(12) United States Patent
Turano

(10) Patent No.: US 11,771,114 B2
(45) Date of Patent: *Oct. 3, 2023

(54) METHODS FOR HIGH TAURINE PRODUCTION USING NOVEL DECARBOXYLASES

(71) Applicant: PLANT SENSORY SYSTEMS LLC, Baltimore, MD (US)

(72) Inventor: Frank J. Turano, Baltimore, MD (US)

(73) Assignee: PLANT SENSORY SYSTEMS, LLC, Baltimore, MD (US)

(*) Notice: Subject to any disclaimer, the term of this patent is extended or adjusted under 35 U.S.C. 154(b) by 617 days.

This patent is subject to a terminal disclaimer.

(21) Appl. No.: 16/763,284

(22) PCT Filed: Nov. 13, 2017

(86) PCT No.: PCT/US2017/061337
§ 371 (c)(1),
(2) Date: May 12, 2020

(87) PCT Pub. No.: WO2019/094051
PCT Pub. Date: May 16, 2019

(65) Prior Publication Data
US 2020/0305468 A1  Oct. 1, 2020

(51) Int. Cl.
*C12N 9/06* (2006.01)
*A23K 50/80* (2016.01)
(Continued)

(52) U.S. Cl.
CPC .............. *A23K 50/80* (2016.05); *A01N 41/08* (2013.01); *A01N 63/50* (2020.01); *A23K 10/10* (2016.05);
(Continued)

(58) Field of Classification Search
None
See application file for complete search history.

(56) References Cited

U.S. PATENT DOCUMENTS

2014/0012140 A1  5/2014  Chen

FOREIGN PATENT DOCUMENTS

| WO | 2017176277 A1 | 10/2017 |
| WO | 2017184175 A1 | 10/2017 |
| WO | 2017/083351 A1 | 5/2018 |

OTHER PUBLICATIONS

Blanc-Mathieu et al., GenBank locus OUS42194, https://www.ncbi.nlm.nih.gov/protein/OUS42194.1?report=genbank&log$=protalign&blast_rank=2&RID=X2Z81KWP013, published Jun. 1, 2017.*
(Continued)

*Primary Examiner* — Erin M. Bowers
(74) *Attorney, Agent, or Firm* — ROTHWELL, FIGG, ERNST & MANBECK, P.C.

(57) ABSTRACT

The present invention describes methods to produce a synthetic or semi-synthetic cysteine synthase/PLP-dependent decarboxylase (sCs/PLP-DC). More particularly, the invention relates to genetic modification of organisms including eukaryotes and prokaryotes to express a functional sCs/PLP-DC. The invention includes methods to produce taurine in organisms that contain native or heterologous (transgenic) taurine biosynthetic pathways or cells that have taurine by enrichment. The invention also relates to methods to increase taurine levels in the cells and to use the said cells or extracts or purifications from the cells that contain the invention to produce plant growth enhancers, food, animal feed, aquafeed, food or drink supplements, animal-feed supplements, dietary supplements, health supplements or taurine.

7 Claims, 1 Drawing Sheet
Specification includes a Sequence Listing.

Motif I = IGxTP(x14-19)KxE(x6)SxKDRI(x7)A(x7)(P/E)G(x6-7)TSGNTG(x3)A(x3)A(x2)G(x11)SxE(x6)AxG
Motif II = P(x6-7)Q(x5)N(x10)EI(x5)G(x9)(S/G)TGxTxxG(x9)(P/G)
Motif III = GxG(K/Y)(x12)D(x21)GxxxGxS(S/A)G(x4-5)A(x13-14)V(x9)YxS
Motif IV = P(x18-25)E(x18-19)PxFxx(Q/F)x(Y/S/F/P)(x9)G(x7)Nx(N/S/V)x(H/F/Y)(x5)P(x5)E(x17-24)G(x6)(S/A)(x9)AR(x7)(K/R)(x11-18)H(Y/S)(x3)K(x5)G
Motif V = (V/T)P(x5)TxGxTxxxAxD(x14)WxHxDxAxxG(x8)(R/N)(x4)GxxRxxSxxWNPHK(x5)Lx(C/Q)(x5)(K/R/H)(x4-5)L
Motif VI = YL(x10-11)DxxDxxIx(C/T)GR(x7)W(x6)G(x30-38)V(x35-38)A(x10)G(x16-18)R (P/G) = P or G residue    x = any amino acid residue    (x14-19) = 14 to 19 residues of any amino acid

(51) Int. Cl.
        *A23K 10/10*      (2016.01)
        *A01N 41/08*      (2006.01)
        *C12N 9/02*       (2006.01)
        *C12N 9/10*       (2006.01)
        *C12N 9/88*       (2006.01)
        *A01N 63/50*      (2020.01)

(52) U.S. Cl.
        CPC ......... *C12N 9/0014* (2013.01); *C12N 9/0071* (2013.01); *C12N 9/1085* (2013.01); *C12N 9/1096* (2013.01); *C12N 9/88* (2013.01); *C12Y 104/99002* (2013.01); *C12Y 114/11017* (2013.01); *C12Y 114/14005* (2013.01); *C12Y 205/01047* (2013.01); *C12Y 206/01077* (2013.01); *C12Y 402/01022* (2013.01)

(56) References Cited

OTHER PUBLICATIONS

International Search Report and Written Opinion issued in corresponding International Application No. PCT/US2017/061337, dated Feb. 14, 2018, 9 pages.
Agnello et al. "Discovery of a Substrate Selectivity Motif in Amino Acid Decarboxylases Unveils a Taurine Biosynthesis Pathway in Prokaryotes," ACS Chemical Biology, Aug. 23, 2013 (Aug. 23, 2013), vol. 8, pp. 2264-2271.
Tevatia et al. "The Taurine Biosynthetic Pathway of Microalgae," Algal Research, Feb. 27, 2015 (Feb. 27, 2015), vol. 9, pp. 21-26.

\* cited by examiner

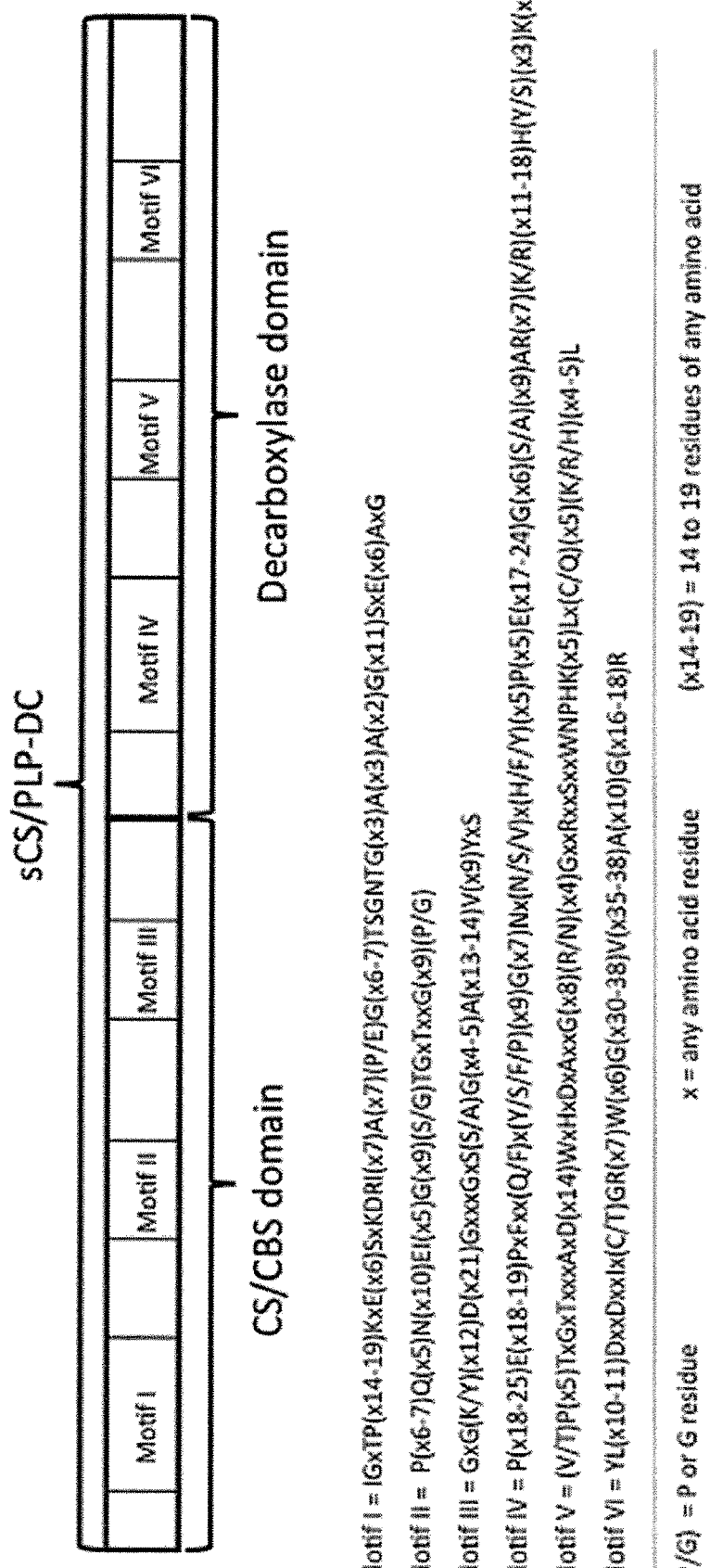

SEQUENCE LISTING

<160> NUMBER OF SEQ ID NOS: 84

<210> SEQ ID NO 1
<211> LENGTH: 2958
<212> TYPE: DNA
<213> ORGANISM: Micromonas pusilla

<400> SEQUENCE: 1

```
atgtccgcgg cgacgggatc attatcccta cccctactcg ggcatctcgc gacctcgcgt      60
aacgcacgcg cgcgtcggaa ccgcgccgcc gcggccatcc ccggcgtctc cctcgggaaa     120
tcgacctcgg ttttcactcc gcgaggtcct aagcgcatcg cgcgcgtcgt cacctcgaag     180
gcgggcccgc attcgaaccc tccgagggcg atatcgaccg tcgacgacgt cctcgcgttc     240
accgtgccca ccgacgagcc cgcggccgag accgcctccc ccgccgacag cgactgcgaa     300
ggcgagttct gcgacatgaa ggagagctcg tgcacgacga gggacctcat cggcagcacg     360
ccgctgctcg atctgagcgc gtactccctg aaccccaccg tgaagatcct cgcgaagtgc     420
gagtacctca acccgtccgg gtccatcaaa gaccgcatcg cgacgcacat cctggacaag     480
gcgatcaaga gcgcgatcct caagcccggg atgaccgtcg tcgcggcgac gtccgggaac     540
accggcgccg cgatcgcgat ggcgtgcgcg ttgcgcgggt acgactacat cgtcatcacc     600
aacgagaaga cgtccaagga aaggtggac gcgatgagag cgtacggcgg cgaggtgatc     660
gtctccccgt ccggggtgtc cccggacgac ccacagcact accagaacat cgagaacaag     720
ctgtgcgagg agaaccccgg gacgtactac ggcgtggatc agtataacaa cccgtacaac     780
gcggacgcgt acgaggcgac gctcgggccg gagatttggc gtcagagcgt gggcgcggtg     840
acgcacttca tcgtcggcgg cagcaccggc ggcacggtca gcggcacggg gaggtacttg     900
aagcaagaga acccggacgt gaggatcgtc ctcgcggacc cgagagggag cgtgttctgg     960
gaccacgtcg tcaacggcgt cgccgccgac gacgtcaagg tgtccaagtc gtgggagacg    1020
gagggcgtcg gcaaggattc catccccggg tgcctcgacg tctcgatcgt ggacgggatg    1080
gtgcgcgcga cggacgagca ggcgttcggc gtgtgccgcg agctcgcgag cagcgacggc    1140
ctcctcgtcg gcggcagcag cggtctgaac ctccacgcct cgcgcgtgtt atccggcgac    1200
gtcgcggacg acagcgtcat cgtcacggtg ttcccggaca cggcgtgaa gtacctgtcg    1260
aagatttaca cgacgactg gctcgactcg aagaagatgg gcggcgcaaa gaactcggac    1320
gggaacgcgg agagagccgc ggagtgcgag gtgtactggc gcccggacgc gctctcgttc    1380
gcggagcgaa aggcggcggc ggacgccgcc gccgccgccg ccgtcgaggg cgacaacctc    1440
tggcccgagg acgagaccga gcgcgagctc aagttcctgg aggaactcgc gccgaagctg    1500
acgcagtacc acagagactc catcaagggc gacgagcgcg tgcacagcaa gctccagtcc    1560
ccggaggagc tcgcggcgac gttcgccgcc gcggggggcgc ccatcgacct cgcggagggc    1620
gacgcccccg cgacggagga gcaactcgcg ctcgcggtgc aggcggtcat ggacaactcg    1680
gtccgctcct cgcacccgat gttcttgaac cagctgtacg ccggcgtcga cgtcgtcgcg    1740
ctcgcggggg agtggaccgc gagcgcgttg aacgccaacg tgcacacgtt tgaagtcgcg    1800
ccggtgctca cggagattga aaagccgtc ctcgcgaaaa ccgcgcggat gtggctgaac    1860
aagcccgggt ctaagacgac gccgccgcac gacggtctgc tcgtccccgg cgggtccctg    1920
gcgaacatgt actcgatgat cctcgcgcgc gatcgcgcgg agccggaggc gaagaccaag    1980
ggcgcgagcg gcaacctcgt cgcgttttgc tcggagcagt cgcactactc gtacaaaaag    2040
tccgcgatgg tcatgggcct cgggatggac aacatgatca aggtgaagtg cgaccagtcc    2100
```

```
ggcgcgatga tcccggcgga gctcgagaag gcggttcagg aggccaagtc ccggggcaag    2160
gtgccgttct acgtcggcac caccgcgggg tccaccgtgc tcggcgcctt tgacgactac    2220
gaaggctgcg cggacgtctg cgaaaagcac gacatgtgga tgcacgtcga cggcgcgtgg    2280
ggcggcgccg cggcgctgtc cccgacgaga aggcacaatc tccagggcgc gaacagagcg    2340
gactcgttct gctggaaccc gcacaagatg ctcgggttgc cgctccagtg ctccatcttc    2400
gtgacgaagc aacccggggc gctgtccaag gcgaacgccg cgcaggcgga ctacttgttc    2460
cagccggaca agaacaacgc cgccgcggac ctcggcgacc gcacgattca gtgcggacgc    2520
aaggcggacc ccctcaagat ctggctcgcg tggaaggcgc gcggagacga aggctgggcg    2580
aatctcgtgg accgctcctt tggcctcgcg gagtacgtcg aggcgtcggt gcgcgagcgg    2640
tgcgaaaaag acggctcgtt cgtcctcgcc gcgcccgcgc agtgcgcgaa catcgggttc    2700
tggtacgtgc cccgcgcct gaggccgttc gatgtcgagt ccgcgaccgc ggaccagctc    2760
acggagattg ggttcgtcgc cccgaagctg aaggaccgga tgcaacggac cggggacgcg    2820
atgatcgggt ccagccgat cgactcgatg aaccttccaa acttttttccg actcgtgctt    2880 ccaaactcga ggcacctgtc gaagaacgcg ctcgacgcta tgctcgatcg catggacgac    2940
atgggcaaag acctgtga                                                  2958
```

<210> SEQ ID NO 2
<211> LENGTH: 985
<212> TYPE: PRT
<213> ORGANISM: Micromonas pusilla

<400> SEQUENCE: 2

```
Met Ser Ala Ala Thr Gly Ser Leu Ser Leu Pro Leu Leu Gly His Leu
1               5                   10                  15

Ala Thr Ser Arg Asn Ala Arg Ala Arg Arg Asn Arg Ala Ala Ala Ala
                20                  25                  30

Ile Pro Gly Val Ser Leu Gly Lys Ser Thr Ser Val Phe Thr Pro Arg
            35                  40                  45

Gly Pro Lys Arg Ile Ala Arg Val Val Thr Ser Lys Ala Gly Pro His
        50                  55                  60

Ser Asn Pro Pro Arg Ala Ile Ser Thr Val Asp Asp Val Leu Ala Phe
65                  70                  75                  80

Thr Val Pro Thr Asp Glu Pro Ala Ala Glu Thr Ala Ser Pro Ala Asp
                85                  90                  95

Ser Asp Cys Glu Gly Glu Phe Cys Asp Met Lys Glu Ser Ser Cys Thr
            100                 105                 110

Thr Arg Asp Leu Ile Gly Ser Thr Pro Leu Leu Asp Leu Ser Ala Tyr
        115                 120                 125

Ser Leu Asn Pro Thr Val Lys Ile Leu Ala Lys Cys Glu Tyr Leu Asn
    130                 135                 140

Pro Ser Gly Ser Ile Lys Asp Arg Ile Ala Thr His Ile Leu Asp Lys
145                 150                 155                 160

Ala Ile Lys Ser Gly Asp Leu Lys Pro Gly Met Thr Val Val Ala Ala
                165                 170                 175

Thr Ser Gly Asn Thr Gly Ala Ala Ile Ala Met Ala Cys Ala Leu Arg
            180                 185                 190

Gly Tyr Asp Tyr Ile Val Ile Thr Asn Glu Lys Thr Ser Lys Glu Lys
        195                 200                 205

Val Asp Ala Met Arg Ala Tyr Gly Gly Glu Val Ile Val Ser Pro Ser
```

```
            210                 215                 220
Gly Val Ser Pro Asp Asp Pro Gln His Tyr Gln Asn Ile Glu Asn Lys
225                 230                 235                 240

Leu Cys Glu Glu Asn Pro Gly Thr Tyr Tyr Gly Val Asp Gln Tyr Asn
                245                 250                 255

Asn Pro Tyr Asn Ala Asp Ala Tyr Glu Ala Thr Leu Gly Pro Glu Ile
                260                 265                 270

Trp Arg Gln Ser Val Gly Ala Val Thr His Phe Ile Val Gly Gly Ser
            275                 280                 285

Thr Gly Gly Thr Val Ser Gly Thr Gly Arg Tyr Leu Lys Gln Glu Asn
            290                 295                 300

Pro Asp Val Arg Ile Val Leu Ala Asp Pro Arg Gly Ser Val Phe Trp
305                 310                 315                 320

Asp His Val Val Asn Gly Val Ala Asp Asp Val Lys Val Ser Lys
                325                 330                 335

Ser Trp Glu Thr Glu Gly Val Gly Lys Asp Ser Ile Pro Gly Cys Leu
                340                 345                 350

Asp Val Ser Ile Val Asp Gly Met Val Arg Ala Thr Asp Glu Gln Ala
            355                 360                 365

Phe Gly Val Cys Arg Glu Leu Ala Ser Ser Asp Gly Leu Leu Val Gly
            370                 375                 380

Gly Ser Ser Gly Leu Asn Leu His Ala Ser Arg Val Leu Ser Gly Asp
385                 390                 395                 400

Val Ala Asp Asp Ser Val Ile Val Thr Val Phe Pro Asp Asn Gly Val
                405                 410                 415

Lys Tyr Leu Ser Lys Ile Tyr Asn Asp Asp Trp Leu Asp Ser Lys Lys
                420                 425                 430

Met Gly Gly Ala Lys Asn Ser Asp Gly Asn Ala Glu Arg Ala Ala Glu
            435                 440                 445

Cys Glu Val Tyr Trp Arg Pro Asp Ala Leu Ser Phe Ala Glu Arg Lys
            450                 455                 460

Ala Ala Ala Asp Ala Ala Ala Ala Ala Val Glu Gly Asp Asn Leu
465                 470                 475                 480

Trp Pro Glu Asp Glu Thr Glu Arg Glu Leu Lys Phe Leu Glu Glu Leu
                485                 490                 495

Ala Pro Lys Leu Thr Gln Tyr His Arg Asp Ser Ile Lys Gly Asp Glu
                500                 505                 510

Arg Val His Ser Lys Leu Gln Ser Pro Glu Glu Leu Ala Ala Thr Phe
            515                 520                 525

Ala Ala Ala Gly Ala Pro Ile Asp Leu Ala Glu Gly Asp Ala Pro Ala
530                 535                 540

Thr Glu Glu Gln Leu Ala Leu Ala Val Gln Ala Val Met Asp Asn Ser
545                 550                 555                 560

Val Arg Ser Ser His Pro Met Phe Leu Asn Gln Leu Tyr Ala Gly Val
                565                 570                 575

Asp Val Val Ala Leu Ala Gly Glu Trp Thr Ala Ser Ala Leu Asn Ala
                580                 585                 590

Asn Val His Thr Phe Glu Val Ala Pro Val Leu Thr Glu Ile Glu Lys
                595                 600                 605

Ala Val Leu Ala Lys Thr Ala Arg Met Trp Leu Asn Lys Pro Gly Ser
            610                 615                 620

Lys Thr Thr Pro Pro His Asp Gly Leu Leu Val Pro Gly Gly Ser Leu
625                 630                 635                 640
```

Ala Asn Met Tyr Ser Met Ile Leu Ala Arg Asp Arg Ala Glu Pro Glu
            645                 650                 655

Ala Lys Thr Lys Gly Ala Ser Gly Asn Leu Val Ala Phe Cys Ser Glu
        660                 665                 670

Gln Ser His Tyr Ser Tyr Lys Lys Ser Ala Met Val Met Gly Leu Gly
    675                 680                 685

Met Asp Asn Met Ile Lys Val Lys Cys Asp Gln Ser Gly Ala Met Ile
690                 695                 700

Pro Ala Glu Leu Glu Lys Ala Val Gln Glu Ala Lys Ser Arg Gly Lys
705                 710                 715                 720

Val Pro Phe Tyr Val Gly Thr Thr Ala Gly Ser Thr Val Leu Gly Ala
                725                 730                 735

Phe Asp Asp Tyr Glu Gly Cys Ala Asp Val Cys Glu Lys His Asp Met
            740                 745                 750

Trp Met His Val Asp Gly Ala Trp Gly Gly Ala Ala Leu Ser Pro
        755                 760                 765

Thr Arg Arg His Asn Leu Gln Gly Ala Asn Arg Ala Asp Ser Phe Cys
770                 775                 780

Trp Asn Pro His Lys Met Leu Gly Leu Pro Leu Gln Cys Ser Ile Phe
785                 790                 795                 800

Val Thr Lys Gln Pro Gly Ala Leu Ser Lys Ala Asn Ala Ala Gln Ala
                805                 810                 815

Asp Tyr Leu Phe Gln Pro Asp Lys Asn Asn Ala Ala Asp Leu Gly
            820                 825                 830

Asp Arg Thr Ile Gln Cys Gly Arg Lys Ala Asp Ala Leu Lys Ile Trp
            835                 840                 845

Leu Ala Trp Lys Ala Arg Gly Asp Glu Gly Trp Ala Asn Leu Val Asp
850                 855                 860

Arg Ser Phe Gly Leu Ala Glu Tyr Val Glu Ala Ser Val Arg Glu Arg
865                 870                 875                 880

Cys Glu Lys Asp Gly Ser Phe Val Leu Ala Ala Pro Ala Gln Cys Ala
                885                 890                 895

Asn Ile Gly Phe Trp Tyr Val Pro Pro Arg Leu Arg Pro Phe Asp Val
            900                 905                 910

Glu Ser Ala Thr Ala Asp Gln Leu Thr Glu Ile Gly Phe Val Ala Pro
        915                 920                 925

Lys Leu Lys Asp Arg Met Gln Arg Thr Gly Asp Ala Met Ile Gly Phe
    930                 935                 940

Gln Pro Ile Asp Ser Met Asn Leu Pro Asn Phe Arg Leu Val Leu
945                 950                 955                 960

Pro Asn Ser Arg His Leu Ser Lys Asn Ala Leu Asp Ala Met Leu Asp
                965                 970                 975

Arg Met Asp Asp Met Gly Lys Asp Leu
            980                 985

<210> SEQ ID NO 3
<211> LENGTH: 2727
<212> TYPE: DNA
<213> ORGANISM: Ostreococcus tauri

<400> SEQUENCE: 3
atgcggacat acacccgatc ttccgagggt ccccgcccat tccacgagag cgcgccgtcg    60
ccagtgcgcg cctccccagt acgccgcgcc gttcacatcg ccgacgcgag cgccggtgct   120

-continued

```
gtcacttccg atcactaccg gcgcgctcgc tcgaacggcg ccgcgcgcgc cgtgcgcggc      180
gccgacgaga cgtcgtcttc agggtttgat tcaacagagg cgtcgctcga gtccgtcgac      240
gacgccctcg agagcgatct ccagcgacgc cgacgacctg gaggagctcc tgaacttaga      300
ttacccggtg gacatgccgg agttcgagaa cgcgctgccg acgataagca ctggcggtcg      360
acgcacgcgc gaatcgcaaa cggagcggtg gtgccacagc agctcatcgg tgggacgccg      420
atgatcgatc ttagtgagtt tagtgcgaac ccaaaggtga agatctatgg gaagtgcgag      480
tacatgaatc cgagtgggag cattaaagat cggattgcgc aggagatttt gactcgggcg      540
ctggagacgg gcgagttgaa acccgggatg acggtcgtgg cggcaacgag tgggaacacc      600
ggggcggcga tcgcgatggc gtgcgcgatt cgtgggtttg attacatcgt gatcacgaat      660
aagaagacga gtaaggagaa gattgacgcc atgaaggcgt acgggggggca agtcatcgtc      720
gcggagagtg gggtcccggc agatcatccg gatcattatc agaacatcga gacgacgatg      780
tgcgcgcaga acccgaacta ttacggcgta aatcagtacg ataatccgta caacgcggat      840
gcgtacgaga agactcttgg tcccgagatt tggtcgcaaa ccaagggggc agtgacgcac      900
ttcatcgcgg gcggttccac aggaggcacc atcactggta ccggtcgcta cttgaagagc      960
gtagatccaa cgatcaaaat catgttagct gatcccaagg gtagcgtttt gtgggactat     1020
ttcgtcaatg acgtgcccga agaggatctt gtggcgaaga gttgggaagt cgagggcgtc     1080
ggcaaggact ccattccggg tgttttgcag acagaataca tcgacggtgc cgtgaaaggt     1140
tgcgacgcga gctcattccg aatttgccga atggtggccg aatcttcggg catcttgctc     1200
ggcggtagct ccggtctgaa cctgcacgcc gctcgagtgc tctcgagcca gatcaaggag     1260
ggtgttatag tcacggtttt gtgcgacagc ggtgtcaagt atttgtcaaa gatcttcaac     1320
gacgaatggc tcgaatcgaa gaatttgaat cagccattgt cggatgtcaa gaacttccaa     1380
gtcgcttgga aaaggacca gtctgaggcg agtgacgacg aagacgcaga ccacggtctg     1440
tggagtcgcg acgatgagga gaaggagctt cgctttctag acgaaatcgc gacgcacatg     1500
gttgagtact accgcaactc cgcgcgcgcc gccgacccgg tcagtacgta caactctccg     1560
ctcgcccttc acgaaaagtt caaggaggtg ggtattccgt tggccatcgg tacgggtgag     1620
gagccggtct cgatgagctt actcaccacc gcgatgaaca cggtgatcca gaacagcgct     1680
cgcacctcgc acccaatgtt aggaggaacg cgcggaggaa gagacggagg aaggatgagg     1740
cggatgggtg agttgtcgtg ggagctcggg gcggcgggtg aggaggagga ggaggaagag     1800
cagggggcagg agggcgagga aatctctcga gaggaggtgc tggcgctctc ggtggagctc     1860
atcgaatcca tcgcttccgg gaaggaaccg ctcgatgcgg cgcgtcttgg gagcttgctt     1920
tggactttga gcaacgcgct gttggaggat ttgacggaca gggacgattt acgcgttccg     1980
gggaactcgc tcgagacgtt tccggtggag ctggtgcgaa acgtcatggg cgccgtcgaa     2040
accctggtcg ttgcgctgac gttcgagccg aagatgcgg tgacgcaacg aagtgggcac     2100
gcaattccgg ccatcggcac acatcgcgtc gctgcgcgcg agatcatcgc cgtgctcttg     2160
caaatcgggt gccaagacat tgacgagcgc atcgcaaagc tcaagctgcc gaacgacggt     2220
cagttcgtcc tcgtgtcgct cgtacgcatg tttttcaagt attcttggag ttcggcgctg     2280
cacgcgaccg tggtgagact gatcttggcc cgctggtga gcccacacga gccgctctgg     2340
gcacccatgt ttgagggcgg ggacgagagt cttcagggct ctctggcagc gtccatgaag     2400
acggcgctcg cgacgaagcc catctccacg agagacggta acgtcgggag cgtgattatt     2460
ctcgccaacg ctctgcacga gctcgaaact tgcgatgacg tcgagcgcca gagcgtgcgg     2520
```

```
acgacgttgc aggaggatgc aacgtggcga gccgccattg acggtgagga tagcccgttg    2580
gcgaacctca acaacgaaca ggctggcgga ctttgtggac caaagccgca gaagtcgcct    2640
gttttcatgg actccggcat gggcgccaac gtcatcagca gccaagagct gctcaggatg    2700
ttgcagcaca tctcgcttgg tcaatga                                        2727

<210> SEQ ID NO 4
<211> LENGTH: 908
<212> TYPE: PRT
<213> ORGANISM: Ostreococcus tauri

<400> SEQUENCE: 4

Met Arg Thr Tyr Thr Arg Ser Ser Glu Gly Pro Arg Pro Phe His Glu
1               5                   10                  15

Ser Ala Pro Ser Pro Val Arg Ala Ser Pro Val Arg Arg Ala Val His
                20                  25                  30

Ile Ala Asp Ala Ser Ala Gly Ala Val Thr Ser Asp His Tyr Arg Arg
            35                  40                  45

Ala Arg Ser Asn Gly Ala Ala Arg Ala Val Arg Gly Ala Asp Glu Thr
        50                  55                  60

Ser Ser Ser Gly Phe Asp Ser Thr Glu Ala Ser Leu Glu Ser Val Asp
65                  70                  75                  80

Asp Ala Leu Glu Ser Asp Leu Gln Arg Arg Arg Pro Gly Gly Ala
                85                  90                  95

Pro Glu Leu Arg Leu Pro Gly Gly His Ala Gly Val Arg Glu Arg Ala
            100                 105                 110

Ala Asp Asp Lys His Trp Arg Ser Thr His Ala Arg Ile Ala Asn Gly
        115                 120                 125

Ala Val Val Pro Gln Gln Leu Ile Gly Gly Thr Pro Met Ile Asp Leu
    130                 135                 140

Ser Glu Phe Ser Ala Asn Pro Lys Val Lys Ile Tyr Gly Lys Cys Glu
145                 150                 155                 160

Tyr Met Asn Pro Ser Gly Ser Ile Lys Asp Arg Ile Ala Gln Glu Ile
                165                 170                 175

Leu Thr Arg Ala Leu Glu Thr Gly Glu Leu Lys Pro Gly Met Thr Val
            180                 185                 190

Val Ala Ala Thr Ser Gly Asn Thr Gly Ala Ala Ile Ala Met Ala Cys
        195                 200                 205

Ala Ile Arg Gly Phe Asp Tyr Ile Val Ile Thr Asn Lys Lys Thr Ser
    210                 215                 220

Lys Glu Lys Ile Asp Ala Met Lys Ala Tyr Gly Gly Gln Val Ile Val
225                 230                 235                 240

Ala Glu Ser Gly Val Pro Ala Asp His Pro Asp His Tyr Gln Asn Ile
                245                 250                 255

Glu Thr Thr Met Cys Ala Gln Asn Pro Asn Tyr Tyr Gly Val Asn Gln
            260                 265                 270

Tyr Asp Asn Pro Tyr Asn Ala Asp Ala Tyr Glu Lys Thr Leu Gly Pro
        275                 280                 285

Glu Ile Trp Ser Gln Thr Lys Gly Ala Val Thr His Phe Ile Ala Gly
    290                 295                 300

Gly Ser Thr Gly Gly Thr Ile Thr Gly Thr Gly Arg Tyr Leu Lys Ser
305                 310                 315                 320

Val Asp Pro Thr Ile Lys Ile Met Leu Ala Asp Pro Lys Gly Ser Val
                325                 330                 335
```

```
Leu Trp Asp Tyr Phe Val Asn Asp Val Pro Glu Asp Leu Val Ala
            340                 345                 350

Lys Ser Trp Glu Val Glu Gly Val Lys Asp Ser Ile Pro Gly Val
            355                 360                 365

Leu Gln Thr Glu Tyr Ile Asp Gly Ala Val Lys Gly Cys Asp Ala Ser
370                 375                 380

Ser Phe Arg Ile Cys Arg Met Val Ala Glu Ser Ser Gly Ile Leu Leu
385                 390                 395                 400

Gly Gly Ser Ser Gly Leu Asn Leu His Ala Ala Arg Val Leu Ser Ser
            405                 410                 415

Gln Ile Lys Glu Gly Val Ile Val Thr Val Leu Cys Asp Ser Gly Val
            420                 425                 430

Lys Tyr Leu Ser Lys Ile Phe Asn Asp Glu Trp Leu Glu Ser Lys Asn
            435                 440                 445

Leu Asn Gln Pro Leu Ser Asp Val Lys Asn Phe Gln Val Ala Trp Lys
            450                 455                 460

Lys Asp Gln Ser Glu Ala Ser Asp Asp Glu Asp Ala Asp His Gly Leu
465                 470                 475                 480

Trp Ser Arg Asp Asp Glu Glu Lys Glu Leu Arg Phe Leu Asp Glu Ile
                485                 490                 495

Ala Thr His Met Val Glu Tyr Tyr Arg Asn Ser Ala Arg Ala Ala Asp
                500                 505                 510

Pro Val Ser Thr Tyr Asn Ser Pro Leu Ala Leu His Glu Lys Phe Lys
                515                 520                 525

Glu Val Gly Ile Pro Leu Ala Ile Gly Thr Gly Glu Glu Pro Val Ser
            530                 535                 540

Met Ser Leu Leu Thr Thr Ala Met Asn Thr Val Ile Gln Asn Ser Ala
545                 550                 555                 560

Arg Thr Ser His Pro Met Leu Gly Gly Thr Arg Gly Gly Arg Asp Gly
                565                 570                 575

Gly Arg Met Arg Arg Met Gly Glu Leu Ser Trp Glu Leu Gly Ala Ala
            580                 585                 590

Gly Glu Glu Glu Glu Glu Glu Gln Gly Gln Glu Gly Glu Glu Ile
            595                 600                 605

Ser Arg Glu Glu Val Leu Ala Leu Ser Val Glu Leu Ile Glu Ser Ile
            610                 615                 620

Ala Ser Gly Lys Glu Pro Leu Asp Ala Ala Arg Leu Gly Ser Leu Leu
625                 630                 635                 640

Trp Thr Leu Ser Asn Ala Leu Leu Glu Asp Leu Thr Asp Arg Asp Asp
                645                 650                 655

Leu Arg Val Pro Gly Asn Ser Leu Glu Thr Phe Pro Val Glu Leu Val
                660                 665                 670

Arg Asn Val Met Gly Ala Val Glu Thr Leu Val Val Ala Leu Thr Phe
            675                 680                 685

Glu Pro Glu Asp Ala Val Thr Gln Arg Ser Gly His Ala Ile Pro Ala
            690                 695                 700

Ile Gly Thr His Arg Val Ala Ala Ala Glu Ile Ile Ala Val Leu Leu
705                 710                 715                 720

Gln Ile Gly Cys Gln Asp Ile Asp Glu Arg Ile Ala Lys Leu Lys Leu
                725                 730                 735

Pro Asn Asp Gly Gln Phe Val Leu Val Ser Leu Val Arg Met Phe Phe
            740                 745                 750
```

```
Lys Tyr Ser Trp Ser Ser Ala Leu His Ala Thr Val Val Arg Leu Ile
            755                 760                 765

Leu Ala Ala Leu Val Ser Pro His Glu Pro Leu Trp Ala Pro Met Phe
    770                 775                 780

Glu Gly Gly Asp Glu Ser Leu Gln Gly Ser Leu Ala Ala Ser Met Lys
785                 790                 795                 800

Thr Ala Leu Ala Thr Lys Pro Ile Ser Thr Arg Asp Gly Asn Val Gly
                805                 810                 815

Ser Val Ile Ile Leu Ala Asn Ala Leu His Glu Leu Glu Thr Cys Asp
            820                 825                 830

Asp Val Glu Arg Gln Ser Val Arg Thr Thr Leu Gln Glu Asp Ala Thr
            835                 840                 845

Trp Arg Ala Ala Ile Asp Gly Glu Asp Ser Pro Leu Ala Asn Leu Asn
850                 855                 860

Asn Glu Gln Ala Gly Gly Leu Cys Gly Pro Lys Pro Gln Lys Ser Pro
865                 870                 875                 880

Val Phe Met Asp Ser Gly Met Gly Ala Asn Val Ile Ser Ser Gln Glu
                885                 890                 895

Leu Leu Arg Met Leu Gln His Ile Ser Leu Gly Gln
            900                 905

<210> SEQ ID NO 5
<211> LENGTH: 969
<212> TYPE: DNA
<213> ORGANISM: Brassica oleracea

<400> SEQUENCE: 5
atggcctctt gtattgctaa tgatgtcacc gaattgattg gaacactcc gttggtgtat      60 ctgaacagtg ttgctgaagg atgtgttggt cgtgttgctg ctaagcttga gatgatggaa    120
ccctgctcca gcgtcaaaga caggattggt tttagcatga tctctgatgc agagaaaaag    180
ggtctgatta aaccaggaga gagtgtgttg attgagccaa cgagtggaaa cacgggagtt    240
gggttagcat tcacggcggc tgccaaggga tacaagctta ttattaccat gccagcttca    300
atgagtgttg agagaagaat cattctctta gcttttggtg ttgagttggt tttgactgat    360
cctgccaagg gcatgaaagg cgctatcgca aaggcggagg agattttggc caaaacacct    420
aatggttaca tgctccaaca gtttgagaac cctgctaacc caagatccca ctatgagaca    480
actggacctg agatttggaa aggcactgat ggtaaaatcg atggctttgt ttctgggatt    540
ggtaccggtg gtaccatcac aggtgcaggg aagtatctta aggaacagaa ccccaacgtt    600
aagctgtatg gagtggaacc aatcgaaagc gctattctat ctggtggaaa gccaggccct    660
cacaagattc aagggatagg tgctggtttt ataccaagtg tgttggaggt taatcttata    720
gatgaagttg ttcaagtttc aagtgatgaa tccatcgaca tggcaaggct tcttgctcgt    780
aaagaaggtc ttcttgtggg aatatcatct ggtgcagcag ctgccgcagc aatcaaactt    840
gcaaagaggc cagaaaacgc cgggaagctt ttcgtggcgg tgttcccgag tttcggagag    900
aggtacctgt cgaccgtact attcgatgcc acaaggaaag aagcagaatc catgaccttc    960
gaggcttga                                                             969

<210> SEQ ID NO 6
<211> LENGTH: 322
<212> TYPE: PRT
<213> ORGANISM: Brassica oleracea

<400> SEQUENCE: 6
```

```
Met Ala Ser Cys Ile Ala Asn Asp Val Thr Glu Leu Ile Gly Asn Thr
1               5                   10                  15

Pro Leu Val Tyr Leu Asn Ser Val Ala Glu Gly Cys Val Gly Arg Val
            20                  25                  30

Ala Ala Lys Leu Glu Met Met Glu Pro Cys Ser Ser Val Lys Asp Arg
            35                  40                  45

Ile Gly Phe Ser Met Ile Ser Asp Ala Glu Lys Lys Gly Leu Ile Lys
        50                  55                  60

Pro Gly Glu Ser Val Leu Ile Glu Pro Thr Ser Gly Asn Thr Gly Val
65                  70                  75                  80

Gly Leu Ala Phe Thr Ala Ala Lys Gly Tyr Lys Leu Ile Ile Thr
                85                  90                  95

Met Pro Ala Ser Met Ser Val Glu Arg Arg Ile Ile Leu Leu Ala Phe
            100                 105                 110

Gly Val Glu Leu Val Leu Thr Asp Pro Ala Lys Gly Met Lys Gly Ala
            115                 120                 125

Ile Ala Lys Ala Glu Glu Ile Leu Ala Lys Thr Pro Asn Gly Tyr Met
        130                 135                 140

Leu Gln Gln Phe Glu Asn Pro Ala Asn Pro Lys Ile His Tyr Glu Thr
145                 150                 155                 160

Thr Gly Pro Glu Ile Trp Lys Gly Thr Asp Gly Lys Ile Asp Gly Phe
                165                 170                 175

Val Ser Gly Ile Gly Thr Gly Gly Thr Ile Thr Gly Ala Gly Lys Tyr
            180                 185                 190

Leu Lys Glu Gln Asn Pro Asn Val Lys Leu Tyr Gly Val Glu Pro Ile
        195                 200                 205

Glu Ser Ala Ile Leu Ser Gly Gly Lys Pro Gly Pro His Lys Ile Gln
        210                 215                 220

Gly Ile Gly Ala Gly Phe Ile Pro Ser Val Leu Glu Val Asn Leu Ile
225                 230                 235                 240

Asp Glu Val Val Gln Val Ser Ser Asp Glu Ser Ile Asp Met Ala Arg
                245                 250                 255

Leu Leu Ala Arg Lys Glu Gly Leu Leu Val Gly Ile Ser Ser Gly Ala
            260                 265                 270

Ala Ala Ala Ala Ile Lys Leu Ala Lys Arg Pro Glu Asn Ala Gly
            275                 280                 285

Lys Leu Phe Val Ala Val Phe Pro Ser Phe Gly Glu Arg Tyr Leu Ser
        290                 295                 300

Thr Val Leu Phe Asp Ala Thr Arg Lys Glu Ala Glu Ser Met Thr Phe
305                 310                 315                 320

Glu Ala

<210> SEQ ID NO 7
<211> LENGTH: 978
<212> TYPE: DNA
<213> ORGANISM: Oryza brachyantha

<400> SEQUENCE: 7
atgggtgagg cgtcgccggc catcgccaag gatgtcaccg agctgattgg gaacacgcca     60
ttggtgtacc tcaaccgcgt gactgaagga tgcgtggggc gcgtcgccgc caagctcgag    120
tccatggaac cctgctccag cgtcaaggac aggattggat acagtatgat cactgatgca    180
gaggagaagg ggctgataat tccaggaaag agtgtgttga ttgagccaac tagtggcaac    240
```

```
acaggcattg gactggcctt catggctgct gcaaagggtt acagacttgt actcacgatg    300
ccagcctcca tgagcatgga gaggagaatc atattgaagg cttttggtgc tgaactgatt    360
cttactgacc cactcttagg aatgaaagga gctgtccaaa aggcagaaga actggcagca    420
aagactccca actcatttat cctccaacaa tttgaaaacc ctgctaaccc aaagatccat    480
tacgagacca cagggcctga aatatggaaa aacacaggag gtaaaattga tggttttgtt    540
tctggtattg ggacaggtgg tactataact ggagctggac gatacctcag agagcaaaat    600
cctaatatca agatctatgg tgtggagcca gtcgagagtg ctgtcctatc tggtggaaag    660
cctgggccac acaagattca aggaattgga gctggtttta ttcctggggt cctggatgtc    720
gacctcattg atgaaactgt acaagtttca agtgatgaag ctatcgagat cgcaaaggct    780
cttgcgctga agaaggatt gctggttgga atatcttcag gtgcagctgc tgcggcagct    840
gttaggcttg ctagcaggcc ggaaaacgca ggaaaacttt tgttgttgt cttcccaagc    900
ttcggtgagc ggtacctttc atcggtgctc ttccagacca tcaagaagga agctgaaaac    960
atggtggtcg agccctga                                                 978
```

<210> SEQ ID NO 8
<211> LENGTH: 325
<212> TYPE: PRT
<213> ORGANISM: Oryza brachyantha

<400> SEQUENCE: 8

```
Met Gly Glu Ala Ser Pro Ala Ile Ala Lys Asp Val Thr Glu Leu Ile
1               5                   10                  15
Gly Asn Thr Pro Leu Val Tyr Leu Asn Arg Val Thr Glu Gly Cys Val
            20                  25                  30
Gly Arg Val Ala Ala Lys Leu Glu Ser Met Glu Pro Cys Ser Ser Val
        35                  40                  45
Lys Asp Arg Ile Gly Tyr Ser Met Ile Thr Asp Ala Glu Glu Lys Gly
    50                  55                  60
Leu Ile Ile Pro Gly Lys Ser Val Leu Ile Glu Pro Thr Ser Gly Asn
65                  70                  75                  80
Thr Gly Ile Gly Leu Ala Phe Met Ala Ala Ala Lys Gly Tyr Arg Leu
                85                  90                  95
Val Leu Thr Met Pro Ala Ser Met Ser Met Glu Arg Arg Ile Ile Leu
            100                 105                 110
Lys Ala Phe Gly Ala Glu Leu Ile Leu Thr Asp Pro Leu Leu Gly Met
        115                 120                 125
Lys Gly Ala Val Gln Lys Ala Glu Glu Leu Ala Ala Lys Thr Pro Asn
    130                 135                 140
Ser Phe Ile Leu Gln Gln Phe Glu Asn Pro Ala Asn Pro Lys Ile His
145                 150                 155                 160
Tyr Glu Thr Thr Gly Pro Glu Ile Trp Lys Asn Thr Gly Gly Lys Ile
                165                 170                 175
Asp Gly Phe Val Ser Gly Ile Gly Thr Gly Gly Thr Ile Thr Gly Ala
            180                 185                 190
Gly Arg Tyr Leu Arg Glu Gln Asn Pro Asn Ile Lys Ile Tyr Gly Val
        195                 200                 205
Glu Pro Val Glu Ser Ala Val Leu Ser Gly Gly Lys Pro Gly Pro His
    210                 215                 220
Lys Ile Gln Gly Ile Gly Ala Gly Phe Ile Pro Gly Val Leu Asp Val
225                 230                 235                 240
```

Asp Leu Ile Asp Glu Thr Val Gln Val Ser Ser Asp Glu Ala Ile Glu
            245                 250                 255

Ile Ala Lys Ala Leu Ala Leu Lys Glu Gly Leu Leu Val Gly Ile Ser
        260                 265                 270

Ser Gly Ala Ala Ala Ala Ala Val Arg Leu Ala Ser Arg Pro Glu
        275                 280                 285

Asn Ala Gly Lys Leu Phe Val Val Phe Pro Ser Phe Gly Glu Arg
    290                 295                 300

Tyr Leu Ser Ser Val Leu Phe Gln Thr Ile Lys Lys Glu Ala Glu Asn
305                 310                 315                 320

Met Val Val Glu Pro
            325

<210> SEQ ID NO 9
<211> LENGTH: 969
<212> TYPE: DNA
<213> ORGANISM: Escherichia_coli

<400> SEQUENCE: 9
atgagtaaga ttttgaaga taactcgctg actatcggtc acacgccgct ggttcgcctg     60
aatcgcatcg gtaacggacg cattctggcg aaggtggaat ctcgtaaccc cagcttcagc    120
gttaagtgcc gtatcggtgc caacatgatt tgggatgccg aaaagcgcgg cgtgctgaaa    180
ccaggcgttg aactggttga accgaccagc ggtaataccg ggattgcact ggcctatgta    240
gctgccgctc gcggttacaa actcacccug accatgccag aaaccatgag tattgaacgc    300
cgcaagctgc tgaaagcgtt aggtgcaaac ctggtgctga cggaaggtgc taaaggcatg    360
aaaggcgcaa tccaaaaagc agaagaaatt gtcgccagca atccagagaa atacctgctg    420
caacaattca gcaatccggc aaaccctgaa attcacgaaa aaaccaccgg tccggagatc    480
tgggaagata ccgacggtca ggttgatgta tttattgctg gcgttgggac tggcggtacg    540
ctgactggcg tcagccgcta cattaaaggc accaaaggca agaccgatct tatctctgtc    600
gccgttgagc aaccgattc tccagttatc gcccaggcac tggctggtga agagattaaa    660
cctggcccgc ataaaattca gggtattggc gctggtttta tcccagctaa cctcgatctc    720
aagctggtcg ataaagtcat tggcatcacc aatgaagaag cgatttctac cgcgcgtcgt    780
ctgatggaag aagaaggtat tcttgcaggt atctcttctg gagcagctgt tgctgcggcg    840
ttgaaactac aagaagatga agctttacc aacaagaata ttgtggttat ctaccgtca    900
tcgggtgagc gttatttaag caccgcattg tttgccgatc tcttcactga gaaagaactg    960
caacagtaa                                                            969

<210> SEQ ID NO 10
<211> LENGTH: 322
<212> TYPE: PRT
<213> ORGANISM: Escherichia coli

<400> SEQUENCE: 10

Met Ser Lys Ile Phe Glu Asp Asn Ser Leu Thr Ile Gly His Thr Pro
1               5                   10                  15

Leu Val Arg Leu Asn Arg Ile Gly Asn Gly Arg Ile Leu Ala Lys Val
            20                  25                  30

Glu Ser Arg Asn Pro Ser Phe Ser Val Lys Cys Arg Ile Gly Ala Asn
        35                  40                  45

Met Ile Trp Asp Ala Glu Lys Arg Gly Val Leu Lys Pro Gly Val Glu
    50                  55                  60

Leu Val Glu Pro Thr Ser Gly Asn Thr Gly Ile Ala Leu Ala Tyr Val
65                  70                  75                  80

Ala Ala Ala Arg Gly Tyr Lys Leu Thr Leu Thr Met Pro Glu Thr Met
                85                  90                  95

Ser Ile Glu Arg Arg Lys Leu Leu Lys Ala Leu Gly Ala Asn Leu Val
            100                 105                 110

Leu Thr Glu Gly Ala Lys Gly Met Lys Gly Ala Ile Gln Lys Ala Glu
        115                 120                 125

Glu Ile Val Ala Ser Asn Pro Glu Lys Tyr Leu Leu Gln Gln Phe Ser
130                 135                 140

Asn Pro Ala Asn Pro Glu Ile His Glu Lys Thr Thr Gly Pro Glu Ile
145                 150                 155                 160

Trp Glu Asp Thr Asp Gly Gln Val Asp Val Phe Ile Ala Gly Val Gly
                165                 170                 175

Thr Gly Gly Thr Leu Thr Gly Val Ser Arg Tyr Ile Lys Gly Thr Lys
            180                 185                 190

Gly Lys Thr Asp Leu Ile Ser Val Ala Val Glu Pro Thr Asp Ser Pro
        195                 200                 205

Val Ile Ala Gln Ala Leu Ala Gly Glu Glu Ile Lys Pro Gly Pro His
210                 215                 220

Lys Ile Gln Gly Ile Gly Ala Gly Phe Ile Pro Ala Asn Leu Asp Leu
225                 230                 235                 240

Lys Leu Val Asp Lys Val Ile Gly Ile Thr Asn Glu Glu Ala Ile Ser
                245                 250                 255

Thr Ala Arg Arg Leu Met Glu Glu Glu Gly Ile Leu Ala Gly Ile Ser
            260                 265                 270

Ser Gly Ala Ala Val Ala Ala Ala Leu Lys Leu Gln Glu Asp Glu Ser
        275                 280                 285

Phe Thr Asn Lys Asn Ile Val Val Ile Leu Pro Ser Ser Gly Glu Arg
290                 295                 300

Tyr Leu Ser Thr Ala Leu Phe Ala Asp Leu Phe Thr Glu Lys Glu Leu
305                 310                 315                 320

Gln Gln

<210> SEQ ID NO 11
<211> LENGTH: 975
<212> TYPE: DNA
<213> ORGANISM: Candidatus kryptonium

<400> SEQUENCE: 11
atgaattacc atcaaaacat acttgagtta atcggcaata ctccgcttgt taagttaacg      60
agggtcacag ctgggataaa ggcaactata ttagccaagc ttgaatttat gaaccctggg     120
ggaagcgtta agataggat agctgtatat atggttgaga aagcaatcaa aaacggatta     180
ctaaacccg gcgggacgat aattgagagc acatctggaa acaccgggat aggattagct     240
atgtatgctg cgttaaaggg attaaagcc attttacga tccctgataa gatgagccaa     300
gagaaaataa acctttaaa agcattcgga gccgaagtta tgtttgtcc gacgaatgta     360
cctccagatt ccccgaaag ttactatgag gtagcaaaaa gactcgccaa agagacacca     420
aattcttatt ttgtaaatca atatcacaat gaggataatg ttgaagccca ctacatgacg     480
acgggaccag atatggac tcaaacgagt ggaagaatcg attatcttgt tgcgggtgcc     540
ggcactggag gaacaatatc aggagtgggg aaattcttaa aggaaaaaaa tccaaatgtt     600

```
aaagttatag cggttgatcc aataggttct gtgtatcacg attggtttaa atataaaaaa      660
cttatagagc caaagattta tatggttgaa ggtattgggg aagatatgtt gtgtgagacg      720
atgcattttg aagttattga tgatataatt caggtaagtg atgctgaagc gttttatatg      780
gcacgtaaac ttgcaaggga agagggaata cttgctggag gttcaagtgg tgcagcggtt      840
cacgcagcaa ttaaagtagc tcaaagttta cccgaggata aagttgttgt ggttatacta      900
cctgatacgg gcaggaatta cataagtaaa atatttaacg atgaatggat gaaagaaaaa      960
ggtttcatcg attaa                                                        975

<210> SEQ ID NO 12
<211> LENGTH: 324
<212> TYPE: PRT
<213> ORGANISM: Candidatus kryptonium

<400> SEQUENCE: 12

Met Asn Tyr His Gln Asn Ile Leu Glu Leu Ile Gly Asn Thr Pro Leu
1               5                   10                  15

Val Lys Leu Thr Arg Val Thr Ala Gly Ile Lys Ala Thr Ile Leu Ala
            20                  25                  30

Lys Leu Glu Phe Met Asn Pro Gly Gly Ser Val Lys Asp Arg Ile Ala
        35                  40                  45

Val Tyr Met Val Glu Lys Ala Ile Lys Asn Gly Leu Leu Lys Pro Gly
    50                  55                  60

Gly Thr Ile Ile Glu Ser Thr Ser Gly Asn Thr Gly Ile Gly Leu Ala
65                  70                  75                  80

Met Tyr Ala Ala Leu Lys Gly Phe Lys Ala Ile Phe Thr Ile Pro Asp
                85                  90                  95

Lys Met Ser Gln Glu Lys Ile Asn Leu Leu Lys Ala Phe Gly Ala Glu
            100                 105                 110

Val Ile Val Cys Pro Thr Asn Val Pro Pro Asp Ser Pro Glu Ser Tyr
        115                 120                 125

Tyr Glu Val Ala Lys Arg Leu Ala Lys Glu Thr Pro Asn Ser Tyr Phe
    130                 135                 140

Val Asn Gln Tyr His Asn Glu Asp Asn Val Glu Ala His Tyr Met Thr
145                 150                 155                 160

Thr Gly Pro Glu Ile Trp Thr Gln Thr Ser Gly Arg Ile Asp Tyr Leu
                165                 170                 175

Val Ala Gly Ala Gly Thr Gly Gly Thr Ile Ser Gly Val Gly Lys Phe
            180                 185                 190

Leu Lys Glu Lys Asn Pro Asn Val Lys Val Ile Ala Val Asp Pro Ile
        195                 200                 205

Gly Ser Val Tyr His Asp Trp Phe Lys Tyr Lys Lys Leu Ile Glu Pro
    210                 215                 220

Lys Ile Tyr Met Val Glu Gly Ile Gly Glu Asp Met Leu Cys Glu Thr
225                 230                 235                 240

Met His Phe Glu Val Ile Asp Asp Ile Ile Gln Val Ser Asp Ala Glu
                245                 250                 255

Ala Phe Tyr Met Ala Arg Lys Leu Ala Arg Glu Glu Gly Ile Leu Ala
            260                 265                 270

Gly Gly Ser Ser Gly Ala Ala Val His Ala Ala Ile Lys Val Ala Gln
        275                 280                 285

Ser Leu Pro Glu Asp Lys Val Val Val Ile Leu Pro Asp Thr Gly
    290                 295                 300
```

Arg Asn Tyr Ile Ser Lys Ile Phe Asn Asp Glu Trp Met Lys Glu Lys
305                 310                 315                 320

Gly Phe Ile Asp

<210> SEQ ID NO 13
<211> LENGTH: 1419
<212> TYPE: DNA
<213> ORGANISM: Chloroflexi bacterium

<400> SEQUENCE: 13

| | | | | | |
|---|---|---|---|---|---|
| atgaaaaaaa | acgatcttcc | cacatccgac | tctcttcgag | tttacgataa | tatattgcaa | 60 |
| gttatcggta | aaacgcccct | ggtgcgcctg | aatcatgtag | ggcacgaaat | aacttgcccg | 120 |
| atatatgcaa | aggtggaatt | ctttaaccct | ggtggttcag | taaaggatcg | catcgccatg | 180 |
| aatatcattg | ctgaagccga | agaagcgaaa | cggcttcgac | ccggtggaac | tgttgttgag | 240 |
| tccacctccg | ggaacaccgg | cctcggtttg | ctatggtct | gcgctataaa | aggatacaag | 300 |
| tcggttttg | tcctgccaga | caagatgagc | caggagaaaa | ttcagttgtt | gcgcgctttc | 360 |
| ggcgccaaag | tggtcgtcac | gccaacttca | gtcgagcctg | atgaccccg | ttcgtattac | 420 |
| agtgttgcca | aacgcattgt | agctgaaacg | cctaatgcca | tcctggcaaa | ccaatatttc | 480 |
| aatcctgaaa | atccaggcag | ccattatgcg | acgactggtc | ctgaaatctg | ggagcagacc | 540 |
| cagggtaaag | tgacagatgt | agtcatcagc | atgggcacag | gcgggactat | ctccggggta | 600 |
| ggacgctatc | tgaaagagcg | aaacccgcac | atacacatta | ttggcgtgga | cgccaccggt | 660 |
| tccatcttgc | tggaaacatg | gcagcgcggc | aaagtgcctg | atgatgtgct | tgccaggccc | 720 |
| tataaagtgg | aaggaatcgg | ggaagatttc | ttgcccggca | cattggaccct | ttctgtgatt | 780 |
| gatgatgtaa | tccgggtcac | agataaagaa | tctttccaat | gggcacgtcg | cctggtcagg | 840 |
| gaagaaggaa | ttttctgcgg | cgggtcatcc | ggtgcaaccc | tggcaggtgc | cttccgctat | 900 |
| gctcaaagcc | ttgattatga | tcggcttgtg | gtcgtacttt | ttcctgattc | aggatcgcgt | 960 |
| tatctgtcaa | aaatctatga | tgacaaatgg | atgtacgaaa | acggcttcat | ggaagtcaaa | 1020 |
| tggaatgagg | tcactcttgg | tgaggttttg | gcatccaaga | gctttcctgg | tgtgatctct | 1080 |
| gtatcgtcag | aggctcacat | gacggatgtg | atcattttgt | tgaaaaagaa | tgatatttcg | 1140 |
| caaacacctg | ttttacaccc | cgacggaaaa | gtggcgggta | tggtcaccga | agcaaacctg | 1200 |
| ctaaagcaca | tgctcgaagc | cgggcataat | cacaccgaag | acgaaacagt | agcctccatt | 1260 |
| cttgaacctg | cgcctccatc | ctatcctgcg | cacatgctgt | tgtctgatgc | cttgccttcc | 1320 |
| tttgttgctg | gaccggttgt | tttggtgagc | gacgccgaac | gcgttgtagg | tttgctgaca | 1380 |
| aaaattgacg | cacttgattt | cattgcccga | acgatatag | | | 1419 |

<210> SEQ ID NO 14
<211> LENGTH: 472
<212> TYPE: PRT
<213> ORGANISM: Chloroflexi bacterium

<400> SEQUENCE: 14

Met Lys Lys Asn Asp Leu Pro Thr Ser Asp Ser Leu Arg Val Tyr Asp
1               5                   10                  15

Asn Ile Leu Gln Val Ile Gly Lys Thr Pro Leu Val Arg Leu Asn His
            20                  25                  30

Val Gly His Glu Ile Thr Cys Pro Ile Tyr Ala Lys Val Glu Phe Phe
        35                  40                  45

Asn Pro Gly Gly Ser Val Lys Asp Arg Ile Ala Met Asn Ile Ile Ala

-continued

```
                 50                  55                  60
Glu Ala Glu Arg Ser Glu Arg Leu Arg Pro Gly Gly Thr Val Val Glu
 65                  70                  75                  80

Ser Thr Ser Gly Asn Thr Gly Leu Gly Leu Ala Met Val Cys Ala Ile
                 85                  90                  95

Lys Gly Tyr Lys Ser Val Phe Val Leu Pro Asp Lys Met Ser Gln Glu
            100                 105                 110

Lys Ile Gln Leu Leu Arg Ala Phe Gly Ala Lys Val Val Val Thr Pro
        115                 120                 125

Thr Ser Val Glu Pro Asp Asp Pro Arg Ser Tyr Tyr Ser Val Ala Lys
    130                 135                 140

Arg Ile Val Ala Glu Thr Pro Asn Ala Ile Leu Ala Asn Gln Tyr Phe
145                 150                 155                 160

Asn Pro Glu Asn Pro Gly Ser His Tyr Ala Thr Thr Gly Pro Glu Ile
                165                 170                 175

Trp Glu Gln Thr Gln Gly Lys Val Thr Asp Val Val Ile Ser Met Gly
            180                 185                 190

Thr Gly Gly Thr Ile Ser Gly Val Gly Arg Tyr Leu Lys Glu Arg Asn
        195                 200                 205

Pro His Ile His Ile Gly Val Asp Ala Thr Gly Ser Ile Leu Leu
    210                 215                 220

Glu Thr Trp Gln Arg Gly Lys Val Pro Asp Asp Val Leu Ala Arg Pro
225                 230                 235                 240

Tyr Lys Val Glu Gly Ile Gly Glu Asp Phe Leu Pro Gly Thr Leu Asp
                245                 250                 255

Leu Ser Val Ile Asp Asp Val Ile Arg Val Thr Asp Lys Glu Ser Phe
            260                 265                 270

Gln Trp Ala Arg Arg Leu Val Arg Glu Glu Gly Ile Phe Cys Gly Gly
        275                 280                 285

Ser Ser Gly Ala Thr Leu Ala Gly Ala Phe Arg Tyr Ala Gln Ser Leu
    290                 295                 300

Asp Tyr Asp Arg Leu Val Val Leu Phe Pro Asp Ser Gly Ser Arg
305                 310                 315                 320

Tyr Leu Ser Lys Ile Tyr Asp Asp Lys Trp Met Tyr Glu Asn Gly Phe
                325                 330                 335

Met Glu Val Lys Trp Asn Glu Val Thr Leu Gly Glu Val Leu Ala Ser
            340                 345                 350

Lys Ser Phe Pro Gly Val Ile Ser Val Ser Ser Glu Ala His Met Thr
        355                 360                 365

Asp Val Ile Ile Leu Lys Lys Asn Asp Ile Ser Gln Thr Pro Val
    370                 375                 380

Leu His Pro Asp Gly Lys Val Ala Gly Met Val Thr Glu Ala Asn Leu
385                 390                 395                 400

Leu Lys His Met Leu Glu Ala Gly His Asn His Thr Glu Asp Glu Thr
                405                 410                 415

Val Ala Ser Ile Leu Glu Pro Ala Pro Pro Ser Tyr Pro Ala His Met
            420                 425                 430

Leu Leu Ser Asp Ala Leu Pro Ser Phe Val Ala Gly Pro Val Val Leu
        435                 440                 445

Val Ser Asp Ala Glu Arg Val Val Gly Leu Leu Thr Lys Ile Asp Ala
    450                 455                 460

Leu Asp Phe Ile Ala Arg Thr Ile
465                 470
```

<210> SEQ ID NO 15
<211> LENGTH: 1803
<212> TYPE: DNA
<213> ORGANISM: Cyprinus carpio

<400> SEQUENCE: 15

| | | | | | | |
|---|---|---|---|---|---|---|
| atgccatcta | gttcagagtc | agttgggact | ggccccatct | gcccacacgc | tgccaaagtc | 60 |
| ctcacaaatg | ctgcaaatgg | agaacctggc | atcaacggag | acgctctttt | gaacggaaag | 120 |
| gctgcacaca | agttaagtgt | gaatggctca | gaccctgtga | gcgaaacaaa | cggtcaccgt | 180 |
| gtgcagagtg | tgaatgtaga | gcacattgag | aacggatcag | aaggcagcat | ggagaggaag | 240 |
| tggattcgac | cggatttgcc | cagcagatgc | acctggaaac | ttggtgaccc | aaatgcagag | 300 |
| tcgcctcaca | agcacttcca | agaacaaaag | acacccagaa | tccttcccaa | cattttaagc | 360 |
| aggattggag | agaccccatt | ggtccgcatg | aacaagattc | ctaaaatgtt | tggcctcaag | 420 |
| tgtgagcttt | tggctaaatg | tgagttcttc | aacgccggtg | gcagcgtgaa | ggacagaatc | 480 |
| agtctgcgaa | tggtagagga | tgcggagaga | gacggcatcc | tgaaacctgg | agacaccatc | 540 |
| attgagccca | cgtcaggaaa | cacagggatc | ggtcttgctt | tggcagcagc | agtcaaaggt | 600 |
| tatcgctgca | tcattgtcat | gcctgagaag | atgagcatgg | aaaaggtgga | cgtgctccgt | 660 |
| gctcttggtg | cagagattgt | tcgtacccct | acctcagccc | ggtttgactc | tcctgagtct | 720 |
| cacgtgggag | tggcttggcg | tttgaagaac | gagattccta | cgctcatat | tctggaccag | 780 |
| taccgcaatc | ccagcaaccc | ccttgcccac | tatgacacca | ctgcagaaga | gattctggag | 840 |
| cagtgtgacg | gtaaaataga | catgctggta | gctggagctg | gcactggtgg | caccatcaca | 900 |
| ggcgtcgctc | gcaagctgaa | ggagaaatgc | cctaatatca | gatagttgg | agtggatccc | 960 |
| gagggctcta | tccttgctga | gccagaggag | ctgaataaga | ctgataagac | tcagtatgag | 1020 |
| gttgaaggca | tcggatatga | cttcatcccc | actgttatgg | acagatctgt | ggtggatagt | 1080 |
| tggtacaagt | ccactgatga | agagtccttt | gccatgtctc | gtatgctcat | cagagaggag | 1140 |
| ggacttctgt | gtggcggtag | ttcaggcacg | gccatggctg | ctgcactgca | tgtagccaaa | 1200 |
| gagctggagg | aaggccagcg | ctgtgtggtg | attctcccag | actccatccg | caactacatg | 1260 |
| tctaaatttc | ttagtgacaa | gtggatgtgt | gaaaagggct | tcctgagtga | ggaggatctt | 1320 |
| gttgtcaaca | agccgtggtg | gtggaatctg | actctacagg | agctccggct | ctccgcccca | 1380 |
| ctcactgtgc | tgcctttagt | gtccattaag | aagaccattc | agatcctgaa | agagaaggct | 1440 |
| tttgaccaag | cccctgtggt | ggacgagacc | gggcagattc | tgggcatggt | cacattgggg | 1500 |
| aacatgctct | cgtccgttct | ggctggcaga | gtcagaccat | ccgatcccat | aaacaaagtt | 1560 |
| ctctacaaac | agtttaaaca | ggtgcgccta | actgataacc | tgggcaagct | ctcacgtatc | 1620 |
| cttgagacgg | accatttcgc | ccttgttgtg | cacgaacaga | ttcagtacat | gagcgatgga | 1680 |
| tcccccaaga | tgaggcagat | ggtgtttggg | gtggtgacag | ccatcgacct | gctgaactac | 1740 |
| gttgccactc | gtgagaggag | ggaacgctcg | ctgtccgagt | gctcgctgtc | agaagatcag | 1800 |
| tga | | | | | | 1803 |

<210> SEQ ID NO 16
<211> LENGTH: 600
<212> TYPE: PRT
<213> ORGANISM: Cyprinus carpio

<400> SEQUENCE: 16

```
Met Pro Ser Ser Ser Glu Ser Val Gly Thr Gly Pro Ile Cys Pro His
1               5                   10                  15

Ala Ala Lys Val Leu Thr Asn Ala Ala Asn Gly Glu Pro Gly Ile Asn
            20                  25                  30

Gly Asp Ala Leu Leu Asn Gly Lys Ala Ala His Lys Leu Ser Val Asn
            35                  40                  45

Gly Ser Asp Pro Val Ser Glu Thr Asn Gly His Arg Val Gln Ser Val
50                  55                  60

Asn Val Glu His Ile Glu Asn Gly Ser Glu Gly Ser Met Glu Arg Lys
65                  70                  75                  80

Trp Ile Arg Pro Asp Leu Pro Ser Arg Cys Thr Trp Lys Leu Gly Asp
                85                  90                  95

Pro Asn Ala Glu Ser Pro His Lys His Phe Gln Arg Thr Lys Thr Pro
            100                 105                 110

Arg Ile Leu Pro Asn Ile Leu Ser Arg Ile Gly Glu Thr Pro Leu Val
            115                 120                 125

Arg Met Asn Lys Ile Pro Lys Met Phe Gly Leu Lys Cys Glu Leu Leu
            130                 135                 140

Ala Lys Cys Glu Phe Phe Asn Ala Gly Gly Ser Val Lys Asp Arg Ile
145                 150                 155                 160

Ser Leu Arg Met Val Glu Asp Ala Glu Arg Asp Gly Ile Leu Lys Pro
                165                 170                 175

Gly Asp Thr Ile Ile Glu Pro Thr Ser Gly Asn Thr Gly Ile Gly Leu
            180                 185                 190

Ala Leu Ala Ala Ala Val Lys Gly Tyr Arg Cys Ile Ile Val Met Pro
            195                 200                 205

Glu Lys Met Ser Met Glu Lys Val Asp Val Leu Arg Ala Leu Gly Ala
            210                 215                 220

Glu Ile Val Arg Thr Pro Thr Ser Ala Arg Phe Asp Ser Pro Glu Ser
225                 230                 235                 240

His Val Gly Val Ala Trp Arg Leu Lys Asn Glu Ile Pro Asn Ala His
                245                 250                 255

Ile Leu Asp Gln Tyr Arg Asn Pro Ser Asn Pro Leu Ala His Tyr Asp
            260                 265                 270

Thr Thr Ala Glu Glu Ile Leu Glu Gln Cys Asp Gly Lys Ile Asp Met
            275                 280                 285

Leu Val Ala Gly Ala Gly Thr Gly Gly Thr Ile Thr Gly Val Ala Arg
            290                 295                 300

Lys Leu Lys Glu Lys Cys Pro Asn Ile Lys Ile Val Gly Val Asp Pro
305                 310                 315                 320

Glu Gly Ser Ile Leu Ala Glu Pro Glu Glu Leu Asn Lys Thr Asp Lys
            325                 330                 335

Thr Gln Tyr Glu Val Glu Gly Ile Gly Tyr Asp Phe Ile Pro Thr Val
            340                 345                 350

Met Asp Arg Ser Val Val Asp Ser Trp Tyr Lys Ser Thr Asp Glu Glu
            355                 360                 365

Ser Phe Ala Met Ser Arg Met Leu Ile Arg Glu Glu Gly Leu Leu Cys
            370                 375                 380

Gly Gly Ser Ser Gly Thr Ala Met Ala Ala Leu His Val Ala Lys
385                 390                 395                 400

Glu Leu Glu Glu Gly Gln Arg Cys Val Val Ile Leu Pro Asp Ser Ile
            405                 410                 415

Arg Asn Tyr Met Ser Lys Phe Leu Ser Asp Lys Trp Met Cys Glu Lys
```

```
                420                 425                 430
Gly Phe Leu Ser Glu Glu Asp Leu Val Val Asn Lys Pro Trp Trp
        435                 440                 445

Asn Leu Thr Leu Gln Glu Leu Arg Leu Ser Ala Pro Leu Thr Val Leu
    450                 455                 460

Pro Leu Val Ser Ile Lys Lys Thr Ile Gln Ile Leu Lys Glu Lys Ala
465                 470                 475                 480

Phe Asp Gln Ala Pro Val Val Asp Glu Thr Gly Gln Ile Leu Gly Met
                485                 490                 495

Val Thr Leu Gly Asn Met Leu Ser Ser Val Leu Ala Gly Arg Val Arg
            500                 505                 510

Pro Ser Asp Pro Ile Asn Lys Val Leu Tyr Lys Gln Phe Lys Gln Val
        515                 520                 525

Arg Leu Thr Asp Asn Leu Gly Lys Leu Ser Arg Ile Leu Glu Thr Asp
    530                 535                 540

His Phe Ala Leu Val Val His Glu Gln Ile Gln Tyr Met Ser Asp Gly
545                 550                 555                 560

Ser Pro Lys Met Arg Gln Met Val Phe Gly Val Val Thr Ala Ile Asp
                565                 570                 575

Leu Leu Asn Tyr Val Ala Thr Arg Glu Arg Arg Glu Arg Ser Leu Ser
            580                 585                 590

Glu Cys Ser Leu Ser Glu Asp Gln
        595                 600

<210> SEQ ID NO 17
<211> LENGTH: 1593
<212> TYPE: DNA
<213> ORGANISM: Beta vulgaris

<400> SEQUENCE: 17
atgggaagcc ttggccctaa cctcaccaac tcctcaaccc ctttaagtgc tacaaccaca     60
ttcaaaccct tagatcatga agaattccga gaacaagccc ataaaatggt ggattacata    120
gcagattact acaaaaacat agaaaatttt cctgttttaa gccgagttga acctggctac    180
ttgctaacat ccctgcctca aacggctccg ctagggccgg agccgtttga ggccatacta    240
ggggatgtta acaagtatat tttcccaggg atgactcatt ggcttaaccc aaatttcttt    300
gccttcttcc ctgctactgt tagctccgcc gctttcgtcg cgatatgctt tgtaatgct     360 tttaatagtg taggcttcaa ttggctagct tcgccggctg ctacggagtt agagatggtt    420
gttatggatt ggcttgcttc tttgctcaag ctccctacct cctttatgtt ctctggcaca    480
ggaggaggtg tactacatgg aactacaagt gaggccatca tttgtacact ggttgcagca    540
agagatcgag caatggagac tgcaaaattt gacaatccat caaaattagt agtttatggc    600
tctgatcaaa cacattctac gttcactaag gcatgcaagt taattggcat accacctaat    660
aatatccgat aatctcaac aaccgtcgag tcaaaattcg ctatgccacc ctctgagttt    720
cgcaagtcca ttgaagcaga tgtggcagct ggttttgtcc cactttatct atgtgtcact    780
ttaggcacca cttctactgc tgcaattgat ccattggaag agctcgtcaa tattgcaggt    840
gattacgaca tttggattca tttggatgct gcttatgctg aagtgcttg atctgccct     900 gaatttaggc actacttaaa cggggttgag cgagttgact cactgagtct cgccccacac    960
aagtggctac taacgtactt ggattgttgt tgcttgtggg tcaagaatcc gagtttgctg   1020
accaaaacac ttagcactaa cccggagtac ttaaaaaaca aactcagcga gtcaaactca   1080
```

```
gtagtggatt ataaagattg gcaaattggt acgggtcgac ggttcaagtc gctccgatta    1140
tggttcgtgt tacgtaccta tggtactatt aatctccaaa accatattag gtccgacatt    1200
tgcatggctc ggactttcga gaatttggtt aaatccgata cccgatttga gattgttgca    1260
cccgctaatt ttgctttggt ttgtttccga ttcaaccctc atagaaagtt taatcccgaa    1320
caaattgagg gtttaaatag ggagctactc gagcgggtca actcaacggg tcgagtttat    1380
attactcata caattgctgg tgggatctac atgttgagat ttgccgtggg gacaacactc    1440
acagaggagc gccacgtgat tgctggttgg gaggtgatta aggaacaagc cgaggttata    1500
tcaatgacat caaaacaggc aacaaatacg gaaaaaactt tatctaccca gcgtcgtcct    1560
acaaatacgt caattgcaga aaagtgtggc tga                                 1593
```

<210> SEQ ID NO 18
<211> LENGTH: 530
<212> TYPE: PRT
<213> ORGANISM: Beta vulgaris

<400> SEQUENCE: 18

```
Met Gly Ser Leu Gly Pro Asn Leu Thr Asn Ser Ser Thr Pro Leu Ser
1               5                   10                  15

Ala Thr Thr Thr Phe Lys Pro Leu Asp His Glu Glu Phe Arg Glu Gln
            20                  25                  30

Ala His Lys Met Val Asp Tyr Ile Ala Asp Tyr Tyr Lys Asn Ile Glu
        35                  40                  45

Asn Phe Pro Val Leu Ser Arg Val Glu Pro Gly Tyr Leu Leu Thr Ser
    50                  55                  60

Leu Pro Gln Thr Ala Pro Leu Gly Pro Glu Pro Phe Glu Ala Ile Leu
65                  70                  75                  80

Gly Asp Val Asn Lys Tyr Ile Phe Pro Gly Met Thr His Trp Leu Asn
                85                  90                  95

Pro Asn Phe Phe Ala Phe Phe Pro Ala Thr Val Ser Ser Ala Ala Phe
            100                 105                 110

Val Gly Asp Met Leu Cys Asn Ala Phe Asn Ser Val Gly Phe Asn Trp
        115                 120                 125

Leu Ala Ser Pro Ala Ala Thr Glu Leu Glu Met Val Val Met Asp Trp
    130                 135                 140

Leu Ala Ser Leu Leu Lys Leu Pro Thr Ser Phe Met Phe Ser Gly Thr
145                 150                 155                 160

Gly Gly Gly Val Leu His Gly Thr Thr Ser Glu Ala Ile Ile Cys Thr
                165                 170                 175

Leu Val Ala Ala Arg Asp Arg Ala Met Glu Thr Ala Lys Phe Asp Asn
            180                 185                 190

Pro Ser Lys Leu Val Val Tyr Gly Ser Asp Gln Thr His Ser Thr Phe
        195                 200                 205

Thr Lys Ala Cys Lys Leu Ile Gly Ile Pro Pro Asn Asn Ile Arg Leu
    210                 215                 220

Ile Ser Thr Thr Val Glu Ser Lys Phe Ala Met Pro Pro Ser Glu Phe
225                 230                 235                 240

Arg Lys Ser Ile Glu Ala Asp Val Ala Ala Gly Phe Val Pro Leu Tyr
                245                 250                 255

Leu Cys Val Thr Leu Gly Thr Thr Ser Thr Ala Ala Ile Asp Pro Leu
            260                 265                 270

Glu Glu Leu Val Asn Ile Ala Gly Asp Tyr Asp Ile Trp Ile His Leu
        275                 280                 285
```

Asp Ala Ala Tyr Ala Gly Ser Ala Cys Ile Cys Pro Glu Phe Arg His
    290                 295                 300

Tyr Leu Asn Gly Val Glu Arg Val Asp Ser Leu Ser Leu Ala Pro His
305                 310                 315                 320

Lys Trp Leu Leu Thr Tyr Leu Asp Cys Cys Cys Leu Trp Val Lys Asn
                325                 330                 335

Pro Ser Leu Leu Thr Lys Thr Leu Ser Thr Asn Pro Glu Tyr Leu Lys
                340                 345                 350

Asn Lys Leu Ser Glu Ser Asn Ser Val Val Asp Tyr Lys Asp Trp Gln
            355                 360                 365

Ile Gly Thr Gly Arg Arg Phe Lys Ser Leu Arg Leu Trp Phe Val Leu
    370                 375                 380

Arg Thr Tyr Gly Thr Ile Asn Leu Gln Asn His Ile Arg Ser Asp Ile
385                 390                 395                 400

Cys Met Ala Arg Thr Phe Glu Asn Leu Val Lys Ser Asp Thr Arg Phe
                405                 410                 415

Glu Ile Val Ala Pro Ala Asn Phe Ala Leu Val Cys Phe Arg Phe Asn
            420                 425                 430

Pro Asn Arg Lys Phe Asn Pro Glu Gln Ile Glu Gly Leu Asn Arg Glu
    435                 440                 445

Leu Leu Glu Arg Val Asn Ser Thr Gly Arg Val Tyr Ile Thr His Thr
450                 455                 460

Ile Ala Gly Gly Ile Tyr Met Leu Arg Phe Ala Val Gly Thr Thr Leu
465                 470                 475                 480

Thr Glu Glu Arg His Val Ile Ala Gly Trp Glu Val Ile Lys Glu Gln
                485                 490                 495

Ala Glu Val Ile Ser Met Thr Ser Lys Gln Ala Thr Asn Thr Glu Lys
            500                 505                 510

Thr Leu Ser Thr Gln Arg Arg Pro Thr Asn Thr Ser Ile Ala Glu Lys
    515                 520                 525

Cys Gly
    530

<210> SEQ ID NO 19
<211> LENGTH: 1443
<212> TYPE: DNA
<213> ORGANISM: Lepisosteus oculatus

<400> SEQUENCE: 19
atggacccag cagagttccg gagacgaggc aaggagatgg ttgacatcat tagcgactat    60
ctagagaaca tcgaacagag gccggtgttt cccgacgtcg agccaggcta cctgagagcg   120
ctggttcctc aagaggcccc ggaagagccg gagtccttcg acgagatcgt cagagacatc   180
gagagggtca tcatgccagg ggtcacccac tggcacagcc ttatttctt tgcctatttt    240 cctactgcca gttcgtttcc tgccatgctt gctgacatgc tgtccggagc tatcggatgc   300
attggatttt cctgggctgc cagtcctgcc tgcacagagc tggaaacggt catgctggac   360
tggctgggga agatgctgaa gttaccagag gaattcctgg ctgggacagc tggtcaaggt   420
gggggtgtga tacagggtac tgctagcgaa gctactttga ttgctctgtt agctgcacga   480
accagaacag tcaaaaagat ccaagcggag aacccaggga cagacgaaga ggacattcta   540
cccaaactgg tggcctacgc ctctgaccag gcacactcct cggtggaaag gcgggggctg   600
ataggtggag tgaaaatgaa gatgatccct tctgatgaca agtttgctgc tcgaggagaa   660

-continued

```
gctctcagac agaccattga agcggacaag gcagctggtc tcatcccctt ctatttctgt    720
gcaactcttg gaacaacacc atcgtgtgca tttgatcgca tcagcgaact tggcccgata    780
tgtaattcag agaacatctg gatgcatatt gatgctgctt atgcaggcag tgctttcatt    840
tgcccagaat tcaggcatct cctcaatgga gtggagtttg cagattcctt caactttaac    900
cctcacaagt ggcttttggt aaactttgac tgctctgcta tgtgggtgaa gaaacgagct    960
gatattgttg gagcttttcaa aatggatcca ctatatctga acatgatca ccaagaatca   1020
ggacttgtca cagattacag acactggcag ataccactgg gccgaagatt tcggtctctg   1080
aaaatgtggt ttgtgttccg tatgtatggg ctcaaaggac tgcagcagta cattcggaag   1140
catgtgagct tggccaagga gtttgagagt ttggtgcgca gcgaccagcg attcgagatc   1200
agcgcggagg tcgtcctggg gcttgtatgc tttcgactga agggatctaa tgctttgaat   1260
gaaaaactcc ttaaaagaat aaatgatacc aggaagatcc accttgtccc ctgccacctg   1320
tcgggcagtt ttgtgctgcg cttcgctgta tgtgcgcgga ccacagagtc aaaacacatc   1380
cagttcgcct ggaagcacat cgcggaaatc gcctcccagc ttctgcagga gccgcggcag   1440
tag                                                                 1443
```

<210> SEQ ID NO 20
<211> LENGTH: 480
<212> TYPE: PRT
<213> ORGANISM: Lepisosteus oculatus

<400> SEQUENCE: 20

```
Met Asp Pro Ala Glu Phe Arg Arg Gly Lys Glu Met Val Asp Ile
1               5                   10                  15

Ile Ser Asp Tyr Leu Glu Asn Ile Glu Gln Arg Pro Val Phe Pro Asp
                20                  25                  30

Val Glu Pro Gly Tyr Leu Arg Ala Leu Val Pro Gln Glu Ala Pro Glu
            35                  40                  45

Glu Pro Glu Ser Phe Asp Glu Ile Val Arg Asp Ile Glu Arg Val Ile
        50                  55                  60

Met Pro Gly Val Thr His Trp His Ser Pro Tyr Phe Phe Ala Tyr Phe
65                  70                  75                  80

Pro Thr Ala Ser Ser Phe Pro Ala Met Leu Ala Asp Met Leu Ser Gly
                85                  90                  95

Ala Ile Gly Cys Ile Gly Phe Ser Trp Ala Ala Ser Pro Ala Cys Thr
            100                 105                 110

Glu Leu Glu Thr Val Met Leu Asp Trp Leu Gly Lys Met Leu Lys Leu
        115                 120                 125

Pro Glu Glu Phe Leu Ala Gly Thr Ala Gly Gln Gly Gly Gly Val Ile
    130                 135                 140

Gln Gly Thr Ala Ser Glu Ala Thr Leu Ile Ala Leu Leu Ala Ala Arg
145                 150                 155                 160

Thr Arg Thr Val Lys Lys Ile Gln Ala Glu Asn Pro Gly Thr Asp Glu
                165                 170                 175

Glu Asp Ile Leu Pro Lys Leu Val Ala Tyr Ala Ser Asp Gln Ala His
            180                 185                 190

Ser Ser Val Glu Arg Ala Gly Leu Ile Gly Gly Val Lys Met Lys Met
        195                 200                 205

Ile Pro Ser Asp Asp Lys Phe Ala Ala Arg Gly Glu Ala Leu Arg Gln
    210                 215                 220

Thr Ile Glu Ala Asp Lys Ala Ala Gly Leu Ile Pro Phe Tyr Phe Cys
```

225                 230                 235                 240
Ala Thr Leu Gly Thr Thr Pro Ser Cys Ala Phe Asp Arg Ile Ser Glu
                245                 250                 255

Leu Gly Pro Ile Cys Asn Ser Glu Asn Ile Trp Met His Ile Asp Ala
            260                 265                 270

Ala Tyr Ala Gly Ser Ala Phe Ile Cys Pro Glu Phe Arg His Leu Leu
        275                 280                 285

Asn Gly Val Glu Phe Ala Asp Ser Phe Asn Asn Pro His Lys Trp
    290                 295                 300

Leu Leu Val Asn Phe Asp Cys Ser Ala Met Trp Val Lys Lys Arg Ala
305                 310                 315                 320

Asp Ile Val Gly Ala Phe Lys Met Asp Pro Leu Tyr Leu Lys His Asp
                325                 330                 335

His Gln Glu Ser Gly Leu Val Thr Asp Tyr Arg His Trp Gln Ile Pro
            340                 345                 350

Leu Gly Arg Arg Phe Arg Ser Leu Lys Met Trp Phe Val Phe Arg Met
        355                 360                 365

Tyr Gly Leu Lys Gly Leu Gln Gln Tyr Ile Arg Lys His Val Ser Leu
    370                 375                 380

Ala Lys Glu Phe Glu Ser Leu Val Arg Ser Asp Gln Arg Phe Glu Ile
385                 390                 395                 400

Ser Ala Glu Val Val Leu Gly Leu Val Cys Phe Arg Leu Lys Gly Ser
                405                 410                 415

Asn Ala Leu Asn Glu Lys Leu Leu Lys Arg Ile Asn Asp Thr Arg Lys
            420                 425                 430

Ile His Leu Val Pro Cys His Leu Ser Gly Ser Phe Val Leu Arg Phe
        435                 440                 445

Ala Val Cys Ala Arg Thr Thr Glu Ser Lys His Ile Gln Phe Ala Trp
    450                 455                 460

Lys His Ile Ala Glu Ile Ala Ser Gln Leu Leu Gln Glu Pro Arg Gln
465                 470                 475                 480

<210> SEQ ID NO 21
<211> LENGTH: 1701
<212> TYPE: DNA
<213> ORGANISM: Danio rerio

<400> SEQUENCE: 21
atggcgtctt ctgcaccttc ttcctcggct ggtgatatgg acccaaacac ggctaattta      60
cgacaacctg ccacaagttt cctgcagaag aacaacagtt tggatgagaa gagtcgtatg     120
gtgggctcct tcaaggagag cgccaagaac cagatgtcgt gcgacaacaa tgagcgcttc     180
acgcgcgatg agacagattt ctccaacctg ttcgcgcgag atctactgcc cgctaaaaac     240
ggcgaggagc ccacaatcca gtttcttctc gaagtggtgg agatcctcac caattatgtg     300
cgcaagacct tcgacagatc caccaaagtg ctggacttcc atcatcctca ccagctgctg     360
gagggaatgg agggcttcaa cctggagctt tctgaccagc ccgagtccct ggagcagatc     420
ctggtggact gcagagacac gctgaaatac ggggtcagaa caggtcatcc tagattcttc     480
aaccagcttt cctccggtct ggacatcatt ggtctggctg agaatggct gacctccact     540 gccaacacca acatgttcac atatgagatt cgcctgtgt tgtcctgat ggagcagctc     600 acactcaaga gatgcgggga gatcatcggc tggccaaacg gagatggaga tgcgctcttc     660
tcacctggtg gtgccatatc aaacatgtac agtgtgatgg ttgcgcggta taaatatttc     720

```
cctgaagtca aaaccaaagg catgtctgcg gctccgcggc tcgtgctgtt cacatctgaa    780
catagtcatt actcaatcaa gaaggcagga gctgttcttg gatttggcaa agaaaacgtc    840
attctcctga agacagatga gaggggggcgt gtcatacctg ctgacttaga ggctaaagtc    900
attgatgcca aacagaaggg atatgtccca ctgtttgtga atgccacggc tggtactaca    960
gtatatggag cgttcgatcc gatcaatgac attgctgaca tctgtgagaa gtacaacttg   1020
tggttacatg tggatggtgc gtggggtgga ggactgttga tgtccagaaa gcatcgtcac   1080
aagctgagcg gcattgagag ggcaaactcc gtcacgtgga accctcataa gatgatgggt   1140
gtgcctttac aatgttcagc catcctggtc agagagaagg gcattctcca gggctgcaac   1200
tccatgtgcg caggttacct cttccagccg gacaaacagt acgacgtgac ctacgacacc   1260
ggagacaagg ccatccagtg cggcagacat gtggacatct tcaaattctg gctcatgtgg   1320
aaggccaagg gcacgattgg gttcgagcag cacattgaca gatgtctgga gctttctgaa   1380
tatctctaca ataaaatcaa gaaccgtgag ggatatgaaa tggtctttga gggccagccc   1440
cagcacacta atgtttgctt ctggtatatt ccaccgagtc tgcgtggcat gccgaacgga   1500
gacgagcgaa gggagaagct gcacagggtg gcgccaaaaa tcaaagcaat gatgatggag   1560
tgcggcacca ccatggtggg ttaccaacca cagggagaca agtcaacttc cttccgaatg   1620
gtggtctcca atcacgccgt caccaagtcg gacatcgatt tcctcatcga tgagatcgag   1680
cggctcggtc aggatctgta a                                             1701

<210> SEQ ID NO 22
<211> LENGTH: 566
<212> TYPE: PRT
<213> ORGANISM: Danio rerio

<400> SEQUENCE: 22

Met Ala Ser Ser Ala Pro Ser Ser Ala Gly Asp Met Asp Pro Asn
1               5                   10                  15

Thr Ala Asn Leu Arg Gln Pro Ala Thr Ser Phe Leu Gln Lys Asn Asn
                20                  25                  30

Ser Leu Asp Glu Lys Ser Arg Met Val Gly Ser Phe Lys Glu Ser Ala
            35                  40                  45

Lys Asn Gln Met Ser Cys Asp Asn Asn Glu Arg Phe Thr Arg Asp Glu
        50                  55                  60

Thr Asp Phe Ser Asn Leu Phe Ala Arg Asp Leu Pro Ala Lys Asn
65                  70                  75                  80

Gly Glu Glu Pro Thr Ile Gln Phe Leu Leu Glu Val Val Glu Ile Leu
                85                  90                  95

Thr Asn Tyr Val Arg Lys Thr Phe Asp Arg Ser Thr Lys Val Leu Asp
            100                 105                 110

Phe His His Pro His Gln Leu Leu Glu Gly Met Glu Gly Phe Asn Leu
        115                 120                 125

Glu Leu Ser Asp Gln Pro Glu Ser Leu Glu Gln Ile Leu Val Asp Cys
    130                 135                 140

Arg Asp Thr Leu Lys Tyr Gly Val Arg Thr Gly His Pro Arg Phe Phe
145                 150                 155                 160

Asn Gln Leu Ser Ser Gly Leu Asp Ile Ile Gly Leu Ala Gly Glu Trp
                165                 170                 175

Leu Thr Ser Thr Ala Asn Thr Asn Met Phe Thr Tyr Glu Ile Ala Pro
            180                 185                 190

Val Phe Val Leu Met Glu Gln Leu Thr Leu Lys Lys Met Arg Glu Ile
```

195                 200                 205
Ile Gly Trp Pro Asn Gly Asp Gly Asp Ala Leu Phe Ser Pro Gly Gly
    210                 215                 220
Ala Ile Ser Asn Met Tyr Ser Val Met Val Ala Arg Tyr Lys Tyr Phe
225                 230                 235                 240
Pro Glu Val Lys Thr Lys Gly Met Ser Ala Ala Pro Arg Leu Val Leu
                245                 250                 255
Phe Thr Ser Glu His Ser His Tyr Ser Ile Lys Lys Ala Gly Ala Val
            260                 265                 270
Leu Gly Phe Gly Lys Glu Asn Val Ile Leu Leu Lys Thr Asp Glu Arg
        275                 280                 285
Gly Arg Val Ile Pro Ala Asp Leu Glu Ala Lys Val Ile Asp Ala Lys
    290                 295                 300
Gln Lys Gly Tyr Val Pro Leu Phe Val Asn Ala Thr Ala Gly Thr Thr
305                 310                 315                 320
Val Tyr Gly Ala Phe Asp Pro Ile Asn Asp Ile Ala Asp Ile Cys Glu
                325                 330                 335
Lys Tyr Asn Leu Trp Leu His Val Asp Gly Ala Trp Gly Gly Gly Leu
            340                 345                 350
Leu Met Ser Arg Lys His Arg His Lys Leu Ser Gly Ile Glu Arg Ala
        355                 360                 365
Asn Ser Val Thr Trp Asn Pro His Lys Met Met Gly Val Pro Leu Gln
    370                 375                 380
Cys Ser Ala Ile Leu Val Arg Glu Lys Gly Ile Leu Gln Gly Cys Asn
385                 390                 395                 400
Ser Met Cys Ala Gly Tyr Leu Phe Gln Pro Asp Lys Gln Tyr Asp Val
                405                 410                 415
Thr Tyr Asp Thr Gly Asp Lys Ala Ile Gln Cys Gly Arg His Val Asp
            420                 425                 430
Ile Phe Lys Phe Trp Leu Met Trp Lys Ala Lys Gly Thr Ile Gly Phe
        435                 440                 445
Glu Gln His Ile Asp Arg Cys Leu Glu Leu Ser Glu Tyr Leu Tyr Asn
    450                 455                 460
Lys Ile Lys Asn Arg Glu Gly Tyr Glu Met Val Phe Glu Gly Gln Pro
465                 470                 475                 480
Gln His Thr Asn Val Cys Phe Trp Tyr Ile Pro Pro Ser Leu Arg Gly
                485                 490                 495
Met Pro Asn Gly Asp Glu Arg Glu Lys Leu His Arg Val Ala Pro
            500                 505                 510
Lys Ile Lys Ala Met Met Met Glu Cys Gly Thr Thr Met Val Gly Tyr
        515                 520                 525
Gln Pro Gln Gly Asp Lys Val Asn Phe Phe Arg Met Val Val Ser Asn
    530                 535                 540
His Ala Val Thr Lys Ser Asp Ile Asp Phe Leu Ile Asp Glu Ile Glu
545                 550                 555                 560
Arg Leu Gly Gln Asp Leu
                565

<210> SEQ ID NO 23
<211> LENGTH: 1353
<212> TYPE: DNA
<213> ORGANISM: Escherichia coli

<400> SEQUENCE: 23

```
atgtatcagg gcaaaaccgt tgagcaactg cgtgaacgta tcaacctgaa tttacgtct    60
cagggcctgg gcaaccaggc cgctattgag cgtgcggttg aatactttct caaagacagc   120
ctgttggttc accatgctca gtgtgtggcg cacctgcact gcccaagtct ggtgattagc   180
caggcggcgg aagtgctgat caacgccact aaccagagta tggactcctg ggaccaaagc   240
ccgtcggcca cgatcattga gatcaaactg atcgaatggc tacgcgagca ggtgggttat   300
gcagcaggcg atgcgggcgt attcaccagc ggcggcaccc agagtaacct gatgggcctg   360
atgctggcgc gcgatgcctt ctttgctcgc ctgggacatt ccattcagca agatggtctg   420
accggtgatc tgagcaaaat taaagtgttc tgctctgaaa gcgcgcactt ctccgtgcag   480
aagaacatgg cgttaatggg gctgggctac cgctccgtca cccaggtgaa gaccgatgcg   540
ttttcacgca tggatctggc tgacctgaaa gacaagctgg cccaggcgaa agccaacggt   600
gagcaggtga tggccattgt tgcgacggct ggtacgacag atgcgggcgc catcgatccg   660
ttagcggata ttgcggcgct ggcggcagaa catcagatct ggatgcacgt ggatgcggca   720
tggggcgggg cgttactgct ttctgagcag tatcgtcact ccctcaacgg ccttgagctg   780
gcagattccg tgacgctgga tttccacaaa cagttcttcc agaccatcag ctgcggtgcg   840
ttcctgttaa agatgcacg ccactacgag ctgatgcgtt accaggcggc gtacctgaac   900
tctgatttcg atgaagaggc tggcgtacca aacctggtat cgaagtcgct gcagaccacg   960
cgtcgtttcg atgcgctgaa gctgtggatg ggcctcgaag cgctgggcaa aaagcagtat  1020
gccgaaatca ttgataatgg cgtaacgctg gcgcgtgatg ttgctgagtt tgtcaaaacc  1080
cagtcgcatc ttgaactggt gatggaacca cagctggcaa gcgtgctgtt ccgcttccgt  1140
cctgaaagcg acgatatggc gttcgttgcg ctgctgaacc agcgtattgg cgacgtgctg  1200
ctggcttcag gtagcgccaa cgtcggcgtg acagaagcgg atggcatcac tgcctgaag  1260
ctgacgctgc tgaacccgac ggtatgcctg gaagatgtga agtcctgct gaccagcgtg  1320
aaggcaacgg cattgagcat tttaagcgcg taa                             1353
```

<210> SEQ ID NO 24
<211> LENGTH: 450
<212> TYPE: PRT
<213> ORGANISM: Escherichia coli

<400> SEQUENCE: 24

```
Met Tyr Gln Gly Lys Thr Val Glu Gln Leu Arg Glu Arg Ile Asn Leu
1               5                   10                  15

Asn Phe Thr Ser Gln Gly Leu Gly Asn Gln Ala Ala Ile Glu Arg Ala
            20                  25                  30

Val Glu Tyr Phe Leu Lys Asp Ser Leu Leu Val His His Ala Gln Cys
        35                  40                  45

Val Ala His Leu His Cys Pro Ser Leu Val Ile Ser Gln Ala Ala Glu
    50                  55                  60

Val Leu Ile Asn Ala Thr Asn Gln Ser Met Asp Ser Trp Asp Gln Ser
65                  70                  75                  80

Pro Ser Ala Thr Ile Ile Glu Ile Lys Leu Ile Glu Trp Leu Arg Glu
                85                  90                  95

Gln Val Gly Tyr Ala Ala Gly Asp Ala Gly Val Phe Thr Ser Gly Gly
            100                 105                 110

Thr Gln Ser Asn Leu Met Gly Leu Met Leu Ala Arg Asp Ala Phe Phe
        115                 120                 125

Ala Arg Leu Gly His Ser Ile Gln Gln Asp Gly Leu Thr Gly Asp Leu
```

130                 135                 140
Ser Lys Ile Lys Val Phe Cys Ser Glu Ser Ala His Phe Ser Val Gln
145                 150                 155                 160

Lys Asn Met Ala Leu Met Gly Leu Gly Tyr Arg Ser Val Thr Gln Val
                165                 170                 175

Lys Thr Asp Ala Phe Ser Arg Met Asp Leu Ala Asp Leu Lys Asp Lys
                180                 185                 190

Leu Ala Gln Ala Lys Ala Asn Gly Glu Gln Val Met Ala Ile Val Ala
                195                 200                 205

Thr Ala Gly Thr Thr Asp Ala Gly Ala Ile Asp Pro Leu Ala Asp Ile
                210                 215                 220

Ala Ala Leu Ala Ala Glu His Gln Ile Trp Met His Val Asp Ala Ala
225                 230                 235                 240

Trp Gly Gly Ala Leu Leu Leu Ser Glu Gln Tyr Arg His Phe Leu Asn
                245                 250                 255

Gly Leu Glu Leu Ala Asp Ser Val Thr Leu Asp Phe His Lys Gln Phe
                260                 265                 270

Phe Gln Thr Ile Ser Cys Gly Ala Phe Leu Leu Lys Asp Ala Arg His
                275                 280                 285

Tyr Glu Leu Met Arg Tyr Gln Ala Ala Tyr Leu Asn Ser Asp Phe Asp
                290                 295                 300

Glu Glu Ala Gly Val Pro Asn Leu Val Ser Lys Ser Leu Gln Thr Thr
305                 310                 315                 320

Arg Arg Phe Asp Ala Leu Lys Leu Trp Met Gly Leu Glu Ala Leu Gly
                325                 330                 335

Lys Lys Gln Tyr Ala Glu Ile Ile Asp Asn Gly Val Thr Leu Ala Arg
                340                 345                 350

Asp Val Ala Glu Phe Val Lys Thr Gln Ser His Leu Glu Leu Val Met
                355                 360                 365

Glu Pro Gln Leu Ala Ser Val Leu Phe Arg Phe Arg Pro Glu Ser Asp
370                 375                 380

Asp Met Ala Phe Val Ala Leu Leu Asn Gln Arg Ile Gly Asp Val Leu
385                 390                 395                 400

Leu Ala Ser Gly Ser Ala Asn Val Gly Val Thr Glu Ala Asp Gly Ile
                405                 410                 415

Thr Cys Leu Lys Leu Thr Leu Leu Asn Pro Thr Val Cys Leu Glu Asp
                420                 425                 430

Val Lys Val Leu Leu Thr Ser Val Lys Ala Thr Ala Leu Ser Ile Leu
                435                 440                 445

Ser Ala
450

<210> SEQ ID NO 25
<211> LENGTH: 1578
<212> TYPE: DNA
<213> ORGANISM: Oncorhynchus mykiss

<400> SEQUENCE: 25
atgagtcacc tacctagatt ctggaacctg ggatggtctt cctttcttga ctggtggagt      60
aatcagagtg ttgtttcaga gcaaggacct tctcccctgt atggtcagca ggaaatgaat     120
gaacctctcc tggacaacag tgaaggccag ctcttcctga ccgaggcttt taaagtcatc     180
gttgaggagg tgctatgtaa aggcacagac gtcaaagaga aggtgtgtga gtggcgcgag     240
ccagaggagt tagctgctct gctagatctg gagctgcgag agaatgggga gccgcaacac     300

```
caactgctgc agagaatacg ggatgtggcc aagtacagtg tcaagaccaa tcatccgcgg    360
ttcttcaatc agctctttgc aggggtggac taccatgcct tgacaggacg attccttacg    420
gaggctctta acactagcca gtatacctac gaggtggctc cagtgtttgt tctgatggaa    480
gacgaggtac tctccaagct acgttctcta gttgggtggg cagagggaga tggcatcttc    540
tgcccaggcg gcaccatgtc taacatgtat gccatgaacg tagcacgcta ccgggccttc    600
ccagaagtaa aactaaaggg aatgtggtcc ctccctcgac tagctgtctt tacatctcaa    660
cagagccact actctgtgat gaaagcggct gcatttcagg gtattgggac gagaacgtg     720
tttaaggtca aagtggatga cagggggttgc atgattccag aagaccttgg tgagacaatt   780
gagctggcga atctcaagg ggcagtgcca ttctttgtcc atgccacatc aggaacgact    840
gtacaaggcg cctttgaccc actggagccc atcgctgaca tctgtgacag acaggggttg    900
tggatgcatg ttgatgcagc ctggggaggg agtgttctct tctcaaagga cacaaacat    960
ctcatgagag gagttgagag agccgattca gtgacttgga atccacacaa gatgatgctg   1020
acgggcttgc agtgttcagc cattctgctc aaggacacca cacacctatt gaaacattgc   1080
cacagtgcgg atgcaaagta cctcttccag caggacaagt tctatgacac gagtctggac   1140
acaggggaca agtcgataca gtgtggccgt aaggttgact gcctgaagct gtggttgatg   1200
tggaaagctg tagggtcaaa aggcttggaa gagcgtgttg acagggcttt cacccataca   1260
agatatctgg tggaggagat gaagagaaga gagggctttg aacttatagg gaagccgttg   1320
tttgtgaacg tgtgttctg gttcatacca cccagtctga ggggaaagga gaacagtcca   1380
gactacaatg acagattgtc aaaggtggct ccagtgatta aggagcgaat gatgaagcag   1440
ggtactatga tgttgggcta ccagcctcag ggtggacgag tcaacttctt ccgcatgata   1500
gtaatctcac cgcagctctc ccaccaagat atgcacattct gtctgaatga gattgagagg   1560
cttgggagtg atttgtaa                                                   1578

<210> SEQ ID NO 26
<211> LENGTH: 525
<212> TYPE: PRT
<213> ORGANISM: Oncorhynchus mykiss

<400> SEQUENCE: 26

Met Ser His Leu Pro Arg Phe Trp Asn Leu Gly Trp Ser Ser Phe Leu
1               5                   10                  15

Asp Trp Trp Ser Asn Gln Ser Val Val Ser Glu Gln Gly Pro Ser Pro
            20                  25                  30

Leu Tyr Gly Gln Gln Glu Met Asn Glu Pro Leu Leu Asp Asn Ser Glu
        35                  40                  45

Gly Gln Leu Phe Leu Thr Glu Ala Phe Lys Val Ile Val Glu Glu Val
    50                  55                  60

Leu Cys Lys Gly Thr Asp Val Lys Glu Lys Val Cys Glu Trp Arg Glu
65                  70                  75                  80

Pro Glu Glu Leu Ala Ala Leu Leu Asp Leu Glu Leu Arg Glu Asn Gly
                85                  90                  95

Glu Pro Gln His Gln Leu Leu Gln Arg Ile Arg Asp Val Ala Lys Tyr
            100                 105                 110

Ser Val Lys Thr Asn His Pro Arg Phe Phe Asn Gln Leu Phe Ala Gly
        115                 120                 125

Val Asp Tyr His Ala Leu Thr Gly Arg Phe Leu Thr Glu Ala Leu Asn
    130                 135                 140
```

Thr Ser Gln Tyr Thr Tyr Glu Val Ala Pro Val Phe Val Leu Met Glu
145                 150                 155                 160

Asp Glu Val Leu Ser Lys Leu Arg Ser Leu Val Gly Trp Ala Glu Gly
            165                 170                 175

Asp Gly Ile Phe Cys Pro Gly Gly Thr Met Ser Asn Met Tyr Ala Met
        180                 185                 190

Asn Val Ala Arg Tyr Arg Ala Phe Pro Glu Val Lys Leu Lys Gly Met
    195                 200                 205

Trp Ser Leu Pro Arg Leu Ala Val Phe Thr Ser Gln Gln Ser His Tyr
210                 215                 220

Ser Val Met Lys Ala Ala Ala Phe Gln Gly Ile Gly Thr Glu Asn Val
225                 230                 235                 240

Phe Lys Val Lys Val Asp Asp Arg Gly Cys Met Ile Pro Glu Asp Leu
            245                 250                 255

Gly Glu Thr Ile Glu Leu Ala Lys Ser Gln Gly Ala Val Pro Phe Phe
        260                 265                 270

Val His Ala Thr Ser Gly Thr Thr Val Gln Gly Ala Phe Asp Pro Leu
    275                 280                 285

Glu Pro Ile Ala Asp Ile Cys Asp Arg Gln Gly Leu Trp Met His Val
290                 295                 300

Asp Ala Ala Trp Gly Gly Ser Val Leu Phe Ser Lys Glu His Lys His
305                 310                 315                 320

Leu Met Arg Gly Val Glu Arg Ala Asp Ser Val Thr Trp Asn Pro His
            325                 330                 335

Lys Met Met Leu Thr Gly Leu Gln Cys Ser Ala Ile Leu Leu Lys Asp
        340                 345                 350

Thr Thr His Leu Leu Lys His Cys His Ser Ala Asp Ala Lys Tyr Leu
    355                 360                 365

Phe Gln Gln Asp Lys Phe Tyr Asp Thr Ser Leu Asp Thr Gly Asp Lys
370                 375                 380

Ser Ile Gln Cys Gly Arg Lys Val Asp Cys Leu Lys Leu Trp Leu Met
385                 390                 395                 400

Trp Lys Ala Val Gly Ser Lys Gly Leu Glu Arg Val Asp Arg Ala
            405                 410                 415

Phe Thr His Thr Arg Tyr Leu Val Glu Glu Met Lys Arg Arg Glu Gly
        420                 425                 430

Phe Glu Leu Ile Gly Lys Pro Leu Phe Val Asn Val Cys Phe Trp Phe
    435                 440                 445

Ile Pro Pro Ser Leu Arg Gly Lys Glu Asn Ser Pro Asp Tyr Asn Asp
450                 455                 460

Arg Leu Ser Lys Val Ala Pro Val Ile Lys Glu Arg Met Met Lys Gln
465                 470                 475                 480

Gly Thr Met Met Leu Gly Tyr Gln Pro Gln Gly Gly Arg Val Asn Phe
            485                 490                 495

Phe Arg Met Ile Val Ile Ser Pro Gln Leu Ser His Gln Asp Met Thr
        500                 505                 510

Phe Cys Leu Asn Glu Ile Glu Arg Leu Gly Ser Asp Leu
    515                 520                 525

<210> SEQ ID NO 27
<211> LENGTH: 1629
<212> TYPE: DNA
<213> ORGANISM: Guillardia theta

<400> SEQUENCE: 27

```
atggtgcccc ccgccttgca tgaagggttc tgcagccctc gaggcaggac ttgttgctct     60
caggtgggac acgtggagtt gttggagagc tgggaaacgc aggggaacaa gctgagatgc    120
gagcaagacc tcctgctggc caaggttccc tctcgcttcc accaccttga ggaagtggcc    180
gagctggatg atatcttcag ggaggtgtat cctctgatcc ggcagtacga gacggagaac    240
gcgctagcag acgagcacaa ggtgctggag ttcaggacgc cagcggagct gaaggaggag    300
gtggacgtgg ggctgcctga ggagggatct gtggagaaat ttgtcgaggg atgcagaagc    360
tctatgaagt acagcgtccg aacgagtcac ccgcgcttca tgaaccagct ctatgctggc    420
agcgacccgg cagggcaggt ggcagagctg ctcagtgctg tgctgaacac caccatccac    480
acgtacgggg cagctccctt cttctccgtg ctggagcggc aggtgatcga aagctgggg    540
aggatgctgg ggtttcagga gcatgtcgac ggcgtctttg cccccggagg ctcgtacgcg    600
aacatggtgg cgctgatagt tgcgaggaac cagcacttcc ctcatgtgcg ggagcatggc    660
tggaggagcg acgacaaacc tgttatcttc acttcttccc atgctcacta ctctgtcgcc    720
aaggctgcca tgatcacggg gatggggtcg aatcaagtgg tcgctgtgcc tacggacgag    780
cagggaagaa tgcagcctgc agcgctggag gaggagatta tgcgagcaaa ggagagcgga    840
cggaagcctt tctacgtgag ctgcacggca gggacgacag tgactggggc gtttgacccg    900
attgacgaga tctgtcagat atgtagaagg catgagatgt ggctgcacac ggatggcgcg    960
tggggaggag ctgcaatatt ctcggaggag cacagaaatc ttctacgagg agttgagggc   1020
gtcgatagct tctgcttgaa tccgcacaag atgctggggg tcccgatgca gtgctccgtg   1080
ctcatcctca caaccacga ggggcgctcg agaggagcaa cagaggaaga gagcttggat   1140
ctcgggcaga agtcgctgca gtgcggaagg aaacctgatt gcctaaagct ctggctctgc   1200
tggaagcgac atggaacccg cgggtttgca aggagggtag atcgcgcgta ccttctcg    1260
cagaagttcg cagaaatggt cagaagggac cccaggttct acctgctgat ggacccgatc   1320
tcctgcaacg tctgcttctt ctacctccct ccctccctcc ggcagcagct ggtggacaga   1380
aacctcaacg acttggaaaa ggaggaggcg cagcggcagc tcaaggagtt ccatgctcga   1440
ctcggtcagg ttactcagat catctacagg aggatgcaga aagacggcaa gatgctcatc   1500
aacttcagcc ctcttaaaga cagagatctg cctcacttct tccgagccgt catgatccag   1560
cagagagtaa cggaagacga tcttgttttc atcctcgatc attttgaaca tctgggaaag   1620
gacctctag                                                           1629
```

<210> SEQ ID NO 28
<211> LENGTH: 542
<212> TYPE: PRT
<213> ORGANISM: Guillardia theta

<400> SEQUENCE: 28

```
Met Val Pro Pro Ala Leu His Glu Gly Phe Cys Ser Pro Arg Gly Arg
1               5                   10                  15

Thr Cys Cys Ser Gln Val Gly His Val Glu Leu Leu Glu Ser Trp Glu
            20                  25                  30

Thr Gln Gly Asn Lys Leu Arg Cys Glu Gln Asp Leu Leu Ala Lys
        35                  40                  45

Val Pro Ser Arg Phe His His Leu Glu Glu Val Ala Glu Leu Asp Asp
    50                  55                  60

Ile Phe Arg Glu Val Tyr Pro Leu Ile Arg Gln Tyr Glu Thr Glu Asn
```

-continued

```
             65                   70                  75                  80
Ala Leu Ala Asp Glu His Lys Val Leu Glu Phe Arg Thr Pro Ala Glu
                    85                  90                  95

Leu Lys Glu Glu Val Asp Val Gly Leu Pro Glu Glu Gly Ser Val Glu
                    100                 105                 110

Lys Phe Val Glu Gly Cys Arg Ser Ser Met Lys Tyr Ser Val Arg Thr
                    115                 120                 125

Ser His Pro Arg Phe Met Asn Gln Leu Tyr Ala Gly Ser Asp Pro Ala
                    130                 135                 140

Gly Gln Val Ala Glu Leu Leu Ser Ala Val Leu Asn Thr Thr Ile His
145                 150                 155                 160

Thr Tyr Gly Ala Ala Pro Phe Phe Ser Val Leu Glu Arg Gln Val Ile
                    165                 170                 175

Glu Lys Leu Gly Arg Met Leu Gly Phe Gln Glu His Val Asp Gly Val
                    180                 185                 190

Phe Ala Pro Gly Gly Ser Tyr Ala Asn Met Val Ala Leu Ile Val Ala
                    195                 200                 205

Arg Asn Gln His Phe Pro His Val Arg Glu His Gly Trp Arg Ser Asp
210                 215                 220

Asp Lys Pro Val Ile Phe Thr Ser Ser His Ala His Tyr Ser Val Ala
225                 230                 235                 240

Lys Ala Ala Met Ile Thr Gly Met Gly Ser Asn Gln Val Val Ala Val
                    245                 250                 255

Pro Thr Asp Glu Gln Gly Arg Met Gln Pro Ala Ala Leu Glu Glu Glu
                    260                 265                 270

Ile Met Arg Ala Lys Glu Ser Gly Arg Lys Pro Phe Tyr Val Ser Cys
                    275                 280                 285

Thr Ala Gly Thr Thr Val Thr Gly Ala Phe Asp Pro Ile Asp Glu Ile
                    290                 295                 300

Cys Gln Ile Cys Arg Arg His Glu Met Trp Leu His Thr Asp Gly Ala
305                 310                 315                 320

Trp Gly Gly Ala Ala Ile Phe Ser Glu Glu His Arg Asn Leu Leu Arg
                    325                 330                 335

Gly Val Glu Gly Val Asp Ser Phe Cys Leu Asn Pro His Lys Met Leu
                    340                 345                 350

Gly Val Pro Met Gln Cys Ser Val Leu Ile Leu Asn Asn His Glu Gly
                    355                 360                 365

Arg Ser Arg Gly Ala Thr Glu Glu Glu Ser Leu Asp Leu Gly Gln Lys
                    370                 375                 380

Ser Leu Gln Cys Gly Arg Lys Pro Asp Cys Leu Lys Leu Trp Leu Cys
385                 390                 395                 400

Trp Lys Arg His Gly Thr Arg Gly Phe Ala Arg Arg Val Asp Arg Ala
                    405                 410                 415

Tyr Thr Phe Ser Gln Lys Phe Ala Glu Met Val Arg Arg Asp Pro Arg
                    420                 425                 430

Phe Tyr Leu Leu Met Asp Pro Ile Ser Cys Asn Val Cys Phe Phe Tyr
                    435                 440                 445

Leu Pro Pro Ser Leu Arg Gln Gln Leu Val Asp Arg Asn Leu Asn Asp
                    450                 455                 460

Leu Glu Lys Glu Glu Ala Gln Arg Gln Leu Lys Glu Phe His Ala Arg
465                 470                 475                 480

Leu Gly Gln Val Thr Gln Ile Ile Tyr Arg Arg Met Gln Lys Asp Gly
                    485                 490                 495
```

Lys Met Leu Ile Asn Phe Ser Pro Leu Lys Asp Arg Asp Leu Pro His
            500                 505                 510

Phe Phe Arg Ala Val Met Ile Gln Gln Arg Val Thr Glu Asp Asp Leu
        515                 520                 525

Val Phe Ile Leu Asp His Phe Glu His Leu Gly Lys Asp Leu
    530                 535                 540

<210> SEQ ID NO 29
<211> LENGTH: 1020
<212> TYPE: DNA
<213> ORGANISM: Escherichia coli

<400> SEQUENCE: 29

| | | | | | |
|---|---|---|---|---|---|
| atgaatgttt | ttattcctga | atactgctcc | cataacaaga | caggggagca | gacaatcatg | 60 |
| gcaatttcat | cgcgtaacac | acttcttgcc | gcactggcat | tcatcgcttt | tcaggcacag | 120 |
| gcggtgaacg | tcaccgtggc | gtatcaaacc | tcagccgaac | cggcgaaagt | ggctcaggcc | 180 |
| gacaacacct | ttgctaaaga | aagcggagca | accgtggact | ggcgtaagtt | tgacagcgga | 240 |
| gccagcatcg | tgcgggcgct | ggcttcaggc | gacgtgcaaa | tcggcaacct | cggttccagc | 300 |
| ccgttagcgg | ttgcagccag | ccaacaggtg | ccgattgaag | tcttcttgct | ggcgtcaaaa | 360 |
| ctgggtaact | ccgaagcgct | ggtggtaaag | aaaactatca | gcaaaccgga | agatctgatt | 420 |
| ggcaaacgca | tcgccgtacc | gtttatctcc | accacccact | acagcctgct | ggcggcactg | 480 |
| aaacactggg | gcattaaacc | cgggcaagtg | gagattgtga | acctgcagcc | gcccgcgatt | 540 |
| atcgctgcct | ggcagcgggg | agatattgat | ggtgcttatg | tctgggcacc | ggcggttaac | 600 |
| gccctggaaa | aagacggcaa | ggtgttgacc | gattctgaac | aggtcgggca | gtggggcgcg | 660 |
| ccaacgctgg | acgtctgggt | ggtgcgcaaa | gattttgccg | agaaacatcc | tgaggtcgtg | 720 |
| aaagcgttcg | ctaaaagcgc | catcgatgct | cagcaaccgt | acattgctaa | cccagacgtg | 780 |
| tggctgaaac | agccggaaaa | catcagcaaa | ctggcgcgtt | taagcggcgt | gcctgaaggt | 840 |
| gacgttccgg | ggctggtgaa | ggggaatacc | tatctgacgc | cgcagcaaca | aacggcagaa | 900 |
| ctgaccggac | cggtgaacaa | agcgatcatc | gacaccgcgc | agttttttgaa | agagcagggc | 960 |
| aaggtcccgg | ctgtagcgaa | tgattacagc | cagtacgtta | cctcgcgctt | cgtgcaataa | 1020 |

<210> SEQ ID NO 30
<211> LENGTH: 320
<212> TYPE: PRT
<213> ORGANISM: Escherichia coli

<400> SEQUENCE: 30

Met Ala Ile Ser Ser Arg Asn Thr Leu Leu Ala Ala Leu Ala Phe Ile
1               5                   10                  15

Ala Phe Gln Ala Gln Ala Val Asn Val Thr Val Ala Tyr Gln Thr Ser
            20                  25                  30

Ala Glu Pro Ala Lys Val Ala Gln Ala Asp Asn Thr Phe Ala Lys Glu
        35                  40                  45

Ser Gly Ala Thr Val Asp Trp Arg Lys Phe Asp Ser Gly Ala Ser Ile
    50                  55                  60

Val Arg Ala Leu Ala Ser Gly Asp Val Gln Ile Gly Asn Leu Gly Ser
65                  70                  75                  80

Ser Pro Leu Ala Val Ala Ala Ser Gln Gln Val Pro Ile Glu Val Phe
                85                  90                  95

Leu Leu Ala Ser Lys Leu Gly Asn Ser Glu Ala Leu Val Val Lys Lys

```
            100                 105                 110
Thr Ile Ser Lys Pro Glu Asp Leu Ile Gly Lys Arg Ile Ala Val Pro
            115                 120                 125

Phe Ile Ser Thr Thr His Tyr Ser Leu Leu Ala Ala Leu Lys His Trp
            130                 135                 140

Gly Ile Lys Pro Gly Gln Val Glu Ile Val Asn Leu Gln Pro Pro Ala
145                 150                 155                 160

Ile Ile Ala Ala Trp Gln Arg Gly Asp Ile Asp Gly Ala Tyr Val Trp
                165                 170                 175

Ala Pro Ala Val Asn Ala Leu Glu Lys Asp Gly Lys Val Leu Thr Asp
            180                 185                 190

Ser Glu Gln Val Gly Gln Trp Gly Ala Pro Thr Leu Asp Val Trp Val
            195                 200                 205

Val Arg Lys Asp Phe Ala Glu Lys His Pro Glu Val Val Lys Ala Phe
            210                 215                 220

Ala Lys Ser Ala Ile Asp Ala Gln Gln Pro Tyr Ile Ala Asn Pro Asp
225                 230                 235                 240

Val Trp Leu Lys Gln Pro Glu Asn Ile Ser Lys Leu Ala Arg Leu Ser
                245                 250                 255

Gly Val Pro Glu Gly Asp Val Pro Gly Leu Val Lys Gly Asn Thr Tyr
                260                 265                 270

Leu Thr Pro Gln Gln Gln Thr Ala Glu Leu Thr Gly Pro Val Asn Lys
            275                 280                 285

Ala Ile Ile Asp Thr Ala Gln Phe Leu Lys Glu Gln Gly Lys Val Pro
290                 295                 300

Ala Val Ala Asn Asp Tyr Ser Gln Tyr Val Thr Ser Arg Phe Val Gln
305                 310                 315                 320

<210> SEQ ID NO 31
<211> LENGTH: 1017
<212> TYPE: DNA
<213> ORGANISM: Roseobacter denitrificans

<400> SEQUENCE: 31
atgacatttc tttcacggat cacgtccggc acagcgattg ccctgacggc gaccatcatg      60
agcatcggcg cggctgatgc caaaaacttc aagatcgccg tgggcgacag cggcggcagc     120
agccaggaag ccaccggttt ggctttcatc gaagcccttg aggagctttc gggcggcgag     180
cacactgcaa cgctgtttct gaacggacag ttggggtccg agcaagacac agtcaacgac     240
gcggccatcg gctcgctcga catgtcgatc ctggcgatca caacgtgac  accgttctcg     300 ccaactgttg gcgtcttctc gcttccatac gtgatcctga gcctcgaaga tgctgaaaag     360
ctgacccagg gcccgatcgg tcaggaactg acagaaaaca caatcgaaga cgcaggcgtt     420
cgtatcgtgg cctggaccta cacgggtttc gccgcctga  ccaattccaa aaagccggtc     480
acatccgttg ccgatctgca aggtctcgtc attcgcgttc caagaacga  aatcatgatc     540 gacacctaca aggcctgggg catcagccca acgccgatgg catggtcgga aacctttgcg     600
ggcctgcaaa ccggcgttgt cgacggtcag gacaacccct acaccaccat caacgcgatg     660
aagttctacg aagtacaaaa gtacgtcacg aacatccgct acatcttctc catcgaacct     720
ctgatcgtgt ccgagcaggt gtttcaggag ctttccgctg aagatcagga aatcattctg     780
gaagcaggca agcgcgcgac ggccgcgtct gcacagttcc tgcgcgacaa ggaagcagag     840
atcaaggaac tgctggtcga aaaaggcatg cagatcgacc acccggtcaa caatgagcag     900
```

```
gagttcattg atctggcgac agcagctgtc tggccgaagt tctacgacag catcggcggc    960
atcgaaaaga tgaacgctgt tctggctgaa atcggccgcg agccggtctc cgaataa      1017
```

<210> SEQ ID NO 32
<211> LENGTH: 338
<212> TYPE: PRT
<213> ORGANISM: Roseobacter denitrificans

<400> SEQUENCE: 32

```
Met Thr Phe Leu Ser Arg Ile Thr Ser Gly Thr Ala Ile Ala Leu Thr
1               5                   10                  15

Ala Thr Ile Met Ser Ile Gly Ala Ala Asp Ala Lys Asn Phe Lys Ile
                20                  25                  30

Ala Val Gly Asp Ser Gly Gly Ser Ser Gln Glu Ala Thr Gly Leu Ala
            35                  40                  45

Phe Ile Glu Ala Leu Glu Glu Leu Ser Gly Gly Glu His Thr Ala Thr
        50                  55                  60

Leu Phe Leu Asn Gly Gln Leu Gly Ser Glu Gln Asp Thr Val Asn Asp
65                  70                  75                  80

Ala Ala Ile Gly Ser Leu Asp Met Ser Ile Leu Ala Ile Asn Asn Val
                85                  90                  95

Thr Pro Phe Ser Pro Thr Val Gly Val Phe Ser Leu Pro Tyr Val Ile
                100                 105                 110

Leu Ser Leu Glu Asp Ala Glu Lys Leu Thr Gln Gly Pro Ile Gly Gln
            115                 120                 125

Glu Leu Thr Glu Asn Thr Ile Glu Asp Ala Gly Val Arg Ile Val Ala
        130                 135                 140

Trp Thr Tyr Thr Gly Phe Arg Arg Leu Thr Asn Ser Lys Lys Pro Val
145                 150                 155                 160

Thr Ser Val Ala Asp Leu Gln Gly Leu Val Ile Arg Val Pro Lys Asn
                165                 170                 175

Glu Ile Met Ile Asp Thr Tyr Lys Ala Trp Gly Ile Ser Pro Thr Pro
                180                 185                 190

Met Ala Trp Ser Glu Thr Phe Ala Gly Leu Gln Thr Gly Val Val Asp
            195                 200                 205

Gly Gln Asp Asn Pro Tyr Thr Thr Ile Asn Ala Met Lys Phe Tyr Glu
        210                 215                 220

Val Gln Lys Tyr Val Thr Asn Ile Arg Tyr Ile Phe Ser Ile Glu Pro
225                 230                 235                 240

Leu Ile Val Ser Glu Gln Val Phe Gln Glu Leu Ser Ala Glu Asp Gln
                245                 250                 255

Glu Ile Ile Leu Glu Ala Gly Lys Arg Ala Thr Ala Ala Ser Ala Gln
                260                 265                 270

Phe Leu Arg Asp Lys Glu Ala Glu Ile Lys Glu Leu Leu Val Glu Lys
            275                 280                 285

Gly Met Gln Ile Asp Asp Pro Val Asn Asn Glu Gln Glu Phe Ile Asp
        290                 295                 300

Leu Ala Thr Ala Ala Val Trp Pro Lys Phe Tyr Asp Ser Ile Gly Gly
305                 310                 315                 320

Ile Glu Lys Met Asn Ala Val Leu Ala Glu Ile Gly Arg Glu Pro Val
                325                 330                 335

Ser Glu
```

<210> SEQ ID NO 33

<211> LENGTH: 852
<212> TYPE: DNA
<213> ORGANISM: Escherichia coli

<400> SEQUENCE: 33

| | | | | | |
|---|---|---|---|---|---|
| atgagtgaac | gtctgagcat | taccccgctg | gggccgtata | tcggcgcaca | aatttcgggt | 60 |
| gccgacctga | cgcgcccgtt | aagcgataat | cagtttgaac | agctttacca | tgcggtgctg | 120 |
| cgccatcagg | tggtgtttct | acgcgatcaa | gctattacgc | cgcagcagca | acgcgcgctg | 180 |
| gcccagcgtt | ttggcgaatt | gcatattcac | cctgtttacc | cgcatgccga | aggggttgac | 240 |
| gagatcatcg | tgctggatac | ccataacgat | aatccgccag | ataacgacaa | ctggcatacc | 300 |
| gatgtgacat | ttattgaaac | gccacccgca | ggggcgattc | tggcagctaa | agagttacct | 360 |
| tcgaccggcg | gtgatacgct | ctggaccagc | ggtattgcgg | cctatgaggc | gctctctgtt | 420 |
| cccttccgcc | agctgctgag | tgggctgcgt | gcggagcatg | atttccgtaa | atcgttcccg | 480 |
| gaatacaaat | accgcaaaac | cgaggaggaa | catcaacgct | ggcgcgaggc | ggtcgcgaaa | 540 |
| aacccgccgt | tgctacatcc | ggtggtgcga | acgcatccgg | tgagcggtaa | acaggcgctg | 600 |
| tttgtgaatg | aaggctttac | tacgcgaatt | gttgatgtga | gcgagaaaga | gagcgaagcc | 660 |
| ttgttaagtt | ttttgtttgc | ccatatcacc | aaaccggagt | tcaggtgcg | ctggcgctgg | 720 |
| caaccaaatg | atattgcgat | ttgggataac | cgcgtgaccc | agcactatgc | caatgccgat | 780 |
| tacctgccac | agcgacggat | aatgcatcgg | gcgacgatcc | ttggggataa | accgttttat | 840 |
| cgggcggggt | aa | | | | | 852 |

<210> SEQ ID NO 34
<211> LENGTH: 283
<212> TYPE: PRT
<213> ORGANISM: Escherichia coli

<400> SEQUENCE: 34

Met Ser Glu Arg Leu Ser Ile Thr Pro Leu Gly Pro Tyr Ile Gly Ala
1               5                   10                  15

Gln Ile Ser Gly Ala Asp Leu Thr Arg Pro Leu Ser Asp Asn Gln Phe
            20                  25                  30

Glu Gln Leu Tyr His Ala Val Leu Arg His Gln Val Val Phe Leu Arg
        35                  40                  45

Asp Gln Ala Ile Thr Pro Gln Gln Gln Arg Ala Leu Ala Gln Arg Phe
    50                  55                  60

Gly Glu Leu His Ile His Pro Val Tyr Pro His Ala Glu Gly Val Asp
65                  70                  75                  80

Glu Ile Ile Val Leu Asp Thr His Asn Asp Asn Pro Pro Asp Asn Asp
                85                  90                  95

Asn Trp His Thr Asp Val Thr Phe Ile Glu Thr Pro Pro Ala Gly Ala
            100                 105                 110

Ile Leu Ala Ala Lys Glu Leu Pro Ser Thr Gly Gly Asp Thr Leu Trp
        115                 120                 125

Thr Ser Gly Ile Ala Ala Tyr Glu Ala Leu Ser Val Pro Phe Arg Gln
    130                 135                 140

Leu Leu Ser Gly Leu Arg Ala Glu His Asp Phe Arg Lys Ser Phe Pro
145                 150                 155                 160

Glu Tyr Lys Tyr Arg Lys Thr Glu Glu Glu His Gln Arg Trp Arg Glu
                165                 170                 175

Ala Val Ala Lys Asn Pro Pro Leu Leu His Pro Val Val Arg Thr His
            180                 185                 190

Pro Ser Gly Lys Gln Ala Leu Phe Val Asn Glu Gly Phe Thr Thr
    195                 200                 205

Arg Ile Val Asp Val Ser Glu Lys Glu Ser Glu Ala Leu Leu Ser Phe
    210                 215                 220

Leu Phe Ala His Ile Thr Lys Pro Glu Phe Gln Val Arg Trp Arg Trp
225                 230                 235                 240

Gln Pro Asn Asp Ile Ala Ile Trp Asp Asn Arg Val Thr Gln His Tyr
                245                 250                 255

Ala Asn Ala Asp Tyr Leu Pro Gln Arg Arg Ile Met His Arg Ala Thr
                260                 265                 270

Ile Leu Gly Asp Lys Pro Phe Tyr Arg Ala Gly
                275                 280

<210> SEQ ID NO 35
<211> LENGTH: 1146
<212> TYPE: DNA
<213> ORGANISM: Escherichia coli

<400> SEQUENCE: 35
atgagtctga aatgttctg gttttaccg acccacggtg acgggcatta tctgggaacg      60
gaagaaggtt cacgcccggt tgatcacggt tatctgcaac aaattgcgca agcggcggat    120
cgtcttggct ataccggtgt gctaattcca acggggcgct cctgcgaaga tgcgtggctg    180
gttgccgcat cgatgatccc ggtgacgcag cggctgaagt ttcttgtcgc cctgcgtccc    240
agcgtaacct cacctaccgt tgccgcccgc caggccgcca cgcttgaccg tctctcaaat    300
ggacgtgcgt tgtttaacct ggtcacaggc agcgatccac aagagctggc aggcgacgga    360
gtgttccttg atcatagcga gcgctacgaa gcctcggcgg aatttaccca ggtctggcgg    420
cgtttattgc agagagaaac cgtcgatttc aacggtaaac atattcatgt gcgcggagca    480
aaactgctct cccggcgat caacagccg tatccgccac tttactttgg cggatcgtca     540
gatgtcgccc aggagctggc ggcagaacag gttgatctct acctcacctg gggcgaaccg    600
ccggaactgg ttaaagagaa aatcgaacaa gtgcgggcga agctgccgc gcatggacgc    660 aaaattcgtt tcggtattcg tctgcatgtg attgttcgtg aaactaacga cgaagcgtgg    720
caggccgccg agcggttaat ctcgcatctt gatgatgaaa ctatcgccaa agcacaggcc    780
gcattcgccc ggacggattc cgtagggcaa cagcgaatgg cggcgttaca taacggcaag    840
cgcgacaatc tggagatcag ccccaattta tgggcgggcg ttggcttagt gcgcggcggt    900
gccgggacgg cgctggtggg cgatggtcct acgtcgctg cgcgaatcaa cgaatatgcc    960
gcgcttggca tcgacagttt tgtgctttcg ggctatccgc atctggaaga agcgtatcgg   1020
gttggcgagt gctgttccc gcttctggat gtcgccatcc cggaaattcc ccagccgcag   1080
ccgctgaatc cgcaaggcga agcggtggcg aatgatttta tcccccgtaa agtcgcgcaa   1140
agctaa                                                              1146

<210> SEQ ID NO 36
<211> LENGTH: 381
<212> TYPE: PRT
<213> ORGANISM: Escherichia coli

<400> SEQUENCE: 36

Met Ser Leu Asn Met Phe Trp Phe Leu Pro Thr His Gly Asp Gly His
1               5                   10                  15

Tyr Leu Gly Thr Glu Glu Gly Ser Arg Pro Val Asp His Gly Tyr Leu

```
                 20                  25                  30
Gln Gln Ile Ala Gln Ala Ala Asp Arg Leu Gly Tyr Thr Gly Val Leu
             35                  40                  45
Ile Pro Thr Gly Arg Ser Cys Glu Asp Ala Trp Leu Val Ala Ala Ser
         50                  55                  60
Met Ile Pro Val Thr Gln Arg Leu Lys Phe Leu Val Ala Leu Arg Pro
 65                  70                  75                  80
Ser Val Thr Ser Pro Thr Val Ala Ala Arg Gln Ala Ala Thr Leu Asp
                 85                  90                  95
Arg Leu Ser Asn Gly Arg Ala Leu Phe Asn Leu Val Thr Gly Ser Asp
             100                 105                 110
Pro Gln Glu Leu Ala Gly Asp Gly Val Phe Leu Asp His Ser Glu Arg
         115                 120                 125
Tyr Glu Ala Ser Ala Glu Phe Thr Gln Val Trp Arg Arg Leu Leu Gln
     130                 135                 140
Arg Glu Thr Val Asp Phe Asn Gly Lys His Ile His Val Arg Gly Ala
145                 150                 155                 160
Lys Leu Leu Phe Pro Ala Ile Gln Gln Pro Tyr Pro Pro Leu Tyr Phe
                 165                 170                 175
Gly Gly Ser Ser Asp Val Ala Gln Glu Leu Ala Ala Glu Gln Val Asp
             180                 185                 190
Leu Tyr Leu Thr Trp Gly Glu Pro Pro Glu Leu Val Lys Glu Lys Ile
         195                 200                 205
Glu Gln Val Arg Ala Lys Ala Ala His Gly Arg Lys Ile Arg Phe
     210                 215                 220
Gly Ile Arg Leu His Val Ile Val Arg Glu Thr Asn Asp Glu Ala Trp
225                 230                 235                 240
Gln Ala Ala Glu Arg Leu Ile Ser His Leu Asp Asp Glu Thr Ile Ala
                 245                 250                 255
Lys Ala Gln Ala Ala Phe Ala Arg Thr Asp Ser Val Gly Gln Gln Arg
             260                 265                 270
Met Ala Ala Leu His Asn Gly Lys Arg Asp Asn Leu Glu Ile Ser Pro
         275                 280                 285
Asn Leu Trp Ala Gly Val Gly Leu Val Arg Gly Gly Ala Gly Thr Ala
     290                 295                 300
Leu Val Gly Asp Gly Pro Thr Val Ala Ala Arg Ile Asn Glu Tyr Ala
305                 310                 315                 320
Ala Leu Gly Ile Asp Ser Phe Val Leu Ser Gly Tyr Pro His Leu Glu
                 325                 330                 335
Glu Ala Tyr Arg Val Gly Glu Leu Leu Phe Pro Leu Leu Asp Val Ala
             340                 345                 350
Ile Pro Glu Ile Pro Gln Pro Gln Pro Leu Asn Pro Gln Gly Glu Ala
         355                 360                 365
Val Ala Asn Asp Phe Ile Pro Arg Lys Val Ala Gln Ser
     370                 375                 380

<210> SEQ ID NO 37
<211> LENGTH: 576
<212> TYPE: DNA
<213> ORGANISM: Escherichia coli

<400> SEQUENCE: 37
atgcgtgtca tcaccctggc gggtagtcct cgctttcctt ctcgctccag ctccttgctg        60
gaatatgcgc gggaaaaact aaatggcctg gatgtagagg tttatcactg gaatctgcaa      120
```

```
aacttcgccc cggaagatct actttatgct cgtttcgata gtccggcact caagaccttc    180
accgaacagc tgcaacaggc cgatgggctg attgtcgcca cgcctgtgta taaagccgcc    240
tattccggtg cgttgaaaac cctgctcgac ctgctgccag aacgcgcttt gcaaggcaaa    300
gtggtgctac cgctggcgac gggcggtacc gtggcccatc tgctggcggt cgattatgcc    360
cttaaaccag ttttaagcgc actgaaagct caggagatcc tgcacggcgt gtttgccgat    420
gactcacaag taattgatta ccatcacaga ccccagttca cgccaaatct gcaaccccgt    480
cttgataccg cgctagaaac tttctggcag gcattgcacc gccgcgatgt tcaggttcct    540
gaccttctgt ctctgcgagg taatgcccat gcgtaa                              576
```

<210> SEQ ID NO 38
<211> LENGTH: 191
<212> TYPE: PRT
<213> ORGANISM: Escherichia coli

<400> SEQUENCE: 38

```
Met Arg Val Ile Thr Leu Ala Gly Ser Pro Arg Phe Pro Ser Arg Ser
1               5                   10                  15

Ser Ser Leu Leu Glu Tyr Ala Arg Glu Lys Leu Asn Gly Leu Asp Val
            20                  25                  30

Glu Val Tyr His Trp Asn Leu Gln Asn Phe Ala Pro Glu Asp Leu Leu
        35                  40                  45

Tyr Ala Arg Phe Asp Ser Pro Ala Leu Lys Thr Phe Thr Glu Gln Leu
    50                  55                  60

Gln Gln Ala Asp Gly Leu Ile Val Ala Thr Pro Val Tyr Lys Ala Ala
65                  70                  75                  80

Tyr Ser Gly Ala Leu Lys Thr Leu Leu Asp Leu Leu Pro Glu Arg Ala
                85                  90                  95

Leu Gln Gly Lys Val Val Leu Pro Leu Ala Thr Gly Gly Thr Val Ala
            100                 105                 110

His Leu Leu Ala Val Asp Tyr Ala Leu Lys Pro Val Leu Ser Ala Leu
        115                 120                 125

Lys Ala Gln Glu Ile Leu His Gly Val Phe Ala Asp Asp Ser Gln Val
    130                 135                 140

Ile Asp Tyr His His Arg Pro Gln Phe Thr Pro Asn Leu Gln Thr Arg
145                 150                 155                 160

Leu Asp Thr Ala Leu Glu Thr Phe Trp Gln Ala Leu His Arg Arg Asp
                165                 170                 175

Val Gln Val Pro Asp Leu Leu Ser Leu Arg Gly Asn Ala His Ala
            180                 185                 190
```

<210> SEQ ID NO 39
<211> LENGTH: 1146
<212> TYPE: DNA
<213> ORGANISM: Corynebacterium glutamicum

<400> SEQUENCE: 39

```
atgacattaa ctttccattg gttcctatcc acttcaggcg attcccgcgg catcatcggc    60
ggcggtcacg gtgcagaaaa atccggcacc tcccgcgaat tgagccacag ctacctcaag    120
cagttggcgc tagctgccga gaccaacggt tttgaatctg tcctgacacc aacgggcacg    180
tggtgcgaag atgcgtggat tactgacgct tctttgattg aggcgacaaa acgcttgaag    240
ttcctcgttg cgcttcgccc tgggcagatt ggacctacgc tgtctgctca aatggcttct    300
```

```
actttccagc gtctgtctgg caaccgtttg ctgatcaatg tggtcaccgg tggggaagat    360
gcggagcagc gtgcgtttgg tgatttcttg aacaaggagg agcgctacgc ccgtaccgga    420
gaattcttgg atatcgtgag ccgcttgtgg cgaggcgaaa ccgtcacgca ccacggtgaa    480
cacctgcagg tggagcaagc tagccttgcg catccgccag agattattcc ggagattctt    540
tttggtggat cgtcgccagc tgcaggtgag gtggctgcac gttatgcgga cacctatctc    600
acgtggggtg aaactcccga tcaggtggcg cagaaaatca actggatcaa cgagctagca    660
gcacagcgcg gccgggaact gcgccatgga atccgcttcc atgtgatcac ccgcgatacg    720
tctgaagaag catgggtggt ggcagagaag ttgattagcg gggtcactcc agaacaggtc    780
gctaaggctc aagccgggtt tgcaacgtct aagtcggagg ggcagcgccg gatggctgag    840
ctgcacagca aggtcgtgc ctttactagt ggctcaactg ctcgtgatct ggaggtgtat    900
cccaatgtgt gggcaggcgt cggttttgctt cgcggaggtg caggaacagc ccttgtgggc    960
tcgcatgaag aggtcgccga tcgcatcgaa gaatacgcag cactcggctt ggatcagttt    1020
gtactgtcgg gttatccaaa cttggaggag gccttccact tcggtgaggg tgtgattccg    1080
gagctgctgc ccgcggtgt ggatatcaaa aatcaagaat cacgagtttt ggaacctgtt    1140
gggtaa                                                                1146
```

<210> SEQ ID NO 40
<211> LENGTH: 381
<212> TYPE: PRT
<213> ORGANISM: Corynebacterium glutamicum

<400> SEQUENCE: 40

```
Met Thr Leu Thr Phe His Trp Phe Leu Ser Thr Ser Gly Asp Ser Arg
1               5                   10                  15

Gly Ile Ile Gly Gly Gly His Gly Ala Glu Lys Ser Gly Thr Ser Arg
            20                  25                  30

Glu Leu Ser His Ser Tyr Leu Lys Gln Leu Ala Leu Ala Ala Glu Thr
        35                  40                  45

Asn Gly Phe Glu Ser Val Leu Thr Pro Thr Gly Thr Trp Cys Glu Asp
    50                  55                  60

Ala Trp Ile Thr Asp Ala Ser Leu Ile Glu Ala Thr Lys Arg Leu Lys
65                  70                  75                  80

Phe Leu Val Ala Leu Arg Pro Gly Gln Ile Gly Pro Thr Leu Ser Ala
                85                  90                  95

Gln Met Ala Ser Thr Phe Gln Arg Leu Ser Gly Asn Arg Leu Leu Ile
            100                 105                 110

Asn Val Val Thr Gly Gly Glu Asp Ala Glu Gln Arg Ala Phe Gly Asp
        115                 120                 125

Phe Leu Asn Lys Glu Glu Arg Tyr Ala Arg Thr Gly Glu Phe Leu Asp
    130                 135                 140

Ile Val Ser Arg Leu Trp Arg Gly Glu Thr Val Thr His His Gly Glu
145                 150                 155                 160

His Leu Gln Val Glu Gln Ala Ser Leu Ala His Pro Pro Glu Ile Ile
                165                 170                 175

Pro Glu Ile Leu Phe Gly Gly Ser Ser Pro Ala Gly Glu Val Ala
            180                 185                 190

Ala Arg Tyr Ala Asp Thr Tyr Leu Thr Trp Gly Glu Thr Pro Asp Gln
        195                 200                 205

Val Ala Gln Lys Ile Asn Trp Ile Asn Glu Leu Ala Ala Gln Arg Gly
    210                 215                 220
```

Arg Glu Leu Arg His Gly Ile Arg Phe His Val Ile Thr Arg Asp Thr
225                 230                 235                 240

Ser Glu Glu Ala Trp Val Val Ala Glu Lys Leu Ile Ser Gly Val Thr
            245                 250                 255

Pro Glu Gln Val Ala Lys Ala Gln Ala Gly Phe Ala Thr Ser Lys Ser
        260                 265                 270

Glu Gly Gln Arg Arg Met Ala Glu Leu His Ser Lys Gly Arg Ala Phe
    275                 280                 285

Thr Ser Gly Ser Thr Ala Arg Asp Leu Glu Val Tyr Pro Asn Val Trp
290                 295                 300

Ala Gly Val Gly Leu Leu Arg Gly Gly Ala Gly Thr Ala Leu Val Gly
305                 310                 315                 320

Ser His Glu Glu Val Ala Asp Arg Ile Glu Glu Tyr Ala Ala Leu Gly
                325                 330                 335

Leu Asp Gln Phe Val Leu Ser Gly Tyr Pro Asn Leu Glu Glu Ala Phe
            340                 345                 350

His Phe Gly Glu Gly Val Ile Pro Glu Leu Leu Arg Arg Gly Val Asp
        355                 360                 365

Ile Lys Asn Gln Glu Ser Arg Val Leu Glu Pro Val Gly
    370                 375                 380

<210> SEQ ID NO 41
<211> LENGTH: 924
<212> TYPE: DNA
<213> ORGANISM: Corynebacterium glutamicum

<400> SEQUENCE: 41
atgacgtccc cgcataattt tgtcagtggt gctattgatc tgggtgaggt gaaagcgcgt      60
gcggatgcgc gccagaaggc ccatgagcag gggccggtaa ctcagggcat tgctagttcc     120
cttgatgtga ccatggagaa cctggagaat gaggtgctgc gtcgttccac gcaggttccg     180
gtgattgttc tcgtgggtac cccgcgcagc cctgattcgg agcagttgaa gtcggatctg     240
accacgcttg ctgctgaaag tggcaggaag ttcatttttcg ttatgtcaa tgctgatacc     300 gatgctgatg tggcccaggt gtttggggtg cagggcttgc cgtcggtgat tgctgtggca     360
gcgggacgcc ctctggctga tttccagggc ggacagccag cggatgcact aaagcagtgg     420
actgatcagg tggttcaggc tgtgggtgga cagctggaag gactgccaga ggaggccaca     480
gacggcgaac aagaagacgc tcctgtggaa gacccccgct tcgatgctgc cactgatgct     540
ctaaaccgtg gcgctttcga tgaggcgatt gcggtttatg agtccatttt ggcgcaggag     600
ccaaacaacg ctgatgcgaa gcaggcacgc gataccgcaa agctgttggg ccggcttgcc     660
acggtggatc cttcggtgga tgttgtcgct gctgcagatg ctgatccaac aaacgttgat     720
ctggcctaca cagcagctga cgcggctgtt gttgcgggtg atcctgaggc tgcctttgat     780
cgtttaattg ctctgctgac catcagcgct ggcgatcaga gaatcaggt gaaggaacgt     840 ttgctggagc tgtttggcat gtttgagacc gccgatcccc gtgtgctgca ggcgcgagga     900
aagatggcca gcgcgctgtt ctaa                                           924

<210> SEQ ID NO 42
<211> LENGTH: 307
<212> TYPE: PRT
<213> ORGANISM: Corynebacterium glutamicum

<400> SEQUENCE: 42

```
Met Thr Ser Pro His Asn Phe Val Ser Gly Ala Ile Asp Leu Gly Glu
1               5                   10                  15

Val Lys Ala Arg Ala Asp Ala Arg Gln Lys Ala His Glu Gln Gly Pro
            20                  25                  30

Val Thr Gln Gly Ile Ala Ser Ser Leu Asp Val Thr Met Glu Asn Leu
                35                  40                  45

Glu Asn Glu Val Leu Arg Arg Ser Thr Gln Val Pro Val Ile Val Leu
    50                  55                  60

Val Gly Thr Pro Arg Ser Pro Asp Ser Glu Gln Leu Lys Ser Asp Leu
65                  70                  75                  80

Thr Thr Leu Ala Ala Glu Ser Gly Arg Lys Phe Ile Phe Gly Tyr Val
                85                  90                  95

Asn Ala Asp Thr Asp Ala Asp Val Ala Gln Val Phe Gly Val Gln Gly
                100                 105                 110

Leu Pro Ser Val Ile Ala Val Ala Ala Gly Arg Pro Leu Ala Asp Phe
            115                 120                 125

Gln Gly Gly Gln Pro Ala Asp Ala Leu Lys Gln Trp Thr Asp Gln Val
    130                 135                 140

Val Gln Ala Val Gly Gly Gln Leu Glu Gly Leu Pro Glu Glu Ala Thr
145                 150                 155                 160

Asp Gly Glu Gln Glu Asp Ala Pro Val Glu Asp Pro Arg Phe Asp Ala
                165                 170                 175

Ala Thr Asp Ala Leu Asn Arg Gly Ala Phe Asp Glu Ala Ile Ala Val
            180                 185                 190

Tyr Glu Ser Ile Leu Ala Gln Glu Pro Asn Asn Ala Asp Ala Lys Gln
    195                 200                 205

Ala Arg Asp Thr Ala Lys Leu Leu Gly Arg Leu Ala Thr Val Asp Pro
    210                 215                 220

Ser Val Asp Val Val Ala Ala Asp Ala Asp Pro Thr Asn Val Asp
225                 230                 235                 240

Leu Ala Tyr Thr Ala Ala Asp Ala Ala Val Val Ala Gly Asp Pro Glu
                245                 250                 255

Ala Ala Phe Asp Arg Leu Ile Ala Leu Leu Thr Ile Ser Ala Gly Asp
                260                 265                 270

Gln Lys Asn Gln Val Lys Glu Arg Leu Leu Glu Leu Phe Gly Met Phe
    275                 280                 285

Glu Thr Ala Asp Pro Arg Val Leu Gln Ala Arg Gly Lys Met Ala Ser
    290                 295                 300

Ala Leu Phe
305
```

<210> SEQ ID NO 43
<211> LENGTH: 387
<212> TYPE: DNA
<213> ORGANISM: Roseobacter denitrificans

<400> SEQUENCE: 43

```
atgaccaaaa cactgacagc tcaggacttg tccgacacct tgacgccctt caatcgccat    60
gacgttgatg gcgtcatgac acatttcgcc gatgattgcg tgttctacac cgtgggcggg   120
gatgaagcct atggcgccaa agtcgaaggc gcagaagcga ttgccaaagc attctctgcc   180
gtctgggcgg gcatgaagga cgcccattgg gatcatcaca gccactttgt gcatggggat   240
cgcgccgtat ccgaatggac gttctccgga actggcgcgg acggcatgcg catcgaagca   300
cagggcgctg acctctttac cctgcgcgac ggcaagatca tcgtgaaaca ggccctgcgc   360
```
aaatcccgcc cgcccttcaa ggcttaa                                       387

<210> SEQ ID NO 44
<211> LENGTH: 128
<212> TYPE: PRT
<213> ORGANISM: Roseobacter denitrificans

<400> SEQUENCE: 44

Met Thr Lys Thr Leu Thr Ala Gln Asp Leu Ser Asp Thr Phe Asp Ala
1               5                   10                  15

Phe Asn Arg His Asp Val Asp Gly Val Met Thr His Phe Ala Asp Asp
            20                  25                  30

Cys Val Phe Tyr Thr Val Gly Gly Asp Glu Ala Tyr Gly Ala Lys Val
        35                  40                  45

Glu Gly Ala Glu Ala Ile Ala Lys Ala Phe Ser Ala Val Trp Ala Gly
    50                  55                  60

Met Lys Asp Ala His Trp Asp His His Ser His Phe Val His Gly Asp
65                  70                  75                  80

Arg Ala Val Ser Glu Trp Thr Phe Ser Gly Thr Gly Ala Asp Gly Met
                85                  90                  95

Arg Ile Glu Ala Gln Gly Ala Asp Leu Phe Thr Leu Arg Asp Gly Lys
            100                 105                 110

Ile Ile Val Lys Gln Ala Leu Arg Lys Ser Arg Pro Pro Phe Lys Ala
        115                 120                 125

<210> SEQ ID NO 45
<211> LENGTH: 1395
<212> TYPE: DNA
<213> ORGANISM: Roseobacter denitrificans

<400> SEQUENCE: 45
atgccacata gaccaaagca ctggcccaag gccagctacg atcccaaata cgatcctatc      60
gtcgacgcgg gtcccggtca caaccgggac cacgcaccga cctattggat tggtacggcg     120
gggacgccac ctgaagatga cgggccggtg tcgggtgaca tcgatgcgga tgtcgtcgtt     180
gtcggctctg gctatacagg tctgtctacc gcaatccacc tggcgaagga ccacggcatc     240
aaggcgcatg tccttgaagc caacacagtc gcctggggct gttccacccg caatggcggg     300
caggcacaga tttcttccgg tcgtctcaag cggtcggagt ggatcaagcg gtggggcgtg     360
gatgtcgcca aaggcatgca cgccgaggtc tgtgaagcct tcgaactgtt caatgatctg     420
atcgggtcag atgacattga ttgcgacccg caaaccgggg gccatttcta tattgcccac     480
cgcgaaaagg tcatggcgaa gctggaaaag gaatgtgccg tcctgaacga cacgtttggc     540
tatggctctc gcattctgtc gcgcgacgaa ctacacgaaa aatacgtgcg ggatcaggaa     600
gcacacggtg cccttgggaa accggacggg acctcgatcc acgcggcaaa actggccttc     660
agctacgtgc gtcttgcgcg caaactcggc gccaagatcc acacggccag cccggtcatg     720
gggtggaaga ccgtgaacgg tgtgcatcac ctcaccacgc ccggtggcac ggtgcgcgca     780
cgtgccgtgg ccttggcgac agcgggctac acaccgccgg ggctgaacga aaagaccaag     840
caccggctca tgccgatcct gtcaaactcc atcgtgacgc gtccgctgag cgatgaggaa     900
aaggcgggat gcggttttca ggtgaaatct ccgctgactg acacgcgcac cttgcggcac     960
tactaccgct atctgcccga cggacgggtc cagatcggca gccgcagtgc gattacaggt    1020
cgagacgcag agaaccccag acatctggag cttctgcaga aaggtctcta tcgcaagttc    1080

-continued

```
cccgtgctcg aaggcattga actggattac tcctggtggg gatgggtgga tgtcagccat    1140
gacatgatgc cacgcatttt ccagccaaac ccgaagcaaa caatctttta tgcgatgggc    1200
tacggcggca acgggtgat gtattccgca caggccggca agcgcatggc gcaaatggtt     1260
gcgggcgaag gcaaggacct caaacttccg atcttcacct cgcaactgcc aagccacggt    1320
gttctgacac ccttccgcag gttgggccag cgcatggcct accctacta ctaccttcgc    1380 gatgaaattc tctga                                                    1395
```

<210> SEQ ID NO 46
<211> LENGTH: 464
<212> TYPE: PRT
<213> ORGANISM: Roseobacter denitrificans

<400> SEQUENCE: 46

```
Met Pro His Arg Pro Lys His Trp Pro Lys Ala Ser Tyr Asp Pro Lys
1               5                   10                  15

Tyr Asp Pro Ile Val Asp Ala Gly Pro Gly His Asn Arg Asp His Ala
            20                  25                  30

Pro Thr Tyr Trp Ile Gly Thr Ala Gly Thr Pro Pro Glu Asp Asp Gly
        35                  40                  45

Pro Val Ser Gly Asp Ile Asp Ala Asp Val Val Val Gly Ser Gly
    50                  55                  60

Tyr Thr Gly Leu Ser Thr Ala Ile His Leu Ala Lys Asp His Gly Ile
65                  70                  75                  80

Lys Ala His Val Leu Glu Ala Asn Thr Val Ala Trp Gly Cys Ser Thr
                85                  90                  95

Arg Asn Gly Gly Gln Ala Gln Ile Ser Ser Gly Arg Leu Lys Arg Ser
            100                 105                 110

Glu Trp Ile Lys Arg Trp Gly Val Asp Val Ala Lys Gly Met His Ala
        115                 120                 125

Glu Val Cys Glu Ala Phe Glu Leu Phe Asn Asp Leu Ile Gly Ser Asp
    130                 135                 140

Asp Ile Asp Cys Asp Pro Gln Thr Gly Gly His Phe Tyr Ile Ala His
145                 150                 155                 160

Arg Glu Lys Val Met Ala Lys Leu Glu Lys Glu Cys Ala Val Leu Asn
                165                 170                 175

Asp Thr Phe Gly Tyr Gly Ser Arg Ile Leu Ser Arg Asp Glu Leu His
            180                 185                 190

Glu Lys Tyr Val Arg Asp Gln Glu Ala His Gly Ala Leu Trp Glu Pro
        195                 200                 205

Asp Gly Thr Ser Ile His Ala Ala Lys Leu Ala Phe Ser Tyr Val Arg
    210                 215                 220

Leu Ala Arg Lys Leu Gly Ala Lys Ile His Thr Ala Ser Pro Val Met
225                 230                 235                 240

Gly Trp Lys Thr Val Asn Gly Val His Leu Thr Thr Pro Gly Gly
                245                 250                 255

Thr Val Arg Ala Arg Ala Val Ala Leu Ala Thr Ala Gly Tyr Thr Pro
            260                 265                 270

Pro Gly Leu Asn Glu Lys Thr Lys His Arg Leu Met Pro Ile Leu Ser
        275                 280                 285

Asn Ser Ile Val Thr Arg Pro Leu Ser Asp Glu Glu Lys Ala Gly Cys
    290                 295                 300

Gly Phe Gln Val Lys Ser Pro Leu Thr Asp Thr Arg Thr Leu Arg His
305                 310                 315                 320
```

Tyr Tyr Arg Tyr Leu Pro Asp Gly Arg Val Gln Ile Gly Ser Arg Ser
            325                 330                 335

Ala Ile Thr Gly Arg Asp Ala Glu Asn Pro Arg His Leu Glu Leu Leu
            340                 345                 350

Gln Lys Gly Leu Tyr Arg Lys Phe Pro Val Leu Glu Gly Ile Glu Leu
            355                 360                 365

Asp Tyr Ser Trp Trp Gly Trp Val Asp Val Ser His Asp Met Met Pro
    370                 375                 380

Arg Ile Phe Gln Pro Asn Pro Lys Gln Thr Ile Phe Tyr Ala Met Gly
385                 390                 395                 400

Tyr Gly Gly Asn Gly Val Met Tyr Ser Ala Gln Ala Gly Lys Arg Met
            405                 410                 415

Ala Gln Met Val Ala Gly Glu Gly Lys Asp Leu Lys Leu Pro Ile Phe
            420                 425                 430

Thr Ser Gln Leu Pro Ser His Gly Val Leu Thr Pro Phe Arg Arg Leu
            435                 440                 445

Gly Gln Arg Met Ala Tyr Pro Tyr Tyr Tyr Leu Arg Asp Glu Ile Leu
    450                 455                 460

<210> SEQ ID NO 47
<211> LENGTH: 1392
<212> TYPE: DNA
<213> ORGANISM: Roseobacter denitrificans

<400> SEQUENCE: 47

```
atggacggca atttcaatga aaatgatatc tcccgcgtcg tcgaagcaga ccgcgcgcat      60
atctggcacc atctgagcca gcacaaacct tacgagacaa cagacccgcg catcattgtc     120
gaaggcaagg gcatgaaggt ttgggaccag aagggcaaag agcatcttga tgccgtctcc     180
ggtggggtct ggaccgtcaa tgtcggctat ggccgcgaac gcatcgccaa cgccgtgcgg     240
gaccagttgg tcaagttgaa ctatttcgcc ggctccgcag gctccatccc cggtgccatg     300
ttcgccgagc gtctgatcga agatgccg gggctgagcc gcgtttatta ctgcaattcc      360
ggctccgagg cgaatgaaaa agccttcaag atggtccgcc agatcgcgca caaacgctat     420
ggcggcaaaa agcacaaggt gctttatcgc gagcgtgact atcacggcac caccatttcc     480
gccctttccg caggcgggca ggacgaacgg aacgcacaat atggcccctt cacgcccggt     540
ttcgtgcgcg tgccccattg ccttgaatac cgcgcctttg aacaggaagg ggcgccacag     600
gaaaactacg tgtctgggc gcggatcag atcgaaaagg taatcctcgc cgaagggccc      660
gataccgtgg gcggcctgtg ccttgaaccg gtcactgcag gtggcggggt gatcacgccc     720
cccgatggct actgggagcg tgtgcaggaa atctgccaca aatacgacat cctgctgcat     780
atcgacgagg tcgtatgcgg cgtcggtcgg accggcacat ggttcggcta tcagcactac     840
ggcatccagc cggatatggt cacgatggcc aagggtgtcg cgtccggtta cgcggcgatc     900
gcctgccttg tgaccaatga aaagtcttc gacatgttca aggatgacgc ctcggatccg      960
ctgaactact ccgcgacat ctcgaccttt gggggctgca cggcgggtcc ggcagctgcg     1020
ctggaaaacc tgtcgatcat cgaagaagaa ggctgctgg acaacaccac ggaacagggg    1080
gcctatatgc tcgactgtct gggcggcttg atggacaagc acaagatcat cggccaggtg    1140
cgcggcaagg gctgttcct cggtgccgaa ctggtcgagg atcgcgacac gcgcaaaccg    1200
gttgacgaaa ggctcgcgca agcggtggtc gcggactgca tgcaacaggg tgtgatcatc    1260
ggcgtgacca accgctctct gccgggcaag aacaacacgc tgtgtttctc gcccgccctg    1320
```

```
atcgccagca aggatgacat tgaccacatc tgcgacgcgg tggacggtgc gctgtcgcgc    1380
gttttcggct aa                                                        1392
```

<210> SEQ ID NO 48
<211> LENGTH: 463
<212> TYPE: PRT
<213> ORGANISM: Roseobacter denitrificans

<400> SEQUENCE: 48

```
Met Asp Gly Asn Phe Asn Glu Asn Asp Ile Ser Arg Val Val Glu Ala
1               5                   10                  15

Asp Arg Ala His Ile Trp His His Leu Ser Gln His Lys Pro Tyr Glu
            20                  25                  30

Thr Thr Asp Pro Arg Ile Ile Val Glu Gly Lys Gly Met Lys Val Trp
        35                  40                  45

Asp Gln Lys Gly Lys Glu His Leu Asp Ala Val Ser Gly Gly Val Trp
    50                  55                  60

Thr Val Asn Val Gly Tyr Gly Arg Glu Arg Ile Ala Asn Ala Val Arg
65                  70                  75                  80

Asp Gln Leu Val Lys Leu Asn Tyr Phe Ala Gly Ser Ala Gly Ser Ile
                85                  90                  95

Pro Gly Ala Met Phe Ala Glu Arg Leu Ile Glu Lys Met Pro Gly Leu
            100                 105                 110

Ser Arg Val Tyr Tyr Cys Asn Ser Gly Ser Glu Ala Asn Glu Lys Ala
        115                 120                 125

Phe Lys Met Val Arg Gln Ile Ala His Lys Arg Tyr Gly Gly Lys Lys
    130                 135                 140

His Lys Val Leu Tyr Arg Glu Arg Asp Tyr His Gly Thr Thr Ile Ser
145                 150                 155                 160

Ala Leu Ser Ala Gly Gly Gln Asp Glu Arg Asn Ala Gln Tyr Gly Pro
                165                 170                 175

Phe Thr Pro Gly Phe Val Arg Val Pro His Cys Leu Glu Tyr Arg Ala
            180                 185                 190

Phe Glu Gln Glu Gly Ala Pro Gln Glu Asn Tyr Gly Val Trp Ala Ala
        195                 200                 205

Asp Gln Ile Glu Lys Val Ile Leu Ala Glu Gly Pro Asp Thr Val Gly
    210                 215                 220

Gly Leu Cys Leu Glu Pro Val Thr Ala Gly Gly Val Ile Thr Pro
225                 230                 235                 240

Pro Asp Gly Tyr Trp Glu Arg Val Gln Glu Ile Cys His Lys Tyr Asp
                245                 250                 255

Ile Leu Leu His Ile Asp Glu Val Val Cys Gly Val Gly Arg Thr Gly
            260                 265                 270

Thr Trp Phe Gly Tyr Gln His Tyr Gly Ile Gln Pro Asp Met Val Thr
        275                 280                 285

Met Ala Lys Gly Val Ala Ser Gly Tyr Ala Ala Ile Ala Cys Leu Val
    290                 295                 300

Thr Asn Glu Lys Val Phe Asp Met Phe Lys Asp Ala Ser Asp Pro
305                 310                 315                 320

Leu Asn Tyr Phe Arg Asp Ile Ser Thr Phe Gly Gly Cys Thr Ala Gly
                325                 330                 335

Pro Ala Ala Ala Leu Glu Asn Leu Ser Ile Ile Glu Glu Glu Gly Leu
            340                 345                 350
```

Leu Asp Asn Thr Thr Glu Gln Gly Ala Tyr Met Leu Asp Cys Leu Gly
        355                 360                 365

Gly Leu Met Asp Lys His Lys Ile Ile Gly Gln Val Arg Gly Lys Gly
370                 375                 380

Leu Phe Leu Gly Ala Glu Leu Val Asp Arg Asp Thr Arg Lys Pro
385                 390                 395                 400

Val Asp Glu Arg Leu Ala Gln Ala Val Val Ala Asp Cys Met Gln Gln
            405                 410                 415

Gly Val Ile Ile Gly Val Thr Asn Arg Ser Leu Pro Gly Lys Asn Asn
            420                 425                 430

Thr Leu Cys Phe Ser Pro Ala Leu Ile Ala Ser Lys Asp Asp Ile Asp
        435                 440                 445

His Ile Cys Asp Ala Val Asp Gly Ala Leu Ser Arg Val Phe Gly
    450                 455                 460

<210> SEQ ID NO 49
<211> LENGTH: 951
<212> TYPE: DNA
<213> ORGANISM: Escherichia coli

<400> SEQUENCE: 49
atgaatttcc aacaactaaa gataatccgc gaggctgcac gtcaggatta caacctgaca      60
gaggttgcga atatgctttt tacctcacag tcaggcgtca gccgtcatat tcgggaactg     120
gaggatgaac ttggcatcga atatttgtt cgacgaggta agcgactgct gggcatgact      180
gaaccgggca agcattact ggtcattgca gaacgtattc tgaatgaagc cagtaatgtt      240
cgtcggcttg cagacctgtt taccaacgat acgtctggcg ttctcactat tgcaacgacg     300
catactcagg cacgttatag cttgccagag gtcattaaag cttttcgcga acttttcccg     360
gaggttcggc tcgagctaat ccaggggacg ccacaggaaa ttgcgacatt gttgcaaaat     420
ggcgaagctg atattggtat cgccagcgag cgtttgagta atgacccgca gctcgtcgcc     480
ttcccgtggt ttcgttggca ccatagttg cttgttccac acgatcatcc cttgacgcaa      540
atttcaccat tgacgctgga atcaatagcg aagtggccgt taatcactta ccgacagggg     600
attacggggc gctcacgtat tgatgacgca tttgccccgca aaggtttgct ggcagatatt     660
gtattaagtg cgcaggattc tgatgtcatt aaaacctatg ttgctcttgg gcttgggatc     720
ggattagttg ccgagcaatc cagtggcgaa caagaggaag agaatttaat ccgcctggat     780
acgcggcatc ttttgatgc taatactgtc tggttgggac tgaagcgagg acaacttcag     840
cgtaactatg tctggcgctt tctggaactt tgtaatgcag actgtcagt gaggatatc       900 aagcggcagg tgatggaaag cagtgaagag gaaattgatt atcagatata g             951

<210> SEQ ID NO 50
<211> LENGTH: 316
<212> TYPE: PRT
<213> ORGANISM: Escherichia coli

<400> SEQUENCE: 50

Met Asn Phe Gln Gln Leu Lys Ile Ile Arg Glu Ala Ala Arg Gln Asp
1               5                   10                  15

Tyr Asn Leu Thr Glu Val Ala Asn Met Leu Phe Thr Ser Gln Ser Gly
            20                  25                  30

Val Ser Arg His Ile Arg Glu Leu Glu Asp Glu Leu Gly Ile Glu Ile
        35                  40                  45

Phe Val Arg Arg Gly Lys Arg Leu Leu Gly Met Thr Glu Pro Gly Lys

```
                50                  55                  60
Ala Leu Leu Val Ile Ala Glu Arg Ile Leu Asn Glu Ala Ser Asn Val
 65                  70                  75                  80

Arg Arg Leu Ala Asp Leu Phe Thr Asn Asp Thr Ser Gly Val Leu Thr
                 85                  90                  95

Ile Ala Thr Thr His Thr Gln Ala Arg Tyr Ser Leu Pro Glu Val Ile
            100                 105                 110

Lys Ala Phe Arg Glu Leu Phe Pro Glu Val Arg Leu Glu Leu Ile Gln
        115                 120                 125

Gly Thr Pro Gln Glu Ile Ala Thr Leu Leu Gln Asn Gly Glu Ala Asp
    130                 135                 140

Ile Gly Ile Ala Ser Glu Arg Leu Ser Asn Asp Pro Gln Leu Val Ala
145                 150                 155                 160

Phe Pro Trp Phe Arg Trp His His Ser Leu Leu Val Pro His Asp His
                165                 170                 175

Pro Leu Thr Gln Ile Ser Pro Leu Thr Leu Glu Ser Ile Ala Lys Trp
            180                 185                 190

Pro Leu Ile Thr Tyr Arg Gln Gly Ile Thr Gly Arg Ser Arg Ile Asp
        195                 200                 205

Asp Ala Phe Ala Arg Lys Gly Leu Leu Ala Asp Ile Val Leu Ser Ala
    210                 215                 220

Gln Asp Ser Asp Val Ile Lys Thr Tyr Val Ala Leu Gly Leu Gly Ile
225                 230                 235                 240

Gly Leu Val Ala Glu Gln Ser Ser Gly Glu Gln Glu Glu Glu Asn Leu
                245                 250                 255

Ile Arg Leu Asp Thr Arg His Leu Phe Asp Ala Asn Thr Val Trp Leu
            260                 265                 270

Gly Leu Lys Arg Gly Gln Leu Gln Arg Asn Tyr Val Trp Arg Phe Leu
        275                 280                 285

Glu Leu Cys Asn Ala Gly Leu Ser Val Glu Asp Ile Lys Arg Gln Val
    290                 295                 300

Met Glu Ser Ser Glu Glu Glu Ile Asp Tyr Gln Ile
305                 310                 315

<210> SEQ ID NO 51
<211> LENGTH: 927
<212> TYPE: DNA
<213> ORGANISM: Corynebacterium glutamicum

<400> SEQUENCE: 51
atggacaacg acggcggaga catgcgaatc gacgacctac gcagcttcat ttcagtcgcc      60
caatcaggcc acctcaccga aaccgccgaa agattaggca tcccgcagcc cacactttcc     120
agacgaatca gccgagtgga aaaacacgca ggcaccccac ttttcgaccg cgccggccgc     180
aaactcgtcc tcaaccaacg aggccacgcc ttcctcaacc acgccagcgc catcgtcgca     240
gaattcaact ccgccgcaac tgaaatcaaa cgcctcatgg acccagaaaa aggcacaatc     300
cgactggact tcatgcattc cttgggcact tggatggtcc ccgaacttat ccgaacattc     360
cgcgccgaac accccaatgt agaattccaa ctccaccaag cggcagcaat gctcctggta     420
gatcgtgttt tggctgatga aactgacctc gcattagttg ccccaaaacc tgccgaggtt     480
ggtacctctt tagggtgggc gccactgctt cgtcaacgac ttgccctagc tgttcccgca     540
gatcaccggc ttgcctcttt ttctggccaa ggagaattgc cgttgattag tgcgacggaa     600
gaacctttcg tggcgatgcg agcaggtttc ggcacccgac tcctcatgga tgcattagcc     660
```

```
gaagaagccg ttttgttcc caatgtggtt ttcgaatcca tggagctcac caccgtcgca    720
gggcttgtca gcgcaggtct cggcgttggt gtggttccga tggatgatcc gtaccttccc    780
acagtgggaa tcgtgcaacg cccacttagt ccacccgcat atagggaact cggtctggta    840
tggaggctta acgcgggacc tgcaccggcc gtggataact tccggaagtt cgtggcggga    900
tcgagatatg cattagaaga gggctga                                        927
```

<210> SEQ ID NO 52
<211> LENGTH: 308
<212> TYPE: PRT
<213> ORGANISM: Corynebacterium glutamicum

<400> SEQUENCE: 52

```
Met Asp Asn Asp Gly Gly Asp Met Arg Ile Asp Asp Leu Arg Ser Phe
1               5                   10                  15

Ile Ser Val Ala Gln Ser Gly His Leu Thr Glu Thr Ala Glu Arg Leu
            20                  25                  30

Gly Ile Pro Gln Pro Thr Leu Ser Arg Arg Ile Ser Arg Val Glu Lys
        35                  40                  45

His Ala Gly Thr Pro Leu Phe Asp Arg Ala Gly Arg Lys Leu Val Leu
    50                  55                  60

Asn Gln Arg Gly His Ala Phe Leu Asn His Ala Ser Ala Ile Val Ala
65                  70                  75                  80

Glu Phe Asn Ser Ala Ala Thr Glu Ile Lys Arg Leu Met Asp Pro Glu
                85                  90                  95

Lys Gly Thr Ile Arg Leu Asp Phe Met His Ser Leu Gly Thr Trp Met
            100                 105                 110

Val Pro Glu Leu Ile Arg Thr Phe Arg Ala Glu His Pro Asn Val Glu
        115                 120                 125

Phe Gln Leu His Gln Ala Ala Ala Met Leu Leu Val Asp Arg Val Leu
    130                 135                 140

Ala Asp Glu Thr Asp Leu Ala Leu Val Gly Pro Lys Pro Ala Glu Val
145                 150                 155                 160

Gly Thr Ser Leu Gly Trp Ala Pro Leu Leu Arg Gln Arg Leu Ala Leu
                165                 170                 175

Ala Val Pro Ala Asp His Arg Leu Ala Ser Phe Ser Gly Gln Gly Glu
            180                 185                 190

Leu Pro Leu Ile Ser Ala Thr Glu Glu Pro Phe Val Ala Met Arg Ala
        195                 200                 205

Gly Phe Gly Thr Arg Leu Leu Met Asp Ala Leu Ala Glu Glu Ala Gly
    210                 215                 220

Phe Val Pro Asn Val Val Phe Glu Ser Met Glu Leu Thr Thr Val Ala
225                 230                 235                 240

Gly Leu Val Ser Ala Gly Leu Gly Val Gly Val Pro Met Asp Asp
                245                 250                 255

Pro Tyr Leu Pro Thr Val Gly Ile Val Gln Arg Pro Leu Ser Pro Pro
            260                 265                 270

Ala Tyr Arg Glu Leu Gly Leu Val Trp Arg Leu Asn Ala Gly Pro Ala
        275                 280                 285

Pro Ala Val Asp Asn Phe Arg Lys Phe Val Ala Gly Ser Arg Tyr Ala
    290                 295                 300

Leu Glu Glu Gly
305
```

<210> SEQ ID NO 53
<211> LENGTH: 1362
<212> TYPE: DNA
<213> ORGANISM: Corynebacterium glutamicum

<400> SEQUENCE: 53

```
atgcttgccg accttcccat cgccttaaac ccacacgaac caacatccat ccccacgcag      60
ctcacagaac agatccgtcg tctcgtggcg aggggaattc tcaccccagg agacccgctt     120
cccagcagtc gctcactatc cacccaattg ggggtatccc gcggcagtgt ggtgaccgct     180
tatgaccaat tggccggtga aggctacctc agcaccgccc gcggttccgg tacaacgatc     240
aacccagatc tgcatttgtt gaagcctgtg aaattgaga agaaggagac gtcgagaagc     300
gtcccgcccc cgctgctcaa cctgagcccc ggcgtgcccg ataccgcgac gctcgccgat     360
tccgcatggc gcgctgcgtg gcgcgaagcc tgcgccaagc acccacgca ctcccctgag     420
cagggacttt tgaggctgcg gatcgagatc gccgaccacc tgcgccagat gcgtggcctc     480
atggtcgagc cggagcagat catcgtcacc gccggcgcgc gcgaggggct gagtctgctg     540
ctgcgcacca tggatgcgcc tgcccgcatc ggcgtcgaat cgcccggcta ccccagcctg     600
cgccgcatcc gcaggtgct tggccatgag acgatcgatg tgccgaccga cgaatccggc     660
ctcgtacccc gcgcgctgcc ccacgacctc aacgcgctac tggtaacccc tagccatcaa     720
tatccctacg gcggctcgct gcccgccgat cgccgcaccg cgctagtcgc gtgggctgag     780
gcaaacgatg cgttgcttat tgaagacgac ttcgattctg agctgcgcta cgtcggtatg     840
ccgcttccgc cgctgcgtgc gctggcgccc gatcgcacga ttctgctcgg cacgttttcc     900
tccgtgatca caccacaagt cgcctgcgga tacctcatcg cgccgacgcc ccaggcgcgc     960
gtgctcgcca cgcttcgcgg gattctcggc cagccagtcg cgccatcac ccaacacgcg    1020
ctcgcgtcct acctcgcctc aggcgcttta cgacgccgca cccaacgttt gcggcgcctt    1080
taccgacacc gccgctccat cgtccaagac ccctcggtg acctcccgaa tacgcagctt    1140
cgccccatca acggtggcct ccacgcagtt ctcctttgcg acaaacccca agacctcgtc    1200
gtcaccacac tcgcctcccg aggccttaac gtcaccgcgc tttcccacta ctggggcggc    1260
accggcgcag acaacggcat cgtcttcggc ttcggctccc acgacgaaga caccctcaga    1320
tgggtgcttg ctgagatcag cgatgcggtg tctctaggct aa                      1362
```

<210> SEQ ID NO 54
<211> LENGTH: 453
<212> TYPE: PRT
<213> ORGANISM: Corynebacterium glutamicum

<400> SEQUENCE: 54

```
Met Leu Ala Asp Leu Pro Ile Ala Leu Asn Pro His Glu Pro Thr Ser
 1               5                  10                  15

Ile Pro Thr Gln Leu Thr Glu Gln Ile Arg Arg Leu Val Ala Arg Gly
             20                  25                  30

Ile Leu Thr Pro Gly Asp Pro Leu Pro Ser Ser Arg Ser Leu Ser Thr
         35                  40                  45

Gln Leu Gly Val Ser Arg Gly Ser Val Val Thr Ala Tyr Asp Gln Leu
     50                  55                  60

Ala Gly Glu Gly Tyr Leu Ser Thr Ala Arg Gly Ser Gly Thr Thr Ile
65                  70                  75                  80

Asn Pro Asp Leu His Leu Leu Lys Pro Val Glu Ile Glu Lys Lys Glu
                 85                  90                  95
```

Thr Ser Arg Ser Val Pro Pro Leu Leu Asn Leu Ser Pro Gly Val
            100                 105                 110

Pro Asp Thr Ala Thr Leu Ala Asp Ser Ala Trp Arg Ala Trp Arg
            115                 120                 125

Glu Ala Cys Ala Lys Pro Pro Thr His Ser Pro Glu Gln Gly Leu Leu
130                 135                 140

Arg Leu Arg Ile Glu Ile Ala Asp His Leu Arg Gln Met Arg Gly Leu
145                 150                 155                 160

Met Val Glu Pro Glu Gln Ile Ile Val Thr Ala Gly Ala Arg Glu Gly
                165                 170                 175

Leu Ser Leu Leu Leu Arg Thr Met Asp Ala Pro Ala Arg Ile Gly Val
            180                 185                 190

Glu Ser Pro Gly Tyr Pro Ser Leu Arg Arg Ile Pro Gln Val Leu Gly
            195                 200                 205

His Glu Thr Ile Asp Val Pro Thr Asp Glu Ser Gly Leu Val Pro Arg
        210                 215                 220

Ala Leu Pro His Asp Leu Asn Ala Leu Leu Val Thr Pro Ser His Gln
225                 230                 235                 240

Tyr Pro Tyr Gly Gly Ser Leu Pro Ala Asp Arg Arg Thr Ala Leu Val
                245                 250                 255

Ala Trp Ala Glu Ala Asn Asp Ala Leu Leu Ile Glu Asp Asp Phe Asp
            260                 265                 270

Ser Glu Leu Arg Tyr Val Gly Met Pro Leu Pro Pro Leu Arg Ala Leu
            275                 280                 285

Ala Pro Asp Arg Thr Ile Leu Leu Gly Thr Phe Ser Ser Val Ile Thr
        290                 295                 300

Pro Gln Val Ala Cys Gly Tyr Leu Ile Ala Pro Thr Pro Gln Ala Arg
305                 310                 315                 320

Val Leu Ala Thr Leu Arg Gly Ile Leu Gly Gln Pro Val Gly Ala Ile
                325                 330                 335

Thr Gln His Ala Leu Ala Ser Tyr Leu Ala Ser Gly Ala Leu Arg Arg
            340                 345                 350

Arg Thr Gln Arg Leu Arg Arg Leu Tyr Arg His Arg Ser Ile Val
            355                 360                 365

Gln Asp Thr Leu Gly Asp Leu Pro Asn Thr Gln Leu Arg Pro Ile Asn
370                 375                 380

Gly Gly Leu His Ala Val Leu Leu Cys Asp Lys Pro Gln Asp Leu Val
385                 390                 395                 400

Val Thr Thr Leu Ala Ser Arg Gly Leu Asn Val Thr Ala Leu Ser His
                405                 410                 415

Tyr Trp Gly Gly Thr Gly Ala Asp Asn Gly Ile Val Phe Gly Phe Gly
            420                 425                 430

Ser His Asp Glu Asp Thr Leu Arg Trp Val Leu Ala Glu Ile Ser Asp
        435                 440                 445

Ala Val Ser Leu Gly
        450

<210> SEQ ID NO 55
<211> LENGTH: 177
<212> TYPE: DNA
<213> ORGANISM: Arabidopsis thaliana

<400> SEQUENCE: 55
atggctgctt atggtcaaat ctcctcggga atgactgtag atcctcaggt tctctcttcc    60

-continued

```
tccagaaaca ttggagtttc cctatcacct ctccggagaa cactaatcgg cgccggagtt      120
aggtctacta gtatctctct ccgtcaatgt tctctctccg ttagatcgat taaaatc         177
```

<210> SEQ ID NO 56
<211> LENGTH: 59
<212> TYPE: PRT
<213> ORGANISM: Arabidopsis thaliana

<400> SEQUENCE: 56

Met Ala Ala Tyr Gly Gln Ile Ser Ser Gly Met Thr Val Asp Pro Gln
1               5                   10                  15

Val Leu Ser Ser Ser Arg Asn Ile Gly Val Ser Leu Ser Pro Leu Arg
            20                  25                  30

Arg Thr Leu Ile Gly Ala Gly Val Arg Ser Thr Ser Ile Ser Leu Arg
        35                  40                  45

Gln Cys Ser Leu Ser Val Arg Ser Ile Lys Ile
    50                  55

<210> SEQ ID NO 57
<211> LENGTH: 70
<212> TYPE: DNA
<213> ORGANISM: Escherichia coli

<400> SEQUENCE: 57

```
ctgcgcgcgt tacagcgccg cctgacgccc tggcatggag aagtacaatg attccgggga     60
tccgtcgacc                                                             70
```

<210> SEQ ID NO 58
<211> LENGTH: 70
<212> TYPE: DNA
<213> ORGANISM: Escherichia coli

<400> SEQUENCE: 58

```
aggggggcgag gggaccgtcc actctcgtat taccccgccc gataaaacgg tgtaggctgg     60
agctgcttcg                                                             70
```

<210> SEQ ID NO 59
<211> LENGTH: 70
<212> TYPE: DNA
<213> ORGANISM: Escherichia coli

<400> SEQUENCE: 59

```
attagacttt aacaataacg ggaaatctga actgcccgga gtttaccgtg attccgggga     60
tccgtcgacc                                                             70
```

<210> SEQ ID NO 60
<211> LENGTH: 70
<212> TYPE: DNA
<213> ORGANISM: Escherichia coli

<400> SEQUENCE: 60

```
aaaagcccgc ttttatagcg ggattttgc tatatctgat aatcaatttc tgtaggctgg      60
agctgcttcg                                                             70
```

<210> SEQ ID NO 61
<211> LENGTH: 70
<212> TYPE: DNA
<213> ORGANISM: Escherichia coli

<400> SEQUENCE: 61
attcgccagc gcatctggca gcccactcaa ctggaaggaa acaattatg attccgggga    60 tccgtcgacc                                                          70

<210> SEQ ID NO 62
<211> LENGTH: 70
<212> TYPE: DNA
<213> ORGANISM: Escherichia coli

<400> SEQUENCE: 62
tcttcactgg cgttgccatt atttcttcct tagctttgcg cgactttacg tgtaggctgg   60
agctgcttcg                                                          70

<210> SEQ ID NO 63
<211> LENGTH: 70
<212> TYPE: DNA
<213> ORGANISM: Escherichia coli

<400> SEQUENCE: 63
gttatcaatg ttaacaaaaa aagaacaatt ggttataagg agagagtatg attccgggga   60
tccgtcgacc                                                          70

<210> SEQ ID NO 64
<211> LENGTH: 70
<212> TYPE: DNA
<213> ORGANISM: Escherichia coli

<400> SEQUENCE: 64
gcaatcccgc cagcgccagt ttaatgatgt tacgcatggg cattacctcg tgtaggctgg   60
agctgcttcg                                                          70

<210> SEQ ID NO 65
<211> LENGTH: 29
<212> TYPE: DNA
<213> ORGANISM: Corynebacterium glutamicum

<400> SEQUENCE: 65
cgcggatccc tttccattgg ttcctatcc                                     29

<210> SEQ ID NO 66
<211> LENGTH: 41
<212> TYPE: DNA
<213> ORGANISM: Corynebacterium glutamicum

<400> SEQUENCE: 66
cttcgatgcg atcggcgacc tcgggaggtg ccggattttt c                       41

<210> SEQ ID NO 67
<211> LENGTH: 41
<212> TYPE: DNA
<213> ORGANISM: Corynebacterium glutamicum

<400> SEQUENCE: 67
gaaaaatccg gcacctcccg aggtcgccga tcgcatcgaa g                       41

<210> SEQ ID NO 68
<211> LENGTH: 29
<212> TYPE: DNA
<213> ORGANISM: Corynebacterium glutamicum

<400> SEQUENCE: 68
cccaagcttc ccaacaggtt ccaaaactc                                    29

<210> SEQ ID NO 69
<211> LENGTH: 29
<212> TYPE: DNA
<213> ORGANISM: Corynebacterium glutamicum

<400> SEQUENCE: 69
cgcggatccg cataattttg tcagtggtg                                    29

<210> SEQ ID NO 70
<211> LENGTH: 40
<212> TYPE: DNA
<213> ORGANISM: Corynebacterium glutamicum

<400> SEQUENCE: 70
acctgattct tctgatcgcc ctggcgcgca tccgcacgcg                        40

<210> SEQ ID NO 71
<211> LENGTH: 41
<212> TYPE: DNA
<213> ORGANISM: Corynebacterium glutamicum

<400> SEQUENCE: 71
cgcgtgcgga tgcgcgccag ggcgatcaga agaatcaggt g                      41

<210> SEQ ID NO 72
<211> LENGTH: 30
<212> TYPE: DNA
<213> ORGANISM: Corynebacterium glutamicum

<400> SEQUENCE: 72
cccaagcttt agaacagcgc gctggccatc                                   30

<210> SEQ ID NO 73
<211> LENGTH: 29
<212> TYPE: DNA
<213> ORGANISM: Corynebacterium glutamicum

<400> SEQUENCE: 73
cgcggatccc aacgacggcg gagacatgc                                    29

<210> SEQ ID NO 74
<211> LENGTH: 43
<212> TYPE: DNA
<213> ORGANISM: Corynebacterium glutamicum

<400> SEQUENCE: 74
ccatcggaac cacaccaacg ccggccggcg cggtcgaaaa gtg                    43

<210> SEQ ID NO 75
<211> LENGTH: 43
<212> TYPE: DNA
<213> ORGANISM: Corynebacterium glutamicum

<400> SEQUENCE: 75
cacttttcga ccgcgccggc cggcgttggt gtggttccga tgg                    43

<210> SEQ ID NO 76
<211> LENGTH: 30
<212> TYPE: DNA
<213> ORGANISM: Corynebacterium glutamicum

```
<400> SEQUENCE: 76
cccaagcttg gccggcgcgg tcgaaaagtg                                        30

<210> SEQ ID NO 77
<211> LENGTH: 30
<212> TYPE: DNA
<213> ORGANISM: Corynebacterium glutamicum

<400> SEQUENCE: 77
cgcggatccc cttcccatcg ccttaaaccc                                        30

<210> SEQ ID NO 78
<211> LENGTH: 41
<212> TYPE: DNA
<213> ORGANISM: Corynebacterium glutamicum

<400> SEQUENCE: 78
cgaggtcttg ggtttgtcg cctgggaagc gggtctcctg g                            41

<210> SEQ ID NO 79
<211> LENGTH: 41
<212> TYPE: DNA
<213> ORGANISM: Corynebacterium glutamicum

<400> SEQUENCE: 79
ccaggagacc cgcttcccag gcgacaaacc ccaagacctc g                           41

<210> SEQ ID NO 80
<211> LENGTH: 31
<212> TYPE: DNA
<213> ORGANISM: Corynebacterium glutamicum

<400> SEQUENCE: 80
cccaagcttg cctagagaca ccgcatcgct g                                      31

<210> SEQ ID NO 81
<211> LENGTH: 102
<212> TYPE: DNA
<213> ORGANISM: Artificial Sequence
<220> FEATURE:
<223> OTHER INFORMATION: Synthetic construct

<400> SEQUENCE: 81
acccgttttt tgggctaacg ggaggaatta accatggtgt agatgggcgc atcgtaaccg       60
tgcatctgcc agtttgaggg gacgacgaca gtatcggcct ca                         102

<210> SEQ ID NO 82
<211> LENGTH: 3291
<212> TYPE: DNA
<213> ORGANISM: Bathycoccus prasinos

<400> SEQUENCE: 82
atgctgtgca taaacatcac cccgaagttc gtgcggatac gccgaggcgt tgcgttatca       60
actcattcgt cgtctttgcg aaattgtcaa attttgtcgt caaacgcaga gagaggaacg      120
aaaacgcagc gccttcttct tagtggtaat caaaaactcg taattgattc ttcgacgagc      180
gatgatgctt cgatgggaag ccatttcagt cgtcgtgcac gtcgtcactt ttcctctcca      240
ttcgcgaggg tttccgacaa gcggagacac gcgctcgtca cttccgcatc ctcgaacaac      300
aacaacaaaa tcacgagtgc aaaaagtggt ttgaacagca ccagtggtgg tgaatctcgt      360
ctccgcgcga tcaacaatcc ctcgcagcag cgagaacaac aagggttagc ggacgcactc      420
```

```
gctgcgggga aatctgcaaa atcgccgccg gggtcgtcac gaggacaaga agaaaaagaa    480
atgatcgacc agacgtacga gttgaacggt aacaacttcg cggaacaaac gatcgcgacg    540
ccgtcggatg gaccgatcga tgtgttgcac gcctcttcga agcagacgaa gagttggcaa    600
gcggtgagga gagcggtgac gactgggccg gtgcaatcga acgcgttgat tggagggacg    660
ccgttgattg acgtgacgag cgtgttgagt ttgaatcctt caaaggtgaa gatttacgcg    720
aagtgcgagt atatgaatcc gagtggaagc attaaggatc gaattgcgag ttatatttta    780
caagcggcga ttgatgctgg ggatttgaag gaggggatga cggtggtggc ggcgacgagc    840
gggaacaccg ggagcgccat cgcggcggcg tgcgccattc gcgggtttga ttacatcgtc    900
attacgaata agaaatgttc gatagagaag atcgatagca tgagagcgta tggtgggacg    960
gttattgtcg cgaagagtgg cgtagctgcg gacgatccag agcattatca aaatatcgag   1020
aacacgatgg tggcggaaaa tccggggaag tatttcggcg tgaaccagta cgataacttg   1080
aacaacgcgt tggcttacga ggcgacgtta gggccggaaa ttatcgcgca aacgaaagga   1140
ctcatcacgc actttgtcgc tgggtcgagt acgggtggga cgctgacggg taccagtcgg   1200
tatttgaagg cggtgaaccc ggagatcaag tccgtgttgg cggatccgcg agggtcggta   1260
ttgtgggata atttcgttaa cgacgttccg gaaaacgagt taattgttgg taagtgggag   1320
attgaaggcg tcgggaaaga ttctattccg ggtgttttgt cctggacgt cgtcgatggc   1380
gcgcaaagag gagacgacgc gtcgagtttt tacacgtgtc gcaaagtcgc gagagatttg   1440
ggcgttttag ttggaggctc cgccgggttg aatttacacg cgtgcgcggt cttgagcggt   1500
aaaatcgaca acggcgtcat cgtgaccgtt ttgccagact ctggggtgaa atacctgtcc   1560
aagattttca cgacgattg gatgaacgag aaaggattca cggcaagga aaagagtccc   1620
gaggatggag aaatctattg gcgaccgggc gcgaacgatc cgtgcgagaa ccaaaagagt   1680
agcagaatgt ttccgataaa cgcgtgctct ttacaacacg acacgagaaa gcaatgcaac   1740
gacgacgagt tgaacccgag agaacaaacg gaagcggagt tgagattttt ggaagagacg   1800
gcggcgagaa tggtcgaata ccatcgtcaa tccgtaaaaa ttggcgaaga accggtagta   1860
ttgatgaata ctccggaaag cattcgagcg atgttttccg aagctggcgt tgggatgacc   1920
tttgagcacc aagaaccggc gtggagcgag caacagttga gagacgccgt gacgaccatc   1980
ttgcaaacgt ccgtgcgttc atcgtcgccg ttattttga accaattata cgccggtgtc   2040
gacccggtcg cgttagccgg cgaatgggtc tccgcggcgt tgaactcaaa cgtgcacacg   2100
ttcgaagtcg cgccatcgtt gacggagatt gagaaatcat gcttggagaa agtcgcgcgg   2160
tgttggttga agaccaacga cggcgtcgag actcccgaac acgacggttt gttcgtccca   2220
ggtggatcgt tatcgatttt atattccatc ttgttagcca gagacgtcgc ggactcttcc   2280
attcgcaagg ctggcatgga cagaaataac aagttggtag cttttttgcag cgaaaacgcg   2340
cattactcgt acaaaaaatc cgccatcgtt accggtttag gcgaagaaaa cttggtcgcg   2400
gtgaaatgtc tgccgaacgg tgccatggat ccgggcgctt tgcgtgcggc gattgcatcg   2460
gccatcgcgg caggcaaaac gccgttctac gtcggcacga ccgcgggtac aactgtttta   2520
ggcgcttttg atccgttcag cgaaatcttt gacgtcgtcg acgagtttca aaatgccaac   2580
gggaaatcgc aacgcatttg gacccacatc gacggcgcgt ggggcggtgg tgccatgctt   2640
tccaaagagc acaatcatct catggacggc gcggaacgct cggattcttt ctcttggaac   2700
ccgcacaaaa tgctcggcat gcctttgcaa tgctcggtgt ttgtctgcaa gcacgccggc   2760
```

-continued

```
tctttatcta aagcgaacgg cgccaaggcg aatatctct tccaaccgga caagaataac    2820
tctggcgcgg acttgggcga ccgaaccatt cagtgtggac gcaaagcaga cgccgtgaag   2880
ttatggttgg cgtggaaatt gcgaggcgac gaaggtttcg ccaagtgcat cgatcggtcc   2940
tttcacttgg cgaaattcgt ccaactcgaa gttgaaaact cggacggcaa gttcgttctc   3000
gtccaaccgg cccaatgctc caacgtcggg ttctggtacg ttccgccgcg cttgcgccca   3060
ttcaaccgga caactgcgac tgaagaagat tgggccgaac tcggttacgt cgctccaaag   3120
ttgaaaaacg ccatgcaaaa agccggcgac gccatgattg gcttccaacc catcgccagc   3180
atgggctacg tcaactttt ccgcctggtg ttaccgaacc cgagacacat cacggaaatg    3240
gatctgagag cgatgttgga tcgcatggac acctacggcc aagaattta a             3291
```

<210> SEQ ID NO 83
<211> LENGTH: 1096
<212> TYPE: PRT
<213> ORGANISM: Bathycoccus prasinos

<400> SEQUENCE: 83

```
Met Leu Cys Ile Asn Ile Thr Pro Lys Phe Val Arg Ile Arg Arg Gly
1               5                  10                  15

Val Ala Leu Ser Thr His Ser Ser Leu Arg Asn Cys Gln Ile Leu
            20                  25                  30

Ser Ser Asn Ala Glu Arg Gly Thr Lys Thr Gln Arg Leu Leu Leu Ser
        35                  40                  45

Gly Asn Gln Lys Leu Val Ile Asp Ser Ser Thr Ser Asp Asp Ala Ser
    50                  55                  60

Met Gly Ser His Phe Ser Arg Arg Ala Arg Arg His Phe Ser Ser Pro
65                  70                  75                  80

Phe Ala Arg Val Ser Asp Lys Arg Arg His Ala Leu Val Thr Ser Ala
                85                  90                  95

Ser Ser Asn Asn Asn Asn Lys Ile Thr Ser Ala Lys Ser Gly Leu Asn
            100                 105                 110

Ser Thr Ser Gly Gly Glu Ser Arg Leu Arg Ala Ile Asn Asn Pro Ser
        115                 120                 125

Gln Gln Arg Glu Gln Gln Gly Leu Ala Asp Ala Leu Ala Ala Gly Lys
    130                 135                 140

Ser Ala Lys Ser Pro Pro Gly Ser Ser Arg Gly Gln Glu Glu Lys Glu
145                 150                 155                 160

Met Ile Asp Gln Thr Tyr Glu Leu Asn Gly Asn Asn Phe Ala Glu Gln
                165                 170                 175

Thr Ile Ala Thr Pro Ser Asp Gly Pro Ile Asp Val Leu His Ala Ser
            180                 185                 190

Ser Lys Gln Thr Lys Ser Trp Gln Ala Val Arg Arg Ala Val Thr Thr
        195                 200                 205

Gly Pro Val Gln Ser Asn Ala Leu Ile Gly Gly Thr Pro Leu Ile Asp
    210                 215                 220

Val Thr Ser Val Leu Ser Leu Asn Pro Ser Lys Val Lys Ile Tyr Ala
225                 230                 235                 240

Lys Cys Glu Tyr Met Asn Pro Ser Gly Ser Ile Lys Asp Arg Ile Ala
                245                 250                 255

Ser Tyr Ile Leu Gln Ala Ala Ile Asp Ala Gly Asp Leu Lys Glu Gly
            260                 265                 270

Met Thr Val Val Ala Ala Thr Ser Gly Asn Thr Gly Ser Ala Ile Ala
        275                 280                 285
```

```
Ala Ala Cys Ala Ile Arg Gly Phe Asp Tyr Ile Val Ile Thr Asn Lys
        290                 295                 300
Lys Cys Ser Ile Glu Lys Ile Asp Ser Met Arg Ala Tyr Gly Gly Thr
305                 310                 315                 320
Val Ile Val Ala Lys Ser Gly Val Ala Ala Asp Asp Pro Glu His Tyr
                325                 330                 335
Gln Asn Ile Glu Asn Thr Met Val Ala Glu Asn Pro Gly Lys Tyr Phe
            340                 345                 350
Gly Val Asn Gln Tyr Asp Asn Leu Asn Asn Ala Leu Ala Tyr Glu Ala
                355                 360                 365
Thr Leu Gly Pro Glu Ile Ile Ala Gln Thr Lys Gly Leu Ile Thr His
370                 375                 380
Phe Val Ala Gly Ser Ser Thr Gly Gly Thr Leu Thr Gly Thr Ser Arg
385                 390                 395                 400
Tyr Leu Lys Ala Val Asn Pro Glu Ile Lys Ser Val Leu Ala Asp Pro
                405                 410                 415
Arg Gly Ser Val Leu Trp Asp Asn Phe Val Asn Asp Val Pro Glu Asn
                420                 425                 430
Glu Leu Ile Val Gly Lys Trp Glu Ile Glu Gly Val Gly Lys Asp Ser
            435                 440                 445
Ile Pro Gly Val Leu Ser Trp Asp Val Val Asp Gly Ala Gln Arg Gly
450                 455                 460
Asp Asp Ala Ser Ser Phe Tyr Thr Cys Arg Lys Val Ala Arg Asp Leu
465                 470                 475                 480
Gly Val Leu Val Gly Gly Ser Ala Gly Leu Asn Leu His Ala Cys Ala
                485                 490                 495
Val Leu Ser Gly Lys Ile Asp Asn Gly Val Ile Val Thr Val Leu Pro
                500                 505                 510
Asp Ser Gly Val Lys Tyr Leu Ser Lys Ile Phe Asn Asp Asp Trp Met
            515                 520                 525
Asn Glu Lys Gly Phe Thr Gly Lys Glu Lys Ser Pro Glu Asp Gly Glu
530                 535                 540
Ile Tyr Trp Arg Pro Gly Ala Asn Asp Pro Cys Glu Asn Gln Lys Ser
545                 550                 555                 560
Ser Arg Met Phe Pro Ile Asn Ala Cys Ser Leu Gln His Asp Thr Arg
                565                 570                 575
Lys Gln Cys Asn Asp Asp Glu Leu Asn Pro Arg Glu Gln Thr Glu Ala
                580                 585                 590
Glu Leu Arg Phe Leu Glu Glu Thr Ala Ala Arg Met Val Glu Tyr His
            595                 600                 605
Arg Gln Ser Val Lys Ile Gly Glu Glu Pro Val Val Leu Met Asn Thr
610                 615                 620
Pro Glu Ser Ile Arg Ala Met Phe Ser Glu Ala Gly Val Gly Met Thr
625                 630                 635                 640
Phe Glu His Gln Glu Pro Ala Trp Ser Glu Gln Leu Arg Asp Ala
                645                 650                 655
Val Thr Thr Ile Leu Gln Thr Ser Val Arg Ser Ser Pro Leu Phe
                660                 665                 670
Leu Asn Gln Leu Tyr Ala Gly Val Asp Pro Val Ala Leu Ala Gly Glu
            675                 680                 685
Trp Val Ser Ala Ala Leu Asn Ser Asn Val His Thr Phe Glu Val Ala
690                 695                 700
```

Pro Ser Leu Thr Glu Ile Glu Lys Ser Cys Leu Glu Lys Val Ala Arg
705                 710                 715                 720

Cys Trp Leu Lys Thr Asn Asp Gly Val Glu Thr Pro Glu His Asp Gly
            725                 730                 735

Leu Phe Val Pro Gly Gly Ser Leu Ser Ile Leu Tyr Ser Ile Leu Leu
        740                 745                 750

Ala Arg Asp Val Ala Asp Ser Ser Ile Arg Lys Ala Gly Met Asp Arg
    755                 760                 765

Asn Asn Lys Leu Val Ala Phe Cys Ser Glu Asn Ala His Tyr Ser Tyr
770                 775                 780

Lys Lys Ser Ala Ile Val Thr Gly Leu Gly Glu Glu Asn Leu Val Ala
785                 790                 795                 800

Val Lys Cys Leu Pro Asn Gly Ala Met Asp Pro Gly Ala Leu Arg Ala
            805                 810                 815

Ala Ile Ala Ser Ala Ile Ala Ala Gly Lys Thr Pro Phe Tyr Val Gly
        820                 825                 830

Thr Thr Ala Gly Thr Thr Val Leu Gly Ala Phe Asp Pro Phe Ser Glu
    835                 840                 845

Ile Phe Asp Val Val Asp Glu Phe Gln Asn Ala Asn Gly Lys Ser Gln
850                 855                 860

Arg Ile Trp Thr His Ile Asp Gly Ala Trp Gly Gly Gly Ala Met Leu
865                 870                 875                 880

Ser Lys Glu His Asn His Leu Met Asp Gly Ala Glu Arg Ser Asp Ser
            885                 890                 895

Phe Ser Trp Asn Pro His Lys Met Leu Gly Met Pro Leu Gln Cys Ser
        900                 905                 910

Val Phe Val Cys Lys His Ala Gly Ser Leu Ser Lys Ala Asn Gly Ala
    915                 920                 925

Lys Ala Glu Tyr Leu Phe Gln Pro Asp Lys Asn Asn Ser Gly Ala Asp
930                 935                 940

Leu Gly Asp Arg Thr Ile Gln Cys Gly Arg Lys Ala Asp Ala Val Lys
945                 950                 955                 960

Leu Trp Leu Ala Trp Lys Leu Arg Gly Asp Glu Gly Phe Ala Lys Cys
            965                 970                 975

Ile Asp Arg Ser Phe His Leu Ala Lys Phe Val Gln Leu Glu Val Glu
        980                 985                 990

Asn Ser Asp Gly Lys Phe Val Leu Val Gln Pro Ala Gln Cys Ser Asn
    995                 1000                1005

Val Gly Phe Trp Tyr Val Pro Arg Leu Arg Pro Phe Asn Arg
    1010                1015                1020

Thr Thr Ala Thr Glu Glu Asp Trp Ala Glu Leu Gly Tyr Val Ala
    1025                1030                1035

Pro Lys Leu Lys Asn Ala Met Gln Lys Ala Gly Asp Ala Met Ile
    1040                1045                1050

Gly Phe Gln Pro Ile Ala Ser Met Gly Tyr Val Asn Phe Phe Arg
    1055                1060                1065

Leu Val Leu Pro Asn Pro Arg His Ile Thr Glu Met Asp Leu Arg
    1070                1075                1080

Ala Met Leu Asp Arg Met Asp Thr Tyr Gly Gln Glu Phe
    1085                1090                1095

<210> SEQ ID NO 84
<211> LENGTH: 909
<212> TYPE: PRT

<213> ORGANISM: Artificial Sequence
<220> FEATURE:
<223> OTHER INFORMATION: Synthetic construct

<400> SEQUENCE: 84

```
Met Ala Phe Thr Val Pro Thr Asp Glu Pro Ala Ala Glu Thr Ala Ser
1               5                   10                  15

Pro Ala Asp Ser Asp Cys Glu Gly Asp Tyr Cys Asp Ile Lys Glu Thr
            20                  25                  30

Ala Cys Ser Thr Arg Gln Val Ile Gly Ser Thr Pro Leu Val Glu Ile
        35                  40                  45

Ser Glu Tyr Ser Ile Asn Pro Lys Ile Arg Leu Leu Gly Lys Cys Glu
    50                  55                  60

Tyr Met Glu Pro Cys Ser Ser Ile Lys Asp Arg Ile Gly Ser His Met
65                  70                  75                  80

Ile Glu Arg Ala Glu Lys Thr Gly Glu Ile Lys Pro Gly Met Thr Ile
                85                  90                  95

Ile Gly Gly Thr Ser Gly Asn Thr Gly Ala Gly Leu Ala Leu Ala Ala
            100                 105                 110

Ala Ile Arg Gly Phe Asp Tyr Val Ile Thr Ser Asn Asp Lys Met Ser
        115                 120                 125

Lys Glu Arg Ile Glu Gly Met Lys Ala Phe Gly Ala Gln Leu Val Leu
    130                 135                 140

Ala Pro Thr Gly Val Pro Ala Asp His Pro Asp His Tyr Asn Gln Ile
145                 150                 155                 160

Glu Thr Thr Met Cys Ala Gln Asn Pro Ala Asn Phe Tyr Ala Leu Asn
                165                 170                 175

Gln Tyr Asp Asn Pro Tyr Asn Gly Glu Ser His Tyr Glu Ile Thr Gly
            180                 185                 190

Pro Glu Ile Trp Lys Gln Thr Ile Gly Ala Ile Thr His Phe Val Ala
        195                 200                 205

Gly Ala Ser Thr Gly Gly Thr Val Ser Gly Thr Ala Arg Tyr Ile Lys
    210                 215                 220

Glu Val Asn Pro Thr Ile Lys Leu Met Ile Ala Asp Pro Lys Gly Ser
225                 230                 235                 240

Ile Leu Trp Asp Tyr Phe Val Asn Asp Val Glu Glu Glu Asp Leu Val
                245                 250                 255

Ala Lys Ser Trp Glu Ile Glu Gly Ile Gly Lys Gly Ser Ile Pro Ala
            260                 265                 270

Val Leu Asp Thr Asn Leu Ile Asp Gly Ala Ile Arg Gly Ser Asp Ala
        275                 280                 285

Gln Ala Ile Asp Ile Cys Arg Met Val Ala Glu Ser Asp Gly Ile Leu
    290                 295                 300

Leu Gly Gly Ser Ser Gly Leu Asn Leu His Ala Ser Arg Leu Ala Ser
305                 310                 315                 320

Ser Gln Ile Ala Asp Asp Ser Leu Ile Val Thr Ile Leu Pro Asp Gln
                325                 330                 335

Gly Ile Arg Tyr Met Ser Lys Val Phe Asp Asp Ser Trp Leu Glu Ser
            340                 345                 350

Lys Gly Met Gly Gly Ala Lys Glu Ser Asp Gly Asn Ala Glu Lys Glu
        355                 360                 365

Ala Asp Cys Glu Ile Tyr Trp Lys Pro Asp Ala Ile Ser Phe Ala Glu
    370                 375                 380

Arg Lys Ala Ala Ala Ala Ala Ala Ala Ala Ala Ala Val Glu Gly His
```

```
             385                 390                 395                 400
         Asn Leu Trp Pro Glu Glu Gln Thr Glu Ala Glu Leu Lys Phe Leu Glu
                         405                 410                 415

Glu Ile Ala Pro Lys Met Val Glu Tyr His Arg Asn Ser Met Lys Ala
                         420                 425                 430

Asp Glu Arg Ile His Ser Lys Leu Gln Ser Pro Glu Ala Leu Ala Glu
                         435                 440                 445

Thr Phe Ala Glu Ala Gly Ser Pro Leu Asp Leu Gly Ser Gly Asp Ala
                 450                 455                 460

Pro Val Ser Glu Glu Gln Ile Ala Ile Asp Val Gln Ile Tyr Ile Gln
         465                 470                 475                 480

Asn Gly Met Lys Thr Ser His Pro Arg Phe Met Ala Gln Leu Tyr Ser
                             485                 490                 495

Gly Val Asp Ile Ile Gly Leu Thr Gly Asp Trp Thr Ser Thr Gly Phe
                         500                 505                 510

Asn Thr Asn Val His Thr Tyr Glu Ile Ala Pro Ile Val Ser Glu Leu
                         515                 520                 525

Glu Lys Gly Leu Met Glu Lys Ser Gly Arg Leu Trp Val Gln Lys Pro
                 530                 535                 540

Glu Ser Lys Thr Ser Pro Pro His Asp Gly Ile Phe Leu Pro Gly Gly
         545                 550                 555                 560

Ser Met Ser Asn Met Tyr Ser Ile Met Val Ala Arg Asp Lys Ala Phe
                             565                 570                 575

Pro Gln Ala Lys Thr Lys Gly Leu Trp Ala Ala Pro Arg Met Ala Ile
                         580                 585                 590

Phe Thr Ser Gln Gln Ser His Tyr Ser Tyr Lys Lys Ser Ala Met Val
                     595                 600                 605

Leu Gly Ile Gly Met Glu Asn Met Ile Lys Val Arg Cys Asp Glu Ser
                 610                 615                 620

Gly Ser Met Ile Pro Glu Asp Leu Glu Ala Ser Ile Val Gln Ala Lys
         625                 630                 635                 640

Ser Lys Asp Lys Val Pro Phe Tyr Val Asn Ala Thr Ala Gly Thr Thr
                             645                 650                 655

Val Ile Gly Ala Phe Asp Pro Leu Gln Ala Cys Ala Asp Ile Cys Glu
                         660                 665                 670

Arg His Asn Met Trp Leu His Val Asp Ala Ala Trp Gly Gly Gly Ala
                         675                 680                 685

Ser Met Ser Pro Lys His Arg His Asn Leu Asn Gly Gly Glu Arg Ala
                 690                 695                 700

Asn Ser Leu Thr Trp Asn Pro His Lys Met Met Gly Val Pro Leu Gln
         705                 710                 715                 720

Cys Ser Ala Ile Leu Val Lys Glu Pro Gly Val Leu Gln Lys Ala Asn
                             725                 730                 735

Ser Gly Cys Ala Gly Tyr Leu Phe Gln Pro Asp Lys Gln Asn Ala Ser
                         740                 745                 750

Ala Asp Ile Gly Asp Lys Ala Ile Gln Cys Gly Arg Lys Ala Asp Ala
                         755                 760                 765

Phe Lys Leu Trp Leu Ala Trp Lys Ala Lys Gly Gln Val Gly Trp Asp
                 770                 775                 780

Asn Met Ile Asn Lys Cys Phe Ala Met Ala Glu Tyr Leu His Gly Ser
         785                 790                 795                 800

Leu Arg Glu Arg Ser Glu Lys Asp Ala Thr Phe Val Ile Ala Gln Pro
                             805                 810                 815
```

-continued

```
Ala Asp Cys Thr Asn Val Ala Phe Trp Tyr Ile Pro Pro Arg Leu Arg
            820                 825                 830

Pro Tyr Gln Ile Glu Ser Gly Thr Ala Gln Asp Ile Thr Glu Leu Gly
        835                 840                 845

Phe Ile Ala Pro Lys Ile Lys Ala Arg Met Met Arg Ser Gly Asp Thr
    850                 855                 860

Met Val Gly Tyr Gln Pro Met Asp Thr Met Asp Ile Pro Asn Phe Phe
865                 870                 875                 880

Arg Met Val Phe Pro Asn Thr Arg His Val Thr Lys Gln Ala Val Asp
                885                 890                 895

Ala Leu Ile Gln Arg Ile Gln Asp Leu Gly Lys Asp Leu
            900                 905
```

METHODS FOR HIGH TAURINE PRODUCTION USING NOVEL DECARBOXYLASES

CROSS REFERENCE TO RELATED APPLICATION(S)

This application is a 35 U.S.C. § 371 National Stage of International Patent Application No. PCT/US2017/061337, filed Nov. 13, 2017, designating the United States, the disclosure of which is incorporated by reference in entirety.

SEQUENCE SUBMISSION

The present application is being filed along with a Sequence Listing in electronic format. The Sequence Listing is entitled SyntheticCSDC.txt, created on Oct. 30, 2017 and is 178 kb in size. The information in the electronic format of the Sequence Listing is incorporated herein by reference in their entirety

FIELD OF THE INVENTION

The present invention is in the field of recombinant genes and peptides for the production of taurine or 2-aminoethanesulfonic acid. The present invention relates to methods and materials for making semi-synthetic or synthetic peptides for taurine production. The present invention describes methods to engineer or synthetize peptides and uses thereof for taurine production. The invention includes semi-synthetic peptides made from modifications, replacements or inclusions of polynucleotides to modify amino acids in natural peptides or synthetic peptides made from synthetic polynucleotides or polynucleotides modified by directed evolution or gene shuffling, and their uses for taurine synthesis production. In some embodiments, the invention is aimed to semi-synthesize peptides by fusion and modification of polynucleotides to engineer a peptide for taurine synthesis. In some embodiments, the invention is aimed to synthesize polynucleotides to engineer a peptide that produces taurine. In other embodiments, the invention is aimed to polynucleotides derived by directed evolution to engineer a peptide that produces taurine. The present invention also describes preferred motifs for semi-synthetic or synthetic peptides to make the novel peptides for taurine synthesis. The present invention includes the production of taurine in eukaryotic and unicellular organisms. Unicellular organisms include single cell eukaryotes and prokaryotes, and unicellular organisms include bacteria, microbes, archaea, protozoa, yeast, unicellular algae and unicellular fungi. The invention also relates to methods to increase taurine levels in the cells with the semi-synthetic or synthetic peptides for taurine production by binding taurine or decreasing taurine degradation. The invention includes use in organisms that contain native or heterologous taurine biosynthetic pathways or cells that have taurine by enrichment. The invention also relates to methods to increase taurine levels in the cells and to use the said cells or extracts or purifications from the cells that contain the invention to produce taurine, plant growth enhancers, food, animal feed, aquafeed, food or drink supplements, animal-feed supplements, dietary supplements, or health supplements.

The publications and other materials used herein to illuminate the background of the invention or provide additional details respecting the practice are incorporated by reference and, for convenience, are respectively grouped in the Bibliography.

BACKGROUND OF THE INVENTION

Taurine is an Essential Compound for Animals

Taurine is essential for human neonatal development (1) and plays an important role in brain development (2, 3). Taurine is involved in the modulation of intracellular calcium homeostasis (4, 5) and may balance glutamate activity, protecting neurons against glutamate excitotoxicity (6, 7). Taurine is also an osmoregulator (8). Taurine is essential for heart function (9), protects the integrity of hepatic tissue (10), and plays a role in photoprotection (11).

Taurine as a Dietary Supplement

Taurine is biosynthesized in most animals and can be found in meat and seafood. Those who do not produce sufficient levels of taurine must acquire it through dietary supplement. Dietary taurine is required for the normal development and growth of cats (12, 13), human infants (14), and carnivorous fish (15-23). Taurine also improves the health and/or growth of other fish species (24-28) and shrimp (29). Taurine is a feed attractant for fish (20, 30).

Taurine as a Pharmaceutical or Therapeutic

Taurine is used as a pharmaceutical and therapeutic. Taurine has been used in the treatment of cardiovascular diseases (31, 32), elevated blood pressure (33), seizure disorders (34), hepatic disorders (35), and alcoholism (36) and may be useful in the treatment of diabetes (37), Alzheimer's disease (38), and ocular disorders (39). Taurine has been shown to prevent obesity (40) and control cholesterol (41, 42). Taurine acts as an antioxidant and protects against toxicity of various substance (43-45). Taurine has been shown to prevent oxidative stress induced by exercise (46) and is used in energy drinks to improve performance (47). Taurine can also be used in topical applications to treat dermatological conditions (48).

Taurine as a Plant Growth Stimulator

Exogenous application of taurine has been reported to increase crop harvest, yield, and biomass (49). Applications of taurine by foliar spray, soil and roots application, and seed immersion increase crop production and seedling growth (49). Exogenous applications of taurine have also been shown to increase photosynthetic capacity of isolated plant cells (protoplasts and chloroplasts) (49).

Metabolic Pathways that Synthesize Taurine

Several metabolic pathways that synthesize taurine or hypotaurine in animals have been described (50). Agnello et al. (51) provided the first data to suggest that prokaryotes may have intact taurine biosynthetic pathways. More recent studies have shown that several algal and microalgal species can synthesize taurine (52), suggesting taurine synthesis is more prevent in nature than what was thought less than a decade ago. The use of polynucleotides and their corresponding peptides and methods for the use of polynucleotides and their corresponding peptides to make taurine in cells have been described in the literature (50, 53, 54).

Methods to Increase Taurine in Cells

The present invention could be combined with other methods or processes to increase taurine in the cell. These methods or processes have been discussed in the literature and in prior inventions (55, 56) and they are described below.

Taurine Enrichment

Other studies have shown that multicellular organisms such as rotifers that contain no or low levels of taurine can be enriched with taurine by diffusion (dissolved method) (57-59), or with liposomes (60). Taurine enrichment methods could also be used with unicellular organisms and in combination with the present invention to increase taurine levels in the cell.

Periplasmic-Binding or Taurine-Binding Proteins

In bacteria, periplasmic binding proteins or substrate-binding proteins bind specific molecules as part of a multi-component (peptide) system that is involved in the binding and transportation of specific molecules from the periplasmic space, outside of the bacterium, to the inside of the cell (61-63). In the ABC transporter system, the substrate-binding protein delivers the bound molecule to transporter proteins on the bacterial membrane where the bound molecule is released into the cell in an energy-dependent manner. In the absence of membrane-bound proteins or energy-dependent releasing peptides (ATP-binding proteins) the substrate molecules remain bound to the substrate-binding protein. In the tripartite ATP-independent periplasmic (TRAP) transporter systems, the substrate-binding protein delivers the bound molecule to membrane bound protein complex (with two peptides) and releases the bound molecule into the cell in an ATP-independent process. In the absence of membrane-bound proteins the substrate molecule remains bound to the substrate-binding protein. Methods to increase pools of sulfonic acids, such as taurine, by expressing only the substrate-binding protein from an ABC transporter or TRAP system, TauA or TauK, respectively, in the cells have been described for use in plant tissues (54, 64). The present invention describes methods to express substrate-specific binding proteins in the cell of a unicellular organism to increase taurine in the cell.

Sulfonic Acid or Taurine Degradation

In the absence of sulfur, bacteria utilize the sulfonic acid uptake and degradation pathway or the taurine uptake and degradation pathway to mobilize carbon, nitrogen or sulfur (65-68). Genes and their corresponding peptides involved in the uptake and degradation of taurine are usually on the same operon and are induced in the absence of nitrogen (69, 70) or sulfur (65) or in the presence of taurine (68, 71). The genes for the degradation enzymes and their corresponding gene products are the TauX and TauY genes (70) that encode taurine dehydrogenase (TDH), the TauD gene (65) that encodes taurine dioxygenase (TDO), the Tpa gene (72) that encodes taurine-pyruvate aminotransferase (TPAT) or the SsuDE (SsuD or SsuE) genes (66) that encode the two-component alkanesulfonate monooxygenase (2CASM).

Transcriptional Regulators

Translational regulators, Cbl or TauR, control the expression and induction of the taurine degradation pathways in bacteria (65, 72). Cbl is a LysR-type transcriptional regulator of the sulfonic acid uptake and degradation pathway or the taurine uptake and degradation pathway in several bacteria (73, 74). The Cbl gene is found in Proteobacteria including members of the Alphaproteobacteria, Betaproteobacteria, and Gammaproteobacteria. In bacteria that lack Cbl or Cbl-like transcriptional regulators there is a MocR subfamily of activators, which include TauR, that control the taurine uptake and degradation system. The TauR is found in Rhizobiales and Rhodobacterales of the Alphaproteobacteria, in Burkholderiaceae and Comamonadaceae of the Betaproteobacteria, in Enterobacteriales, Oceanospirillales and Psychromonadales from the Gammaproteobacteria, and in Rhizobiales and *Rhodobacter* of the Alphaproteobacteria. This invention describes how to decrease the expression of these genes or decrease the activities of their corresponding proteins in the cell of a unicellular organism to increase taurine in the cell.

SUMMARY OF THE INVENTION

The invention provides methods and compositions for semi-synthetic or synthetic polynucleotides and corresponding peptides to cysteine synthetase/PLP decarboxylase (CS/PLP-DC) for taurine or 2-aminoethanesulfonic acid production (55, 56). The CS/PLP-DC polynucleotide and the resulting peptide increased levels of taurine production in eukaryotic (55) and prokaryotic (56) systems using plants and bacteria, respectively. This invention describes the semi-synthetic and synthetic assembly and use of synthetic CS/PLP-DC (sCS/PLP-DC) polynucleotides and corresponding peptides for taurine synthesis. In addition, the invention describes preferred motifs and their use in sCS/PLP-DC peptides for taurine synthesis.

This invention describes the semi-synthetic assembly of sCS/PLP-DC genes and corresponding peptides from cysteine synthase (CS) and decarboxylase (DC) genes or cystathionine beta-synthase (CBS) and DC genes. This invention describes semi-synthetic methods that include polynucleotide fusion and nucleotide modifications, such as insertions, deletions and substitutes, and methods of directed evolution. CS or CBS genes and a range of known DC genes can be used and include but are not limited to sulfinoalanine decarboxylase (SAD) glutamate decarboxylase (GAD), aromatic amino acid decarboxylase (AAAD) or 2,4-diaminobutyrate decarboxylase (BABD). This invention describes synthetic methods that include CS/PLP-DC-like genes and corresponding peptides. This invention describes semi-synthetic and synthetic methods that include the use of polynucleotides and corresponding peptides to synthesize an sCS/PLP-DC with conserved domains or motifs necessary for functional CS/PLP-DC or sCS/PLP-DC peptides that increase taurine production (FIG. 1). In addition, the invention provides methods for the synthesis of sCS/PLP-DC peptides using directed evolution.

The invention encompasses the use of sCS/PLP-DC polynucleotides in combination with nucleotides and peptides for substrate-binding proteins, such as the TauA or TauK genes, to increase taurine in cells or the use of polynucleotides for peptides that degrade taurine as described in (54, 56). This invention describes methods to use cells with increased taurine pools of the sulfonic acids, such as taurine, by binding taurine in the cell with specific bacterial substrate-binding proteins or by blocking or inhibiting taurine degradation.

This invention also describes the use of the sCS/PLP-DC polynucleotides in combination with methods to block taurine degradation by methods of silencing, mutating or knocking out genes for enzymes in the taurine degradation pathway(s) (56) including the TauX or TauY genes that encode TDH, the TauD gene that encodes TDO, the SsuD or SsuE genes that encode 2CASM, or the Tpa gene that encodes TPAT, or by methods of silencing, mutating or knocking out the Cbl gene that encodes LysR-type transcriptional regulator or the TauR gene that encodes a MocR transcriptional regulator. This invention describes the use of polynucleotides for taurine-binding proteins or taurine degradation proteins and their corresponding peptides in unicellular organisms that are capable of producing taurine due to the presence of endogenous (native) or heterologous (gene transfer) taurine biosynthetic pathways or in cells enriched with taurine.

The invention can be used to increase taurine in eukaryotic and prokaryotic cells and in unicellular organisms that produce taurine through a native or endogenous taurine (52) or heterologous pathway (75) or in cells enriched with taurine (57-60, 75).

The invention provides isolated cells comprising polynucleotides which do not express a functional taurine degradation enzyme. Some isolated cells of the invention comprise: (i) exogenous DNA which disrupts the expression of the endogenous gene or renders the corresponding peptide for the degradation enzyme non-functional, (ii) a basepair mutation that disrupts the expression of the gene or renders the corresponding peptide for the degradation enzyme non-functional, or (iii) a deletion of the entire polynucleotide or a portion of the polynucleotide which disrupts the expression of the gene or renders the corresponding peptide for the degradation enzyme non-functional. The non-functional DNA could be due to changes in the promoter, a portion of the coding region, coding region, or terminator to a polynucleotide which encodes taurine degradation enzyme, that includes TauX, TauY, TauD, Tpa, SsuD, or SsuE or translational activators of those genes including Cbl or TauR genes in a manner where the genes products are not functional. The invention also provides isolated cells comprising non-functional genes or gene products of taurine degradation enzymes from the suppression or decreased accumulation of the corresponding RNA due to antisense RNA or RNA interference.

The invention provides isolated cells comprising exogenous DNA which express enzymes of the sCS/PLP-DC biosynthetic pathway and polynucleotides or methods which result in a non-functional or silenced taurine degradation enzyme. In one embodiment, an isolated cell comprises two separate expression cassettes. A first expression cassette comprises a first promoter operably linked to a first polynucleotide, and a second cassette comprises polynucleotides which result in a non-functional taurine degradation enzyme. In some embodiments, the first polynucleotide encodes sCS/PLP-DC. The second polynucleotide comprises the promoter, a portion of the coding region, coding region, or terminator to genes for a taurine degradation enzyme that results in a non-functional TauX, TauY, TauD, Tpa, SsuD, or SsuE or a non-functional translational activator including Cbl or TauR genes. The genes can be made non-functional in such a manner where the genes are not expressed, the gene products are not functional, or the target polynucleotide is silenced.

The invention also describes how to use the cells, fractions of the cells, or extracts from the cells for the present invention for a variety of purposes, including as an additive, feed ingredient, extract or meal. This invention describes the use of polynucleotides and their corresponding polypeptides that either bind or degrade taurine.

The invention provides methods for increasing taurine in the cells of the invention by growing or treating the cells with an agent that increases sulfur or nitrogen concentration.

The invention also provides nutritional supplements, feed supplements, and pharmaceutical compositions comprising an extract or meal from the cell of the invention,

BRIEF DESCRIPTION OF THE FIGURE

FIG. 1 shows a diagram of the sCS/PLP-DC peptide with the CS/CBS and the decarboxylase region domains. Motifs (I-VI) associated with sCS/PLP-DC peptides are indicated. The specific motifs are indicated using standard single letter amino acid abbreviations. X represents any amino acid, and numbers indicate the spaces between conserved residues.

DETAILED DESCRIPTION OF THE INVENTION

The present invention provides methods and materials for the production of taurine (2-aminoethanesulfonic acid) using sCS/PLP-DC. In preferred embodiments, the invention provides methods for the genetic transformation of eukaryotic and prokaryotic cells with sCS/PLP-DC polypeptides and expression of the corresponding sCS/PLP-DC peptides. Another embodiment of the invention is organisms with genes that encode proteins that bind taurine or with silenced or knocked out genes for taurine degradation. The preferred embodiment for eukaryotes is in plants. Another embodiment of the invention is in unicellular organisms. The invention also provides methods of using eukaryotic and prokaryotic cells or unicellular organisms such as algae, microalgae, bacteria, fungi, yeast, or unicellular cellular organisms with increased levels of endogenous taurine or taurine derivatives such as hypotaurine that can be purified or used as a food- or feed-supplement, dietary supplement, as a component of a health supplement or therapy or for plant growth or yield.

The invention describes methods for the use of polynucleotides that encode a functional sCS/PLP-DC peptide using polynucleotides that correspond to CS/PLP-DC, CS, CBS, AAAD, GAD, BABD, or SAD peptides in eukaryotes, prokaryotes or unicellular organisms. The preferred embodiments of the invention are in plants and unicellular organisms but other organisms may be used.

The present invention describes the methods for the synthesis of DNA constructs from polynucleotides and use of vectors and the methods for making transformed eukaryotic organisms, including plants and fungi, and unicellular organisms, including bacteria microbes, fungi, yeast, algae and microalgae that produce taurine due to the presence of sCS/PLP-DC peptide. The present invention describes methods to produce extracts or cells with enhanced taurine production and that result in cells or items with increased nutritional, pharmaceutical, or therapeutic value. The invention can be used in cells enriched with taurine, that contain a native taurine biosynthetic pathway(s), or that contain taurine from the insertion of a heterologous pathway by transformation or gene transfer.

The present invention describes the methods and use of the sCS/PLP-DC constructs alone or in conjunction with polynucleotides and corresponding peptides that bind taurine or with polynucleotides or methods that inhibit taurine degradation. Present invention describes methods to synthesize polynucleotides and vectors and the methods for making transformed organisms including unicellular organisms, microbes, fungi yeast, algae and microalgae. The present invention is unique in that it describes a method to produce taurine that has advantages of enhanced taurine production or hypotaurine and that result in cells with increased nutritional, pharmaceutical, or therapeutic value.

The invention provides methods to develop isolated cells and organisms comprising exogenous DNA that expresses enzymes of sCS/PLP-DC and taurine binding protein. In one embodiment, an isolated cell comprises two separate expression cassettes. A first expression cassette comprises a first promoter operably linked to an sCS/PLP-DC polynucleotide and a second expression cassette comprises another promoter operably linked to a second polynucleotide. The second polynucleotide encodes a taurine binding protein (TauA or TauK).

The present invention describes the methods for the synthesis of sCS/PLP-DC constructs to inhibit taurine degradation from polynucleotides and vectors and the methods for making transformed organisms including unicellular organisms, microbes, fungi yeast, algae and microalgae. The present invention is unique in that it describes a method to produce taurine that has advantages of enhanced taurine production or hypotaurine and that result in cells with increased nutritional, pharmaceutical, or therapeutic value The present invention describes the insertion of the sCS/PLP-DC polynucleotides in conjunction with polynucleotides that encode functional taurine binding proteins (TauA or TauK) or polynucleotides that silence or knocked-out genes for proteins involved in taurine degradation (TauD, SsuD, SsuE, TauX, TauY, or Tpa) or transcriptional regulators (cbl or TauR) that control taurine degradation in unicellular organisms, or their use in taurine biosynthetic pathway in unicellular organisms where the pathway does not exist or has not clearly been identified.

Enzymes of Taurine Biosynthetic Pathways

Examples of amino acid sequences that can be used for assembly of the sCS/PLP-DC biosynthetic pathways are provided in the sequence listing: SEQ ID NO:2 (CS/PLP-DC), SEQ ID NO:4 (CS/PLP-DC), SEQ ID NO:6 (CS), SEQ ID NO:8 (CS), SEQ ID NO:10 (CS), SEQ ID NO:12 (CBS), SEQ ID NO:14 (CBS), SEQ ID NO:16 (CBS), SEQ ID NO:18 (AAAD), SEQ ID NO:20 (AAAD), SEQ ID NO:22 (GAD), SEQ ID NO:24 (BABD), SEQ ID NO:26 (SAD), SEQ ID NO:28 (SAD) and SEQ ID NO:83 (CS/PLP-DC). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for CS/PLP-DC from *Micromonas pusilla, Ostreococcus tauri*, or *Bathycoccus prasinos*; CS from *Brassica oleracea, Oryza brachyantha*, or *Escherichia coli*; CBS from *Candidatus kryptonium, Chloroflexi bacterium* or *Cyprinus carpio*; AAAD from *Beta vulgaris* or *Lepisosteus oculatus*; GAD from *Danio rerio*; BABD from *Escherichia coli*; or SAD from *Oncorhynchus mykiss* or *Guillardia theta* may differ to a certain degree from the amino acid sequences of CS/PLP-DC, CS, CBS, AAAD, GAD, BABD, or SAD in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Substrate Binding Proteins

Examples of amino acid sequences of substrate binding proteins or periplasmic binding proteins that bind taurine are provided in the sequence listing: SEQ ID NO:30 (TauA) and SEQ ID NO:32 (TauK). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for TauA from *Escherichia coli* or TauK from *Roseobacter denitrificans* may differ to a certain degree from the amino acid sequences of TauA or TauK in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Enzymes of Taurine Degradation Pathways

Examples of amino acid sequences of enzymes in degradation pathways are provided in the sequence listing: SEQ ID NO:34 (TDO), SEQ ID NO:36 (SsuD), SEQ ID NO:38 (SsuE), SEQ ID NO:40 (SsuD), SEQ ID NO:42 (SsuE), SEQ ID NO:44 (TauX), SEQ ID NO:46 (TauY), and SEQ ID NO:48 (Tpa). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for TDO, SsuD or SsuE from *Escherichia coli*, SsuD or SsuE from *Corynebacterium glutamicum*, TauX, TauY, or Tpa from *Roseobacter denitrificans* may differ to a certain degree from the amino acid sequences of TDO, SsuD, SsuE, TauX, TauY, or Tpa in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Translational Regulators

Examples of amino acid sequences of translational regulators are provided in the sequence listing: SEQ ID NO:50 or SEQ ID NO:52 (cbl), or SEQ ID NO:54 (TauR). The invention is not limited to the use of these amino acid sequences. Those of ordinary skill in the art know that organisms of a wide variety of species commonly express and utilize homologous proteins, which include the insertions, substitutions and/or deletions discussed above, and effectively provide similar function. For example, the amino acid sequences for cbl from *Escherichia coli*, or cbl from *Corynebacterium glutamicum* or TauR from *Corynebacterium glutamicum* may differ to a certain degree from the amino acid sequences of cbl or TauR in another species and yet have similar functionality with respect to catalytic and regulatory function. Amino acid sequences comprising such variations are included within the scope of the present invention and are considered substantially or sufficiently similar to a reference amino acid sequence. Although it is not intended that the present invention be limited by any theory by which it achieves its advantageous result, it is believed that the identity between amino acid sequences that is necessary to maintain proper functionality is related to maintenance of the tertiary structure of the polypeptide such that specific interactive sequences will be properly located and will have the desired activity, and it is contemplated that a polypeptide including these interactive sequences in proper spatial context will have activity.

Another manner in which similarity may exist between two amino acid sequences is where there is conserved substitution between a given amino acid of one group, such as a non-polar amino acid, an uncharged polar amino acid, a charged polar acidic amino acid, or a charged polar basic amino acid, with an amino acid from the same amino acid group. For example, it is known that the uncharged polar amino acid serine may commonly be substituted with the uncharged polar amino acid threonine in a polypeptide without substantially altering the functionality of the polypeptide. Whether a given substitution will affect the functionality of the enzyme may be determined without undue experimentation using synthetic techniques and screening assays known to one with ordinary skill in the art.

One of ordinary skill in the art will recognize that changes in the amino acid sequences, such as individual substitutions, deletions or additions to a nucleic acid, peptide, polypeptide, or protein sequence which alters, adds or deletes a single amino acid or a small percentage of amino acids in the encoded sequence is "sufficiently similar" when the alteration results in the substitution of an amino acid with a chemically similar amino acid. Thus, any number of amino acid residues selected from the group of integers consisting of from 1 to 15 can be so altered. Thus, for example, 1, 2, 3, 4, 5, 7 or 10 alterations can be made. Conservatively modified variants typically provide similar biological activity as the unmodified polypeptide sequence from which they are derived. Conserved substitutions of functionally similar amino acids are known by those of ordinary skill in the art. The following three groups each contain amino acids that are conserved substitutions for one another: (1) Alanine (A), Serine (S), and Threonine (T); (2) Aspartic acid (D) and Glutamic acid (E); (3) Asparagine (N) and Glutamine (Q).

Directed Evolution and Gene Shuffling

The invention is not limited to the fusing of the polynucleotides and corresponding amino acids from CS or CBS with decarboxylases to make a sCS/PLP-DC. Those of ordinary skill in the art know that methods such as directed evolution, gene shuffling, site-directed mutagenesis, saturation mutagenesis, randomized mutagenesis, PCR mutagenesis, sequence saturated mutagenesis and computational modeling can be used to increase catalytic activity or maximize efficiency in specific organisms [see reviews and references therein (76-78)].

Suitable Polynucleotides

Suitable polynucleotides encoding enzymes of taurine biosynthetic and degradation pathways, taurine specific substrate binding proteins, and translational regulators of taurine degradation pathways are described below. The invention is not limited to the use of these sequences, however. In fact, any nucleotide sequence that encodes an enzyme of CS/PLP-DC, or a CS or CBS with a DC including AAAD, GAD, BABD, or SAD can be used in an expression vector to produce recombinant protein with sCS/PLP-DC activity in a eukaryote, prokaryote or unicellular organism alone or in combination with the expression for a taurine-binding protein or an impaired or absent degradation taurine pathway(s) due to suppression, mutation silencing of degradation enzymes or regulators of the degradation taurine pathway.

A suitable polynucleotide for CS/PLP-DC is provided in SEQ ID NO:1, SEQ ID NO: 3, or SEQ ID NO:82. Other suitable polynucleotides for use in accordance with the invention may be obtained by the identification of polynucleotides that selectively hybridize to the polynucleotides of SEQ ID NO:1, SEQ ID NO:3, or SEQ ID NO:82 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:1, SEQ ID NO: 3, or SEQ ID NO:82 when it used as a reference for sequence comparison or polynucleotides that encode polypeptides that have substantial identity to amino acid sequence of SEQ ID NO:2, SEQ ID NO:4, or SEQ ID NO:83 when it is used as a reference for sequence comparison.

A suitable polynucleotide for CS is provided in SEQ ID NO:5, SEQ ID NO:7 or SEQ ID NO:9. Other suitable polynucleotides for use in accordance with the invention may be obtained by the identification of polynucleotides that selectively hybridize to the polynucleotides of SEQ ID NO:5, SEQ ID NO:7 or SEQ ID NO:9 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:5, SEQ ID NO:7 or SEQ ID NO:9 when it used as a reference for sequence comparison or polynucleotides that encode polypeptides that have substantial identity to amino acid sequence of SEQ ID NO:6, SEQ ID NO:8 or SEQ ID NO:10 when it is used as a reference for sequence comparison.

A suitable polynucleotide for CBS is provided in SEQ ID NO:11, SEQ ID NO:13 or SEQ ID NO:15. Other suitable polynucleotides for use in accordance with the invention may be obtained by the identification of polynucleotides that selectively hybridize to the polynucleotides of SEQ ID NO:11, SEQ ID NO:13 or SEQ ID NO:15 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:11, SEQ ID NO:13 or SEQ ID NO:15 when it used as a reference for sequence comparison or polynucleotides that encode polypeptides that have substantial identity to amino acid sequence of SEQ ID NO:12, SEQ ID NO:14 or SEQ ID NO:16 when it is used as a reference for sequence comparison.

A suitable polynucleotide for AAAD is provided in SEQ ID NO:17 or SEQ ID NO:19. Other suitable polynucleotides for use in accordance with the invention may be obtained by the identification of polynucleotides that selectively hybridize to the polynucleotides of SEQ ID NO:17 or SEQ ID NO:19 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:17 or SEQ ID NO:19 when it used as a reference for sequence comparison or polynucleotides that encode polypeptides that have substantial identity to amino acid sequence of SEQ ID NO:18 or SEQ ID NO:20 when it is used as a reference for sequence comparison.

A suitable polynucleotide for GAD is provided in SEQ ID NO:21. Other suitable polynucleotides for use in accordance with the invention may be obtained by the identification of polynucleotides that selectively hybridize to the polynucleotides SEQ ID NO:21 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:21 when it used as a reference for sequence comparison or polynucleotides that encode polypeptides that have substantial identity to amino acid sequence of SEQ ID NO:22 when it is used as a reference for sequence comparison.

A suitable polynucleotide for BABD is provided in SEQ ID NO:23. Other suitable polynucleotides for use in accordance with the invention may be obtained by the identification of polynucleotides that selectively hybridize to the polynucleotides SEQ ID NO:23 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:23 when it used as a reference for sequence comparison or polynucleotides that encode polypeptides that have substantial identity to amino acid sequence of SEQ ID NO:24 when it is used as a reference for sequence comparison.

A suitable polynucleotide for SAD is provided in SEQ ID NO:25 or SEQ ID NO:27. Other suitable polynucleotides for use in accordance with the invention may be obtained by the identification of polynucleotides that selectively hybridize to the polynucleotides of SEQ ID NO:25 or SEQ ID NO:27 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:25 or SEQ ID NO:27 when it is used as a reference for sequence comparison or polynucleotides that encode polypeptides that have substantial identity to amino acid sequence of SEQ ID NO:26 or SEQ ID NO:28 when it is used as a reference for sequence comparison.

Suitable polynucleotides for a taurine-binding protein are provided in SEQ ID NO:29 or SEQ ID NO:31. Other suitable polynucleotides for use in accordance with the invention may be obtained by the identification of polynucleotides that selectively hybridize to the polynucleotides of SEQ ID NO:29 or SEQ ID NO:31 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:29 or SEQ ID NO:31 when it is used as a reference for sequence comparison or polynucleotides that encode polypeptides that have substantial identity to amino acid sequence of SEQ ID NO:30 or SEQ ID NO:32 when it is used as a reference for sequence comparison.

A suitable polynucleotide for TDO is provided in SEQ ID NO:33. Other suitable polynucleotides for use in accordance with the invention may be obtained by the identification of polynucleotides that selectively hybridize to the polynucleotides of SEQ ID NO:33 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:33 when it is used as a reference for sequence comparison or polynucleotides that encode polypeptides that have substantial identity to amino acid sequence of SEQ ID NO:34 when it is used as a reference for sequence comparison.

Suitable polynucleotides for a SsuD are provided in SEQ ID NO:35 and SEQ ID NO:39. Other suitable polynucleotides for use in accordance with the invention may be obtained by the identification of polynucleotides that selectively hybridize to the polynucleotides of SEQ ID NO:35 and SEQ ID NO:39 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:35 and SEQ ID NO:39 when it is used as a reference for sequence comparison or polynucleotides that encode polypeptides that have substantial identity to amino acid sequence of SEQ ID NO:36 or SEQ ID NO:40 when it is used as a reference for sequence comparison.

Suitable polynucleotides for a SsuE are provided in SEQ ID NO:37 and SEQ ID NO:41. Other suitable polynucleotides for use in accordance with the invention may be obtained by the identification of polynucleotides that selectively hybridize to the polynucleotides of SEQ ID NO:37 and SEQ ID NO:41 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:37 and SEQ ID NO:41 when it is used as a reference for sequence comparison or polynucleotides that encode polypeptides that have substantial identity to amino acid sequence of SEQ ID NO:38 and SEQ ID NO:42 when it is used as a reference for sequence comparison.

A suitable polynucleotide for TauX is provided in SEQ ID NO:43. Other suitable polynucleotides for use in accordance with the invention may be obtained by the identification of polynucleotides that selectively hybridize to the polynucleotides of SEQ ID NO:43 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:43 when it is used as a reference for sequence comparison or polynucleotides that encode polypeptides that have substantial identity to amino acid sequence of SEQ ID NO:44 when it is used as a reference for sequence comparison.

A suitable polynucleotide for TauY is provided in SEQ ID NO:45. Other suitable polynucleotides for use in accordance with the invention may be obtained by the identification of polynucleotides that selectively hybridize to the polynucleotides of SEQ ID NO:45 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:45 when it is used as a reference for sequence comparison or polynucleotides that encode polypeptides that have substantial identity to amino acid sequence of SEQ ID NO:46 when it is used as a reference for sequence comparison.

A suitable polynucleotide for Tpa is provided in SEQ ID NO:47. Other suitable polynucleotides for use in accordance with the invention may be obtained by the identification of polynucleotides that selectively hybridize to the polynucleotides of SEQ ID NO:47 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:47 when it is used as a reference for sequence comparison or polynucleotides that encode polypeptides that have substantial identity to amino acid sequence of SEQ ID NO:48 when it is used as a reference for sequence comparison.

Suitable polynucleotides for a cbl are provided in SEQ ID NO:49 and SEQ ID NO:51. Other suitable polynucleotides for use in accordance with the invention may be obtained by the identification of polynucleotides that selectively hybridize to the polynucleotides of SEQ ID NO:49 and SEQ ID NO:51 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:49 and SEQ ID NO:51 when it is used as a reference for sequence comparison or polynucleotides that encode polypeptides that have substantial identity to amino acid sequence of SEQ ID NO:50 or SEQ ID NO:52 when it is used as a reference for sequence comparison.

A suitable polynucleotide for TauR is provided in SEQ ID NO:53. Other suitable polynucleotides for use in accordance with the invention may be obtained by the identification of polynucleotides that selectively hybridize to the polynucleotides of SEQ ID NO:53 by hybridization under low stringency conditions, moderate stringency conditions, or high stringency conditions. Still other suitable polynucleotides for use in accordance with the invention may be obtained by the identification of polynucleotides that have substantial identity of the nucleic acid of SEQ ID NO:53 when it is used as a reference for sequence comparison or polynucleotides that encode polypeptides that have substantial identity to amino acid sequence of SEQ ID NO:54 when it is used as a reference for sequence comparison.

Another embodiment of the invention is a polynucleotide (e.g., a DNA construct) that encodes a protein that functions as an sCS/PLP-DC that selectively hybridizes to either SEQ ID NO:1, SEQ ID NO:3, SEQ ID NO:5, SEQ ID NO:7, SEQ ID NO:9, SEQ ID NO:11, SEQ ID NO:13, SEQ ID NO:15, SEQ ID NO:17, SEQ ID NO:19, SEQ ID NO:21, SEQ ID NO:23, SEQ ID NO:25, SEQ ID NO:27, or SEQ ID:82. Selectively hybridizing sequences typically have at least 40% sequence identity, preferably 60-90% sequence identity, and most preferably 95% sequence identity with each other.

Another embodiment of the invention is a polynucleotide that encodes an sCS/PLP-DC polypeptide that has substantial identity to the amino acid sequence of SEQ ID NO:2, SEQ ID NO:4, SEQ ID NO:6, SEQ ID NO:8, SEQ ID NO:10, SEQ ID NO:12, SEQ ID NO:14, SEQ ID NO:16, SEQ ID NO:18, SEQ ID NO:20, SEQ ID NO:22, SEQ ID NO:24, SEQ ID NO:26, SEQ ID NO:28, SEQ ID:83, or SEQ ID:84. Substantial identity of amino acid sequences for these purposes normally means sequence identity of between 50-100%, preferably at least 55%, preferably at least 60%, more preferably at least 70%, 80%, 90%, and most preferably at least 95%.

Another embodiment of the invention is a polynucleotide (e.g., a DNA construct) that encodes a protein that functions as a TauA, TauK, TauD, TauX, TauY, Tpa, or TauR that selectively hybridizes to SEQ ID NO:29, SEQ ID NO:31, SEQ ID NO:33, SEQ ID NO:43, SEQ ID NO:45, SEQ ID NO:47, or SEQ ID NO:53, respectively; or functions as a SsuD that selectively hybridizes to either SEQ ID NO:35 or SEQ ID NO:39; or functions as a SsuE that selectively hybridizes to either SEQ ID NO:37 or SEQ ID NO:41; or functions as a cbl that selectively hybridizes to either SEQ ID NO:49, SEQ ID NO:51. Selectively hybridizing sequences typically have at least 40% sequence identity, preferably 60-90% sequence identity, and most preferably 100% sequence identity with each other.

Another embodiment of the invention is a polynucleotide that encodes a polypeptide that has substantial identity to the amino acid sequence of SEQ ID NO:30, SEQ ID NO:32, SEQ ID NO:34, SEQ ID NO:36, SEQ ID NO:38, SEQ ID NO:40, SEQ ID NO:42, SEQ ID NO:44, SEQ ID NO:46, SEQ ID NO:48, SEQ ID NO:50, SEQ ID NO:52, or SEQ ID NO:54. Substantial identity of amino acid sequences for these purposes normally means sequence identity of between 50-100%, preferably at least 55%, preferably at least 60%, more preferably at least 70%, 80%, 90%, and most preferably at least 100%.

The process of encoding a specific amino acid sequence may involve DNA sequences having one or more base changes (i.e., insertions, deletions, substitutions) that do not cause a change in the encoded amino acid, or which involve base changes which may alter one or more amino acids, but do not eliminate the functional properties of the polypeptide encoded by the DNA sequence.

It is therefore understood that the invention encompasses more than the specific polynucleotides encoding the proteins described herein. For example, modifications to a sequence, such as deletions, insertions, or substitutions in the sequence, which produce "silent" changes that do not substantially affect the functional properties of the resulting polypeptide, are expressly contemplated by the present invention. Furthermore, because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations" and represent one species of conservatively modified variation. Every nucleic acid sequence herein that encodes a polypeptide also describes every possible silent variation of the nucleic acid. One of ordinary skill in the art will recognize that each amino acid has more than one codon, except for methionine and tryptophan that ordinarily have the codons AUG and UGG, respectively. It is known by those of ordinary skill in the art, "universal" code is not completely universal. Some mitochondrial and bacterial genomes diverge from the universal code, e.g., some termination codons in the universal code specify amino acids in the mitochondria or bacterial codes. Thus, each silent variation of a nucleic acid, which encodes a polypeptide of the present invention, is implicit in each described polypeptide sequence and incorporated in the descriptions of the invention.

It is understood that alterations in a nucleotide sequence, which reflect the degeneracy of the genetic code, or which result in the production of a chemically equivalent amino acid at a given site, are contemplated. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a biologically equivalent product.

Nucleotide changes which result in alteration of the amino-terminal and carboxy-terminal portions of the encoded polypeptide molecule would also not generally be expected to alter the activity of the polypeptide. In some cases, it may in fact be desirable to make mutations in the sequence in order to study the effect of alteration on the biological activity of the polypeptide. Each of the proposed modifications is well within the routine skill in the art.

When the nucleic acid is prepared or altered synthetically, one of ordinary skill in the art can take into account the known codon preferences for the intended host where the nucleic acid is to be expressed. For example, although nucleic acid sequences of the present invention may be expressed in different species, sequences can be modified to account for the specific codon preferences and GC-content preferences of the organism, as these preferences have been shown to differ (79-84).

Cloning Techniques

For purposes of promoting an understanding of the principles of the invention, reference will now be made to particular embodiments of the invention and specific language will be used to describe the same. The materials, methods and examples are illustrative only and not limiting. Unless mentioned otherwise, the techniques employed or contemplated herein are standard methodologies well known to one of ordinary skill in the art. Specific terms, while employed below and defined at the end of this section, are used in a descriptive sense only and not for purposes of limitation. The practice of the present invention will employ, unless otherwise indicated, conventional techniques of botany, microbiology, mycology, phycology, tissue culture, molecular biology, chemistry, biochemistry, biotechnology, recombinant DNA technology and synthetic biology, which are within the skill of the art (85-94).

A suitable polynucleotide for use in accordance with the invention may be obtained by cloning techniques using cDNA or genomic libraries, DNA, or cDNA from eukaryotes (i.e. fish, plants, or, mammals), bacteria, algae, microalgae, diatoms, yeast or fungi which are available commercially or which may be constructed using standard methods known to persons of ordinary skill in the art. Suitable nucleotide sequences may be isolated from DNA libraries obtained from a wide variety of species by means of nucleic acid hybridization or amplification methods, such as polymerase chain reaction (PCR) procedures, using as probes or primers nucleotide sequences selected in accordance with the invention.

Furthermore, nucleic acid sequences may be constructed using chemical synthesis or amplified. The product of amplification is termed an amplicon. Moreover, if the particular nucleic acid sequence is of a length that makes chemical synthesis of the entire length impractical, the sequence may be broken up into smaller segments that may be synthesized and ligated together to form the entire desired sequence by methods known in the art. Alternatively, individual components or DNA fragments may be amplified by PCR and adjacent fragments can be amplified together using fusion-PCR (95), overlap-PCR (96) or chemical (de novo) synthesis (97-101) using a vendor (e.g. DNA2.0, GE life technologies, GENEART, Gen9, GenScript) by methods known in the art.

A suitable polynucleotide for use in accordance with the invention may be constructed by recombinant DNA technology, for example, by cutting or splicing nucleic acids using restriction enzymes and mixing with a cleaved (cut with a restriction enzyme) vector with the cleaved insert (DNA of the invention) and ligated using DNA ligase. Alternatively, amplification techniques, such as PCR, can be used, where restriction sites are incorporated in the primers that otherwise match the nucleotide sequences (especially at the 3' ends) selected in accordance with the invention. The desired amplified recombinant molecule is cut or spliced using restriction enzymes and mixed with a cleaved vector and ligated using DNA ligase. In another method, after amplification of the desired recombinant molecule, DNA linker sequences are ligated to the 5' and 3' ends of the desired nucleotide insert with ligase, the DNA insert is cleaved with a restriction enzyme that specifically recognizes sequences present in the linker sequences and the desired vector. The cleaved vector is mixed with the cleaved insert, and the two fragments are ligated using DNA ligase. In yet another method, the desired recombinant molecule is amplified with primers that have recombination sites (e.g. Gateway) incorporated in the primers, that otherwise match the nucleotide sequences selected in accordance with the invention. The desired amplified recombinant molecule is mixed with a vector containing the recombination site and recombinase, the two molecules are fused together by recombination.

The recombinant expression cassette or DNA construct includes a promoter that directs transcription in a specific organism, operably linked to the polynucleotide encoding an sCS/PLP-DC, an sCS/PLP-DC with a TauA, or an sCS/PLP-DC with a TauK. In various aspects of the invention described herein, a variety of different types of promoters are described and used. As used herein, a polynucleotide is "operably linked" to a promoter or other nucleotide sequence when it is placed into a functional relationship with the promoter or other nucleotide sequence. The functional relationship between a promoter and a desired polynucleotide insert typically involves the polynucleotide and the promoter sequences being contiguous such that transcription of the polynucleotide sequence will be facilitated. Two nucleic acid sequences are further said to be operably linked if the nature of the linkage between the two sequences does not (1) result in the introduction of a frame-shift mutation; (2) interfere with the ability of the promoter region sequence to direct the transcription of the desired nucleotide sequence, or (3) interfere with the ability of the desired nucleotide sequence to be transcribed by the promoter sequence region. Typically, the promoter element is generally upstream (i.e., at the 5' end) of the nucleic acid insert coding sequence.

While a promoter sequence can be ligated to a coding sequence prior to insertion into a vector, in other embodiments, a vector is selected that includes a promoter operable in the host cell into which the vector is to be inserted. In addition, certain preferred vectors have a region that codes a ribosome binding site positioned between the promoter and the site at which the DNA sequence is inserted so as to be operatively associated with the DNA sequence of the invention to produce the desired polypeptide, i.e., the DNA sequence of the invention in-frame.

Suitable Peptide Linkers

Peptide linkers are known to those skilled in the art to connect protein domains or peptides. In general, linkers that contain the amino acids, glycine and serine, are useful linkers (102, 103). Other suitable linkers that can be used in the invention are known to those of ordinary skill in the art (104-109).

Suitable Promoters: Unicellular Organisms

A wide variety of promoters are known to those of ordinary skill in the art, as are other regulatory elements that can be used alone or in combination with promoters. A wide variety of promoters that direct transcription in unicellular organisms can be used in connection with the present invention (110-112). The features (binding sites and regulatory elements) necessary for the identification and use of functional bacterial promoters are known to those of ordinary skill in the art (113-115). For purposes of describing the present invention, promoters are divided into two types, namely, constitutive promoters and non-constitutive promoters (111, 116). Constitutive promoters are classified as providing for a range of constitutive expression. Some are weak constitutive promoters, and others are strong constitutive promoters (117). Other promoters are considered non-constitutive promoters (118-122). A selected promoter can be an endogenous promoter, i.e. a promoter native to the species and or cell type being transformed. Alternatively, the promoter can be a foreign promoter, which promotes transcription of a length of DNA. The promoter may be of viral origin, including a cauliflower mosaic virus promoter (CaMV 35S) (117), and SV40 promoters from viruses have been used to express target genes (123). The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed unicellular organism that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a unicellular organism in accordance with the invention, a DNA construct is provided that includes a non-constitutive promoter operably linked to a polynucleotide encoding the desired polypeptide of the invention. The construct is incorporated into a unicellular organism to provide a transformed organism that expresses the polynucleotide in response to a signal. It is understood that the non-constitutive promoter does not continuously produce the transcript or RNA of the invention. But in this embodiment the selected promoter for inclusion of the invention advantageously induces or increases transcription of the gene for the desired polypeptide of the invention in response to a signal, such as a chemical or environmental cue or other stress signal including biotic and/or abiotic stresses or other conditions.

Terminators: Unicellular Organisms

Terminators are typically located downstream (3') of the gene, after the stop codon (TGA, TAG or TAA). Terminators play an important role in the processing and stability of RNA as well as in translation and may also control gene expression (124-133). The identification and use of terminators that are required to express genes in unicellular organisms are known to those of ordinary skill in the art.

Suitable Vectors: Unicellular Organisms

A wide variety of vectors may be employed to transform a unicellular organism with a construct made or selected in accordance with the invention, including high- or low-copy number plasmids, phage vectors and cosmids. Vector systems, expression cassettes, culture methods, and transformation methods are known by those of ordinary skill in the art. The vectors can be chosen such that operably linked promoter and polynucleotides that encode the desired polypeptide of the invention are incorporated into the genome of the unicellular organism. Other vectors that can operably link promoter and polynucleotides that encode the polypeptide of the invention are incorporated into the host but are not incorporated into the host genome. The vector DNA with the clone polynucleotides are autonomously or semi autonomously replicated in the cell. Although the preferred embodiment of the invention is expressed in bacteria, other embodiments may include expression in prokaryotic or unicellular eukaryotic organisms including, but not limited to, yeast, fungi, algae, microalgae, or microbes.

It is known by those of ordinary skill in the art that there exist numerous expression systems available for expression of a nucleic acid encoding a protein of the present invention. There are many commercially available recombinant vectors to transform a unicellular organism. Standard molecular and cloning techniques (89, 92, 134) are available to make a recombinant expression cassette that expresses the polynucleotide that encodes the desired polypeptide of the invention. No attempt will be made to describe in detail the various methods known for the expression of proteins in prokaryotes or eukaryotes. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter to direct transcription, a ribosome-binding site for translational initiation, and a transcription/translation terminator.

Expression in Prokaryotes

Protocols for transformation as well as commonly used vectors with control sequences including promoters for transcription initiation (some with an operator), together with ribosome binding site sequences for use in prokaryotes are known to those of ordinary skill in the art. Commonly used prokaryotic control sequences include promoters for transcription initiation, optionally with an operator, along with ribosome binding site sequences. Commonly used prokaryotic promoters include the beta lactamase (135), lactose (135), and tryptophan (136) promoters. The vectors usually contain selectable markers to identify transfected or transformed cells. Some commonly used selectable markers include the genes for resistance to ampicillin, tetracycline, or chloramphenicol. The vectors are typically a plasmid or phage. Bacterial cells are transfected or transformed with the plasmid vector DNA. Phage DNA can be infected with phage vector particles or transfected with naked phage DNA. The plasmid and phage DNA for the vectors are commercially available from numerous vendors known to those of ordinary skill in the art. Those of ordinary skill in the art know the molecular techniques and DNA vectors that are used in bacterial systems (137-141). In bacteria one messenger RNA can encode for one peptide (referred to as monocistronic) or several independent peptides (referred to as polycistronic). It is known to those of ordinary skill in the art that a portion of a polycistronic messenger RNA can be knocked-out (142) or that heterologous or exogenous genes can be expressed on a monocistronic or polycistronic messenger RNA (140, 141). Genes can be expressed by modification of bacterial DNA (genomic) through the use of knock-in, gene insertion, or by allelic exchange (143-148). Specific gene targeting has been used in bacteria using PCR-based methods (149) and CRISPR/Cas (150-152).

Expression in Algae and Microalgae

Protocols for transformation as well as commonly used vectors with control sequences include promoters for transcription initiation, optionally with an operator, together with ribosome binding site sequences for use in algae and microalgae are known to those of ordinary skill in the art (111, 153-164). Specific gene targeting systems have been used in algae including ZFNs (165) and transcription activator-like effector nucleases (TALENs) (166).

Transformation of Host Cells: Unicellular Organisms

Transformation of a unicellular organism can be accomplished in a wide variety of ways within the scope of a person of ordinary skill in the art (110, 112, 162, 167). Those of ordinary skill in the art can use different algal, diatom, fungal, yeast and bacteria gene transfer techniques that include, but not limited to, *Agrobacterium*-mediated (168) glass beads and polyethylene glycol (PEG) (169, 170), electroporation (171-174), microprojectile bombardment or ballistic particle acceleration (175-179), silicon carbide whisker methods (180, 181), viral infection (182, 183), or transposon/transposase complexes (184). Transformation can be targeted to organellular genomes (185). Other methods to edit, incorporate or move genes into bacteria, fungal, or algal genomes include, but are not limited to, Zinc-finger nucleases (ZFNs), transcription activator like effector nucleases (TALENs), or clustered regularly interspaced short palindromic repeats/Cas (CRISPR/Cas).

Suitable Unicellular Organisms

A wide variety of unicellular host cells may be used in the invention, including prokaryotic and unicellular eukaryotic host cells. These cells or organisms may include yeast, fungi, algae, microalgae, microbes, or unicellular photosynthetic organisms. Preferred host cells for this invention are bacteria including archaebacteria and eubacteria. Proteobacteria such as members of Aiphaproteobacteria, Betaproteobacteria, Gammaproteobacteria, Deltaproteobacteria, and Epsilonproteobacteria can host the invention. Other bacteria including methanotrophs, methylotrophs, or members of the genera *Methylobacterium*, *Methylobacterium*, *Methylomonas*, *Methylobacter*, *Methylococcus*, *Methylosinus*, *Methylocyctis*, *Methylomicrobium*, and *Methanomonas* (186) can be used with the invention. These include, but are not limited to, *Methylobacterium extorquens*, *Methylobacterium populi*, *Methylobacterium radiotolerans*, *Methylobacterium nodulans*, and *Methylobacterium* spp. Other methylotrophic bacteria include but are not limited to *Methylophilus*, *Methylobacillus*, *Methylobacterium*, *Hyphomicrobium*, *Xanthobacter*, *Bacillus*, *Paracoccus*, *Nocardia*, *Arthrobacter*, *Rhodopseudomonas*, and *Pseudomonas*. Some vectors developed for use in *Methylobacterium* include, but are not limited to, pCM62, pCM66, pCM80, pCM160, pHC41, pHC90, pHC91, pHC115, pLC 290, or pLC291. Other bacterial genera that can host the invention include, but are not limited to, *Bacillus*, *Salmonella*, *Lactococcus*, *Streptococcus*, *Brevibacterium* and Coryneform bacteria. Some specific bacterial species that can be used for the invention include, but are not limited to, *Bacillus subtilis*, *Brevibacterium ammoniagene*, *Corynebacterium crenatum*, *Corynebacterim pekinese*, *Corynebacterium glutamicumas*, *Erwinia citreus*, *Erwinia herbicola*, *Escherichia coli*, *Fusarium venenatum*, *Gluconobacter oxydans*, *Propionibacterium freudenreicheii*, and *Propionibacterium denitrificans* (187).

Unicellular algae, unicellular photosynthetic organisms, and microscopic algae (microphytes or microalgae) cells may be used in the invention. These include, but are not limited to diatoms, green algae (Chlorophyta), and members of the Euglenophyta, Dinoflagellata, Chrysophyta, Phaeophyta, red algae (Rhodophyta), Heterokontophyta, and Cyanobacteria. The invention can also be used to increase the taurine by binding taurine with a taurine binding protein or knocking out genes for taurine degradation that have been shown to synthesize taurine (52) or may have the capability to synthesize taurine (52). These include but are not limited to *Coccomyxa* species, *Chlorella* species, *Trebouxia impressa*, *Tetraselmis species*, *Chlamydomonas reinhardtii*, *Micromonas pusilla*, *Ostreococcus tauri*, *Navicula radiosa*, *Phaeodactylum tricornutum*, *Pseudo-nitzschia multiseries*, *Fragilariopsis cylindrus*, *Thalassiosira weissflogii*, *Nannochloropsis oceanica*, *Aureococcus anophagefferens*, *Saccharina japonica*, *Sargassum* species and *Bigelowiella natans*.

Protozoa that may be used in the invention include, but are not limited to, ciliates, amoebae and *flagellates*. Yeast and unicellular fungi that can be used include, but are not limited to, *Ashbya gossypii*, *Blakeslea trispora*, *Candida flareri*, *Eremothecium ashbyii*, *Mortierella isabellina*, *Pichia pastoris*, *Saccharomyces cerevisiae*, and *Saccharomyces pombe*.

Expression in Non Plant Eukaryotes

Protocols for transformation, as well as commonly used vectors, are known to those of ordinary skill in the art. Also known to those of ordinary skill in the art are control sequences that include promoters for transcription initiation and ribosome binding site sequences for use in unicellular eukaryotes. The present invention can be expressed in a variety of eukaryotic expression systems such as yeast and protozoa. The vectors usually have expression control sequences, such as promoters, an origin of replication, enhancer sequences, termination sequences, ribosome binding sites, RNA splice sites, polyadenylation sites, transcriptional terminator sequences, and selectable markers (188, 189). There are numerous vectors that can be used with the invention that are known to those of ordinary skill in the art and include, but are not limited to, pREP, pRIP, pD912, pD1201, pD1211, pD1221, pD1231, pYES2/NT, pYSG-IBA, or pESC-TRP. Synthesis of heterologous proteins and fermentation of products in yeast are known to those of ordinary skill in the art (190, 191). Protozoa that can be used include, but are not limited to, ciliates, amoebae and *flagellates*. Yeast and fungi that can be used with the invention and the molecular protocols for transformation, and the vectors required for expression of genes in these systems, are known to those of ordinary skill in the art (192-197). Also available are plasmid vectors, which may be integrative, autonomously replicating high copy-number vectors, or autonomously replicating low copy number vectors (198, 199). The most common vectors that complement a chromosomal mutation in the host include functional genes such as URA3, HISS, LEU2, TRP1 and LYS2. Specific gene editing or targeting has been used in unicellular fungi using PCR-based methods (200-202), Zinc-finger nucleases (ZFNs) (203), transcription activator like effector nucleases (TALENs) (204), and clustered regularly interspaced short palindromic repeats/Cas (CRISPR/Cas) (205, 206).

The present invention can be expressed in a variety of eukaryotic expression systems such as yeast, insect cell lines, and mammalian cells which are known to those of ordinary skill in the art. For each host system, suitable vectors are commercially available (e.g., Invitrogen, Startagene, GE Healthcare Life Sciences). The vectors usually have expression control sequences, such as promoters, an origin of replication, enhancer sequences, termination sequences, ribosome binding sites, RNA splice sites, polyadenylation sites, transcriptional terminator sequences, and selectable markers. Synthesis of heterologous proteins and fermentation of products in yeast are well known to those of ordinary skill in the art (190, 191). Yeast and fungi that can be used include, but are not limited to, *Ashbya gossypii, Blakeslea trispora, Candida flareri, Eremothecium ashbyii, Mortierella isabellina, Pichia pastoris, Saccharomyces cerevisiae* and *Saccharomyces* sp. Molecular protocols for transformation and the vectors required for expression in these systems are known to those of ordinary skill in the art (193, 194, 196, 207, 208).

Insect cell lines that include, but are not limited to, black-fly larvae, mosquito larvae, silkworm, armyworm, moth, and *Drosophila* cell lines can be used to express proteins of the present invention using baculovirus-derived vectors (209). In addition, mammalian cell lines can be used to express proteins of the present invention (210). A number of suitable host cell lines capable of expressing intact proteins have been developed in the art, and include the HEK293, BHK21, and CHO cell line.

A protein of the present invention, once expressed in any of the non-plant eukaryotic systems, can be isolated from the organism by lysing the cells and applying standard protein isolation techniques to the lysates or the pellets. The monitoring of the purification process can be accomplished by using western blot techniques, radioimmunoassay, or other standard immunoassay techniques.

Expression in Plants

Protocols for plant transformation, as well as commonly used vectors, are known to those of ordinary skill in the art. Also known to those of ordinary skill in the art are control sequences that include promoters for transcription initiation and ribosome binding site sequences for use in plants. A wide variety of promoters are known to those of ordinary skill in the art as are other regulatory elements that can be used alone or in combination with promoters. A wide variety of promoters that direct transcription in plants cells can be used in connection with the present invention. For purposes of describing the present invention, promoters are divided into two types, namely, constitutive promoters and non-constitutive promoters. Constitutive promoters are classified as providing for a range of constitutive expression. Thus, some are weak constitutive promoters, and others are strong constitutive promoters. Non-constitutive promoters include tissue-preferred promoters, tissue-specific promoters, cell-type specific promoters, and inducible-promoters.

Suitable Plant Promoters

Of particular interest in certain embodiments of the present invention are inducible-promoters that respond to various forms of environmental stresses, or other stimuli, including, for example, mechanical shock, heat, cold, salt, flooding, drought, salt, anoxia, pathogens, such as bacteria, fungi, and viruses, and nutritional deprivation, including deprivation during times of flowering and/or fruiting, and other forms of plant stress. For example, the promoter selected in alternate forms of the invention, can be a promoter that is induced by one or more of the following, but not limited to, abiotic stresses such as wounding, cold, desiccation, ultraviolet-B (211), heat shock (212) or other heat stress, drought stress or water stress. The promoter may further be one induced by biotic stresses including pathogen stress, such as stress induced by a virus (213) or fungi (214, 215), stresses induced as part of the plant defense pathway (216) or by other environmental signals, such as light (217), carbon dioxide (218, 219), hormones or other signaling molecules such as auxin, hydrogen peroxide and salicylic acid (220, 221), sugars and gibberellin (222) or abscisic acid and ethylene (223).

In other embodiments of the invention, tissue-specific promoters are used. Tissue-specific expression patterns as controlled by tissue- or stage-specific promoters that include, but is not limited to, fiber-specific, green tissue-specific, root-specific (224, 225), stem-specific, and flower-specific. Examples of the utilization of tissue-specific expression includes, but is not limited to, the expression in leaves of the desired peptide for the protection of plants against foliar pathogens, the expression in roots of the desired peptide for the protection of plants against root pathogens, and the expression in roots or seedlings of the desired peptide for the protection of seedlings against soil-borne pathogens. In many cases, however, protection against more than one type of pathogen may be sought, and expression in multiple tissues will be desirable.

Of particular interest in certain embodiments of the present invention seed-specific promoters are used. Examples of the utilization of seed-specific promoters for expression includes, but is not limited to, napin (226), sunflower seed-specific promoter (227, 228), phaseolin (229), beta-conglycinin (230), zein (231), and rice glutelin (232).

Although some promoters from dicotyledons have been shown to be operational in monocotyledons and vice versa, ideally dicotyledonous promoters are selected for expression in dicotyledons, and monocotyledonous promoters are selected for expression in monocotyledons. There are also promoters that control expression of genes in green tissue or for genes involved in photosynthesis from both monocotyledons and dicotyledons such as the maize phosphoenol carboxylase gene (233). A promoter selected can be an endogenous promoter, i.e. a promoter native to the species and or cell type being transformed. Alternatively, the promoter can be a foreign promoter, which promotes transcription of a length of DNA of viral, microbes, bacterial or eukaryotic origin, invertebrates, vertebrates including those from plants and plant viruses. For example, in certain preferred embodiments, the promoter may be of viral origin, including a cauliflower mosaic virus promoter (CaMV), such as CaMV 35S or19S, a figwort mosaic virus promoter (FMV 35S), or the coat protein promoter of tobacco mosaic virus (TMV). The promoter may further be, for example, a promoter for the small subunit of ribulose-1, 3-biphosphate carboxylase. Promoters of bacterial origin (microbe promoters) include the octopine synthase promoter, the nopaline synthase promoter and other promoters derived from native Ti plasmids (234).

The promoters may further be selected such that they require activation by other elements known to those of ordinary skill in the art, so that production of the protein encoded by the nucleic acid sequence insert may be regulated as desired. In one embodiment of the invention, a DNA construct comprising a non-constitutive promoter operably linked to a polynucleotide encoding the desired polypeptide of the invention is used to make a transformed plant that selectively increases the level of the desired polypeptide of the invention in response to a signal. The term "signal" is used to refer to a condition, stress or stimulus that results in or causes a non-constitutive promoter to direct expression of a coding sequence operably linked to it. To make such a plant in accordance with the invention, a DNA construct is provided that includes a non-constitutive promoter operably linked to a polynucleotide encoding the desired polypeptide of the invention. The construct is incorporated into a plant genome to provide a transformed plant that expresses the polynucleotide in response to a signal.

In alternate embodiments of the invention, the selected promoter is a tissue-preferred promoter, a tissue-specific promoter, a cell-type-specific promoter, an inducible promoter or other type of non-constitutive promoter. It is readily apparent that such a DNA construct causes a plant transformed thereby to selectively express the gene for the desired polypeptide of the invention. Therefore, under specific conditions or in certain tissue- or cell-types the desired polypeptide will be expressed. The result of this expression in the plant depends upon the activity of the promoter and in some cases the conditions of the cell or cells in which it is expressed.

It is understood that the non-constitutive promoter does not continuously produce the transcript or RNA of the invention. But in this embodiment the selected promoter for inclusion of the invention advantageously induces or increases transcription of gene for the desired polypeptide of the invention in response to a signal, such as an environmental cue or other stress signal including biotic and/or abiotic stresses or other conditions.

Suitable Plant Terminators

In addition to the selection of a suitable promoter, the DNA constructs require an appropriate transcriptional terminator to be attached downstream of the desired gene of the invention for proper expression in plants. Terminators are typically located downstream (3') of the gene, after the stop codon (TGA, TAG or TAA). Terminators play an important role in the processing and stability of RNA as well as in translation. Most, but not all terminators, contain a polyadenylation sequence or cleavage site. Examples of specific polyadenylation sequences are AAUAAA or AAUAAU. These sequences are known as the near upstream elements (NUEs) (235). NUEs usually reside approximately 30 bp away from a GU-rich region (236-238) which is known as far upstream elements (FUEs). The FUEs enhance processing at the polyadenylation sequence or cleavage site, which is usually a CA or UA in a U-rich region (239). Within the terminator, elements exist that increase the stability of the transcribed RNA (240-242) and may also control gene expression (124, 243).

Several terminators are available and known to persons of ordinary skill in the art. These include, but are not limited to, the tml from CaMV and E9 from rbcS. Another example of a terminator sequence is the polyadenylation sequence from the bovine growth hormone gene. A wide variety of available terminators known to function in plants can be used in the context of this invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Enhancer sequences cooperate with the promoter to increase expression of the polynucleotide insert coding sequence. Enhancers can stimulate promoter activity in host cell. RNA splice sites are sequences that ensure accurate splicing of the transcript. Selectable markers usually confer resistance to an antibiotic, herbicide or chemical or provide color change, which aid the identification of transformed organisms. The vectors also include a RNA stability signal, which are 3'-regulatory sequence elements that increase the stability of the transcribed RNA (241).

Suitable Plant Vectors

A wide variety of vectors may be employed to transform a plant, plant cell or other cells with a construct made or selected in accordance with the invention, including high- or low-copy number plasmids, phage vectors and cosmids. Such vectors, as well as other vectors, are well known in the art. Representative T-DNA vector systems (234, 244) and numerous expression cassettes and vectors and in vitro culture methods for plant cell or tissue transformation and regeneration of plants are known and available (245). The vectors can be chosen such that operably linked promoter and polynucleotides that encode the desired polypeptide of the invention are incorporated into the genome of the plant. Although the preferred embodiment of the invention is expression in plants or plant cells, other embodiments may include expression in prokaryotic or eukaryotic photosynthetic organisms, yeast, fungi, algae, microalgae, microbes, invertebrates or vertebrates.

It is known by those of ordinary skill in the art that there exist numerous expression systems available for expression of a nucleic acid encoding a protein of the present invention. There are many commercially available recombinant vectors to transform a host plant or plant cell. Standard molecular and cloning techniques (89, 92, 134) are available to make a recombinant expression cassette that expresses the polynucleotide that encodes the desired polypeptide of the invention. No attempt to describe in detail the various methods known for the expression of proteins in prokaryotes or eukaryotes will be made. In brief, the expression of isolated nucleic acids encoding a protein of the present invention will typically be achieved by operably linking, for example, the DNA or cDNA to a promoter, followed by incorporation into an expression vector. The vectors can be suitable for replication and integration in either prokaryotes or eukaryotes. Typical expression vectors contain transcription and translation terminators, initiation sequences, and promoters useful for regulation of the expression of the DNA encoding a protein of the present invention. To obtain high-level expression of a cloned gene, it is desirable to construct expression vectors that contain, at the minimum, a strong promoter such as ubiquitin to direct transcription, a ribosome-binding site for translational initiation, and a transcription/translation terminator.

Transit Peptides

A wide variety of plastid transit peptides are known to those of ordinary skill in the art that can be used in connection with the present invention. Suitable transit peptides which can be used to target any sCS/PLP-DC, TauA, or TauK polypeptide to a plastid include, but are not limited to, those described herein and in U.S. Pat. No. 8,779,237 (246), U.S. Pat. No. 8,674,180 (247), U.S. Pat. No. 8,420,888 (248), and U.S. Pat. No. 8,138,393 (249) and in Lee et al. (250) and von Heijne et al. (251). Identification and use of chloroplast plastid targeting sequences for algae are known to those of ordinary skill in the art (252-255). Cloning a nucleic acid sequence that encodes a transit peptide upstream and in-frame of a nucleic acid sequence that encodes a polypeptide involves standard molecular techniques that are known to those of ordinary skill in the art. In addition, The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (256-259), C-terminus (260, 261) or internal (262-264) or tertiary structure (264). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (265, 266), iPSORT (267), SignalP (268), PrediSi (269), ELSpred (270) HSLpred (271) and PSLpred (272), MultiLoc (273), SherLoc (274), ChloroP (275), MITOPROT (276), Predotar (277) and 3D-PSSM (278). Additional methods and protocols are discussed in the literature (273).

Plant Transformation

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (279).

Those of ordinary skill in the art can use different plant gene transfer techniques found in references for, but not limited to, the electroporation, (280-284) microinjection, (285, 286) lipofection, (287) liposome or spheroplast fusions, (288-290) *Agrobacterium*, (291) direct gene transfer, (292) T-DNA mediated transformation of monocots, (293) T-DNA mediated transformation of dicots, (294, 295) microprojectile bombardment or ballistic particle acceleration, (296-299) chemical transfection including $CaCl_2$ precipitation, polyvinyl alcohol, or poly-L-ornithine, (300) silicon carbide whisker methods, (301, 302) laser methods, (303, 304) sonication methods, (305-307) polyethylene glycol methods, (308) vacuum infiltration (309) and transbacter. (310) Other methods to edit, incorporate or move genes into plant genomes include, but are not limited to, Zinc-finger nucleases (ZFNs) (311, 312) transcription activator like effector nucleases (TALENs) and clustered regularly interspaced short palindromic repeats/Cas (CRISPR/Cas) (313-316).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

Suitable Hosts and Plants

A wide variety of host cells may be used in the invention, including prokaryotic and eukaryotic host cells. These cells or organisms may include yeast, fungi, algae, microalgae, microbes, invertebrate, vertebrates or photosynthetic organisms. Preferred host cells are eukaryotic, preferably plant cells, including such as those derived from monocotyledons or dicotyledons, including, acacia, alfalfa, algae, aneth, apple, apricot, artichoke, arugula, asparagus, avocado, banana, barley, beans, beech, beet, bent grass, Bermuda grass, blackberry, blueberry, Blue grass, broccoli, brussel sprouts, bush beans, cabbage, camelina, canola, cantaloupe, carrot, cassava, cauliflower, celery, cherry, chicory, cilantro, citrus, clementines, coffee, corn, cotton, cucumber, duckweed, Douglas fir, eggplant, endive, escarole, eucalyptus, fennel, fescue, figs, forest trees, garlic, gourd, grape, grapefruit, honey dew, jicama, kiwifruit, lettuce, leeks, lemon, lime, Loblolly pine, maize, mango, melon, mushroom, nectarine, nut, oat, okra, onion, orange, ornamental plants, papaya, parsley, pea, peach, peanut, pear, pepper, persimmon, pine, pineapple, plantain, plum, pomegranate, poplar, potato, pumpkin, quince, radiata pine, radicchio, radish, rapeseed, raspberry, rice, rye, rye grass, seaweed, scallion, sorghum, Southern pine, soybean, spinach, squash, strawberry, sugarbeet, sugarcane, sunflower, sweet potato, sweetgum, switchgrass, tangerine, tea, tobacco, tomato, turf, turnip, a vine, watermelon, wheat, yam, and zucchini.

Plastid Transformation: Unicellular Organisms and Plants

The invention can be targeted for transformation into the chloroplast. Chloroplast targeted transformation systems for algae and plants are known by those of ordinary skill in the art (119, 317).

Gene Silencing by Mutagenesis or Using Recombinant Technologies

Genetic modification to silence or inactivate genes or their corresponding gene products of unicellular organisms can be conducted by radiation-, chemical- or UV-based mutagenesis followed by specific screening for biochemical traits or pathways (167, 318-322). Radiation-based mutations can silence or inactive a gene or the corresponding gene product by DNA breakage and repair. Chemical- or UV-based mutations usually result in single DNA basepair changes. Mutations can silence or inactive a gene or the corresponding gene product by one of the following: (1) introduction of a frame-shift mutation; (2) introduction of premature stop codon; (3) interference with the ability of the promoter region sequence to direct the transcription of the desired nucleotide sequence, (4) interference with the ability of the desired nucleotide sequence to be transcribed by the promoter sequence region, or (5) introduction of an amino acid substitution in the gene product to reduce or inhibit activity (enzymatic or binding) or interfere with the function of the gene product.

Targeted gene silencing or knockouts can be made in unicellular organisms using phage or viruses (116, 323-327), transposons (184, 328-331), PCR-assisted targeting (200-202, 332), recombinases or by allelic exchange (143-148), targeted and random bacterial gene disruptions using a group II intron (Targetron) (333, 334), ZNFs (203), TALENs (204), CRISPER-Cas9 or clustered regularly interspaced short palindromic repeats interference (CRISPi) (150-152, 205, 206, 335, 336). In addition, RNA-mediated methods (337-342), or regulatory RNAs (343-345) have been used to silence or suppress gene expression in unicellular organisms and these techniques and protocols are well known to one with ordinary skill in the art.

One of ordinary skill in the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are known to those of ordinary skill in the art and include, for example, a methionine added at the amino terminus to provide an initiation site, additional amino acids (tags) placed on either terminus to create a tag, additional nucleic acids to insert a restriction site or a termination.

In addition to the selection of a suitable promoter, the DNA constructs require an appropriate transcriptional terminator to be attached downstream of the desired gene of the invention for proper expression in unicellular organisms. Several such terminators are available and known to persons of ordinary skill in the art. These include, but are not limited to, the tml from CaMV and E9 from rbcS. A variety of available terminators known to function in unicellular organisms can be used in the present invention. Vectors may also have other control sequence features that increase their suitability. These include an origin of replication, enhancer sequences, ribosome binding sites, RNA splice sites, polyadenylation sites, selectable markers and RNA stability signal. Origin of replication is a gene sequence that controls replication of the vector in the host cell. Selectable markers usually confer resistance to an antibiotic, herbicide or chemical or provide color change, which aid the identification of transformed organisms. The vectors may also include a RNA stability signal, which are 3'-regulatory sequence elements that increase the stability of the transcribed RNA (240, 241).

In addition, polynucleotides that encode an sCS/PLP-DC can be placed in the appropriate vector used to transform unicellular organisms. The polypeptide can be expressed and then isolated from transformed cells, or metabolites can be synthesized and isolated from the transformed cells. Such transgenic organisms can be harvested, and subjected to large-scale protein or metabolite (taurine) extraction and purification techniques.

The vectors may include another polynucleotide insert that encodes a peptide or polypeptide and used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional sCS/PLP-DC, TauA, or TauK to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the vacuole, chloroplast (not in fungi), mitochondrion, peroxisomes, secretory pathway, lysosome, endoplasmic reticulum, nucleus or Golgi apparatus in fungi or algae. There are specific signal polypeptides or signal sequences to direct peptide transport to the periplasmic space in bacteria.(346-348) A signal polypeptide or signal sequence is usually at the amino terminus and normally absent from the mature protein due to protease that removes the signal peptide when the polypeptide reaches its final destination. Signal sequences can be a primary sequence located at the N-terminus (251, 257-259), C-terminus (260, 261) or internal (262-264) or tertiary structure (264). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (265, 266), iPSORT (267), SignalP (268), PrediSi (269), ELSpred (270) HSLpred (271) and PSLpred (272), MultiLoc (273), SherLoc (274), ChloroP (275), MITOPROT (276), Predotar (277) 3D-PSSM (278) and PredAlgo. (255) Additional methods and protocols are discussed in the literature (273).

One of ordinary skill to the art recognizes that modifications could be made to a protein of the present invention without diminishing its biological activity. Some modifications may be made to facilitate the cloning, expression, targeting or to direct the location of the polypeptide in the host, or for the purification or detection of the polypeptide by the addition of a "tag" as a fusion protein. Such modifications are well known to those of skill in the art and include, for example, a methionine added at the amino terminus to provide an initiation site, additional amino acids (tags) placed on either terminus to create a tag, additional nucleic acids to insert a restriction site or a termination.

In addition, polynucleotides that encode a sCS/PLP-DC can be placed in the appropriate plant expression vector used to transform plant cells. The polypeptide can then be isolated from plant callus or the transformed cells can be used to regenerate transgenic plants. Such transgenic plants can be harvested, and the appropriate tissues can be subjected to large-scale protein extraction and purification techniques.

The vectors may include another polynucleotide insert that encodes a peptide or polypeptide used as a "tag" to aid in purification or detection of the desired protein. The additional polynucleotide is positioned in the vector such that upon cloning and expression of the desired polynucleotide a fusion, or chimeric, protein is obtained. The tag may be incorporated at the amino or carboxy terminus. If the vector does not contain a tag, persons with ordinary skill in the art know that the extra nucleotides necessary to encode a tag can be added with the ligation of linkers, adaptors, or spacers or by PCR using designed primers. After expression of the peptide the tag can be used for purification using affinity chromatography, and if desired, the tag can be cleaved with an appropriate enzyme. The tag can also be maintained, not cleaved, and used to detect the accumulation of the desired polypeptide in the protein extracts from the host using western blot analysis. In another embodiment, a vector includes the polynucleotide for the tag that is fused in-frame to the polynucleotide that encodes a functional sCS/PLP-DC to form a fusion protein. The tags that may be used include, but are not limited to, Arg-tag, calmodulin-binding peptide, cellulose-binding domain, DsbA, c-myc-tag, glutathione S-transferase, FLAG-tag, HAT-tag, His-tag, maltose-binding protein, NusA, S-tag, SBP-tag, Strep-tag, and thioredoxin (Trx-Tag). These are available from a variety of manufacturers Clontech Laboratories, Takara Bio Company GE Healthcare, Invitrogen, Novagen Promega and QIAGEN.

The vector may include another polynucleotide that encodes a signal polypeptide or signal sequence ("subcellular location sequence") to direct the desired polypeptide in the host cell, so that the polypeptide accumulates in a specific cellular compartment, subcellular compartment, or membrane. The specific cellular compartments include the apoplast, vacuole, plastids chloroplast, mitochondrion, peroxisomes, secretory pathway, lysosome, endoplasmic reticulum, nucleus or Golgi apparatus. A signal polypeptide or signal sequence is usually at the amino terminus and normally absent from the mature protein due to protease that removes the signal peptide when the polypeptide reaches its final destination. Signal sequences can be a primary sequence located at the N-terminus (256-259), C-terminus (260, 261) or internal (262-264) or tertiary structure (264). If a signal polypeptide or signal sequence to direct the polypeptide does not exist on the vector, it is expected that those of ordinary skill in the art can incorporate the extra nucleotides necessary to encode a signal polypeptide or signal sequence by the ligation of the appropriate nucleotides or by PCR. Those of ordinary skill in the art can identify the nucleotide sequence of a signal polypeptide or signal sequence using computational tools. There are numerous computational tools available for the identification of targeting sequences or signal sequence. These include, but are not limited to, TargetP (265, 266), iPSORT (267), SignalP (349), PrediSi (269 04), ELSpred (270) HSLpred (272) and PSLpred (272), MultiLoc (273), SherLoc (274), ChloroP (275), MITOPROT (276), Predotar (277) and 3D-PSSM (278). Additional methods and protocols are discussed in the literature (273).

Transformation of Host Cell

Transformation of a plant can be accomplished in a wide variety of ways within the scope of a person of ordinary skill in the art. In one embodiment, a DNA construct is incorporated into a plant by (i) transforming a cell, tissue or organ from a host plant with the DNA construct; (ii) selecting a transformed cell, cell callus, somatic embryo, or seed which contains the DNA construct; (iii) regenerating a whole plant from the selected transformed cell, cell callus, somatic embryo, or seed; and (iv) selecting a regenerated whole plant that expresses the polynucleotide. Many methods of transforming a plant, plant tissue or plant cell for the construction of a transformed cell are suitable. Once transformed, these cells can be used to regenerate transgenic plants (279).

Those of ordinary skill in the art can use different plant gene transfer techniques found in references for, but not limited to, the electroporation (280-284), microinjection (285, 286), lipofection (287), liposome or spheroplast fusions (288-290), Agrobacterium (291), direct gene transfer (292), T-DNA mediated transformation of monocots (293), T-DNA mediated transformation of dicots (294, 295), microprojectile bombardment or ballistic particle acceleration (175, 298, 299), chemical transfection including $CaCl_2$ precipitation, polyvinyl alcohol, or poly-L-ornithine (300), silicon carbide whisker methods (301, 302), laser methods (303, 304), sonication methods (305-307), polyethylene glycol methods (308), and vacuum infiltration (309) and transbacter (310). Other methods to edit, incorporate or move genes into plant genomes are found in references of, but not limited to, Zinc-finger nucleases (ZFNs), transcription, activator like effector nucleases (TALENs) and clustered regularly interspaced short palindromic repeats)-Cas (CRISPR/Cas) (311, 312, 350-353).

In one embodiment of the invention, a transformed host cell may be cultured to produce a transformed plant. In this regard, a transformed plant can be made, for example, by transforming a cell, tissue or organ from a host plant with an inventive DNA construct; selecting a transformed cell, cell callus, somatic embryo, or seed which contains the DNA construct; regenerating a whole plant from the selected transformed cell, cell callus, somatic embryo, or seed; and selecting a regenerated whole plant that expresses the polynucleotide.

A wide variety of host cells may be used in the invention, including prokaryotic and eukaryotic host cells. These cells or organisms may include yeast, fungi, algae, microalgae, microbes, invertebrate, vertebrates or photosynthetic organisms. Preferred host cells are eukaryotic, preferably plant cells, such as those derived from monocotyledons or dicotyledons.

One embodiment of the invention (Embodiment Number 1) is a method for the increased production of taurine in an organism by the following steps:
1. operably link a promoter to the 5' end of the polynucleotide for a functional CS or CBS that is linked in-frame, with no linker, with a polynucleotide for a functional DC (using AAAD, GAD, BABD, or SAD) operably linked to a terminator;
2. insert the sCS/PLP-DC polynucleotide construct (from Step 1, Embodiment Number 1) into a vector; and
3. transform the vector containing the sCS/PLP-DC protein (from Step 2, Embodiment Number 1) construct into an organism.

Another embodiment of the invention (Embodiment Number 2) is a method for the increased production of taurine in an organism by the following steps:
1. operably link a promoter to the 5' end of the polynucleotide for functional CS or CBS that is linked in-frame with a short, 3 to 66, polynucleotide (linker) to the 5' end of the polynucleotide for a functional decarboxylase (using AAAD, GAD, BABD, or SAD) operably linked to a terminator;
2. insert the sCS/PLP-DC polynucleotide construct (from Step 1, Embodiment Number 2) into a vector; and;
3. transform the vector containing the sCS/PLP-DC protein construct (from Step 2, Embodiment number 2) into an organism.

Another embodiment of the invention (Embodiment Number 3) is a method for the increased production of taurine in an organism by the following steps:
1. operably link a promoter to the 5' end of the polynucleotide for a truncated functional Tau-binding protein (using TauA or TauK) operably linked to a terminator;
2. insert the taurine-binding protein polynucleotide construct (from Step 1, Embodiment Number 2) into a vector containing the functional sCS/PLP-DC protein construct (from Step 2, Embodiment Number 1 or from Step 2, Embodiment Number 2); and 3. transform the vector containing the sCS/PLP-DC and taurine-binding protein (from Step 2, Embodiment Number 3) constructs into an organism.

Another embodiment of the invention (Embodiment Number 4) is a method for the increased production of taurine in a unicellular organism by the following steps:
1. knockout the gene for a taurine degradation enzyme using chemical or genetic means by replacement or deletion of a promoter, a portion of the coding region, or terminator to one of the following genes, TauX, TauY, TauD, Tpa, SsuD, or SsuE, using a pSC101ts-sacB, allelic exchange or λ-red recombinase method in a unicellular organism; and
2. transform the vector containing a functional sCS/PLP-DC protein construct (from Step 2, Embodiment Number 1 or from Step 2, Embodiment Number 2) into the unicellular organism with the mutation or knocked-out TauX, TauY, TauD, Tpa, SsuD, or SsuE gene (from Step 1, Embodiment Number 4).

Another embodiment of the invention (Embodiment Number 5) is a method for the increased production of taurine in a unicellular organism by the following step:
1. transform the vector containing the sCS/PLP-DC and taurine-binding protein construct (from Step 2, Embodiment Number 3) into the unicellular organism with the mutated or knocked-out TauX, TauY, TauD, Tpa, SsuD, or SsuE gene (from Step 1, Embodiment Number 4).

Another embodiment of the invention (Embodiment Number 6) is a method for the increased production of taurine in a unicellular organism by the following steps:
1. introduce a mutation or knock out the gene for the transcription regulator of the taurine degradation pathway(s) using chemical or genetic means by replacement or deletion of a promoter, a portion of the coding region, or terminator to one of the following genes, cbl, or TauR genes using a pSC101ts-sacB, allelic exchange or k-red recombinase method and select the mutant or knocked-out unicellular organism; and
2. transform the vector containing the functional sCS/PLP-DC protein construct (from Step 2, Embodiment Number 1 or from Step 2, Embodiment Number 2) into the unicellular organism with the mutated or knocked-out cbl or TauR gene (from Step 1, Embodiment Number 6).

Another embodiment of the invention (Embodiment Number 7) is a method for the increased production of taurine in a unicellular organism by the following step:
1. transform the vector containing the sCS/PLP-DC protein and taurine-binding protein construct (from Step 2, Embodiment Number 3) into the unicellular organism with the mutated or knocked-out cbl or TauR gene (from Step 1, Embodiment Number 6).

Once transformed, the organism may be treated with other "active agents" either prior to or during the growth to further increase production of taurine. "Active agent," as used herein, refers to an agent that has a beneficial effect on the taurine or amino acid production by the unicellular organism. Some of these agents may be precursors of end products for the reaction catalyzed by sCS/PLP-DC. These compounds could promote growth, development, biomass and yield, and change in metabolism. A host of molecules could be used to activate sCS/PLP-DC. These include but are not limited to (1) the twenty amino acids that are involved in protein synthesis, (2) the sulfur containing compounds such as sulfite, sulfide, hydrogen sulfide, sulfate, taurine, hypotaurine, cysteate, 2-sulfacetaldehyde, homotaurine, homocysteine, cystathionine, N-acetyl thiazolidine 4 carboxylic acid (ATCA), glutathione, or bile, (3) other non-protein amino acids, such as GABA, citrulline and ornithine, and (4) other nitrogen containing compounds such as polyamines. Depending on the type of gene construct or recombinant expression cassette, other metabolites and nutrients may be used to activate sCS/PLP-DC. These include, but are not limited to, sugars, carbohydrates, lipids, oligopeptides, mono- (glucose, arabinose, fructose, xylose, and ribose) di- (sucrose and trehalose) and polysaccharides, carboxylic acids (succinate, malate and fumarate) and nutrients such as phosphate, molybdate, or iron.

In some embodiments, properties of a transgenic unicellular organism are altered using an agent which increases sulfur concentration in the cell, such as sulfur, sulfite, sulfide, hydrogen sulfide, sulfate, taurine, hypotaurine, homotaurine, cysteate, 2-sulfacetaldehyde, N-acetyl-thiazolidine-4-carboxylic acid (ATCA), glutathione, and bile. In other embodiments, the agent increases nitrogen concentration. Amino acids either naturally occurring in proteins (e.g., cysteine, methionine, glutamate, glutamine, serine, alanine, or glycine) or which do not naturally occur in proteins (e.g., GABA, citrulline, or ornithine) and/or polyamines can be used for this purpose.

Pharmaceutical Compositions

The invention provides pharmaceutical compositions that comprise extracts of one or more transgenic organisms described above. Extracts containing hypotaurine or taurine can be used to synthesize or manufacture taurine derivatives (354, 355), taurine-conjugates (356) or taurine-polymers (357) that may have a wide range of commercial and medicinal applications (358). Some taurine derivatives can function as organogelators (359) or dyes (360) and can be used in nanosensor synthesis (361). Some taurine derivatives have anticonvulsant (354) or anti-cancer (362) properties. Other taurine derivatives are used in the treatment of alcoholism (363, 364). Taurine-conjugated carboxyethyl-ester-polyrotaxanes increase anticoagulant activity (365). Taurine-containing polymers may increase wound healing (366, 367). Taurine linked polymers such as poly gamma-glutamic acid-sulfonates are biodegradable and may have applications in the development of drug delivery systems, environmental materials, tissue engineering, and medical materials (368). Extracts from taurine-containing cells may be used in pharmaceutical or medicinal compositions to deliver taurine, hypotaurine, taurine-conjugates, or taurine-polymers for use in the treatment of congestive heart failure, high blood pressure, hepatitis, high cholesterol, fibrosis, epilepsy, autism, attention deficit-hyperactivity disorder, retinal degeneration, diabetes, and alcoholism. It is also used to improve mental performance and as an antioxidant.

Pharmaceutically acceptable vehicles of taurine, taurine derivatives, taurine-conjugates, or taurine-polymers are tablets, capsules, gel, ointment, film, patch, powder or dissolved in liquid form.

Nutritional Supplements and Feeds

Transgenic cells containing hypotaurine or taurine may be consumed or used to make extracts for nutritional supplements. Transgenic cells that contain hypotaurine or taurine may be used for human consumption. Extracts from transgenic cells containing hypotaurine or taurine may be used as nutritional supplements, as an antioxidant or to improve physical or mental performance. The extracts may be used in the form of a liquid, powder, capsule or tablet.

Transgenic cells containing hypotaurine or taurine may be used as fish or animal feed or used to make extracts for the supplementation of animal feed. Transgenic cells that contain hypotaurine or taurine may be used as animal or fish feed. Extracts from transgenic cells containing taurine may be used as feed supplements in the Rhin of a liquid, powder, capsule or tablet.

Enhancer of Plant Growth or Yield

Transgenic cells that contain hypotaurine or taurine may be used as an enhancer for plant growth or yield. Extracts from transgenic cells containing hypotaurine or taurine may be used as plant enhancers in the form of a liquid, powder, capsule or tablet.

Fermentation and Taurine Purification

Taurine could be purified from the cells or from extracts of the cells or from media from which the cells were grown. The extracted taurine could be used as a food or feed additive, nutrient, pharmaceutical or an enhancer of plant growth or yield. Prokaryotic or eukaryotic cells with the invention can be grown in culture or by fermentation to produce hyptotaurine or taurine. Methods to produce chemical compounds by batch fermentation, fed-batch fermentation, continuous fermentation or in tanks or ponds are well known to one with ordinary skill in the art (187, 369-379).

Methods such as centrifugation, filtration, crystallization, ion exchange, electrodialysis, solvent extraction, decolorization or evaporation to purify or separate chemical compounds from cells or from liquids or media that grew cells are well known to one with ordinary skill in the art. These methods can be used by one with ordinary skill in the art to purify or separate taurine from cells with the invention, or from liquids or media from which cell suspensions or cell cultures containing the invention were grown (370, 372, 373, 380-383).

Definitions

The term "polynucleotide" refers to a natural or synthetic linear and sequential array of nucleotides and/or nucleosides, including deoxyribonucleic acid, ribonucleic acid, and derivatives thereof. It includes chromosomal DNA, self-replicating plasmids, infectious polymers of DNA or RNA and DNA or RNA that performs a primarily structural role. Unless otherwise indicated, nucleic acids or polynucleotide are written left to right in 5' to 3' orientation, Nucleotides are referred to by their commonly accepted single-letter codes. Numeric ranges are inclusive of the numbers defining the range.

The terms "amplified" and "amplification" refer to the construction of multiple copies of a nucleic acid sequence or multiple copies complementary to the nucleic acid sequence using at least one of the nucleic acid sequences as a template. Amplification can be achieved by chemical synthesis using any of the following methods, such as solid-phase phosphoramidate technology or the polymerase chain reaction (PCR). Other amplification systems include the ligase chain reaction system, nucleic acid sequence based amplification, Q-Beta Replicase systems, transcription-based amplification system, and strand displacement amplification. The product of amplification is termed an amplicon.

As used herein "promoter" includes reference to a region of DNA upstream from the start of transcription and involved in recognition and binding of RNA polymerase, either I, II or III, and other proteins to initiate transcription. Promoters include necessary nucleic acid sequences near the start site of transcription, such as, in the case of a polymerase II type promoter, a TATA element. A promoter also optionally includes distal enhancer or repressor elements, which can be located as far as several thousand base pairs from the start site of transcription. In bacteria, the promoter includes a Shine-Dalgarno or ribosomal binding site that can include the sequence AGGAGG (−35 box) and a Pribnow box or RNA polymerase binding site that can include the sequence TATAAT (−10 box).

The term "algal promoter" refers to a promoter capable of initiating transcription in algal cells.

The term "foreign promoter" refers to a promoter, other than the native, or natural, promoter, which promotes transcription of a length of DNA of viral, bacterial or eukaryotic origin, including those from microbes, plants, plant viruses, invertebrates or vertebrates.

The term "microbe" refers to any microorganism (including both eukaryotic and prokaryotic microorganisms), such as bacteria, fungi, yeast, bacteria, algae and protozoa, as well as other unicellular organisms such as yeast, unicellular algae and unicellular fungi.

The term "constitutive" refers to a promoter that is active under most environmental and developmental conditions, such as, for example, but not limited to, the CaMV 35S promoter.

The term "inducible promoter" refers to a promoter that is under chemical (including biomolecules such as sugars, organic acids or amino acids) or environmental control.

The terms "encoding" and "coding"" refer to the process by which a polynucleotide, through the mechanisms of transcription and translation, provides the information to a cell from which a series of amino acids can be assembled into a specific amino acid sequence to produce a functional polypeptide, such as, for example, an active enzyme or ligand binding protein.

The terms "polypeptide," "peptide," "protein" and "gene product" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. Amino acids may be referred to by their commonly known three-letter or one-letter symbols. Amino acid sequences are written left to right in amino to carboxy orientation, respectively. Numeric ranges are inclusive of the numbers defining the range.

The terms "residue," "amino acid residue," and "amino acid" are used interchangeably herein to refer to an amino acid that is incorporated into a protein, polypeptide, or peptide. The amino acid may be a naturally occurring amino acid and may encompass known analogs of natural amino acids that can function in a similar manner as the naturally occurring amino acids.

The term "degradation" in reference to the "taurine degradation pathway", "taurine degradation enzymes", "taurine degradation system", and "taurine degradation proteins" refers to the process of breakdown, catabolism, or dissimilation of taurine.

The terms "sulfinoalanine decarboxylase" and "SAD" refer to the protein (4.1.1.29) that catalyzes the following reaction:

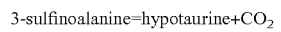

3-sulfinoalanine=hypotaurine+$CO_2$

NOTE: SAD is another name for cysteine-sulfinate decarboxylase, L-cysteine sulfinic acid decarboxylase, cysteine-sulfinate decarboxylase, CADCase/CSADCase, CSAD, cysteic decarboxylase, cysteine sulfinic acid decarboxylase, cysteine sulfinate decarboxylase, sulfoalanine decarboxylase, sulphinoalanine decarboxylase, and 3-sulfino-L-alanine carboxy-lyase.

NOTE: the SAD reaction is also catalyzed by GADL1 (4.1.1.15) (glutamic acid decarboxylase like 1). Although called GADL1 the enzyme has been shown to catalyze the SAD reaction (384, 385).

Other names for hypotaurine are 2-aminoethane sulfinate, 2-aminoethylsulfinic acid, and 2-aminoethanesulfinic acid.

Other names for taurine are 2-aminoethane sulfonic acid, aminoethanesulfonate, L-taurine, taurine ethyl ester, and taurine ketoisocaproic acid 2-aminoethane sulfinate.

The terms "taurine-pyruvate aminotransferase" and "TPAT" refer to the protein (EC 2.6.1.77) that catalyzes the following reaction:

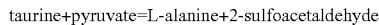
taurine+pyruvate=L-alanine+2-sulfoacetaldehyde

TPAT is another name for taurine transaminase or taurine transaminase aminotransferase The term "Tpa" refers to the gene that encodes TPAT.

The terms "taurine dehydrogenase" and "TDH" refer to the protein (EC:1.4.99.2) that catalyzes the following reaction:

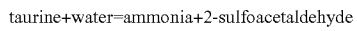
taurine+water=ammonia+2-sulfoacetaldehyde

TDH is another name for taurine:oxidoreductase, taurine: ferricytochrome-c oxidoreductase, The term "TauX" or "TauI" refers to the genes that encode for the small and large subunits of TDH, respectively.

The tell "taurine dioxygenase" and "TDO" refer to the protein (EC:1.14.11.17) that catalyzes the following reaction:

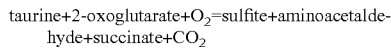
taurine+2-oxoglutarate+$O_2$=sulfite+aminoacetaldehyde+succinate+$CO_2$ TDO is another name for 2-aminoethanesulfonate dioxygenase, alpha-ketoglutarate-dependent taurine dioxygenase, taurine, or 2-oxoglutarate:$O_2$ oxidoreductase.

2-oxoglutarate is another name for alpha-ketoglutarate.

The term "TauD" refers to the gene that encodes TDO.

The term "two-component alkanesulfonate monooxygenase" or "2CASM" that catalyzes the following reaction:

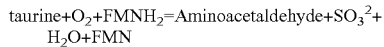
taurine+$O_2$+$FMNH_2$=Aminoacetaldehyde+$SO_3^{2-}$+$H_2O$+FMN or

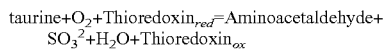
taurine+$O_2$+Thioredoxin$_{red}$=Aminoacetaldehyde+$SO_3^{2-}$+$H_2O$+Thioredoxin$_{ox}$ The term "SssuDE", "SsuD" or "SsuE" refers to the genes that encode the two-component alkanesulfonate monooxygenase (2CASM).

The terms "cysteine synthetase" and "CS" refer to the protein (EC:2.5.1.47) that catalyzes the following reaction:

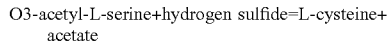
O3-acetyl-L-serine+hydrogen sulfide=L-cysteine+acetate

The terms "cystathionine-β-synthase" and "CBS" refer to the protein (EC:4.2.1.22) that catalyzes the following reaction:

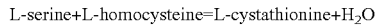
L-serine+L-homocysteine=L-cystathionine+$H_2O$

The terms "cysteine synthetase/PLP decarboxylase" and "CS/PLP-DC" refer to the protein that that forms taurine from: sulfur containing precursors including but not limited to sulfate, sulfite, hypotaurine, cysteamine, 3-sulfinoalanine, cysteine, sulfoacetaldehyde, cysteate, homocysteine or cystathionine.

The term "functional" with reference to sCS/PLP-DC refers to peptides, proteins or enzymes made synthetically, by gene fusion, gene shuffling or directed evolution that catalyzes the CS/PLP-DC reaction.

The term "decarboxylase" refers to enzymes that that catalyzes the removal of a carboxyl group from an organic molecule or the decarboxylation of a particular organic molecule examples of decarboxylases include but are not limited to; sulfinoalanine decarboxylase, glutamate decarboxylase, aromatic amino acid decarboxylase, 2,4-diaminobutyrate decarboxylase, acetoacetate decarboxylase, S-adenosylmethionine decarboxylase, aconitate decarboxylase, aminocarboxymuconate-semialdehyde decarboxylase, aminobenzoate decarboxylase, arginine decarboxylase, aspartate (1 or 4) decarboxylase, dopa decarboxylase, tryptophan decarboxylase, and ornithine decarboxylase.

The term "recombinant" includes reference to a cell or vector that has been modified by the introduction of a heterologous nucleic acid. Recombinant cells express genes that are not normally found in that cell or express native genes that are otherwise abnormally expressed, underexpressed, or not expressed at all as a result of deliberate human intervention, or expression of the native gene may have reduced or eliminated as a result of deliberate human intervention.

The term "recombinant expression cassette" refers to a nucleic acid construct, generated recombinantly or synthetically, with a series of specified nucleic acid elements, which permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid to be transcribed, and a promoter.

The term "transgenic" includes reference to a unicellular, which comprises within its genome a heterologous polynucleotide. Generally, the heterologous polynucleotide is integrated within the genome such that the polynucleotide is passed on to successive generations. The heterologous polynucleotide may be integrated into the genome alone or as part of a recombinant expression cassette. "Transgenic" is also used to include any cell the genotype of which has been altered by the presence of heterologous nucleic acid including those cells altered or created by budding or conjugation propagation from the initial transgenic cell.

The term "vector" includes reference to a nucleic acid used in transfection or transformation of a host cell and into which can be inserted a polynucleotide.

The term "selectively hybridizes" includes reference to hybridization, under stringent hybridization conditions, of a nucleic acid sequence to a specified nucleic acid target sequence to a detectably greater degree (e.g., at least 2-fold over background) than its hybridization to non-target nucleic acid sequences and to the substantial exclusion of non-target nucleic acids. Selectively hybridizing sequences typically have about at least 40% sequence identity, preferably 60-90% sequence identity, and most preferably 100% sequence identity (i.e., complementary) with each other.

The terms "stringent conditions" and "stringent hybridization conditions" include reference to conditions under which a probe will hybridize to its target sequence, to a detectably greater degree than other sequences (e.g., at least 2-fold over background). Stringent conditions are sequence-dependent and will be different in different circumstances. By controlling the stringency of the hybridization and/or washing conditions, target sequences can be identified which can be up to 100% complementary to the probe (homologous probing). Alternatively, stringency conditions can be adjusted to allow some mismatching in sequences so that lower degrees of similarity are detected (heterologous probing). Optimally, the probe is approximately 500 nucleotides in length, but can vary greatly in length from less than 500 nucleotides to equal to the entire length of the target sequence.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide or Denhardt solution. Low stringency conditions include hybridization with a buffer solution of 30 to 35% formamide, 1 M NaCl, 1% SDS (sodium dodecyl sulfate) at 37° C., and a wash in 1× to 2×SSC (20×SSC=3.0 M NaCl/0.3 M trisodium citrate) at 50 to 55° C. Moderate stringency conditions include hybridization in 40 to 45% formamide, 1 M NaCl, 1% SDS at 37° C., and a wash in 0.5× to 1×SSC at 55 to 60° C. High stringency conditions include hybridization in 50% formamide, 1 M NaCl, 1% SDS at 37° C., and a wash in 0.1×SSC at 60 to 65° C. Specificity is typically the function of post-hybridization washes, the critical factors being the ionic strength and temperature of the final wash solution. For DNA-DNA hybrids, the $T_m$ can be approximated (386), where the $T_m=81.5°$ C.+16.6 (log M)+0.41 (% GC)−0.61 (% form)−500/L; where M is the molarity of monovalent cations, % GC is the percentage of guanosine and cytosine nucleotides in the DNA, % form is the percentage of formamide in the hybridization solution, and L is the length of the hybrid in base pairs. $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization and/or wash conditions can be adjusted to hybridize to sequences of the desired identity. For example, if sequences with >90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill in the art will understand that variations in the stringency of hybridization and/or wash solutions are inherently described. An extensive guide to the hybridization of nucleic acids is found in the scientific literature. (134, 387) Unless otherwise stated, in the present application high stringency is defined as hybridization in 4×SSC, 5×Denhardt solution (5 g Ficoll, 5 g polyvinylpyrrolidone, 5 g bovine serum albumin in 500 ml of water), 0.1 mg/ml boiled salmon sperm DNA, and 25 mM Na phosphate at 65° C., and a wash in 0.1×SSC, 0.1% SDS at 65° C.

The following terms are used to describe the sequence relationships between two or more nucleic acids or polynucleotides or polypeptides: "reference sequence", "comparison window", "sequence identity", "percentage of sequence identity", and "substantial identity".

The term "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "comparison window" includes reference to a contiguous and specified segment of a polynucleotide sequence, where the polynucleotide sequence may be compared to a reference sequence and the portion of the polynucleotide sequence in the comparison window may comprise additions or deletions (i.e., gaps) when it is compared to the reference sequence for optimal alignment. The comparison window is usually at least 20 contiguous nucleotides in length, and optionally can be 30, 40, 50, 100 or longer. Those of ordinary skill in the art understand that the inclusion of gaps in a polynucleotide sequence alignment introduces a gap penalty, and it is subtracted from the number of matches.

Methods of alignment of nucleotide and amino acid sequences for comparison are well known to those of ordinary skill in the art. The local homology algorithm, BESTFIT (388), can perform an optimal alignment of sequences for comparison using a homology alignment algorithm called GAP (389), search for similarity using Tfasta and Fasta (390), by computerized implementations of these algorithms widely available on-line or from various vendors (Intelligenetics, Genetics Computer Group). CLUSTAL allows for the alignment of multiple sequences (391-393) and program PileUp can be used for optimal global alignment of multiple sequences (394). The BLAST family of programs can be used for nucleotide or protein database similarity searches. BLASTN searches a nucleotide database using a nucleotide query. BLASTP searches a protein database using a protein query. BLASTX searches a protein database using a translated nucleotide query that is derived from a six-frame translation of the nucleotide query sequence (both strands). TBLASTN searches a translated nucleotide database using a protein query that is derived by reverse-translation. TBLASTX search a translated nucleotide database using a translated nucleotide query.

GAP (389) maximizes the number of matches and minimizes the number of gaps in an alignment of two complete sequences. GAP considers all possible alignments and gap positions and creates the alignment with the largest number of matched bases and the fewest gaps. It also calculates a gap penalty and a gap extension penalty in units of matched bases. Default gap creation penalty values and gap extension penalty values in Version 10 of the Wisconsin Genetics Software Package are 8 and 2, respectively. The gap creation and gap extension penalties can be expressed as an integer selected from the group of integers consisting of from 0 to 100. GAP displays four figures of merit for alignments: Quality, Ratio, Identity, and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the Wisconsin Genetics Software Package is BLOSUM62 (395).

Unless otherwise stated, sequence identity or similarity values refer to the value obtained using the BLAST 2.0 suite of programs using default parameters (396). As those of ordinary skill in the art understand that BLAST searches assume that proteins can be modeled as random sequences and that proteins comprise regions of nonrandom sequences, short repeats, or enriched for one or more amino acid residues, called low-complexity regions. These low-complexity regions may be aligned between unrelated proteins even though other regions of the protein are entirely dissimilar. Those of ordinary skill in the art can use low-complexity filter programs to reduce number of low-complexity regions that are aligned in a search. These filter programs include, but are not limited to, the SEG (397, 398) and XNU (399).

The terms "sequence identity" and "identity" are used in the context of two nucleic acid or polypeptide sequences and include reference to the residues in the two sequences, which are the same when aligned for maximum correspondence over a specified comparison window. When the percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. Where sequences differ in conserved substitutions, the percent sequence identity may be adjusted upwards to correct for the conserved nature of the substitution. Sequences, which differ by such conservative substitutions, are said to have "sequence similarity" or "similarity." Scoring for a conservative substitution allows for a partial rather than a full mismatch (400), thereby increasing the percentage sequence similarity.

The term "percentage of sequence identity" means the value determined by comparing two optimally aligned sequences over a comparison window, wherein the portion of the polynucleotide sequence in the comparison window may comprise gaps (additions or deletions) when compared to the reference sequence for optimal alignment. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

The term "substantial identity" of polynucleotide sequences means that a polynucleotide comprises a sequence that has between 50-100% sequence identity, preferably at least 50% sequence identity, preferably at least 60% sequence identity, preferably at least 70%, more preferably at least 80%, more preferably at least 90%, and most preferably at least 95%, compared to a reference sequence using one of the alignment programs described using standard parameters. One of ordinary skill in the art will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of between 50-100%. Another indication that nucleotide sequences are substantially identical is if two molecules hybridize to each low stringency conditions, moderate stringency conditions or high stringency conditions. Yet another indication that two nucleic acid sequences are substantially identical is if the two polypeptides immunologically cross-react with the same antibody in a western blot, immunoblot or ELISA assay.

The terms "substantial identity" in the context of a peptide indicates that a peptide comprises a sequence with between 55-100% sequence identity to a reference sequence preferably at least 55% sequence identity, preferably 60% preferably 70%, more preferably 80%, most preferably at least 90% or 95% sequence identity to the reference sequence over a specified comparison window. Preferably, optimal alignment is conducted using the homology alignment algorithm (389). Thus, a peptide is substantially identical to a second peptide, for example, where the two peptides differ only by a conserved substitution. Another indication that amino acid sequences are substantially identical is if two polypeptides immunologically cross-react with the same antibody in a western blot, immunoblot or ELISA assay. In addition, a peptide can be substantially identical to a second peptide when they differ by a non-conservative change if the epitope that the antibody recognizes is substantially identical.

All patents, patent applications, and references cited in this disclosure are expressly incorporated herein by reference. The above disclosure generally describes the present invention. A more complete understanding can be obtained by reference to the following specific examples, which are provided for purposes of illustration only and are not intended to limit the scope of the invention.

Example 1

Development of sCS/PLP-DC without the Transit Peptide from a CS and Decarboxylase Using Chemical Synthesis Step 1: Use chemical synthesis to make a DNA construct that contains an sCS/PLP-DC gene from a CS gene fused in-frame with a decarboxylase gene, codon optimized for expression in the target organism.

The CS portion of the sCS/PLP-DC gene is derived as follows from the group below:
  a. from SEQ ID NO:1 by removing nucleotides 4 through 234 (corresponding to the native transit peptide) and 1444 through 2958 (corresponding to the decarboxylase region), encoding the CS portion of the peptide from *Micromonas pusilla* (SEQ ID NO:2 minus amino acids 2 through 78 and minus amino acids 472 to 984, corresponding to the transit and decarboxylase domains, respectively);
  b. from SEQ ID NO:3 by removing nucleotides 4 through 69 (corresponding to the native transit peptide) and 1414 through 2727 (corresponding to the decarboxylase region), encoding the CS portion of the peptide from *Ostreococcus tauri* (SEQ ID NO:4 minus amino acids 2 through 23 and minus amino acids 480 to 905, corresponding to the transit and decarboxylase domains, respectively);
  c. from SEQ ID NO:5 without the stop codon, encoding the CS peptide from *Brassica oleracea* (SEQ ID NO:6);
  d. from SEQ ID NO:7 without the stop codon, encoding the CS peptide from *Oryza* brachyantha (SEQ ID NO:8);
  e. from SEQ ID NO:9 without the stop codon, encoding the CS peptide from *Escherichia coli* (SEQ ID NO:10); or f. from SEQ ID NO:82 by removing nucleotides 4 through 99 (corresponding to the native transit peptide) and 1723 through 3291 (corresponding to the decarboxylase region), encoding the CS portion of the peptide from *Bathycoccus prasinos* (SEQ ID NO:83 minus amino acids 2 through 33 and minus amino acids 575 to 1096, corresponding to the transit and decarboxylase domains, respectively).

The DC portion of the sCS/PLP-DC gene is derived as follows from the group below:
 a. from SEQ ID NO:1 by removing nucleotides 1 through 1413 (corresponding to the native transit and cysteine synthetase peptide regions), encoding a decarboxylase peptide from *Micromonas pusilla* (SEQ ID NO:2 minus amino acids 1 through 471);
 b. from SEQ ID NO:17 encoding the DC peptide from *Beta vulgaris* (SEQ ID NO:18);
 c. from SEQ ID NO:19 encoding the DC peptide from *Lepisosteus oculatus* (SEQ ID NO:20);
 d. from SEQ ID NO:21 encoding the DC peptide from *Danio rerio* (SEQ ID NO:22);
 e. from SEQ ID NO:23 encoding the DC peptide from *Escherichia coli* (SEQ ID NO:24);
 f. from SEQ ID NO:25 encoding the DC peptide from *Oncorhynchus mykiss* (SEQ ID NO:26);
 g. from SEQ ID NO:27 encoding the DC peptide from *Guillardia theta* (SEQ ID NO:28);
 h. from SEQ ID NO:82 by removing nucleotides 1 through 1723 (corresponding to the native transit and cysteine synthetase peptide regions), encoding a decarboxylase peptide from *Bathycoccus prasinos* (SEQ ID NO:83 minus amino acids 1 through 574).

Clone sCS/PLP-DC (from Step 1, EXAMPLE 1) into the vector pCAMBIA1105, pET11, pKK223-3, or pSF-Tac, transform *E. coli*, select for antibiotic resistance, conduct PCR identification of cloned DNA constructs in transformants, and confirm the presence of the DNA construct.

Example 2

Development of sCS/PLP-DC without the Transit Peptide from a CBS and Decarboxylase Using Chemical Synthesis Step 1: Use chemical synthesis to make a DNA construct that contains an sCS/PLP-DC gene from a CBS gene fused in-frame with a decarboxylase gene, codon optimized for expression in the target organism.

The CBS portion of the sCS/PLP-DC gene is derived as follows from the group below:
 a. from SEQ ID NO:11 without the stop codon, encoding the CBS peptide from *Candidatus kryptonium* (SEQ ID NO:12);
 b. from SEQ ID NO:13 without the stop codon, encoding the CBS peptide from *Chloroflexi bacterium* (SEQ ID NO:14); or
 c. from SEQ ID NO:15 without the stop codon, encoding the CBS peptide from *Cyprinus carpio* (SEQ ID NO:16).

The DC portion of the sCS/PLP-DC gene is derived as follows from the group below:
 a. from SEQ ID NO:1 by removing nucleotides 1 through 1413 (corresponding to the native transit and cysteine synthetase peptide regions), encoding a decarboxylase peptide from *Micromonas pusilla* (SEQ ID NO:2 minus amino acids 1 through 471);
 b. from SEQ ID NO:17 encoding the DC peptide from *Beta vulgaris* (SEQ ID NO:18);
 c. from SEQ ID NO:19 encoding the DC peptide from *Lepisosteus oculatus* (SEQ ID NO:20);
 d. from SEQ ID NO:21 encoding the DC peptide from *Danio rerio* (SEQ ID NO:22);
 e. from SEQ ID NO:23 encoding the DC peptide from *Escherichia coli* (SEQ ID NO:24);
 f. from SEQ ID NO:25 encoding the DC peptide from *Oncorhynchus mykiss* (SEQ ID NO:26); or
 g. from SEQ ID NO:27 encoding the DC peptide from *Guillardia theta* (SEQ ID NO:28);
 h. from SEQ ID NO:82 by removing nucleotides 1 through 1723 (corresponding to the native transit and cysteine synthetase peptide regions), encoding a decarboxylase peptide from *Bathycoccus prasinos* (SEQ ID NO:83 minus amino acids 1 through 574).

Clone sCS/PLP-DC (from Step 1, EXAMPLE 2) into the vector pCAMBIA1105, pET11, pKK223-3, or pSF-Tac, transform *E. coli*, select for antibiotic resistance, conduct PCR identification of cloned DNA constructs in transformants and confirm the presence of the DNA construct.

Example 3

Development of an sCS/PLP-DC Gene Using Gene Evolution or Gene Shuffling

Step 1. Use chemical synthesis to make a DNA construct that contains an sCS/PLP-DC gene (from Step 1 EXAMPLE 1 or Step 1 EXAMPLE 2) and subject the sCS/PLP-DC polynucleotide to directed evolution as described by making a mutant library with a non-proof reading taq polymerase for PCR amplification (401, 402) or by DNA shuffling, a method that makes new point mutations and recombines existing mutations (403).

Step 2. Transform vectors with mutated or shuffled sCS/PLP-DC genes into *E. coli*.

Step 3. Grow cultures, harvest cells and supernatant from cultures extract amino acids and subject them to HPLC or GC-MS analysis to validate taurine production.

Step 4. Isolate the sCS/PLP-DC containing vector and sequence the polynucleotide. The resulting sCS/PLP-DC polynucleotide can be used for expression of a CS/PLP-DC peptide similar to SEQ ID NO:84 in other systems.

Example 4

Development of sCS/PLP-DC with a Transit Peptide Using Chemical Synthesis

Step 1. Use chemical synthesis to make a DNA construct that contains a plastid transit peptide fused in-frame with an sCS/PLP-DC gene (from Step 1 EXAMPLE 1; Step 1 EXAMPLE 2; or Step 4 EXAMPLE 3), codon optimized for expression in the target organism.

The plastid transit peptide nucleotide sequence is SEQ ID NO:55 and encodes the peptide SEQ ID NO:56.

The sCS/PLP-DC gene (from Step 1 EXAMPLE 1; Step 1 EXAMPLE 2; or Step 4 EXAMPLE 3) minus the start codon.

Step 2. Clone the transit peptide containing sCS/PLP-DC (TP_sCS/PLP-DC) gene (from Step 1 EXAMPLE 4) into the vector pCAMBIA1105, pET11, pKK223-3, or pSF-Tac, transform *E. coli*, select for antibiotic resistance, conduct PCR identification of cloned DNA constructs in transformants and confirm the presence of the DNA construct.

Example 5

Development of a Transgenic Bacterium with a TauD Knockout that Expresses sCS/PLP-DC without a Transit Peptide Using Chemical Synthesis Step 1: Use PCR to amplify the TauD (SEQ ID NO:33) using 500 ng of DNA from *E. coli* strain K12 and the primers for SEQ ID NO:57 and SEQ ID NO:58. Use the PCR-amplified fragment to knock out TauD with 2red-mediated recombination as described by Datsenko and Wanner (332) and Baba et al. (142).

Step 2: Use chemical synthesis to make a DNA construct that contains a functional sCS/PLP-DC gene (from Step 1 EXAMPLE 1; Step 1 EXAMPLE 2; or Step 4 EXAMPLE 3) without the transit peptide codon optimized for expression in *E. coli*. Clone the sCS/PLP-DC gene into a bacterial expression vector, such as pET11, pKK223-3, or pSF-Tac, so it is functional.

Step 3: Transform the vector with the functional sCS/PLP-DC construct (from Step 2, EXAMPLE 5) into the TauD knockout *E. coli* strain (from Step 1, EXAMPLE 5) and confirm the presence of the DNA construct.

Example 6

Development of a Transgenic Bacterium with a TauD Knockout that Expresses an sCS/PLP-DC without a Transit Peptide and Expresses a Taurine Binding Peptide without a Transit Peptide Using Chemical Synthesis Step 1: Use chemical synthesis to make a DNA construct that contains a taurine binding protein (SEQ ID NO:29 or SEQ ID NO:31) without the transit peptide optimized for expression in *E. coli*. Clone the taurine binding protein into a bacterial expression vector, such as pET11, pKK223-3, or pSF-Tac, so it is functional.

The taurine-binding protein gene is derived as follows from the group below:
 a. from SEQ ID NO:29 by removing nucleotides 4 through 66 (corresponding to the periplasmic transit peptide) and encoding a truncated taurine-binding peptide from *E. coli* (SEQ ID NO:30 minus amino acids 2 through 22); or
 b. from SEQ ID NO:31, by removing nucleotides 4 through 93, (corresponding to the periplasmic transit peptide), optimized for expression in *E. coli* and encoding a truncated taurine-binding peptide from *Roseobacter denitrificans* (SEQ ID NO:32 minus amino acids 2 through 31).

Step 2: Transform the DNA vector with the taurine-binding protein (from Step 1, EXAMPLE 6) into the TauD knockout *E. coli* strain that contains the vector with the pCS/PLP-DC (from Step 3, EXAMPLE 5). Select for antibiotic resistance, and confirm the presence of the DNA constructs.

Example 7

Development of a Transgenic Bacterium with a Cbl Knockout that Expresses sCS/PLP-DC without Transit Peptide Using Chemical Synthesis Step 1: Use PCR to amplify the cbl (SEQ ID NO:49) using 500 ng of DNA from *E. coli* strain K12 and the primers for SEQ ID NO:59 and SEQ ID NO:60. Use the PCR-amplified fragment to knockout cbl with λ red-mediated recombination as described by Datsenko and Wanner (332) and Baba et al. (142)

Step 2: Transform the vector with the functional sCS/PLP-DC construct (from Step 2, EXAMPLE 5) into the cbl knockout *E. coli* strain (from Step 1, EXAMPLE 7) and confirm the presence of the DNA construct.

Example 8

Development of a Transgenic Bacterium with a Cbl Knockout that Expresses sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 6) into the cbl knockout *E. coli* strain that contains the vector with the sCS/PLP-DC (from Step 2, EXAMPLE 7) and confirm the presence of the DNA constructs.

Example 9

Development of a Transgenic Bacterium with an SsuD Knockout that Expresses sCS/PLP-DC without a Transit Peptide Using Chemical Synthesis Step 1: Use PCR to amplify the SsuD (SEQ ID NO:35) using 500 ng of DNA from *E. coli* strain K12 and the primers for SEQ ID NO:61 and SEQ ID NO:62. Use the PCR-amplified fragment to knock out SsuD with X red-mediated recombination as described by Datsenko and Wanner (332) and Baba et al. (142).

Step 2: Transform the vector with the functional sCS/PLP-DC construct (from Step 2, EXAMPLE 5) into the SsuD knockout *E. coli* strain (from Step 1, EXAMPLE 9) and confirm the presence of the DNA construct.

Example 10

Development of a Transgenic Bacterium with an SsuD Knockout that Expresses sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 6) into the SsuD knockout *E. coli* strain that contains the vector with the functional sCS/PLP-DC construct (from Step 2, EXAMPLE 9) and confirm the presence of the DNA constructs.

Example 11

Development of a Transgenic Bacterium with an SsuE Knockout that Expresses sCS/PLP-DC without a Transit Peptide Using Chemical Synthesis Step 1: Use PCR to amplify the SsuE (SEQ ID NO:37) using 500 ng of DNA from *E. coli* strain K12 and the primers for SEQ ID NO:63 and SEQ ID NO:64. Use the PCR-amplified fragment to knockout SsuE with X red-mediated recombination as described by Datsenko and Wanner (332) and Baba et al. (142).

Step 2: Transform the vector with the functional sCS/PLP-DC construct (from Step 2, EXAMPLE 5) into the SsuE knockout *E. coli* strain (from Step 1, EXAMPLE 11) and confirm the presence of the DNA construct.

Example 12

Development of a Transgenic Bacterium with an SsuE Knockout that Expresses sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 6) into the SsuE knockout *E. coli* strain that contains the vector with the functional sCS/PLP-DC (from Step 2, EXAMPLE 12) and confirm the presence of the DNA constructs.

Example 13

Development of Another Type of Transgenic Bacterium with an SsuD Knockout that Expresses sCS/PLP-DC without a Transit Peptide Using Chemical Synthesis Step 1: Use overlap PCR to amplify a knockout fragment for SsuD (SEQ ID NO:39) using genome DNA from *Corynebacterium glutamicum* and the pK19mobsacB vector as described by Buchholz et al. (404). Generate independent DNA fragments using the primer pairs SEQ ID NO:65 and SEQ ID NO:66 and genome DNA from *C. glutamicum* and SEQ ID NO:67 and SEQ ID NO:68 and genome DNA from *C. glutamicum*. Purify each DNA fragment and mix in equal amounts in an overlap PCR using primers SEQ ID NO:65 and SEQ ID NO:68. Clone the resulting fusion product containing the SsuD gene with an internal deletion of 875 bp (SsuD knockout fragment) into pK19mobsacB. Replace the SsuD1 gene with the SsuD knockout fragment by homologous recombination (404).

Step 2: Use chemical synthesis to make a DNA construct that contains an sCS/PLP-DC gene (from Step 1 EXAMPLE 1; Step 1 EXAMPLE 2; or Step 4 EXAMPLE 3) optimized for expression in *C. glutamicum*. Clone the sCS/PLP-DC fragment into a bacterial expression vector, such as pET11, pKK223-3, or pSF-Tac, so it is functional.

Step 3: Transform the vector with the functional sCS/PLP-DC construct (from Step 2, EXAMPLE 13) into the SsuD knockout *C. glutamicum* strain (from Step 1, EXAMPLE 13) and confirm the presence of the DNA construct.

Example 14

Development of Another Type of Transgenic Bacterium with an SsuD Knockout that Expresses sCS/PLP-DC without a Transit Peptide and Expresses a Taurine Binding Peptide without a Transit Peptide Using Chemical Synthesis Step 1: Use chemical synthesis to make a DNA construct that contains a taurine binding protein (SEQ ID NO:29 or SEQ ID NO:31) without the transit peptide. Clone the taurine binding protein into a bacterial expression vector, such as pET11, pKK223-3, or pSF-Tac, so it is functional.

The taurine binding protein gene is derived as follows from the group below:

a. from SEQ ID NO:29 by removing nucleotides 4 through 66 (corresponding to the periplasmic transit peptide) and encoding a truncated taurine-binding peptide from *C. glutamicum* (SEQ ID NO:30 minus amino acids 2 through 22); or b. from SEQ ID NO:31 by removing nucleotides 4 through 93, (corresponding to the periplasmic transit peptide), optimized for expression in *C. glutamicum* and encoding a truncated taurine-binding peptide from *Roseobacter denitrificans* (SEQ ID NO:32 minus amino acids 2 through 31).

Step 2: Transform the DNA vector with the taurine-binding protein (from Step 1, EXAMPLE 14) into the SsuD knockout *C. glutamicum* strain that contains the vector with the functional sCS/PLP-DC (from Step 2, EXAMPLE 13) and confirm the presence of the DNA construct.

Example 15

Development of Another Type of Transgenic Bacterium with an SsuE Knockout that Expresses sCS/PLP-DC without a Transit Peptide Using Chemical Synthesis Step 1: Use overlap PCR to amplify a knockout fragment for SsuE (SEQ ID NO:41) using genome DNA from *Corynebacterium glutamicum* and the pK19mobsacB vector as described by Buchholz et al. (404) Generate independent DNA fragments using the primer pairs SEQ ID NO:69 and SEQ ID NO:70 and genome DNA from *C. glutamicum* and SEQ ID NO:71 and SEQ ID NO:72 and genome DNA from *C. glutamicum*. Purify each DNA fragment and mix in equal amounts in an overlap PCR using primers SEQ ID NO:69 and SEQ ID NO:72. Clone the resulting fusion product, containing the SsuE gene with an internal deletion of 735 bp (SsuE knockout fragment), into pK19mobsacB. Replace the SsuE gene with the SsuE knockout fragment by homologous recombination (404).

Step 2: Transform the vector with the functional sCS/PLP-DC construct (from Step 2, EXAMPLE 13) into the SsuE knockout *C. glutamicum* strain (from Step 1, EXAMPLE 15) and confirm the presence of the DNA construct.

Example 16

Development of Another Transgenic Bacterium with an SsuE Knockout that Expresses an sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 14) into the SsuE knockout *C. glutamicum* strain with the functional sCS/PLP-DC construct (from Step 2, EXAMPLE 15) and confirm the presence of the DNA construct.

Example 17

Development of Another Transgenic Bacterium with a Cbl Knockout that Expresses an sCS/PLP-DC without a Transit Peptide Using Chemical Synthesis Step 1: Use overlap PCR to amplify a knockout fragment for cbl (SEQ ID NO:51) using genome DNA from *Coryne-* bacterium glutamicum, and the pK19mobsacB vector as described by Buchholz et al. (404). Generate independent DNA fragments using the primer pairs SEQ ID NO:73 and SEQ ID NO:74 and genome DNA from *C. glutamicum* and SEQ ID NO:75 and SEQ ID NO:76 and genome DNA from *C. glutamicum*. Purify each DNA fragment and mix in equal amounts in an overlap PCR using primers SEQ ID NO:73 and SEQ ID NO:76. Clone the resulting fusion product, containing the cbl gene with an internal deletion of 563 bp (cbl knockout fragment) into pK19mobsacB. Replace the cbl gene with the cbl knockout fragment by homologous recombination (404).

Step 2: Transform the vector with the functional sCS/PLP-DC construct (from Step 2, EXAMPLE 13) into the cbl knockout *C. glutamicum* strain (from Step 1, EXAMPLE 17) and confirm the presence of the DNA construct.

Example 18

Development of Another Transgenic Bacterium with a Cbl Knockout that Expresses sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 14) into the cbl knockout *C. glutamicum* strain with the functional sCS/PLP-DC construct (from Step 1, EXAMPLE 17) and confirm the presence of the DNA construct.

Example 19

Development of a Transgenic Bacterium with a TauR Knockout that Expresses sCS/PLP-DC without a Transit Peptide Using Chemical Synthesis Step 1: Use overlap PCR to amplify a knockout fragment for TauR (SEQ ID NO:53) using genome DNA from *Corynebacterium glutamicum* and the pK19mobsacB vector as described by Buchholz et al. (404). Generate independent DNA fragments using the primer pairs SEQ ID NO:77 and SEQ ID NO:78 and genome DNA from *C. glutamicum* and SEQ ID NO:79 and SEQ ID NO:80 and genome DNA from *C. glutamicum*. Purify each DNA fragment and mix in equal amounts in an overlap PCR using primers SEQ ID NO:77 and SEQ ID NO:80. Clone the resulting fusion product containing the TauR gene with an internal deletion of 1052 bp (TauR knockout fragment) into pK19mobsacB. Replace the TauR gene with the TauR knockout fragment by homologous recombination (404).

Step 2: Transform the vector with the functional sCS/PLP-DC construct (from Step 2, EXAMPLE 13) into the TauR knockout *C. glutamicum* strain (from Step 1, EXAMPLE 19) and confirm the presence of the DNA construct.

Example 20

Development of a Transgenic Bacterium with a TauR Knockout that Expresses an sCS/PLP-DC without a Transit Peptide and Expresses a Taurine Binding Peptide without a Transit Peptide Using Chemical Synthesis Step 1: Transform the DNA vector with the taurine-binding protein (from Step 1, EXAMPLE 14) into the TauR knockout *C. glutamicum* strain with the functional sCS/PLP-DC construct (from Step 1, EXAMPLE 19) and confirm the presence of the DNA construct.

Example 21

Development of Transgenic *Methylobacterium* that Expresses sCS/PLP-DC without a Transit Peptide Using Chemical Synthesis Step 1: Use chemical synthesis to make a DNA construct that contains an sCS/PLP-DC gene (from Step 1 EXAMPLE 1, Step 1 EXAMPLE 2, or Step 4 EXAMPLE 3) optimized for expression in *Methylobacterium extorquens*. Clone the sCS/PLP-DC fragment into a bacterial expression vector, such as pCM80, pCM160, pHC90, pHC91, pHC115, pLC290, or pLC291 so it is functional.

Step 2: Transform the vector with the functional sCS/PLP-DC construct (from Step 1, EXAMPLE 21) into *Methylobacterium extorquens, Methylobacterium populi, Methylobacterium radiotolerans, Methylobacterium nodula* or *Methylobacterium* spp. and confirm the presence of the DNA construct.

Example 22

Development of a Transgenic Alga that Expresses an sCS/PLP-DC without a Transit Peptide Using Chemical Synthesis Step 1: Use chemical synthesis to make an sCS/PLP-DC gene without a transit peptide (from Step 1 EXAMPLE 1; Step 1 EXAMPLE 2; or Step 4 EXAMPLE 3) codon optimized from expression in algae, *Chlamydomonas reinhardtii* or *Ostreococcus tauri*. Clone the sCS/PLP-DC gene without a transit peptide into an algal expression vector, such as pCB740 or pD1-Kan, so it is functional, and confirm the presence of the DNA construct.

Step 2: Transform the DNA vector with the sCSIPLP-DC (from Step 1, EXAMPLE 22) into *Chlamydomonas reinhardtii* or *Ostreococcus tauri* and confirm the presence of the DNA constructs.

Example 23

Development of a Transgenic Alga that Expresses an sCSIPLP-DC without a Transit Peptide and Expresses a Taurine Binding Protein without a Transit Peptide Using Chemical Synthesis Step 1: Use chemical synthesis to make a DNA construct that contains a taurine binding protein (SEQ ID NO:29 or SEQ ID NO:31) without the transit peptide. Clone the taurine binding protein into an algal expression vector, such as pCB740 or pD1-Kan, so it is functional.

The taurine binding protein gene is derived as follows from the group below:

a. from SEQ ID NO:29 by removing nucleotides 4 through 66 (corresponding to the periplasmic transit peptide), optimized for expression in *Chlamydomonas reinhardtii* or *Ostreococcus tauri* and encoding a truncated taurine-binding peptide from *E. coli* (SEQ ID NO:30 minus amino acids 2 through 22); or b. from SEQ ID NO:31 by removing nucleotides 4 through 93, (corresponding to the periplasmic transit peptide), optimized for expression in *Chlamydomonas reinhardtii* or *Ostreococcus tauri* and encoding a truncated taurine-binding protein from *Roseobacter denitrificans* (SEQ ID NO:32 minus amino acids 2 through 31).

Step 2: Transform the DNA vector with the taurine-binding protein (from Step 1, EXAMPLE 23) into *Chlamydomonas reinhardtii* or *Ostreococcus tauri* that contains sCS/PLS-DC (from Step 2, EXAMPLE 22) and confirm the presence of the DNA constructs.

Example 24

Development of a Transgenic Alga that Expresses an sCS/PLP-DC Gene with a Chloroplast Transit Peptide Using Chemical Synthesis Step 1: Use chemical synthesis to make a TP_sCS/PLP-DC gene with a transit peptide (from Step 1, EXAMPLE 4) codon optimized from expression in algae, *Chlamydomonas reinhardtii* or *Ostreococcus tauri*. Clone the TP_sCS/PLP-DC gene into an algal expression vector, such as pCB740 or pD1-Kan, so it is functional, and confirm the presence of the DNA construct.

Step 2: Transform the DNA vector with the TP_sCS/PLP-DC protein (from Step 1, EXAMPLE 24) into *Chlamydomonas reinhardtii* or *Ostreococcus tauri* and confirm the presence of the DNA constructs.

Example 25

Development of a Transgenic Alga that Expresses a TP_sCS/PLP-DC Gene with a Transit Peptide and Expresses a Taurine Binding Protein with a Chloroplast Transit Peptide Using Chemical Synthesis Step 1: Use chemical synthesis to make a DNA construct that contains a taurine binding protein (SEQ ID NO:29 or SEQ ID NO:31) with the plastid transit peptide (SEQ ID NO:55). Clone the taurine-binding protein into an algal expression vector, such as pCB740 or pD1-Kan, so it is functional.

The nucleotide sequence for the plastid transit peptide (SEQ ID NO:55) encodes the peptide SEQ ID NO:56.

The taurine binding protein gene is derived as follows from the group below:
  a. from SEQ ID NO:29 by removing nucleotides 1 through 66 (corresponding to the periplasmic transit peptide), optimized for expression in *Chlamydomonas reinhardtii* or *Ostreococcus tauri* and encoding a truncated taurine-binding peptide from *E. coli* (SEQ ID NO:30 minus amino acids 1 through 22); or
  b. from SEQ ID NO:31 by removing nucleotides 4 through 93, (corresponding to the periplasmic transit peptide), optimized for expression in *Chlamydomonas reinhardtii* or *Ostreococcus tauri* and encoding a truncated taurine-binding peptide from *Roseobacter denitrificans* (SEQ ID NO:32 minus amino acids 2 through 31).

Step 2: Transform the DNA vector with the taurine-binding protein (from Step 1, EXAMPLE 25) into *Chlamydomonas reinhardtii* or *Ostreococcus tauri* that expresses the TP_sCS/PLP-DC gene with a transit peptide (from Step 2, EXAMPLE 24) and confirm the presence of the DNA constructs.

Example 26

Development of a Transgenic Alga that Expresses an sCS/PLP-DC Gene in the Chloroplast Via Chloroplast Transformation Using Chemical Synthesis Step 1: Make the following construct: an atpA promoter-59UTR (untranslated region) operably linked to sCS/PLP-DC polynucleotide and the atpA terminator (TatpA). Use the chloroplast destination expression for *Chlamydomonas reinhardtii* as described by Oey et al. (121). Use chemical synthesis to make a DNA construct that encodes a sCS/PLP-DC protein (from Step 1 EXAMPLE 1; Step 1 EXAMPLE 2; or Step 4 EXAMPLE 3) optimized for expression in an algal chloroplast. Synthesize the sCS/PLP-DC polynucleotide without a transit peptide and with XbaI at the 5' end and a NcoI site at the 3'end. Clone the sCS/PLP-DC polynucleotide into the XbaI/NcoI site (remove the GFP fragment of the Entry vector). Recombine the atpA/sCS/PLP-DC/atpA cassette from the Entry vector into the Destination vector, pC-Dest/psbA.

Step 2: Transform the DNA vector with the Destination vector containing the atpA promoter/sCS/PLP-DC/TatpA (from Step 1, EXAMPLE 26) into *Chlamydomonas reinhardtii* and confirm the presence of the DNA construct.

Example 27

Development of a Transgenic Fungus that Expresses an sCS/PLP-DC Gene without the Transit Peptide Using Chemical Synthesis Step 1: Use chemical synthesis to make an sCS/PLP-DC gene without a transit peptide (from Step 1 EXAMPLE 1; Step 1 EXAMPLE 2; or Step 4 EXAMPLE 3) codon optimized for expression in a fungus such as yeast, and clone into a fungal expression vector such as pESC-TRP, pYES2/NT, or pYSG-IBA, so it is functional.

Step 2: Transform the DNA vector with the sCS/PLP-DC gene (from Step 1, EXAMPLE 27) into the yeast strain and confirm the presence of the DNA constructs.

Example 28

Development of a Transgenic Fungus that Expresses an sCS/PLP-DC without a Transit Peptide and Expresses a Taurine Binding Protein without a Transit Peptide Using Chemical Synthesis Step 1: Use chemical synthesis to make a DNA construct that contains a taurine binding protein gene without the transit peptide. Clone the taurine binding protein fragment into a fungal expression vector, such as pESC-TRP, pYES2/NT, or pYSG-IBA vector, so it is functional.

The taurine-binding protein gene is derived as follows from the group below:
  a. from SEQ ID NO:29 by removing nucleotides 4 through 66 (corresponding to the periplasmic transit peptide), optimized for expression in yeast, and encoding a truncated taurine-binding peptide (SEQ ID NO:30 minus amino acids 2 through 22); or
  b. from SEQ ID NO:31, by removing nucleotides 4 through 93, (corresponding to the periplasmic transit peptide), optimized for expression in yeast, and encoding a truncated taurine-binding peptide from *Roseobacter denitrificans* (SEQ ID NO:32 minus amino acids 2 through 31).

Step 2: Transform the DNA vector with the taurine-binding protein (from Step 1, EXAMPLE 28) into the yeast strain that contains the vector with sCS/PLP-DC (from Step 2, EXAMPLE 27) and confirm the presence of the DNA constructs.

Example 29

Development of a Transgenic Bacterium with TauX Suppressed and that Expresses an sCS/PLP-DC without the Transit Peptide Using Chemical Synthesis Step 1: Use chemical synthesis to make an antisense construct to silence or suppress TauX (SEQ ID NO: 43) and clone into the pBAD vector as described by Stefan et al. (405). To make the TauX antisense, fuse the polynucleotides for SEQ ID NO:81 to polynucleotides 1 through 360 of SEQ ID NO:43. Clone the TauX antisense fragment into the bacterial expression vector, pBAD, so the TauX antisense fragment can be expressed.

Step 2: Transform the vector with the TauX antisense construct (from Step 1, EXAMPLE 29) into *Roseobacter denitrificans* and confirm the presence of the DNA construct.

Step 3: Use chemical synthesis to make a DNA construct that contains an sC/PLP/DC gene (from Step 1 EXAMPLE 1; Step 1 EXAMPLE 2; or Step 4 EXAMPLE 3) without the transit peptide, optimized for expression in *Roseobacter denitrificans*. Clone the sCS/PLP-DC fragment into a bacterial expression vector, such as pET11, pKK223-3, or pSF-Tac, so it is functional.

Step 4: Transform the vector with the functional sCS/PLP-DC construct (from Step 3, EXAMPLE 29) into the TauX knockdown *Roseobacter denitrificans* strain (from Step 2, EXAMPLE 29) and confirm the presence of the DNA construct.

Example 30

Development of a Transgenic Bacterium with a TauY Suppressed and that Expresses an sCS/PLP-DC without the Transit Peptide Using Chemical Synthesis Step 1: Use chemical synthesis to make an antisense construct to silence or suppress TauY (SEQ ID NO: 45) and clone into the pBAD vector as described by Stefan et al. (405). To make the TauY antisense, fuse the polynucleotides for SEQ ID NO:81 to polynucleotides 1 through 360 of SEQ ID NO:45. Clone the TauY antisense fragment into a bacterial expression vector, pBAD, so the TauY antisense fragment can be expressed.

Step 2: Transform the vector with the TauY antisense construct (from Step 1, EXAMPLE 30) into *Roseobacter denitrificans* and confirm the presence of the DNA construct Step 3: Transform the vector with the functional sCS/PLP-DC construct (from Step 3, EXAMPLE 29) into the TauX knockdown *Roseobacter denitrificans* strain (from Step 2, EXAMPLE 30) and confirm the presence of the DNA construct.

Example 31

Development of a Transgenic Bacterium with a Tpa Suppressed and that Expresses an sCS/PLP-DC without the Transit Peptide Using Chemical Synthesis Step 1: Use chemical synthesis to make an antisense construct to silence or suppress Tpa (SEQ ID NO: 47) and clone into the pBAD vector as described by Stefan et al. (405). To make the Tpa antisense, fuse the polynucleotides for SEQ ID NO:81 to polynucleotides 1 through 360 of SEQ ID NO:47. Clone the Tpa antisense fragment into the bacterial expression vector, pBAD, so Tpa antisense fragment can be expressed.

Step 2: Transform the vector with the Tpa antisense construct (from Step 1, EXAMPLE 31) into *Roseobacter denitrificans* and confirm the presence of the DNA construct.

Step 3: Transform the vector with the functional sCS/PLP-DC construct (from Step 3, EXAMPLE 29) into the Tpa knockdown *Roseobacter denitrificans* strain (from Step 2, EXAMPLE 31) and confirm the presence of the DNA construct.

Example 32

Develop Bacteria with Taurine

Grow bacteria (*E. coli*: EXAMPLES 5-12; *C. glutamicum* EXAMPLES 13-20; or a member of the *Methylobacterium* EXAMPLE 21) with sCS/PLP-DC and induce gene expression with the appropriate inducer associated with the vector. Collect the cells and confirm that the cells express the sCS/PLP-DC peptide (~96.6 kDa) using western blot analysis. Harvest cells and supernatant from cultures. Extract amino acids and subject them to HPLC or GC-MS analysis to validate taurine production.

Example 33

Develop Aquafeed Using Bacterial Cells with Taurine

Grow bacteria with sCS/PLP-DC (such as from EXAMPLE 32) and induce gene expression with the appropriate inducer associated with the vector. Collect the cells and process for use as an additive to feed.

Example 34

Develop an *E. coli* Strain that Produces Taurine

This example demonstrates the use of a TauD knockout that expresses an sCS/PLP-DC (such as from EXAMPLE 5) to produce taurine in *E. coli*. Confirm *E. coli* transformation by selection and PCR analysis. Grow *E. coli* in ZYP media (406) and induce using autoinduction with an 8:1 lactose to glucose ratio. Extract free amino acids from 24, 48, or 72 hour culture to determine the level of taurine using high-performance liquid chromatography (HPLC). Separate bacteria from the supernatant by centrifugation, extract the amino acids, and determine the level of taurine in the pellet and supernatant. Taurine levels should be at least 0.25% of the total extracted free amino acids for the pellet or supernatant.

Example 35

Development of a Transgenic Plant that Constitutively Expresses an sCS/PLP-DC without a Transit Peptide Step 1: Use chemical synthesis to make an sCSlPLP-DC DNA construct that contains a constitutive promoter, such as 35S, fused with the nucleotide sequence for the sCS/PLP-DC gene and a NOS terminator. Clone the DNA construct into a binary vector, such as pCambia1300, pCambia2300, or pCambia3200.

The sCS/PLP-DC gene is derived from Step 1 EXAMPLE 1; Step 1 EXAMPLE 2; or Step 4 EXAMPLE 3, optimized for expression in a dicot (such as *Arabidopsis* or soybean) or a monocot (such as corn).

Step 2: Transform the DNA construct (Step 1, EXAMPLE 35) into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA construct in the transgenic plant.

Example 36

Development of a Transgenic Plant that Constitutively Expresses a TP_CS/PLP-DC Protein with a Plant Plastid Transit Peptide Step 1: Use chemical synthesis to make a DNA construct that contains a constitutive promoter, such as 35S, fused with the nucleotide sequence for a plastid transit peptide (SEQ ID NO: 55), sCS/PLP-DC and a NOS terminator. Clone the DNA construct into a binary vector, such as pCambia1300, pCambia2300, or pCambia3200. The TP_CS/PLP-DC gene is derived from Step 1, EXAMPLE 4, optimized for expression in a dicot (such as *Arabidopsis* or soybean) or a monocot (such as corn).

Step 2: Transform the DNA construct into *Agrobacterium tumefaciens*, select for antibiotic resistance, and confirm the presence of the DNA construct.

Step 3: Transform plant (*Arabidopsis*, soybean, corn, wheat, sugar beet, rice, camelina or canola), select for antibiotic resistance, and confirm the presence of the DNA constructs in the transgenic plant.

Example 37

Development of a Transgenic Plant that Constitutively Expresses an sCS/PLP-DC without a Transit Peptide and Expresses a Taurine Binding Protein without a Transit Peptide Using Chemical Synthesis Step 1: Use chemical synthesis to make a DNA construct that contains a taurine binding protein (SEQ ID NO:29 or SEQ ID NO:31) without the transit peptide. Clone the DNA construct into a binary vector, such as pCambia1300, pCambia2300, or pCambia3200.

The taurine binding protein gene is derived as follows from the group below:

a. from SEQ ID NO:29 by removing nucleotides 4 through 66 (corresponding to the periplasmic transit peptide), optimized for expression in a dicot (such as *Arabidopsis* or soybean) or a monocot (such as corn) and encoding a truncated taurine-binding peptide from *E. coli* (SEQ ID NO:30 minus amino acids 2 through 22); or b. from SEQ ID NO:31 by removing nucleotides 4 through 93, (corresponding to the periplasmic transit peptide), optimized for expression in a dicot (such as *Arabidopsis* or soybean) or a monocot (such as corn) and encoding a truncated taurine-binding protein from *Roseobacter denitrificans* (SEQ ID NO:32 minus amino acids 2 through 31).

Step 2: Transform the DNA construct into *Agrobacterium tumefaciens*, select for antibiotic resistance, and confirm the presence of the DNA construct Step 3: Transform the DNA vector with the taurine-binding protein without a transit peptide (from Step 1, EXAMPLE 37) into a plant (*Arabidopsis*, soybean, corn, wheat, sugar beet, rice, camelina or canola), that contains sCS/PLS-DC without the transit peptide (from Step 3, EXAMPLE 35) and confirm the presence of the DNA constructs.

Example 38

Development of a Transgenic Plant that Constitutively Expresses a TP_CS/PLP-DC Protein with a Plant Plastid Transit Peptide and Expresses a Taurine Binding Protein with a Transit Peptide Using Chemical Synthesis Step 1: Use chemical synthesis to make a DNA construct that contains a constitutive promoter, such as 35S, fused with the nucleotide sequence for a plastid transit peptide (SEQ ID NO: 55), taurine binding protein and a NOS terminator. Clone the DNA construct into a binary vector, such as pCambia1300, pCambia2300, or pCambia3200.

The nucleotide sequence for the plastid transit peptide (SEQ ID NO:55) encodes the peptide SEQ ID NO:56.

The taurine binding protein gene is derived as follows from the group below:

a. from SEQ ID NO:29 by removing nucleotides 1 through 66 (corresponding to the periplasmic transit peptide), optimized for expression in a dicot (such as *Arabidopsis* or soybean) or a monocot (such as corn) and encoding a truncated taurine-binding peptide from *E. coli* (SEQ ID NO:30 minus amino acids 1 through 22); or b. from SEQ ID NO:31 by removing nucleotides 4 through 93, (corresponding to the periplasmic transit peptide), optimized for expression in a dicot (such as *Arabidopsis* or soybean) or a monocot (such as corn) and encoding a truncated taurine-binding peptide from *Roseobacter denitrificans* (SEQ ID NO:32 minus amino acids 2 through 31).

Step 2: Transform the DNA construct into *Agrobacterium tumefaciens*, select for antibiotic resistance, and confirm the presence of the DNA construct.

Step 3: Transform the DNA vector with the taurine-binding protein with the transit peptide (from Step 1, EXAMPLE 38) into (*Arabidopsis*, soybean, corn, wheat, sugar beet, rice, camelina or canola), that contains sCS/PLS- DC with the transit peptide (from Step 3, EXAMPLE 36) and confirm the presence of the DNA constructs.

Example 39

Development of a Transgenic Plant that Expresses an sCS/PLP-DC Gene in the Chloroplast Via Plastid Transformation Using Chemical Synthesis Step 1: Use chemical synthesis to make a DNA construct that contains a functional sCS/PLP-DC gene (Step 1 EXAMPLE 1; Step 1 EXAMPLE 2; or Step 4 EXAMPLE 3) without the transit peptide, codon optimized for expression in *Glycine max* (soybean) chloroplast. Clone the sCS/PLP-DC gene into the soybean plastid transformation vector pCLT312 as described by Dufourmantel et al. (317) so it is functional.

Step 2: Transform the DNA vector with the sCS/PLP-DC-containing soybean plastid transformation vector (from Step 1, EXAMPLE 39) into soybean and confirm the presence of the DNA construct.

The use of the terms "a" and "an" and "the" and similar referents in the context of describing the invention (especially in the context of the following claims) are to be construed to cover both the singular and the plural, unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context. Embodiments of this invention are described herein, including the best mode known to the inventors for carrying out the invention. Variations of those embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

BIBLIOGRAPHY

1. Sturman J A (1988) Taurine in development. *J Nutr* 118(10):1169-1176.
2. Sturman J A & Hayes K C (1980) The biology of taurine in nutrition and development. *Adv Nutr Res* 3:231-299.
3. Chen X C, Pan Z L, Liu D S, & Han X (1998) Effect of taurine on human fetal neuron cells: Proliferation and differentiation. *Adv Exp Med Biol* 442:397-403.
4. El Idrissi A & Trenkner E (1999) Growth factors and taurine protect against excitotoxicity by stabilizing calcium homeostasis and energy metabolism. *J Neurosci* 19:9459-9468.
5. El Idrissi A & Trenkner E (2003) Taurine regulates mitochondrial calcium homeostasis. *Adv Exp Med Biol* 526:527-536.
6. Trenkner E (1990) Possible role of glutamate with taurine in neuron-glia interaction during cerebellar development. *Progr Clin Biol Res* 351:133-140.
7. Wu H, et al. (2005) Mode of action of taurine as a neuroprotector. *Brain Res* 1038:123-131.
8. Schaffer S, Takahashi K, & Azuma J (2000) Role of osmoregulation in the actions of taurine. *Amino Acids* 19:527-546.
9. Chapman R A, Suleiman M S, & Earm Y E (1993) Taurine and the heart. *Cardiovascular Res* 27:358-363.
10. Tabassuma H, Rehmana H, Banerjeeb B D, Raisuddina S, & Parvez S (2006) Attenuation of tamoxifen-induced hepatotoxicity by taurine in mice. *Clinica Chimica Acta* 370:129-136.
11. Rocket N. et al. (2007) The osmolyte taurine protects against ultraviolet B radiation-induced immunosuppression. *J Immunol* 179:3604-3612.
12. Knopf K, Sturman J A, Armstrong M, & Hayes A C (1978) Taurine: An essential nutrient for the cat. *J Nutr* 108:773-778.
13. Morris J G, Rogers Q R, & Pacioretty L M (1990) Taurine: an essential nutrient for cats. *J Small Anim Pract* 31(10):502-509.
14. Chesney R, et al. (1998) The Role of Taurine in Infant Nutrition. *Taurine 3, Advances in Experimental Medicine and Biology*, eds Schaffer S, Lombardini J, & Huxtable R (Springer US), Vol 442, pp 463-476.
15. Gibson G T, et al. (2007) Supplementation of taurine and methionine to all-plant protein diets for rainbow trout (*Oncorhynchus mykiss*). *Aquaculture* 269:514-524.
16. Buentello A, Jirsa D, Barrows F T, & Drawbridge M (2015) Minimizing fishmeal use in juvenile California yellowtail, Seriola lalandi, diets using non-G M soybeans selectively bred for aquafeeds. *Aquaculture* 435(0):403-411.
17. Rossi W, Moxely D, Buentello A, Pohlenz C, & Gatlin D M (2013) Replacement of fishmeal with novel plant feedstuffs in the diet of red drum *Sciaenops ocellatus*: an assessment of nutritional value. *Aquaculture Nutr* 19:72-81.
18. Watson A M, Buentello A, & Place A R (2014) Partial replacement of fishmeal, poultry by-product meal and soy protein concentrate with two non-genetically modified soybean cultivars in diets for juvenile cobia, *Rachycentron canadum*. *Aquaculture* 434(0):129-136.

19. Takagia S, et al. (2008) Taurine is an essential nutrient for yellowtail *Seriola quinqueradiata* fed non-fish meal diets based on soy protein concentrate. *Aquaculture* 280: 198-205.
20. Lunger A N, McLean E, Gaylord T G, Kuhn D, & Craig S R (2007) Taurine supplementation to alternative dietary proteins used in fish meal replacement enhances growth of juvenile cobia (*Rachycentron canadum*). *Aquaculture* 271:401-410.
21. Watson A M, Barrows F T, & Place A R (2013) Taurine supplementation of plant derived protein and n-3 fatty acids are critical for optimal growth and development of cobia, *Rachycentron canadum*. *Lipids* 48(9):899-913.
22. Watson A M, Barrows F T, & Place A R (2013) Taurine supplemented plant protein based diets with alternative lipid sources for juvenile gilthead sea bream, *Sparus aurata*. *J Fish Aquaculture* 4:59-66.
23. Park G S, Takeuchi T, Yokoyama M, & Seikai T (2002) Optimal dietary taurine level for growth of juvenile Japanese flounder *Paralichthys olivaceus*. *Fish Sci* 68:824-829.
24. Gaylord T G, Teague A M, & Barrows F1 (2006) Taurine supplementation of all-plant protein diets for rainbow trout (*Oncorhynchus mykiss*). *J World Aquaculture Soc* 37:509-517.
25. Salze G P & Davis D A (2015) Taurine: a critical nutrient for future fish feeds. *Aquaculture* 437:215-229.
26. Yang H, Tian L, Huang J, Liang G, & Liu Y (2013) Dietary taurine can improve the hypoxia-tolerance but not the growth performance in juvenile grass carp *Ctenopharyngodon idellus*. *Fish Physiol Biochem* 39(5):1071-1078.
27. Kuz'mina V V, Gavrovskaya L K, Rusanova P V, Kulivatskaya E A, & Ryzhova O V (2011) Effect of taurine on the glycemia level and the activity of hydrolases in the intestinal mucosa in carp (*Cyprinus carpio* L.). *Inland Water Biol* 4(2):242-248.
28. Al-Feky S S A, El-Sayed A F M, & Ezzat A A (2016) Dietary taurine enhances growth and feed utilization in larval Nile tilapia (*Oreochromis niloticus*) fed soybean meal-based diets. *Aquaculture Nutr* 22(2):457-464.
29. Yue Y-R, et al. (2012) The effect of dietary taurine supplementation on growth performance, feed utilization and taurine contents in tissues of juvenile white shrimp (*Litopenaeus vannamei*, Boone, 1931) fed with low-fishmeal diets. *Aquaculture Res* DOI: 10.1111/j.1365-2109.2012.03135.x.
30. Brotons Martinez J, Chatzifotis S, Divanach P, & Takeuchi T (2004) Effect of dietary taurine supplementation on growth performance and feed selection of sea bass *Dicentrarchus labrax* fry fed with demand-feeders. *Fish Sci* 70(1):74-79.
31. Milei J, et al. (1992) Reduction of reperfusion injury with preoperative rapid intravenous infusion of taurine during myocardial revascularization. *Amer Heart J* 123: 339-345.
32. Militante J D & Lombardini J B (2002) Treatment of hypertension with oral taurine. *Endocrinol* 147:3276-3284.
33. Fujita T, Ando K, Noda H, Ito Y, & Sato Y (1987) Effects of increased adrenomedullary activity and taurine in young patients with borderline hypertension. *Circulation* 75:525-532.
34. McCown T J, Givens B S, & Breese G R (1987) Amino acid influences on seizures elicited within the inferior colliculus. *Pharmacol Exp Ther* 243:603-608.
35. Matsuyama Y, Morita T, Higuchi M, & Tsujii T (1983) The effect of taurine administration on patients with acute hepatitis. *Progr Clin Biol Res* 125:461-468.
36. Ikeda H (1977) Effects of taurine on alcohol withdrawal. *Lancet* 2:509.
37. Franconi F, Di Leo M A S, Bennardini F, & Ghirlanda G (2004) Is taurine beneficial in reducing risk factors for diabetes mellitus? *Neurochem Res* 29:143-150.
38. Paula-Lima A C, De Felice F G, Brito-Moreira J, & Ferreira S T (2005) Activation of GABAA receptors by taurine and muscimol blocks the neurotoxicity of [beta]-amyloid in rat hippocampal and cortical neurons. *Neuropharmacol* 49:1140-1148.
39. Nakamori K, et al. (1993) Quantitative evaluation of the effectiveness of taurine in protecting the ocular surface against oxidant. *Chem Pharm Bull* 41:335-338.
40. Zhang M, et al. (2004) Beneficial effects of taurine on serum lipids in overweight or obese non-diabetic subjects. *Amino Acids* 26:267-271.
41. Yokogoshi H, et al. (1999) Dietary taurine enhances cholesterol degradation and reduces serum and liver cholesterol concentrations in rats fed a high-cholesterol diet. *J Nutr* 129:1705-1712.
42. Yamamoto K, et al. (2000) Dietary taurine decreases hepatic secretion of cholesterol ester in rats fed a high-cholesterol diet. *Pharmacol* 60:27-33.
43. Green T R, Fellman J H, Eicher A L, & Pratt K L (1991) Antioxidant role and subcellular location of hypotaurine and taurine in human neutrophils. *Biochim Biophys Acta* 1073:91-97.
44. Giirer H, Ozgiines H, Saygin E, & Ercal N (2001) Antioxidant effect of taurine against lead-induced oxidative stress. *Arch Environ Contam and Toxicol* 41:397-402.
45. Das J, Ghosh J, Manna P, & Sil P C (2008) Taurine provides antioxidant defense against NaF-induced cytotoxicity in murine hepatocytes. *Pathophysiol* 15:181-190.
46. Zhang M, et al. (2004) Role of taurine supplementation to prevent exercise-induced oxidative stress in healthy young men. *Amino Acids* 26:203-207.
47. Williams M (2005) Dietary supplements and sports performance: Amino acids. *J Int Soc Sports Nutr* 2:63-67.
48. da Silva D L P, et al. (2008) Penetration profile of taurine in the human skin and its distribution in skin layers. *Pharm Res* 25:1846-1850.
49. Suzuki A, Kajita T, & Furushima M (1989) U.S. Pat. No. 4,877,447.
50. Turano F J, Turano K A, Carlson P S, & Kinnersley A M (2012) U.S. Pat. No. 9,267,148 (Feb. 23, 2016).
51. Agnello G, Chang L L, Lamb C M, Georgiou G, & Stone E M (2013) Discovery of a substrate selectivity motif in amino acid decarboxylases unveils a taurine biosynthesis pathway in prokaryotes. *ACS Chem Biol* 8(10):2264-2271.
52. Tevatia R, et al. (2015) The taurine biosynthetic pathway of microalgae. *Algal Res* 9:21-26.
53. Honjoh K I, et al. (2010) Enhancement of menadione stress tolerance in yeast by accumulation of hypotaurine and taurine: co-expression of cDNA clones, from *Cyprinus carpio*, for cysteine dioxygenase and cysteine sulfinate decarboxylase in *Saccharomyces cerevisiae*. *Amino Acids* 38:1173-1183.
54. Turano F J, Price M B, & Turano K A (2014) U S Patent Application No. 20170283821.
55. Turano F J (2016) International Patent Application No. PCT/US2016/026465.
56. Turano F J (2016) International Patent Application No. PCT/US2016/028958.

57. Matsunari H, et al. (2005) Effect of feeding rotifers enriched with taurine on growth performance and body composition of Pacific cod larvae *Gadus macrocephalus*. *Aquaculture Sci* 53(3):297-304.
58. Salze G, McLean E, & Craig S R (2012) Dietary taurine enhances growth and digestive enzyme activities in larval cobia. *Aquaculture* 362-363:44-49.
59. Takahashi T, Amano T, & Takeuchi T (2005) Establishment of direct enrichment method of taurine to rotifer. *Aquaculture Sci* 53(2):121-126.
60. Hawkyard M, Laurel B, Barr Y, Hamre K, & Langdon C (2015) Evaluation of liposomes for the enrichment of rotifers (*Brachionus* sp.) with taurine and their subsequent effects on the growth and development of northern rock sole (*Lepidopsetta polyxystra*) larvae. *Aquaculture* 441: 118-125.
61. Higgins C F (2001) ABC transporters: physiology, structure and mechanism—an overview. *Res Microbiol* 152:205-210.
62. Berntsson R P A, Smits S H J, Schmitt L, Slotboom D-J, & Poolman B (2010) A structural classification of substrate-binding proteins. *FEBS Lett* 584(12):2606-2617.
63. Mulligan C, Fischer M, & Thomas G H (2011) Tripartite ATP-independent periplasmic (TRAP) transporters in bacteria and archaea. *FEMS Microbiol Rev* 35(1):68-86.
64. Turano F J & Turano K A (2011) U.S. Pat. No. 8,742,204 (Issued Jun. 3, 2014).
65. van der Ploeg J R, et al. (1996) Identification of sulfate starvation-regulated genes in *Escherichia coli*: a gene cluster involved in the utilization of taurine as a sulfur source. *J Bacteriol* 178(18):5438-5446.
66. van der Ploeg J R, Cummings N J, Leisinger T, & Connerton I F (1998) *Bacillus subtilis* genes for the utilization of sulfur from aliphatic sulfonates. *Microbiol* 144(9):2555-2561.
67. Brüggemann C, Denger K, Cook A M, & Ruff J (2004) Enzymes and genes of taurine and isethionate dissimilation in *Paracoccus denitrificans*. *Microbiol* 150(4):805-816.
68. Denger K, Ruff J, Schleheck D, & Cook A M (2004) *Rhodococcus opacus* expresses the xsc gene to utilize taurine as a carbon source or as a nitrogen source but not as a sulfur source. *Microbiol* 150(6):1859-1867.
69. Denger K, Smits T H M, & Cook A M (2006) Genome-enabled analysis of the utilization of taurine as sole source of carbon or of nitrogen by *Rhodobacter sphaeroides* 2.4.1. *Microbiol* 152(11):3197-3206.
70. Krejcik Z, Schleheck D, Hollemeyer K, & Cook A M (2012) A five-gene cluster involved in utilization of taurine-nitrogen and excretion of sulfoacetaldehyde by *Acinetobacter radioresistens* SH164. *Arch Microbiol* 194 (10):857-863.
71. Gorzynska A K, Denger K, Cook A M, & Smits T H M (2006) Inducible transcription of genes involved in taurine uptake and dissimilation by *Silicibacter pomeroyi* DSS-3T. *Arch Microbiol* 185(5):402-406.
72. Novak R T, Gritzer R F, Leadbetter E R, & Godchaux W (2004) Phototrophic utilization of taurine by the purple nonsulfur bacteria *Rhodopseudomonas palustris* and *Rhodobacter sphaeroides*. *Microbiol* 150(6):1881-1891.
73. van der Ploeg J R, Iwanicka-Nowicka R, Kertesz M A, Leisinger T, & Hryniewicz M M (1997) Involvement of CysB and Cbl regulatory proteins in expression of the tauABCD operon and other sulfate starvation-inducible genes in *Escherichia coli*. *J Bacteriol* 179(24):7671-7678.
74. van der Ploeg J R, Iwanicka-Nowicka R, Bykowski T, Hryniewicz M M, & Leisinger T (1999) The *Escherichia coli* ssuEADCB Gene Cluster Is Required for the Utilization of Sulfur from Aliphatic Sulfonates and Is Regulated by the Transcriptional Activator Cbl. *J Biol Chem* 274(41):29358-29365.
75. Feinberg L F & Marx C J (2014).
76. Jäckel C & Hilvert D (2010) Biocatalysts by evolution. *Curr Opin Biotechnol* 21(6):753-759.
77. Lane M D & Seelig B (2014) Advances in the directed evolution of proteins. *Current opinion in chemical biology* 22(Supplement C):129-136.
78. Packer M S & Liu D R (2015) Methods for the directed evolution of proteins. *Nature* 16:379.
79. Bennetzen J L & Hall B D (1982) Codon selection in yeast. *J Biol Chem* 257(6):3026-3031.
80. Gouy M & Gautier C (1982) Codon usage in bacteria: correlation with gene expressivity. *Nucleic Acids Res* 10(22):7055-7074.
81. Campbell W H & Gowri G (1990) Codon Usage in Higher Plants, Green Algae, and Cyanobacteria. *Plant Physiol* 92(1):1-11.
82. Douglas E S & Penny L S (The Plastid Genome of the Cryptophyte Alga, *Guillardia theta*: Complete Sequence and Conserved Synteny Groups Confirm Its Common Ancestry with Red Algae. *J Mol Evol* 48(2):236-244.
83. Yoon H S, Müller K M, Sheath R G, Ott F D, & Bhattacharya D (2006) Defining the major lineages of red algae (rhodophyta). *Journal of Phycology* 42(2):482-492.
84. Fletcher S P, Muto M, & Mayfield S P (2007) Optimization of Recombinant Protein Expression in the Chloroplasts of Green Algae. *Transgenic Microalgae as Green Cell Factories*, eds León R, Galván A, & Fernández E (Springer New York, N.Y., N.Y.), pp 90-98.
85. Langenheim J H & Thimann K V (1982) *Botany: Plant Biology and its Relation to Human Affairs* (John Wiley & Sons Inc., New York).
86. Vasil I K (1984) *Cell Culture and Somatic Cell Genetics of Plants: Laboratory Procedures and Their Applications* (Academic Press, Orlando).
87. Stanier R, Ingrahm J, Wheelis M, & Painter P (1986) *The Microbial World* (Prentice-Hall, New Jersey) 5 Ed.
88. Dhringra O D & Sinclair J B (1985) *Basic plant pathology methods* (CRC Press, Boca Raton, Fla.).
89. Maniatis T, Fritsch E F, & Sambrook J (1985) *Molecular Cloning: A Laboratory Manual: DNA Cloning* (Cold Spring Harbor, New York).
90. Gait (1984) *Oligonucleotide Synthesis-A Practical Approach* (IRL Press, Washington, D.C.).
91. Hames D D & Higgins S J (1984) *Nucleic Acid Hybridization: A Practical Approach* (IRL Press, Washington D.C.).
92. Watson J D, Gilman M, Witowski J, & Zoller M (1992) *Recombinant DNA* (Scientific American Books, New York).
93. Chen Y Y, Galloway K E, & Smolke C D (2012) Synthetic biology: advancing biological frontiers by building synthetic systems. *Genome Biol* 13(2):240.
94. Ceroni F, Carbonell P, Francois J-M, & Haynes K A (2015) Editorial—Synthetic Biology: Engineering Complexity and Refactoring Cell Capabilities. *Front Bioeng Biotechnol* 3:120.
95. Szewczyk E, et al. (2006) Fusion PCR and gene targeting in *Aspergillus nidulans*. *Nature Protocols* 1:3111-3121.
96. Ho S N, Hunt H D, Horton R M, Pullen J K, & Pease L R (1989) Site-directed mutagenesis by overlap extension using the polymerase chain reaction. *Gene* 77:51-59.

97. Fuhrmann M, Oertel W, & Hegemann P (1999) A synthetic gene coding for the green fluorescent protein (GFP) is a versatile reporter in *Chlamydomonas reinhardtii*. *Plant J* 19:353-361.
98. Mandecki W & Bolling T J (1988) FokI method of gene synthesis. *Gene* 68:101-107.
99. Stemmer W P, Crameri, A., Ha, K. D., Brennan, T. M. and Heyneker, H. L. (1995) Single-step assembly of a gene and entire plasmid from large numbers of oligodeoxyribonucleotides. *Gene* 164:49-53.
100. Gao X, Yo P, Keith A, Ragan T J, & Harris T K (2003) Thermodynamically balanced inside-out (TBIO) PCR-based gene synthesis: a novel method of primer design for high-fidelity assembly of longer gene sequences. *Nucleic Acids Res* 31:e143.
101. Young L & Dong Q (2004) Two-step total gene synthesis method. *Nucleic Acids Res* 32:e59.
102. Trinh R, Gurbaxani B, Morrison S L, & Seyfzadeh M (2004) Optimization of codon pair use within the (GGGGS) 3 linker sequence results in enhanced protein expression. *Mol Immunol* 40(10):717-722.
103. Chang T W & Yu L (1999) Genetic engineering. (Google Patents).
104. Kuusinen A, Arvola M, & Keinanen K (1995) Molecular dissection of the agonist binding site of an AMPA receptor. *EMBO J* 14(24):6327-6332.
105. Robinson C R & Sauer R T (1998) Optimizing the stability of single-chain proteins by linker length and composition mutagenesis. *PNAS* 95(11):5929-5934.
106. Armstrong N & Gouaux E (2000) Mechanisms for activation and antagonism of an AMPA-sensitive glutamate receptor: crystal structures of the GluR2 ligand binding core. Neuron 28(1):165-181.
107. Arai R, Ueda H, Kitayama A, Kamiya N, & Nagamune T (2001) Design of the linkers which effectively separate domains of a bifunctional fusion protein. *Protein Eng* 14(8):529-532.
108. Wriggers W, Chakravarty S, & Jennings P A (2005) Control of protein functional dynamics by peptide linkers. *Biopolymers* 80(6):736-746.
109. Reddy Chichili V P, Kumar V, & Sivaraman J (2013) Linkers in the structural biology of protein-protein interactions. *Protein Sci: Pub Protein Soc* 22(2):153-167.
110. Rosano G L & Ceccarelli E A (2014) Recombinant protein expression in microbial systems. *Front Microbiol* 5:341.
111. Hlavova M, Turoczy Z, & Bisova K (2015) Improving microalgae for biotechnology—From genetics to synthetic biology. *Biotechnol Adv* 33:1194-1203.
112. çelik E & çalik P (2012) Production of recombinant proteins by yeast cells. *Biotechnol Adv* 30(5):1108-1118.
113. de Jong A, Pietersma H, Cordes M, Kuipers O P, & Kok J (2012) PePPER: a webserver for prediction of prokaryote promoter elements and regulons. *BMC Genomics* 13:299.
114. Lee D J, Minchin S D, & Busby S J W (2012) Activating Transcription in Bacteria. *Annu Rev Microbiol* 66(1):125-152.
115. Meysman P, et al. (2014) Structural properties of prokaryotic promoter regions correlate with functional features. *PLoS ONE* 9(2):e88717.
116. Fujiwara T, Ohnuma M, Yoshida M, Kuroiwa T, & Hirano T (2013) Gene targeting in the red alga *Cyanidioschyzon merolae*: Single- and multi-copy insertion using authentic and chimeric selection markers. *PLoS ONE* 8(9):e73608.
117. Mikami K, Hirata K, Takahashi M, Uji T, & Saga N (2011) Transient transformation of red algal cells: Breakthrough toward genetic transformation of marine crop porphyra species. *Genetic Transformation*, ed Alvarez M (InTech).
118. Manuell A L et al. (2007) Robust expression of a bioactive mammalian protein in *Chlamydomonas* chloroplast. *Plant Biotechnol J* 5(3):402-412.
119. Cui Y, Qin S, & Jiang P (2014) Chloroplast Transformation of *Platymonas* (*Tetraselmis*) *subcordiformis* with the bar Gene as Selectable Marker. *PLoS ONE* 9(6): e98607.
120. Oey M, et al. (2013) RNAi Knock-Down of LHCBM1, 2 and 3 Increases Photosynthetic H2 Production Efficiency of the Green Alga *Chlamydomonas reinhardtii*. *PLoS ONE* 8(4):e61375.
121. Oey M, Ross I L, & Hankamer B (2014) Gateway-assisted vector construction to facilitate expression of foreign proteins in the chloroplast of single celled algae. *PLoS ONE* 9(2):e86841.
122. Wang B, Wang J, Zhang W, & Meldrum D R (2012) Application of synthetic biology in cyanobacteria and algae. *Front Microbiol* 3:344.
123. Wang J, Jiang P, Cui Y, Guan X, & Qin S (2010) Gene transfer into conchospores of *Porphyra haitanensis* (Bangiales, Rhodophyta) by glass bead agitation. *Phycologia* 49(4):355-360.
124. Ingelbrecht I L, Herman L M, Dekeyser R A, Van Montagu M C, & Depicker A G (1989) Different 3' end regions strongly influence the level of gene expression in plant cells. *Plant Cell* 1:671-680.
125. Zaret K S & Sherman F (1982) DNA sequence required for efficient transcription termination in yeast. *Cell* 28:563-573.
126. Helden Jv, Rios A F, & Collado-Vides J (2000) Discovering regulatory elements in non-coding sequences by analysis of spaced dyads. *Nucleic Acids Res* 28(8):1808-1818.
127. Graber J H (2003) Variations in yeast 3'-processing cis-elements correlate with transcript stability. *Trends Genet* 19(9):473-476.
128. Wodniok S, Simon A, Glöckner G, & Becker B (2007) Gain and loss of polyadenylation signals during evolution of green algae. *BMC Evol Biol* 7(1):1-12.
129. Shen Y, Liu Y, Liu L, Liang C, & Li Q Q (2008) Unique Features of Nuclear mRNA Poly(A) Signals and Alternative Polyadenylation in *Chlamydomonas reinhardtii*. Genetics 179(1):167-176.
130. Schiackow M, et al. (2013) Genome-wide analysis of poly(A) site selection in *Schizosaccharomyces pombe*. *RNA (New York, N.Y.)* 19(12):1617-1631.
131. Yamanishi M, et al. (2013) A genome-wide activity assessment of terminator regions in *Saccharomyces cerevisiae* provides a "Terminatome" toolbox. *ACS Synth Biol* 2(6):337-347.
132. Chen Y-J, et al. (2013) Characterization of 582 natural and synthetic terminators and quantification of their design constraints. *Nat Meth* 10(7):659-664.
133. Leavitt J M & Alper H S (2015) Advances and current limitations in transcript-level control of gene expression. *Curr Opin Biotechnol* 34:98-104.
134. Ausubel F M, et al. (1995) *Curr Protoc Mol Biol* (Greene Publishing and Wiley-Interscience, New York).
135. Chan H W & Wells R D (1974) Structural uniqueness of lactose operator. *Nature* 252:205-209.
136. Goeddel D V, et al. (1980) Synthesis of human fibroblast interferon by *E. coli Nucleic Acids Res* 8:4057-4074.

137. Marx C J & Lidstrom M E (2001) Development of improved versatile broad-host-range vectors for use in methylotrophs and other Gram-negative bacteria. *Microbiol* 147:2065-2075.
138. Atomi H, Imanaka T, & Fukui T (2012) Overview of the genetic tools in the Archaea. *Front Microbiol* 3:337.
139. Farkas J A, Picking J W, & Santangelo T J (2013) Genetic techniques for the archaea. *Annu Rev Genet* 47:539-561.
140. Tan S (2001) A modular polycistronic expression system for overexpressing protein complexes in *Escherichia coli*. *Protein Expr Purif* 21(1):224-234.
141. Tan S, Kern R C, & Selleck W (2005) The pST44 polycistronic expression system for producing protein complexes in *Escherichia coli*. *Protein Expr Purif* 40(2): 385-395.
142. Baba T, et al. (2006) Construction of *Escherichia coli* K-12 in-frame, single-gene knockout mutants: the Keio collection. *Mol Syst Biol* 2:2006.0008-2006.0008.
143. Reyrat J M, Pelicic V, Gicquel B, & Rappuoli R (1998) Counterselectable markers: untapped tools for bacterial genetics and pathogenesis. *Infect Immun* 66(9):4011-4017.
144. Nakashima N & Miyazaki K (2014) Bacterial cellular engineering by genome editing and gene silencing. *Int J Mol Sci* 15(2):2773-2793.
145. Ried J L & Collmer A (1987) An nptI-sacB-sacR cartridge for constructing directed, unmarked mutations in gram-negative bacteria by marker exchange-eviction mutagenesis. *Gene* 57(2-3):239-246.
146. Murphy K C, Campellone K G, & Poteete A R (2000) PCR-mediated gene replacement in *Escherichia coli*. *Gene* 246 (1-2):321-330.
147. Sun W, Wang S, & Curtiss R (2008) Highly efficient method for introducing successive multiple scarless gene deletions and markerless gene insertions into the *Yersinia pestis* chromosome. *Appl Environ Microbiol* 74:4241-4245.
148. Costantino N & Court D L (2003) Enhanced levels of X, Red-mediated recombinants in mismatch repair mutants. *PNAS* 100(26):15748-15753.
149. Datsenko K A & Wanner B L (2000) One-step inactivation of chromosomal genes in *Escherichia coli* K-12 using PCR products. *PNAS* 97(12):6640-6645.
150. Lv L, Ren Y-L, Chen J-C, Wu Q, & Chen G-Q (2015) Application of CRISPRi for prokaryotic metabolic engineering involving multiple genes, a case study: Controllable P(3HB-co-4HB) biosynthesis. *Metab Eng* 29:160-168.
151. Peters J M, et al. (2015) Bacterial CRISPR: accomplishments and prospects. *Curr Opin Microbiol* 27:121-126.
152. Selle K & Barrangou R (2015) Harnessing CRISPR-Cas systems for bacterial genome editing. *Trends Microbiol* 23(4):225-232.
153. Rehnstam-Holm A-S & Godhe A (2003) Genetic engineering of algal species. *Biotechnology*, ed Doelle H W (UNESCO, Eolss Publishers, Oxford, U K).
154. Rosa L, Galván-Cejudo A, & Fernández E eds (2007) *Transgenic Microalgae as Green Cell Factories* (Springer Science+Business Media, LLC, New York, N.Y.), Vol 616.
155. Leon R & Fernandez E (2007) Nuclear transformation of eukaryotic microalgae: historical overview, achievements and problems. *Adv Exp Med Biol* 616:1-11.
156. Mikami K, Hirata R, Takahashi M, Uji T, & Saga N (2011) Transient transformation of red algal cells: Breakthrough toward genetic transformation of marine crop *Porphyra* Species. *Genetic Transformation*, ed Alvarez M (InTech).
157. Umen J G & Olson B J (2012) Genomics of Volvocine Algae. *Advances in botanical research* 64:185-243.
158. Liu L et al. (2013) Development of a new method for genetic transformation of the green alga *Chlorella ellipsoidea*. *Mol Biotechnol* 54(2):211-219.
159. Gimpel J A, Specht E A, Georgianna D R, & Mayfield S P (2013) Advances in microalgae engineering and synthetic biology applications for biofuel production. *Current Opin Chemical Biol* 17(3):489-495.
160. Rasala B A, Chao S-S, Pier M, Barrera D J, & Mayfield S P (2014) Enhanced genetic tools for engineering multigene traits into green algae. *PLoS ONE*.
161. Rasala B A, et al. (2010) Production of therapeutic proteins in algae, analysis of expression of seven human proteins in the chloroplast of *Chlamydomonas reinhardtii*. *Plant Biotechnol J* 8(6):719-733.
162. Potvin G & Zhang Z (2010) Strategies for high-level recombinant protein expression in transgenic microalgae: a review. *Biotechnol Adv* 28(6):910-918.
163. León-Bañares R, González-Ballester D, Galván A, & Fernández E (2004) Transgenic microalgae as green cell-factories. *Trends Biotechnol* 22(1):45-52.
164. Heitzer M & Zschoernig B (2007) Construction of modular tandem expression vectors for the green alga *Chlamydomonas reinhardtii* using the Cre/lox-system. *Biotechniques* 43(3):324, 326, 328 passim.
165. Sizova I, Greiner A, Awasthi M, Kateriya S, & Hegemann P (2013) Nuclear gene targeting in *Chlamydomonas* using engineered zinc-finger nucleases. *Plant J* 73(5):873-882.
166. Daboussi F, et al. (2014) Genome engineering empowers the diatom *Phaeodactylum tricornutum* for biotechnology. *Nat Commun* 5.
167. Hlavova M, Turoczy Z, & Bisova K (2015) Improving microalgae for biotechnology—From genetics to synthetic biology. *Biotechnol Adv* 33(6 Pt 2):1194-1203.
168. Pratheesh P T, Vineetha M, & Kurup G M (2013) An efficient protocol for the *Agrobacterium*-mediated genetic transformation of microalga *Chlamydomonas reinhardtii*. *Molecular Biotechnol* 56(6):507-515.
169. Kindle K L (1998) Nuclear Transformation: Technology and Applications. *The Molecular Biology of Chloroplasts and Mitochondria in Chlamydomonas*, eds Rochaix J D, Goldschmidt-Clermont M, & Merchant S (Springer Netherlands, Dordrecht), pp 41-61.
170. Ohnuma M, Yokoyama T, Inouye T, Sekine Y, & Tanaka K (2008) Polyethylene Glycol (PEG)-Mediated Transient Gene Expression in a Red Alga, *Cyanidioschyzon merolae* 10D. *Plant Cell Physiol* 49(1):117-120.
171. Shimogawara K, Fujiwara S, Grossman A, & Usuda H (1998) High-efficiency transformation of *Chlamydomonas reinhardtii* by electroporation. *Genetics* 148(4):1821-1828.
172. Hayashi M, Hirono M, & Kamiya R (2001) Recovery of flagellar dynein function in a *Chlamydomonas* actin/dynein-deficient mutant upon introduction of muscle actin by electroporation. *Cell Motil Cytoskeleton* 49(3):146-153.
173. van Ooijen G, Knox K, Kis K, Bouget F-Y, & Millar A J (2012) Genomic transformation of the Picoeukaryote *Ostreococcus tauri*. *J Vis Exp* (65):4074.
174. Vieler A, et al. (2012) Genome, functional gene annotation, and nuclear transformation of the Heterokont Oleaginous Alga *Nannochloropsis oceanica* CCMP1779. *PLoS Genetics* 8(11):e1003064.
175. Boynton J E, et al. (1988) Chloroplast transformation in *Chlamydomonas* with high velocity microprojectiles. *Science* 240(4858):1534-1538.
176. Apt K E, Kroth-Pancic P G, & Grossman A R (1996) Stable nuclear transformation of the diatom *Phaeodactylum tricornutum. Mol Gen Genet* 252(5):572-579.
177. Dunahay T G, Jarvis E E, & Roessler P G (1995) Genetic transformation of the diatoms cyclotella cryptica and navicula saprophila. *J Phycol* 31(6):1004-1012.
178. Falciatore A, Casotti R, Leblanc C, Abrescia C, & Bowler C (1999) Transformation of Nonselectable Reporter Genes in Marine Diatoms. *Marine Biotechnol* (New York N.Y.) 1(3):239-251.
179. Zaslayskaia L A, Lippmeier J C, Kroth P G, Grossman A R, & Apt K E (2000) Transformation of the diatom *Phaeodactylum tricornutum* (Bacillariophyceae) with a variety of selectable marker and reporter genes. *J Phycol* 36(2):379-386.
180. Dunahay T G (1993) Transformation of *Chlamydomonas reinhardtii* with silicon carbide whiskers. *Biotechniques* 15(3):452-455, 457-458, 460.
181. Te M R, Lohuis, & Miller D J (1998) Genetic transformation of dinoflagellates (Amphidinium and Symbiodinium): expression of GUS in microalgae using heterologous promoter constructs. *Plant J* 13(3):427-435.
182. Henry E C & Meints R H (Recombinant viruses as transformation vectors of marine macroalgae. *J Appl Phycol* 6(2):247-253.
183. Van Etten J L & Meints R H (1999) Giant viruses infecting algae. *Annu Rev Microbiol* 53:447-494.
184. Kojima H & Kawata Y (2001) A mini-transposon/transposase complex as a new tool for the genetic transformation of microalgae. *Photosynthetic Microorganisms in Environment Biotechnology*, eds Kojima H & Lee Y K (Springer-Verlag, Berlin, Germany), pp 41-61.
185. Lapidot M, Raveh D, Sivan A, Arad S M, & Shapira M (2002) Stable chloroplast transformation of the unicellular red alga *Porphyridium* species. *Plant Physiol* 129(1): 7-12.
186. Jiang H, et al. (2010) Methanotrophs: Multifunctional bacteria with promising applications in environmental bioengineering. *Biochem Eng J* 49(3):277-288.
187. Demain A L (2007) The business of biotechnology. *Indust Biotechnol* 3:269-283.
188. Romanos M A, Scorer C A, & Clare J J (1992) Foreign gene expression in yeast: a review. *Yeast (Chichester, England)* 8(6):423-488.
189. Agmon N, et al. (2015) Yeast Golden Gate (yGG) for the Efficient Assembly of *S. cerevisiae* Transcription Units. *ACS Synth Biol* 4(7):853-859.
190. Sherman F (1991) Getting started with yeast. *Methods in Enzymology, Guide to Yeast Genetics and Molecular Biology*, eds Guthrie C & Fink G R (Acad. Press, New York), Vol 194, pp 3-21.
191. Sherman F, Fink G R, & Hick J B (1982) *Methods in Yeast Genetics* (Cold Spring Harbor Laboratory, New York).
192. Olmedo-Monfil V, CortEs-Penagos C, & Herrera-Estrella A (2004) Three Decades of Fungal Transformation, Vol 267, pp 297-313.
193. Weld R J, Plummer K M, Carpenter M A, & Ridgway H J (2006) Approaches to functional genomics in filamentous fungi. *Cell Res* 16(1):31-44.
194. Kawai S, Hashimoto W, & Murata K (2010) Transformation of *Saccharomyces cerevisiae* and other fungi: Methods and possible underlying mechanism. *Bioengineered Bugs* 1(6):395-403.
195. van den Berg M A & Maruthachalam K eds (2015) *Genetic Transformation Systems in Fungi, Volume 1* (Springer, New York, N.Y.).
196. Rivera A L, Magana-Ortiz D, Gomez-Lim M, Fernandez F, & Loske A M (2014) Physical methods for genetic transformation of fungi and yeast. *Physics of life reviews* 11(2):184-203.
197. Vickers C E, Bydder S F, Zhou Y, & Nielsen L K (2013) Dual gene expression cassette vectors with antibiotic selection markers for engineering in *Saccharomyces cerevisiae. Microbial Cell Factories* 12(1):1-11.
198. Sherman F (1997) Yeast genetics. *The Encyclopedia of Molecular Biology and Molecular Medicine*, ed Meyers R A (VCH Publisher, Weinheim, Germany), Vol 6, pp 302-325.
199. Romanos M A, Scorer C A, & Clare J J (1992) Foreign gene expression in yeast: a review. *Yeast (Chichester, England)* 8.
200. Baudin A, Ozier-Kalogeropoulos O, Denouel A, Lacroute F, & Cullin C (1993) A simple and efficient method for direct gene deletion in *Saccharomyces cerevisiae. Nucleic Acids Res* 21(14):3329-3330.
201. Longtine M S, et al. (1998) Additional modules for versatile and economical PCR-based gene deletion and modification in *Saccharomyces cerevisiae. Yeast (Chichester, England)* 14(10):953-961.
202. Krawchuk M D & Wahls W P (1999) High-efficiency gene targeting in *Schizosaccharomyces pombe* using a modular, PCR-based approach with long tracts of flanking homology. *Yeast (Chichester, England)* 15(13):1419-1427.
203. Epinat J-C, et al. (2003) A novel engineered meganuclease induces homologous recombination in yeast and mammalian cells. *Nucleic Acids Res* 31(11):2952-2962.
204. Li T, et al. (2011) Modularly assembled designer TAL effector nucleases for targeted gene knockout and gene replacement in eukaryotes. *Nucleic Acids Res*.
205. DiCarlo J E, et al. (2013) Genome engineering in *Saccharomyces cerevisiae* using CRISPR-Cas systems. *Nucleic Acids Res* 41(7):4336-43.
206. Jacobs J Z, Ciccaglione K M, Tournier V, & Zaratiegui M (2014) Implementation of the CRISPR-Cas9 system in fission yeast. *Nat Commun* 5.
207. Olmedo-Monfil V, Cortes-Penagos C, & Herrera-Estrella A (2004) Three decades of fungal transformation: key concepts and applications. *Methods Mol Biol* 267: 297-313.
208. van den Berg M A & Maruthachalam K (2015) *Genetic Transformation Systems in Fungi, Volume 1* (Springer International Publishing, Cham).
209. van Oers M M, Pijlman G P, & Vlak J M (2015) Thirty years of baculovirus-insect cell protein expression: from dark horse to mainstream technology. *J Gen Virol* 96(1): 6-23.
210. Almo S C & Love J D (2014) Better and faster: improvements and optimization for mammalian recombinant protein production. *Curr Opin Struct Biol* 26:39-43.
211. van Der Krol A R, et al. (1999) Developmental and wound-, cold-, desiccation-, ultraviolet-B-stress-induced modulations in the expression of the *petunia* zinc finger transcription factor gene ZPT2-2. *Plant Physiol* 121(4): 1153-1162.

212. Shinmyo A, et al. (1998) Metabolic engineering of cultured tobacco cells. *Biotechnol Bioeng* 58(2-3):329-332.
213. Sohal A K, Pallas J A, & Jenkins G I (1999) The promoter of a *Brassica napus* lipid transfer protein gene is active in a range of tissues and stimulated by light and viral infection in transgenic *Arabidopsis*. *Plant Mol Biol* 41(1):75-87.
214. Cormack R S, et al. (2002) Leucine zipper-containing WRKY proteins widen the spectrum of immediate early elicitor-induced WRKY transcription factors in parsley. *Biochimica et Biophysica Acta* 1576(1-2):92-100.
215. Eulgem T, Rushton P J, Schmelzer E, Hahlbrock K, & Somssich I E (1999) Early nuclear events in plant defence signalling: rapid gene activation by WRKY transcription factors. *EMBO J* 18(17):4689-4699.
216. Lebel E, et al. (1998) Functional analysis of regulatory sequences controlling PR-1 gene expression in A rabidopsis. *Plant J* 16(2):223-233.
217. Ngai N, Tsai F Y, & Coruzzi G (1997) Light-induced transcriptional repression of the pea AS1 gene: identification of cis-elements and transfactors. *Plant J* 12(5): 1021-1034.
218. Kucho K, Ohyama K, & Fukuzawa H (1999) CO(2)-responsive transcriptional regulation of CAH1 encoding carbonic anhydrase is mediated by enhancer and silencer regions in *Chlamydomonas reinhardtii*. *Plant Physiol* 121(4):1329-1338.
219. Kucho K, Yoshioka S, Taniguchi F, Ohyama K, & Fukuzawa H (2003) Cis-acting elements and DNA-binding proteins involved in CO2-responsive transcriptional activation of Cah1 encoding a periplasmic carbonic anhydrase in *Chlamydomonas reinhardtii*. *Plant Physiol* 133 (2):783-793.
220. Chen W, Chao G, & Singh K B (1996) The promoter of a H2O2-inducible, *Arabidopsis* glutathione S-transferase gene contains closely linked OBF- and OBP1-binding sites. *Plant J* 10(6):955-966.
221. Chen W & Singh K B (1999) The auxin, hydrogen peroxide and salicylic acid induced expression of the *Arabidopsis* GST6 promoter is mediated in part by an ocs element. *Plant J* 9(6):667-677.
222. Andrade M A, O'Donoghue S I, & Rost B (1998) Adaptation of protein surfaces to subcellular location. *J Mol Biol* 276.
223. Leubner-Metzger G, Petruzzelli L, Waldvogel R, Vogeli-Lange R, & Meins F, Jr. (1998) Ethylene-responsive element binding protein (EREBP) expression and the transcriptional regulation of class I beta-1,3-glucanase during tobacco seed germination. *Plant Mol Biol* 38(5): 785-795.
224. de Framond A J (1991) A metallothionein-like gene from maize (*Zea mays*). Cloning and characterization. *FEBS Letters* 290(1-2):103-106.
225. Hudspeth R L, Hobbs S L, Anderson D M, Rajasekaran K, & Grula J W (1996) Characterization and expression of metallothionein-like genes in cotton. *Plant Mol Biol* 31(3):701-705.
226. Kridl J C, et al. (1991) Isolation and characterization of an expressed napin gene from *Brassica rapa*. *Seed Science Research* 1(04):209-219.
227. Zavallo D, Lopez Bilbao M, Hopp H E, & Heinz R (2010) Isolation and functional characterization of two novel seed-specific promoters from sunflower (*Helianthus annuus* L.). *Plant Cell Rep* 29(3):239-248.
228. Kim M J, et al. (2006) Seed-specific expression of sesame microsomal oleic acid desaturase is controlled by combinatorial properties between negative cis-regulatory elements in the SeFAD2 promoter and enhancers in the 5'-UTR intron. *Mol Genet Genom* 276(4):351-368.
229. Bustos M M, et al. (1989) Regulation of beta-glucuronidase expression in transgenic tobacco plants by an A/T-rich, cis-acting sequence found upstream of a French bean beta-phaseolin gene. *Plant Cell* 1(9):839-853.
230. Fujiwara T & Beachy R N (1994) Tissue-specific and temporal regulation of a beta-conglycinin gene: roles of the R Y repeat and other cis-acting elements. *Plant Mol Biol* 24(2):261-272.
231. Wienand U, Langridge P, & Feix G (1981) Isolation and characterization of a genomic sequence of maize coding for a zein gene. *Molec Gen Genet* 182(3):440-444.
232. Takaiwa F, Oono K, Wing D, & Kato A (1991) Sequence of three members and expression of a new major subfamily of glutelin genes from rice. *Plant Mol Biol* 17:875-885.
233. Hudspeth R L, Grula J W, Dai Z, Edwards G E, & Ku M S (1992) Expression of maize phosphoenolpyruvate carboxylase in transgenic tobacco: Effects on biochemistry and physiology. *Plant Physiol* 98(2):458-464.
234. Herrera-Estrella L, Depicker A, van Montagu M, & Schell J (1983) Expression of chimaeric genes transferred into plant cells using a Ti-plasmid-derived vector. *Nature* 303:209-213.
235. Nagaya S, Kawamura K, Shinmyo A, & Kato K (2010) The HSP terminator of *Arabidopsis thaliana* increases gene expression in plant cells. *Plant Cell Physiol* 51(2): 328-332.
236. Mogen B D, MacDonald M H, Graybosch R, & Hunt A G (1990) Upstream sequences other than AAUAAA are required for efficient messenger RNA 3'-end formation in plants. *Plant Cell* 2(12):1261-1272.
237. Mogen B D, MacDonald M H, Leggewie G, & Hunt A G (1992) Several distinct types of sequence elements are required for efficient mRNA 3' end formation in a pea rbcS gene. *Mol Cell Biol* 12(12):5406-5414.
238. Rothnie H M, Reid J, & Hohn T (1994) The contribution of AAUAAA and the upstream element UUUGUA to the efficiency of mRNA 3'-end formation in plants. *EMBO J* 13(9):2200-2210.
239. Bassett C L (2007) *Regulation of Gene Expression in Plants: The Role of Transcript Structure and Processing* (Springer Press, New York).
240. Ohme-Takagi M, Taylor C B, Newman T C, & Green P J (1993) The effect of sequences with high A U content on mRNA stability in tobacco. *PNAS* 90(24):11811-11815.
241. Newman T C, Ohme-Takagi M, Taylor C B, & Green P J (1993) DST sequences, highly conserved among plant SAUR genes, target reporter transcripts for rapid decay in tobacco. *Plant Cell* 5(6):701-714.
242. Gutiérrez R A, Macintosh G C, & Green P J (1999) Current perspectives on mRNA stability in plants: multiple levels and mechanisms of control. *Trends Plant Sci* 4:429-438.
243. An G, et al. (1989) Functional analysis of the 3' control region of the potato wound-inducible proteinase inhibitor II gene. *Plant Cell* 1:115-122.
244. An G, Watson B D, Stachel S, Gordon M P, & Nester E W (1985) New cloning vehicles for transformation of higher plants. *EMBO J* 4:277-284.
245. Gruber M Y & Cosby W L (1993) Vectors for plant transformation. *Methods in Plant Molecular Biology and Biotechnology*, eds Glick B R & Thompson J E (CRC Press, Baco Raton, Fla.), pp 89-119.

246. Hatzfeld Y (2014) U.S. Pat. No. 8,779,237.
247. Franklin S, Somanchi A, Espina K, Rudenko G, & Chua P (2014) U.S. Pat. No. 8,674,180.
248. Feng P C C, Malven M, & Flasinski S (2013) U.S. Pat. No. 8,420,888.
249. Manjunath S, et al. (2012) U.S. Pat. No. 8,138,393.
250. Lee D W, et al. (2008) *Arabidopsis* nuclear-encoded plastid transit peptides contain multiple sequence subgroups with distinctive chloroplast-targeting sequence motifs. *Plant Cell* 20(6):1603-1622.
251. von Heijne G, et al. (1991) CHLPEP: a database of chloroplast transit peptides. *Plant Mol Biol Rep* 9:104-126.
252. Waller R F, Reed M B, Cowman A F, & McFadden G I (2000) Protein trafficking to the plastid of *Plasmodium falciparum* is via the secretory pathway. *EMBO J* 19(8):1794-1802.
253. Minge M A, et al. (2010) A phylogenetic mosaic plastid proteome and unusual plastid-targeting signals in the green-colored dinoflagellate *Lepidodinium chlorophorum*. *BMC Evol Biol* 10(1):1-11.
254. Li H-m & Teng Y-S (2013) Transit peptide design and plastid import regulation. *Trends Plant Sci* 18(7):360-366.
255. Tardif M, et al. (2012) PredAlgo: A New Subcellular Localization Prediction Tool Dedicated to Green Algae. *Mol Biol Evol* 29(12):3625-3639.
256. von Heijne G (1986) Mitochondrial targeting sequences may form amphiphilic helices. *EMBO J* 5:1335-1342.
257. Swinkels B W, Gould S J, Bodnar A G, Rachubinski R A, & Subramani S (1991) A novel, cleavable peroxisomal targeting signal at the amino-terminus of the rat 3-ketoacyl-CoA thiolase. *EMBO J* 10(11):3255-3262.
258. Rusch S L & Kendall D A (1995) Protein transport via amino-terminal targeting sequences: Common themes in diverse systems. *Mol Membrane Biol* 12(4):295-307.
259. Soll J & Tien R (1998) Protein translocation into and across the chloroplastic envelope membranes. *Plant Mol Biol* 38:191-207.
260. Gould S J, Keller G A, & Subramani S (1988) Identification of peroxisomal targeting signals located at the carboxy terminus of four peroxisomal proteins. *J Cell Biol* 107(3):897-905.
261. Gould S J, Keller G A, Hosken N, Wilkinson J, & Subramani S (1989) A conserved tripeptide sorts proteins to peroxisomes. *J Cell Biol* 108(5):1657-1664.
262. McCammon M T, McNew J A, Willy P J, & Goodman J M (1994) An internal region of the peroxisomal membrane protein PMP47 is essential for sorting to peroxisomes. *J Cell Biol* 124(6):915-925.
263. Cokol M, Nair R, & Rost B (2000) Finding nuclear localization signals. *EMBO Rep* 1(5):411-415.
264. Helenius A & Aebi M (2001) Intracellular functions of N-linked glycans. *Science* 291(5512):2364-2369.
265. Emanuelsson O, Brunak S, von Heijne G, & Nielsen H (2007) Locating proteins in the cell using TargetP, SignalP and related tools. *Nature Protoc* 2(4):953-971.
266. Emanuelsson O, Nielsen H, Brunak S, & von Heijne G (2000) Predicting subcellular localization of proteins based on their N-terminal amino acid sequence. *J Mol Biol* 300(4):1005-1016.
267. Bannai H, Tamada Y, Maruyama O, Nakai K, & Miyano S (2002) Extensive feature detection of N-terminal protein sorting signals. *Bioinformatics* 18(2):298-305.
268. Bendtsen J D, Nielsen H, von Heijne G, & Brunak S (2004) Improved prediction of signal peptides: SignalP 3.0. *J Mol Biol* 340(4):783-795.
269. Hiller K, Grote A, Scheer M, Munch R, & Jahn D (2004) PrediSi: prediction of signal peptides and their cleavage positions. *Nucleic Acids Res* 32(Web Server issue):W375-379.
270. Bhasin M & Raghava G P (2004) ESLpred: SVM-based method for subcellular localization of eukaryotic proteins using dipeptide composition and PSI-BLAST. *Nucleic Acids Res* 32(Web Server issue):W414-419.
271. Garg A, Bhasin M, & Raghava G P (2005) Support vector machine-based method for subcellular localization of human proteins using amino acid compositions, their order, and similarity search. *J Biol Chem* 280(15):14427-14432.
272. Bhasin M, Garg A, & Raghava G P (2005) PSLpred: prediction of subcellular localization of bacterial proteins. *Bioinformatics* 21(10):2522-2524.
273. Hoglund A, Donnes P, Blum T, Adolph H W, & Kohlbacher O (2006) MultiLoc: prediction of protein subcellular localization using N-terminal targeting sequences, sequence motifs and amino acid composition. *Bioinformatics* 22(10):1158-1165.
274. Shatkay H, et al. (2007) SherLoc: high-accuracy prediction of protein subcellular localization by integrating text and protein sequence data. *Bioinformatics* 23(11):1410-1417.
275. Emanuelsson O, Nielsen H, & von Heijne G (1999) ChloroP, a neural network-based method for predicting chloroplast transit peptides and their cleavage sites. *Protein Sci* 8(5):978-984.
276. Claros M G & Vincens P (1996) Computational method to predict mitochondrially imported proteins and their targeting sequences. *Eur J Biochem* 241(3):779-786.
277. Small I, Peeters N, Legeai F, & Lurin C (2004) Predotar: A tool for rapidly screening proteomes for N-terminal targeting sequences. *Proteomics* 4(6):1581-1590.
278. Kelley L A, MacCallum R M, & Sternberg M J (2000) Enhanced genome annotation using structural profiles in the program 3D-PSSM. *J Mol Biol* 299(2):499-520.
279. Shahin E A (1985) Totipotency of tomato protoplasts. *Theor Appl Genet* 69:235-240.
280. Fromm M, Taylor L P, & V. W (1985) Expression of genes transferred into monocot and dicot plant cells by electroporation. *PNAS* 82:5824-5828.
281. Fromm M E, Taylor L P, & Walbot V (1986) Stable transformation of maize after gene transfer by electroporation. *Nature* 319(6056):791-793.
282. Riggs C D & Bates G W (1986) Stable transformation of tobacco by electroporation: evidence for plasmid concatenation. *PNAS* 83(15):5602-5606.
283. D'Halluin K, Bonne E, Bossut M, De Beuckeleer M, & Leemans J (1992) Transgenic maize plants by tissue electroporation. *Plant Cell* 4:1495-1505.
284. Laursen C M, Krzyzek R A, Flick C E, Anderson P C, & Spencer T M (1994) Production of fertile transgenic maize by electroporation of suspension culture cells *Plant Mol Biol* 24:51-61
285. Crossway A, et al. (1986) Integration of foreign DNA following microinjection of tobacco mesophyll protoplasts. *Molecular and General Genetics* 202:179-185.
286. Griesbach R J (1983) Protoplast microinjection. *Plant Mol Biol Rep* 1:32-37.
287. Sporlein B & Koop H-U (1991) Lipofectin: direct gene transfer to higher plants using cationic liposomes. *Theor Appl Genet* 83:1-5.

288. Ohgawara T, Uchimiya H, & Harada H (1983) Uptake of liposome-encapsulated plasmid DNA by plant protoplasts and molecular fate of foreign DNA *Protoplasma* 116:145-148.
289. Deshayes A, Herrera-Estrella L, & Caboche M (1985) Liposome-mediated transformation of tobacco mesophyll protoplasts by an *Escherichia coli* plasmid. *EMBO J* 4(11):2731-2737.
290. Christou P, Murphy J E, & Swain W F (1987) Stable transformation of soybean by electroporation and root formation from transformed callus. *PNAS* 84(12):3962-3966.
291. Horsch R B, et al. (1985) A Simple and General Method for Transferring Genes into Plants. *Science* 227:1229-1231.
292. Paszkowski J, et al. (1984) Direct gene transfer to plants. *Embo J* 3(12):2717-2722.
293. Hooykaas-Van Slogteren G M, Hooykaas P J, & Schilperoort R A (1984) Expression of Ti plasmid genes in monocotyledonous plants infected with *Agrobacterium tumefaciens*. *Nature* 311:763-764.
294. Rogers S G, Horsch, R. B., and Fraley, R. T. 1986. Gene transfer in plants: Production of transformed plants using Ti-plasmid vectors. (1986) Gene transfer in plants: Production of transformed plants using Ti-plasmid vectors. *Methods Enzymol* 118:627-640.
295. Bevan M W & Chilton M-D (1982) T-DNA of the *Agrobacterium* Ti and Ri plasmids. *Annu Rev Genet* 16:357-384.
296. Klein T M, et al. (1988) Transfer of foreign genes into intact maize cells with high-velocity microprojectiles. *PNAS* 85(12):4305-4309.
297. Klein T M, Gradziel T, Fromm M E, & Sanford J C (1988) Factors influencing gene delivery into *Zea mays* cells by high-velocity microprojectiles. *Biotechnol* 6:559-563.
298. McCabe D E, Swain W F, Martinell B J, & Christou P (1988) Stable transformation of soybean (*Glycine max*) by particle acceleration. *Biotechnol* 6:923-926.
299. Sanford J C, Smith F D, & Rushell J A (1993) Optimizing the biolistic process for different biological application. *The Methods in Enzymology*, ed Wu R (Academic Press, Orlando), Vol 217, pp 483-509.
300. Freeman J P, et al. (1984) A comparison of methods for plasmid delivery into plant protoplasts. *Plant Cell Physiol* 25:1353-1365.
301. Frame B R, et al. (1994) Production of fertile transgenic maize plants by silicon carbide whisker-mediated transformation. *Plant J* 6:941-948.
302. Thompson J A, Drayton P, Frame B, Wang K, & Dunwell J M (1995) Maize transformation utilizing silicon carbide whiskers: a review. *Euphytica* 85:75-80.
303. Guo Y, Liang H, & Berns M W (1995) Laser-mediated gene transfer in rice. Physiol *Plantarum* 93:19-24.
304. Badr Y A, Kereim M A, Yehia M A, Fouad O O, & Bahieldin A (2005) Production of fertile transgenic wheat plants by laser micropuncture. *Photochem Photobiol Sci* 4:803-807.
305. Bao S, Thrall B D, & Miller D L (1997) Transfection of a reporter plasmid into cultured cells by sonoporation in vitro. *Ultrasound Med Biol* 23:953-959.
306. Finer K R & Finer J J (2000) Use of *Agrobacterium* expressing green fluorescent protein to evaluate colonization of sonication-assisted *Agrobacterium*-mediated transformation-treated soybean cotyledons. *Lett Appl Microbiol* 30(5):406-410.
307. Amoah B K, Wu H, Sparks C, & Jones H D (2001) Factors influencing *Agrobacterium*-mediated transient expression of uidA in wheat inflorescence tissue. *J Exp Bot* 52(358): 1135-1142.
308. Krens F A, Molendijk L, Wullems G J, & Schilperoort R A (1982) In Vitro transformation of plant protoplasts with Ti-plasmid DNA. *Nature* 296:72-74.
309. Bechtold N & Pelletier G (1998) In planta *Agrobacterium*-mediated transformation of adult *Arabidopsis thaliana* plants by vacuum infiltration. *Meth Mol Biol* 82:259-266.
310. Broothaerts W, et al. (2005) Gene transfer to plants by diverse species of bacteria. *Nature* 433:629-633.
311. Urnov F D, Rebar E J, Holmes M C, Zhang H S, & Gregory P D (2010) Genome editing with engineered zinc finger nucleases. *Nature Rev. Genetics* 11(9):636-646.
312. Weinthal D, Tovkach A, Zeevi V, & Tzfira T (2010) Genome editing in plant cells by zinc finger nucleases. *Trends Plant Sci* 15(6):308-321.
313. Gaj T, Gersbach C A, & Barbas C F (2013) ZFN, TALEN and CRISPR/Cas-based methods for genome engineering. *Trends Biotechnol* 31(7):397-405.
314. Sprink T, Metje J, & Hartung F (2015) Plant genome editing by novel tools: TALEN and other sequence specific nucleases. *Curr Opin Biotechnol* 32:47-53.
315. Bortesi L & Fischer R (2015) The CRISPR/Cas9 system for plant genome editing and beyond. *Biotechnol Adv* 33(1):41-52.
316. Kumar V & Jain M (2015) The CRISPR-Cas system for plant genome editing: advances and opportunities. *J Exp Bot* 66(1):47-57.
317. Dufourmantel N, et al. (2004) Generation of fertile transplastomic soybean. *Plant Mol Biol* 55(4):479-489.
318. Miller J H (1992) *A short course in bacterial genetics: a laboratory manual and handbook for Escherichia coli and related bacteria* (Cold Spring Harbor Laboratory Press, Plainview, N.Y.).
319. Parekh S, Vinci V A, & Strobel R J (2000) Improvement of microbial strains and fermentation processes. *Appl Microbiol Biotechnol* 54(3):287-301.
320. Forsburg S L (2001) The art and design of genetic screens: Yeast. *Nature Rev Genetics* 2(9):659-668.
321. Flynn T, Ghirardi M L, & Seibert M (2002) Accumulation of 02-tolerant phenotypes in H2-producing strains of *Chlamydomonas reinhardtii* by sequential applications of chemical mutagenesis and selection. *Int J Hydrogen Energy* 27(11-12):1421-1430.
322. Doan T T Y & Obbard J P (2012) Enhanced intracellular lipid in *Nannochloropsis* sp. via random mutagenesis and flow cytometric cell sorting. *Algal Res* 1(1):17-21.
323. Bernheim A G, Libis V K, Lindner A B, & Wintefinute E H (2016) Phage-mediated delivery of targeted sRNA constructs to knock down gene expression in *E. coli*. (109):e53618.
324. Zhang R, et al. (2014) High-Throughput genotyping of green algal mutants reveals random distribution of mutagenic insertion sites and endonucleolytic cleavage of transforming DNA. *Plant Cell* 26(4):1398-1409.
325. Dent R M, Haglund C M, Chin B L, Kobayashi M C, & Niyogi K K (2005) Functional genomics of eukaryotic photosynthesis using insertional mutagenesis of *Chlamydomonas reinhardtii*. *Plant Physiol* 137(2):545-556.
326. Colombo S L, et al. (2002) Use of the bleomycin resistance gene to generate tagged insertional mutants of *Chlamydomonas reinhardtii* that require elevated CO2 for optimal growth. *Funct Plant Biol* 29(3):231-241.

327. Gonzalez-Ballester D, et al. (2011) Reverse genetics in *Chlamydomonas*: a platform for isolating insertional mutants. *Plant Methods* 7(1):1-13.
328. Kleckner N, Bender J, & Gottesman S (1991) Uses of transposons with emphasis on Tn10. *Methods Enzymol* 204:139-180.
329. Wu-Scharf D, Jeong B-r, Zhang C, & Cerutti H (2000) Transgene and transposon silencing in *Chlamydomonas reinhardtii* by a DEAH-Box RNA helicase. *Science* 290 (5494):1159-1162.
330. Casas-Mollano J A, et al. (2008) Diversification of the core RNA interference machinery in *Chlamydomonas reinhardtii* and the role of DCL1 in transposon silencing. *Genetics* 179(1):69-81.
331. Goryshin I Y, Jendrisak J, Hoffman L M, Meis R, & Reznikoff W S (2000) Insertional transposon mutagenesis by electroporation of released Tn5 transposition complexes. *Nat Biotech* 18(1):97-100.
332. Datsenko K A & Wanner B L (2000) One-step inactivation of chromosomal genes in *Escherichia coli* K-12 using PCR products. *PNAS* 97.
333. Zhong J, Karberg M, & Lambowitz A M (2003) Targeted and random bacterial gene disruption using a group II intron (targetron) vector containing a retrotransposition-activated selectable marker. *Nucleic Acids Res* 31(6):1656-1664.
334. Minoda A, Sakagami R, Yagisawa F, Kuroiwa T, Sc. Tanaka K (2004) Improvement of culture conditions and evidence for nuclear transformation by homologous recombination in a red alga, *Cyanidioschyzon merolae* 10D. *Plant Cell Physiol* 45(6):667-671.
335. Qi Lei S, et al. (2013) Repurposing CRISPR as an RNA-guided platform for sequence-specific control of gene expression. *Cell* 152(5):1173-1183.
336. Jiang W, Bikard D, Cox D, Zhang F, & Marraffini L A (2013) RNA-guided editing of bacterial genomes using CRISPR-Cas systems. *Nat Biotechnol* 31(3):233-239.
337. Zhao T, Wang W, Bai X, & Qi Y (2009) Gene silencing by artificial microRNAs in *Chlamydomonas*. *Plant J* 58(1):157-164.
338. Si T, HamediRad M, & Zhao H (2015) Regulatory RNA-assisted genome engineering in microorganisms. *Curr Opin Biotechnol* 36:85-90.
339. Meng J, et al. (2012) A genome-wide inducible phenotypic screen identifies antisense RNA constructs silencing *Escherichia coli* essential genes. *FEMS microbiology letters* 329(1):45-53.
340. Xiao H & Zhao H (2014) Genome-wide RNAi screen reveals the E3 SUMO-protein ligase gene SIZ1 as a novel determinant of furfural tolerance in *Saccharomyces cerevisiae*. *Biotechnol Biofuels* 7(1):1-11.
341. Bao Z, et al. (2015) Homology-integrated CRISPR-Cas (HI-CRISPR) system for one-step multigene disruption in *Saccharomyces cerevisiae*. *ACS Synth Biol* 4(5):585-594.
342. De Backer M D, et al. (2001) An antisense-based functional genomics approach for identification of genes critical for growth of *Candida albicans*. *Nat Biotech* 19(3):235-241.
343. Na D, et al. (2013) Metabolic engineering of *Escherichia coli* using synthetic small regulatory RNAs. *Nat Biotech* 31(2):170-174.
344. Ohnuma M, et al. (2009) Transient gene suppression in a red alga, *Cyanidioschyzon merolae* 10D. *Protoplasma* 236(1-4):107-112.
345. Molnar A, et al. (2009) Highly specific gene silencing by artificial microRNAs in the unicellular alga *Chlamydomonas reinhardtii*. *Plant J* 58:165-174.
346. Nakai K & Kanehisa M (1991) Expert system for predicting protein localization sites in gram-negative bacteria. *Proteins: Struct, Funct, and Bioinf* 11(2):95-110.
347. Bendtsen J D, Nielsen H, von Heijne G, & Brunak S (2004) Improved prediction of signal peptides: SignalP 3.0. *J Mol Biol* 340(4):783-795.
348. Bendtsen J D, Kiemer L, Fausbøll A, & Brunak S (2005) Non-classical protein secretion in bacteria. *BMC Microbiol* 5(1):1-13.
349. Bendtsen J D, Jensen L T, Blom N, von Heijne G, & Brunak S (2004) Feature based prediction of non-classical protein secretion. *Protein Eng Des Sel* 17.
350. Gaj T, Gersbach C A, & Barbas C F, 3rd (2013) ZFN, TALEN, and CRISPR/Cas-based methods for genome engineering. *Trends Biotechnol* 31(7):397-405.
351. Kumar V & Jain M (2015) The CRISPR-Cas system for plant genome editing: advances and opportunities. *J Exp Bot* 66(1):47-57.
352. Bortesi L & Fischer R (2015) The CRISPR/Cas9 system for plant genome editing and beyond. *Biotechnol Adv* 33(1):41-52.
353. Sprink T, Metje J, & Hartung F (2015) Plant genome editing by novel tools: TALEN and other sequence specific nucleases. *Curr Opin Biotechnol* 32(Supplement C):47-53.
354. Andersen L, Sundman L-O, Inge-Britt Linden I-B, Kontro P, & Simo S O (1984) Synthesis and anticonvulsant properties of some 2-Aminoethanesulfonic acid (Taurine) derivatives. *J Pharm Sci* 73:106-108.
355. Herdeis C & Weis C E (1999) U.S. Pat. No. 5,889,183.
356. Tserng K-Y, Hachey D L, & Klein P D (1977) An improved procedure for the synthesis of glycine and taurine conjugates of bile acids. *J Lipid Res* 18:404-407.
357. Fong D W & Hoots J E (1992) U.S. Pat. No. 5,128,419.
358. Seeberger S, Griffin R J, Hardcastle I R, & Golding B T (2007) A new strategy for the synthesis of taurine derivatives using the 'safety-catch' principle for the protection of sulfonic acids. *Org Biomol Chem* 5:132-138.
359. Suzuki M, Nakajima Y, Sato T, Shirai H, & Hanabusa K (2006) Fabrication of TiO2 using L-lysine-based organogelators as organic templates: control of the nanostructures. *Chem Commun* (4):377-379.
360. Mikhalenko S A, Soloveva L I, & Lukyanets E A (2004) Phthalocyanines and related compounds: XXXVIII. Synthesis of symmetric taurine- and choline-substituted phthalocyanines. *Russ J Gen Chem* 74:1775-1800.
361. Capone R, Blake S, Restrepo M R, Yang J, & Mayer M (2007) Designing nanosensors based on charged derivatives of *Gramicidin A*. *J Amer Chem Soc* 129:9737-9745.
362. Gupta R C, Win T, & Bittner S (2005) Taurine analogues; A new class of therapeutics: Retrospect and prospects *Curr Med Chem* 12:2021-2039.
363. Johnson B A (2008) Update on neuropharmacological treatments for alcoholism: Scientific basis and clinical findings. *Biochem Pharmacol* 75:34-56.
364. Tambour S & Quertemont E (2007) Preclinical and clinical pharmacology of alcohol dependence. *Fund Clin Pharmacol* 21:9-28.
365. Joung Y K, Sengoku Y, Ooya T, Park K D, & Yui N (2005) Anticoagulant supramolecular-structured polymers: Synthesis and anticoagulant activity of taurine-conjugated carboxyethylester-polyrotaxanes. *Sci Tech Adv Materials* 6:484-490.
366. Ozmeriç N, et al. (2000) Chitosan film enriched with an antioxidant agent, taurine, in fenestration defects. *J Biomed Materials Res Part A* 51:500-503.

367. Degim Z, et al. (2002) An investigation on skin wound healing in mice with a taurinechitosan gel formulation. *Amino Acids* 22:187-198.
368. Matsusaki M, Serizawa T, Kishida A, Endo T, & Akashi M (2002) Novel functional biodegradable polymer: Synthesis and anticoagulant activity of poly(γ-Glutamic Acid) sulfonate (γ-PGA-sulfonate). *Bioconjugate Chem* 13:23-28.
369. Roubos J A, van Straten G, & van Boxtel A J B (1999) An evolutionary strategy for fed-batch bioreactor optimization; concepts and performance. *J Biotechnol* 67(2-3): 173-187.
370. Oka T (1999) Amino acids, production processes. *Encyclopedia of Bioprocess Technology: Fermentation, Biocatalysis, and Bioseparation*, eds Flickinger M C & Drew S W (Wiley, London).
371. Borowitzka M A (1999) Commercial production of microalgae: ponds, tanks, tubes and fermenters. *J Biotechnol* 70(1-3):313-321.
372. Hermann T (2003) Industrial production of amino acids by coryneform bacteria. *J Biotechnol* 104(1-3):155-172.
373. Ikeda M (2003) Amino acid production processes. *Adv Biochem Eng Biotechnol* 79:1-35.
374. Ikeda M (2005) Towards bacterial strains overproducing l-tryptophan and other aromatics by metabolic engineering. *Appl Microbiol Biotechnol* 69(6):615-626.
375. Richmond A & Hu Q eds (2013) *Handbook of Microalgal Culture: Biotechnology and Applied Phycology* (Wiley-Blackwell, Hoboken, N.J.), 2nd Ed.
376. Cardozo K H, et al. (2007) Metabolites from algae with economical impact. *Comp Biochem Physiol C Toxicol Pharmacol* 146(1-2):60-78.
377. Milledge J J (2011) Commercial application of microalgae other than as biofuels: a brief review. *Reviews in Environ Sci Biotechnol* 10:31-41.
378. Xu Q, Li S, Huang H, & Wen J (2012) Key technologies for the industrial production of fumaric acid by fermentation. *Biotechnol adv* 30(6):1685-1696.
379. Dufossé L, Fouillaud M, Caro Y, Mapari S A S, & Sutthiwong N (2014) Filamentous fungi are large-scale producers of pigments and colorants for the food industry. *Curr Opin Biotechnol* 26:56-61.
380. Höfler A, et al. (1998) U.S. Pat. No. 5,840,358
381. Lee I, Lee K, Namgoong K, & Lee Y-S (2002) The use of ion exclusion chromatography as approved to the nomial ion exchange chromatography to achieve a more efficient lysine recovery from fermentation broth. *Enzyme Microb Technol* 30(6):798-803.
382. Binder M & Uffmann K-E (2002) U.S. Pat. No. 6,465,025.
383. Leuchtenberger W, Huthmacher K, & Drauz K (2005) Biotechnological production of amino acids and derivatives: current status and prospects. *Appl Microbiol Biotechnol* 69(1):1-8.
384. Liu P, et al. (2012) Role of Glutamate Decarboxylase-like Protein 1 (GADL1) in Taurine Biosynthesis. *J Biol Chem* 287(49):40898-40906.
385. Winge I, et al. (2015) Mammalian CSAD and GADL1 have distinct biochemical properties and patterns of brain expression. *Neurochem Int* 90:173-184.
386. Meinkoth J & G. W (1984) Hybridization of nucleic acids immobilized on solid supports. *Anal Biochem* 138: 267-284.
387. Tijssen P (1993) Overview of principles of hybridization and the strategy of nucleic acid probe assays. *Laboratory Techniques in Biochemistry and Molecular Biology—Hybridization with Nucleic Acid Probes: Part I*, (Elsevier, New York).
388. Smith T F & Waterman M S (1981) Comparison of biosequences. *Adv Appl Math* 2:482-489.
389. Needleman S B & Wunsch C D (1970) A general method applicable to the search for similarities in the amino acid sequence of two proteins. *J Mol Biol* 48:443-453.
390. Pearson W R & Lipman D J (1988) Improved tools for biological sequence comparison. *PNAS* 85:2444-2448.
391. Higgins D G, Bleasby A J, & Fuchs R (1992) CLUSTAL V: improved software for multiple sequence alignment. *Comp Appl Biosci* 8(2):189-191.
392. Higgins D G & Sharp P M (1988) CLUSTAL: a package for performing multiple sequence alignment on a microcomputer. *Gene* 73(1):237-244.
393. Higgins D G & Sharp P M (1989) Fast and sensitive multiple sequence alignments on a microcomputer. *Comp Appl Biosci* 5(2):151-153.
394. Feng D F & Doolittle R F (1987) Progressive sequence alignment as a prerequisite to correct phylogenetic trees. *J Mol Evol* 25(4):351-360.
395. Henikoff S & Henikoff J (1989) Amino acid substitution matrices from protein blocks *PNAS* 89:10915-10919.
396. Altschul S F, et al. (1997) Gapped BLAST and PSI-BLAST: a new generation of protein database search programs. *Nucleic Acids Res* 25:3389-3402.
397. Wootton J C & Federhen S (1993) Statistics of local complexity in amino acid sequences and sequence databases. *Comp Chem* 17:149-163.
398. Wootton J C & Federhen S (1996) Analysis of compositionally biased regions in sequence databases. *Methods Enzymol* 266:554-571.
399. Claverie J-M & States D J (1993) Information enhancement methods for large scale sequence analysis. *Comp Chem* 17:191-201.
400. Myers E W & Miller W (1988) Optimal alignments in linear-space. *Comp App Biol Sci* 4:11-17.
401. Cadwell R C & Joyce G F (1994) Mutagenic PCR. *PCR Meth Appl* 3(6):5136-140.
402. Lin-Goerke J L, Robbins D J, & Burczak J D (1997) PCR-based random mutagenesis using manganese and reduced dNTP concentration. *Biotechniques* 23(3):409-412.
403. Stemmer W P (1994) Rapid evolution of a protein in vitro by DNA shuffling. *Nature* 370(6488):389-391.
404. Buchholz J, et al. (2013) Platform engineering of *Corynebacterium glutamicum* with reduced pyruvate dehydrogenase complex activity for improved production of L-lysine, L-valine, and 2-ketoisovalerate. *Appl Environ Microbiol* 79(18):5566-5575.
405. Stefan A, Schwarz F, Bressanin D, & Hochkoeppler A (2010) Shine-Dalgarno sequence enhances the efficiency of lacZ repression by artificial anti-lac antisense RNAs in *Escherichia coli*. *J Biosci Bioeng* 110(5):523-528.
406. Studier F W (2014) Stable Expression Clones and Auto-Induction for Protein Production in *E. coli*. Structural Genomics: Methods and Protocols, Methods in Molecular Biology, ed Chen Y W (Springer, New York).

What is claimed is:

1. A cell comprising:
   (a) a unit expressing a synthetic or semi-synthetic cysteine synthetase/PLP decarboxylase (sCS/PLP-DC), wherein
      (i) exogenous DNA comprises a single expression cassette, wherein the single expression cassette comprises a promoter operably linked to a polynucleotide which encodes a cysteine synthetase (CS) fused in-frame with a PLP-dependent decarboxylase (DC) or
      (ii) exogenous DNA comprises a single expression cassette, wherein the single expression cassette comprises a promoter operably linked to a polynucleotide which encodes a cystathionine beta synthase (CBS) fused in-frame with a PLP-dependent DC; or
   (b) two units expressed as one polycistronic message, wherein
      (i) an exogenous DNA comprises a single expression cassette, wherein the single expression cassette comprises a promoter operably linked to a polynucleotide which encodes a sCS/PLP-DC protein and
      (ii) a second polynucleotide which encodes a taurine-binding protein,
wherein the expression units are expressed in the cell and wherein the cell produces taurine.

2. The cell of claim 1, wherein the sCS/PLP-DC polynucleotide encodes a polypeptide with the amino acid sequence SEQ ID NO:84.

3. The cell of claim 1, wherein the sCS/PLP-DC polynucleotide encodes a polypeptide with the amino acid sequence with 90% identity to SEQ ID NO:84.

4. The cell of claim 1, wherein the sCS/PLP-DC polynucleotide encodes a polypeptide with the amino acid sequence with 80% identity to SEQ ID NO:84.

5. The cell of claim 1, wherein the cell is a prokaryotic cell.

6. The prokaryotic cell of claim 5, wherein the function of the TauD, TauX, TauY, SsuD, SsuE, Tpa, cbl or TauR gene(s) in the prokaryotic cell is disrupted by a genetic knock out resulting in negligible expression of the corresponding gene products TDO, TDH, TDH, SsuD, SsuE, Tpa, cbl or TauR identified herein as TauD/KO, TauX/KO, TauY/KO, SsuD/KO, SsuE/KO, Tpa/KO, cbl/KO or TauR/KO.

7. The prokaryotic cell of claim 5, wherein the prokaryotic cell is a bacteria selected from the group consisting of Proteobacteria, Alphaproteobacteria, Betaproteobacteria, Deltaproteobacteria, Epsilonproteobacteria, methanotrophs, *Methylobacterium, Bacillus, Salmonella, Lactococcus, Streptococcus, Brevibacterium, Coryneform bacteria, Bacillus subtilis, Brevibacterium ammoniagene, Corynebacterium crenatum, Corynebacterim pekinese, Corynebacterium glutamicumas glutamicum, Erwinia citreus, Erwinia herbicola, Escherichia coli, Fusarium venenatum, Gluconobacter oxydans, Propionibacterium freudenreicheii,* and *Propionibacterium denitrificans.*

* * * * *